United States Patent
Rome et al.

(10) Patent No.: US 9,597,372 B2
(45) Date of Patent: Mar. 21, 2017

(54) VAULT COMPLEXES FOR CYTOKINE DELIVERY

(71) Applicant: The Regents of the University of California, Oakland, CA (US)

(72) Inventors: Leonard H. Rome, Los Angeles, CA (US); Valerie A. Kickhoefer, Sherman Oaks, CA (US); Steven M. Dubinett, Los Angeles, CA (US); Sherven Sharma, Culver City, CA (US); Upendra K. Kar, Dhenkanal (IN)

(73) Assignees: The Regents of the University of California, Oakland, CA (US); The United States of America as represented by the Department of Veterans Affairs, Washington, DC (US)

( * ) Notice: Subject to any disclaimer, the term of this patent is extended or adjusted under 35 U.S.C. 154(b) by 79 days.

(21) Appl. No.: 14/553,146

(22) Filed: Nov. 25, 2014

(65) Prior Publication Data

US 2015/0150944 A1    Jun. 4, 2015

Related U.S. Application Data

(63) Continuation of application No. 13/505,420, filed as application No. PCT/US2010/055146 on Nov. 2, 2010, now Pat. No. 8,920,807.

(60) Provisional application No. 61/257,358, filed on Nov. 2, 2009.

(51) Int. Cl.

| | | |
|---|---|---|
| *C12N 5/00* | (2006.01) | |
| *C12P 21/06* | (2006.01) | |
| *C07K 14/435* | (2006.01) | |
| *A61K 38/19* | (2006.01) | |
| *A61K 38/00* | (2006.01) | |
| *C07K 14/52* | (2006.01) | |
| *A61K 47/48* | (2006.01) | |
| *A61K 35/12* | (2015.01) | |
| *A61K 48/00* | (2006.01) | |
| *C07H 21/00* | (2006.01) | |
| *C07K 7/06* | (2006.01) | |
| *C07K 14/47* | (2006.01) | |
| *C12N 5/0783* | (2010.01) | |
| *C12N 9/96* | (2006.01) | |
| *C12N 15/86* | (2006.01) | |
| *G01N 33/535* | (2006.01) | |

(52) U.S. Cl.
CPC ............ *A61K 38/195* (2013.01); *A61K 38/00* (2013.01); *A61K 47/48853* (2013.01); *C07K 14/521* (2013.01); *A61K 35/12* (2013.01); *A61K 48/00* (2013.01); *C07H 21/00* (2013.01); *C07K 7/06* (2013.01); *C07K 14/47* (2013.01); *C07K 2319/00* (2013.01); *C12N 5/0636* (2013.01); *C12N 9/96* (2013.01); *C12N 15/86* (2013.01); *G01N 33/535* (2013.01)

(58) Field of Classification Search
CPC ................. A61K 38/00; A61K 38/195; A61K 47/48853; C01K 14/521
See application file for complete search history.

(56) References Cited

U.S. PATENT DOCUMENTS

| | | | |
|---|---|---|---|
| 5,139,941 A | 8/1992 | Muzyczka et al. | |
| 5,252,479 A | 10/1993 | Srivastava | |
| 5,436,146 A | 7/1995 | Shenk et al. | |
| 5,665,557 A | 9/1997 | Murray et al. | |
| 5,981,276 A | 11/1999 | Sodroski et al. | |
| 6,110,740 A | 8/2000 | Rome et al. | |
| 6,143,520 A | 11/2000 | Marasco et al. | |
| 6,156,879 A | 12/2000 | Rome et al. | |
| 6,555,347 B1 | 4/2003 | Rome et al. | |
| 7,482,319 B2 | 1/2009 | Rome et al. | |
| 8,124,109 B2 | 2/2012 | Kickhoefer et al. | |
| 8,318,182 B2 | 11/2012 | Kickhoefer et al. | |
| 8,551,781 B2 | 10/2013 | Rome et al. | |
| 8,834,896 B2 * | 9/2014 | Kickhoefer | A61K 39/118 424/234.1 |
| 8,920,807 B2 * | 12/2014 | Rome | A61K 38/00 424/184.1 |
| 8,933,203 B2 * | 1/2015 | Rome | B82Y 5/00 424/130.1 |
| 9,114,173 B2 * | 8/2015 | Rome | B82Y 5/00 |
| 9,181,312 B2 * | 11/2015 | Rome | C07K 14/005 |
| 2006/0148086 A1 | 7/2006 | Rome et al. | |
| 2009/0226435 A1 | 9/2009 | Khare | |

(Continued)

FOREIGN PATENT DOCUMENTS

| | | |
|---|---|---|
| WO | WO-93/24641 A2 | 12/1993 |
| WO | WO-93/24641 A3 | 12/1993 |

(Continued)

OTHER PUBLICATIONS

Kickhoefer et al., (ACS Nano. 2009;3(1):27-36. Epub Dec. 19, 2008).*
Allen, T.M. et al. (Mar. 19, 2004). "Drug Delivery Systems: Entering the Mainstream," *Science* 303:1818-1822.
Almand, B. et al. (2001). "Increased Production of Immature Myeloid Cells in Cancer Patients: A Mechanism of Immunosuppression in Cancer," *The Journal of Immunology* 166:678-689.
Altschul, S.F. et al. (1990). "Basic Local Alignment Search Tool," *J. Mol. Biol.* 215:403-410.
Anderson, D.H. et al. (Nov. 2007). "Draft Crystal Structure of the Vault Shell at 9-Å Resolution," *PLoS Biol.* 5(11): e318, 10 pages.
Andersson, A. et al. (2009). "IL-7 promotes CXCR3 Ligand-Dependent T Cell Antitumor Reactivity in Lung Cancer," *J. Immunol.* 182:6951-6958.

(Continued)

*Primary Examiner* — Cherie M Stanfield
(74) *Attorney, Agent, or Firm* — Suzannah K. Sundby, Esq.; Canady + Lortz LLP

(57) ABSTRACT

The invention relates to compositions of vault complexes containing recombinant cytokine fusion proteins that include a cytokine and a vault targeting domain, and methods of using the vault complexes to deliver the cytokines to a cell or subject, and methods for using the compositions to treat cancer, such as lung cancer.

12 Claims, 7 Drawing Sheets

(56) References Cited

U.S. PATENT DOCUMENTS

| | | | |
|---|---|---|---|
| 2010/0086610 | A1 | 4/2010 | Rome et al. |
| 2012/0003201 | A1 | 1/2012 | Nicholas et al. |
| 2013/0078273 | A1 | 3/2013 | Kickhoefer et al. |
| 2013/0122037 | A1 | 5/2013 | Kickhoefer et al. |
| 2013/0344564 | A1 | 12/2013 | Rome et al. |
| 2014/0377301 | A1 | 12/2014 | Kickhoefer et al. |

FOREIGN PATENT DOCUMENTS

| | | | | |
|---|---|---|---|---|
| WO | WO-94/12649 | A2 | 6/1994 | |
| WO | WO-94/12649 | A3 | 6/1994 | |
| WO | WO-94/13788 | A1 | 6/1994 | |
| WO | WO-99/49025 | A2 | 9/1999 | |
| WO | WO-99/49025 | A3 | 9/1999 | |
| WO | WO-99/62547 | A1 | 12/1999 | |
| WO | WO-2004/081533 | A2 | 9/2004 | |
| WO | WO-2004/081533 | A3 | 9/2004 | |
| WO | WO 2009117566 | A1 * | 9/2009 | ......... A61K 39/0011 |
| WO | WO-2009117566 | A1 | 9/2009 | |
| WO | WO-2011/053991 | A2 | 5/2011 | |
| WO | WO-2011/053991 | A3 | 5/2011 | |

OTHER PUBLICATIONS

Baratelli, F. et al. (Jul. 22, 2008). "Pre-Clinical Characterization of GMP Grade CCL21-Gene Modified Dendritic Cells for Application in a Phase I Trial in Non-Small Cell Lung Cancer," *Journal of Translation Medicine* 6:38, 17 pages.

Berger, W. et al. (2009, e-pub. Sep. 19, 2008). "Vaults and the Major Vault Protein: Novel Roles in Signal Pathway Regulation and Immunity," *Cell Mol. Life Sci.* 66(1):43-61.

Boesen, J.J.B. et al. (1994). "Circumvention of Chemotherapy-Induced Myelosuppression by Transfer of the *mdr1* Gene," *Biotherapy* 6:291-302.

Boon, T. et al. (1994). "Tumor Antigens Recognized by T Lymphocytes," *Annu. Rev. Immunol.* 12:337-365.

Bout, A. et al. (1994). "Lung Gene Therapy: In Vivo Adenovirus-Mediated Gene Transfer to Rhesus Monkey Airway Epithelium," *Human Gene Therapy* 5:3-10.

Champion, C.I. et al. (Apr. 2009). "A Vault Nanoparticle Vaccine Induces Protective Mucosal Immunity," *PLoS ONE* 4(4):e5409, 12 pages.

Chen, H. et al. (Feb. 24, 2009). "Anti-CTLA-4 Therapy Results in Higher CD4$^+$ICOS$^{hi}$ T Cell Frequency and IFN-$\gamma$ Levels in Both Nonmalignant and Malignant Prostate Tissues," *PNAS* 106(8):2729-2734.

Chugani, D.C. et al. (Jan. 1991). "Vault Immunofluorescence in Brain: New Insights Regarding the Origin of Microglia," *The Journal of Neuroscience* 11:256-268.

Chugani, D.C. et al. (1993). "Evidence that Vault Ribonucleoprotein Particles Localize to the Nuclear Pore Complex," *Journal of Cell Science* 106:23-29.

Clowes. M.M. et al. (Feb. 1994). "Long-Term Biological Response of Injured Rat Carotid Artery Seeded with Smooth Muscle Cells Expressing Retrovirally Introduced Human Genes," *J. Clin. Invest.* 93:644-651.

Diaz-Montero, C.M. et al. (Jan. 2009). "Increased Circulating Myeloid-Derived Suppressor Cells Correlate with Clinical Cancer Stage, Metastatic Tumor Burden, and Doxorubicin-Cyclophosphamide Chemotherapy," *Cancer Immunol. Immunother.* 58(1):49-59.

Dieu-Nosjean, M.-C. et al. (Sep. 20, 2008). "Long-Term Survival for Patients with Non-Small-Cell Lung Cancer with Intratumoral Lymphoid Structures," *Journal of Clinical Oncology* 26(27):4410-4417.

Esfandiary, R. et al. (Apr. 2009, e-pub. Aug. 6, 2008). "Structural Stability of Vault Particles," *Journal of Pharmaceutical Sciences* 98(4):1376-1386, doi: 10.1002/jps.21508.

Fisher, K.J. et al. (Jan. 1996). "Transduction with Recombinant Adeno-Associated Virus for Gene Therapy is Limited by Leading-Strand Synthesis," *Journal of Virology* 70(1):520-532.

Goldsmith, L.E. et al. (Mar. 13, 2007, e-pub. Feb. 16, 2007). "Vault Nanocapsule Dissociation into Halves Triggered at Low pH," *Biochemistry* 46(10):2865-2875.

Goldsmith, L.E. et al. (Oct. 2009, e-pub. Sep. 23, 2009). "Utilization of a Protein 'Shuttle' to Load Vault Nanocapsules with Gold Probes and Proteins," *ACS Nano* 3(10):3175-3183.

Greish, K. (Aug.-Sep. 2007). "Enhanced Permeability and Retention of Macromolecular Drugs in Solid Tumors: A Royal Gate for Targeted Anticancer Nanomedicines," *Journal of Drug Targeting* 15(7-8): 457-464.

Grossman, M. et al. (1993). "Retroviruses: Delivery Vehicle to the Liver," *Current Opinion in Genetics and Development* 3:110-114.

Gunn, M.D. et al. (Jan. 1998). "A Chemokine Expressed in Lymphoid High Endothelial Venules Promotes the Adhesion and Chemotaxis of Naïve T Lymphocytes," *Proc. Natl. Acad. Sci. USA* 95:258-263.

Herrmann, C. et al. (Mar. 22, 1999). "Recombinant Major Vault Protein is Targeted to Neuritic Tips of PC12 Cells," *The Journal of Cell Biology* 144(6):1163-1172.

Hiraoka, K. et al. (2006). "Concurrent Infiltration by CD8$^+$ T cells and CD4$^+$ T Cells is a Favourable Prognostic Factor in Non-Small-Cell Lung Carcinoma," *British Journal of Cancer* 94(2):275-280.

Hu, Y. et al. (2002). "A Very Early Induction of Major Vault Protein Is Accompanied by Increased Drug Resistance in U-937 Cells," *Int. J. Cancer* 97:149-156.

Izquierdo, M.A. et al. (1996). "Relationship of LRP-Human Major Vault Protein to in vitro and Clinical Resistance to Anticancer Drugs," *Cytotechnology* 19:191-197.

Izquierdo, M.A. et al. (Mar. 1996). "Broad Distribution of the Multidrug Resistance-Related Vault Lung Resistance Protein in Normal Human Tissues and Tumors," *American Journal of Pathology* 148(3):877-887.

Johnson, S.K. et al. (2000). "Immune Cell Infiltrates and Prognosis in Primary Carcinoma of the Lung," *Lung Cancer* 27(1):27-35.

Ju, S. et al. (Aug. 15, 2009). "CD13$^+$CD4$^+$CD25$^{th}$ Regulatory T Cells Exhibit Higher Suppressive Function and Increase with Tumor Stage in Non-Small Cell Lung Cancer Patients," *Cell Cycle* 8(16):2578-2585.

Kaddis, C.S. et al. (2007, e-pub. Apr. 16, 2007). "Sizing Large Proteins and Protein Complexes by Electrospray Ionization Mass Spectrometry and Ion Mobility," *J. Am. Soc. Mass Spectrom* 18:1206-1216.

Kar, U.K. et al. (Jul. 2012). "Vault Nanocapsules as Adjuvants Favor Cell-Mediated Over Antibody-Mediated immune Responses Following Immunization of Mice," *PLoS ONE* 7(7):e38553, 13 pages.

Kedersha, N.L. et al. (Sep. 1986). "Isolation and Characterization of a Novel Ribonucleoprotein Particle: Large Structures Contain a Single Species of Small RNA," *J. Cell Biol.* 103:699-709.

Kedersha, N.L. et al. (Apr. 1990). "Vaults. II. Ribonucleoprotein Structures are Highly Conserved Among Higher and Lower Eukaryotes," *J. Cell Biol.* 110:895-901.

Kedersha, N.L. et al. (1990). "Vaults: Large Cytoplasmic RNP's that Associate with Cytoskeletal Elements," *Molecular Biology Reports* 14:121-122.

Kedersha, N.L. et al. (Jan. 1991). "Vaults. III. Vault Ribonucleoprotein Particles Open into Flower-like Structures with Octagonal Symmetry," *J. Cell Biol.* 112:225-235.

Kickhoefer, V.A. et al. (Apr. 15, 1993). "Vault Ribonucleoprotein Particles from Rat and Bullfrog Contain a Related Small RNA that is Transcribed by RNA Polymerase III," *J. Biol. Chem.* 268(11):7868-7873.

Kickhoefer, V.A. et al. (1994). "The Sequence of a cDNA Encoding the Major Vault Protein from *Rattus norvegicus*," *Gene* 151:257-260.

Kickhoefer, V.A. et al. (May 1996). "Vaults are the Answer, What is the Question?" *Trends in Cell Biology* 6:174-178.

Kickhoefer, V.A. et al. (Apr. 10, 1998). "Vaults are Up-Regulated in Multidrug Resistant Cancer Cell Lines," *J. Biol. Chem.* 273(15):8971-8974.

(56) References Cited

OTHER PUBLICATIONS

Kickhoefer, V.A. et al. (Sep. 6, 1999). "The 193-kD Vault Protein, VPARP, Is a Novel Poly(ADP-ribose) Polymerase," *J. Cell Biol.* 146(5):917-928.

Kickhoefer, V.A. et al. (Nov. 12, 1999). "Vaults and Telomerase Share a Common Subunit, TEP1," *J. Biol. Chem.* 274:32712-32717.

Kickhoefer, V.A. et al. (Jan. 8, 2001). "The Telomerase/Vault-Associated Protein TEP1 is Required for Vault RNA Stability and Its Association with the Vault Particle," *J. Cell Biol.* 152:157-164.

Kickhoefer, V.A. et al. (Mar. 22, 2005). "Engineering of Vault Nanocapsules with Enzymatic and Fluorescent Properties," *PNAS* 102(12):4348-4352.

Kiem, H.-P. et al. (Mar. 15, 1994). "Retrovirus-Mediated Gene Transduction Into Canine Peripheral Blood Repopulating Cells," *Blood* 83(6):1467-1473.

Kirk, C.J. et al. (Dec. 15, 2001). "The Dynamics of the T-Cell Antitumor Response: Chemokine-Secreting Dendritic Cells Can Prime Tumor-Reactive T Cells Extranodally," *Cancer Research* 61:8794-8802.

Kong, L.B. et al. (Apr. 1999). "Structure of the Vault, a Ubiquitous Cellular Component," *Structure* 7:371-379.

Kong, L.B. et al. (2000). "RNA Location and Modeling of a WD40 Repeat Domain within the Vault," *RNA* 6:890-900.

Kozarsky, K.F. et al. (1993). "Gene Therapy: Adenovirus Vectors," *Current Opinion in Genetics and Development* 3:499-503.

Kusmartsev, S.A. et al. (1989). "Suppressor Activity of Bone Marrow and Spleen Cells in C57BI/6 Mice During Carcinogenesis Induced by 7,12-Dimethylbenz(a)anthracene," *Eksp Onkol* 11(5):23-26. (English Abstract Only).

Kusmartsev, S.A. et al. (1998). "Immunosuppressive Cells in Bone Marrow of Patients with Stomach Cancer," *Adv. Exp. Med. Biol.* 451:189-194.

Kusmartsev, S.A. et al. (2000). "Gr-1+ Myeloid Cells Derived from Tumor-Bearing Mice Inhibit Primary T Cell Activation Induced Through CD3/CD28 Costimulation," *The Journal of Immunology* 165:779-785.

Lai, C.-Y. et al. (2009, e-pub. Feb. 18, 2009). "Vault Nanoparticles Containing an Adenovirus-Derived Membrane Lytic Protein Facilitate Toxin and Gene Transfer," *ACS Nano* 3(3):691-699.

Li, C. et al. (Feb. 1, 2007). "Identification of Pancreatic Cancer Stem Cells," *Cancer Research* 67(3):1030-1037.

Li, L. et al. (2009). "The Prevalence of FOXP3+ Regulatory T-Cells in Peripheral Blood of Patients with NSCLC," *Cancer Biotherapy Radiopharmaceuticals* 24(3):357-367.

Liang, C.-M. et al. (Sep. 2007, e-pub. Jun. 13, 2007). "Local Expression of Secondary Lymphoid Tissue Chemokine Delivered by Adeno-Associated Virus within the Tumor Bed Stimulates Strong Anti-Liver Tumor Immunity," *Journal of Virology* 81(17):9502-9511.

Liu, C. et al. (May 15, 2007). "Expansion of Spleen Myeloid Suppressor Cells Represses NK Cell Cytotoxicity in Tumor-Bearing Host," *Blood* 109(10):4336-4342.

Liu, C.-Y. et al. (2010, e-pub. Jul. 2, 2009). "Population Alterations of L-Arginase- and Inducible Nitric Oxide Synthase-Expressed CD11b+/CD14−/CD15+/CD33+ Myeloid Suppressor Cells and CD8+ T Lymphocytes in Patients with Advanced-Stage Non-Small Cell Lung Cancer," *J. Cancer Res. Clin. Oncol.* 136:35-45.

Liu, Y. et al. (Jun. 2004). "Vault Poly(ADP-Ribose) Polymerase is Associated with Mammalian Telomerase and is Dispensable for Telomerase Function and Vault Structure In Vivo," *Molecular and Cell Biology* 24(12):5314-5323.

Maeda, H. et al. (2000). "Tumor Vascular Permeability and the EPR Effect in Macromolecular Therapeutics: A Review," *Journal of Controlled Release* 65:271-284.

Mastrangeli, A. et al. (1993). "Diversity of Airway Epithelial Cell Targets for In Vivo Recombinant Adenovirus-Mediated Gene Transfer," *J. Clin. Invest.* 91:225-234.

Mikyas, Y. et al. (2004). "Cryoelectron Microscopy Imaging of Recombinant and Tissue Derived Vaults: Localization of the MVP N Termini and VPARP," *J. Mol. Biol.* 344:91-105.

Needleman, S.B. et al. (1970). "A General Method Applicable to the Search for Similarities in the Amino Acid Sequence of Two Proteins," *J. Mol. Biol.* 48:443-453.

Ng, B.C. et al. (Oct. 2008, e-pub on Sep. 20, 2008). "Encapsulation of Semiconductoring Polymers in Vault Protein Cages," *Nano Letters* 8(10):3503-3509.

Novak, L. et al. (Jun. 2007). "Characterization of the CCL21-Mediated Melanoma-Specific Immune Responses and in situ Melanoma Eradication," *Mol. Cancer Ther.* 6(6):1755-1764.

Pearson, W.R. et al. (Apr. 1988). "Improved Tools for Biological Sequence Comparison," *Proc. Natl. Acad. Sci. USA* 85:2444-2448.

Poderycki, M.J. et al. (2005). "The p80 Homology Region of TEP1 is Sufficient for its Associated with the Telomerase and Vault RNAs, and the Vault Particle," *Nucleic Acids Research* 33(3):893-902.

Poderycki, M.J. et al. (Oct. 3, 2006, e-pub. Sep. 7, 2006). "The Vault Exterior Shell is a Dynamic Structure that Allows Incorporation of Vault-Associated Proteins into Its Interior," *Biochemistry* 45(39):12184-12193.

Raval-Fernandes, S. et al. (1999). "Cloning of a cDNA Encoding a Sequence-Specific Single-Stranded-DNA-Binding Protein from *Rattus norvegicus*," *Gene* 237:201-207.

Raval-Fernandes, S. et al. (Oct. 1, 2005). "increased Susceptibility of Vault Poly(ADP-Ribose) Polymerase-Deficient Mice to Carcinogen-Induced Tumorigenesis," *Cancer Res.* 65(19):8846-8852.

Rome, L. et al. (Aug./Sep. 1991). "Unlocking Vaults: Organelles in Search of a Function," *Trends in Cell Biology* 1:47-50.

Rome, L.H. (Jun. 1995). "Multidrug Resistance: Locked in the Vault?" *Nature Medicine* 1(6):527.

Rosenfeld, M.A. et al. (Apr. 19, 1991). "Adenovirus-Mediated Transfer of a Recombinant α1-Antitrypsin Gene to the Lung Epithelium in Vivo," *Science* 252:431-434.

Rosenfeld, M.A. et al. (Jan. 10, 1992). "In Vivo Transfer of the Human Cystic Fibrosis Transmembrane Conductance Regulator Gene to the Airway Epithelium," *Cell* 68:143-155.

Sakaguchi, S. (May 26, 2000). Regulatory T Cells: Key Controllers of Immunologic Self-Tolerance. *Cell* 101(5):455-458.

Salmons, B. et al. (1993). "Targeting of Retroviral Vectors for Gene Therapy," *Human Gene Therapy* 4:129-141.

Samulski, R.J. et al. (Oct. 1987). "A Recombinant Plasmid from Which an Infectious Adeno-Associated Virus Genome Can Be Excised in Vitro and Its Use to Study Viral Replication," *Journal of Virology* 61(10):3096-3101.

Samulski, R.J. et al. (Sep. 1989). "Helper-Free Stocks of Recombinant Adeno-Associated Viruses: Normal Integration Does Not Require Viral Gene Expression," *Journal of Virology* 63(9):3822-3828.

Scheper, R.J. et al. (1996). "Role of LRP/Major Vault Protein in Multidrug Resistance," Chapter 7 in *Multidrug Resistance in Cancer Cells: Molecular, Biochemical, Physiological and Biological Aspects*, Gupta, S. et al. eds., John Wiley & Sons, Chichester, England.

Schroeijers, A.B. et al. (Feb. 15, 2000). "The $M_r$ 193,000 Vault Protein is Up-Regulated in Multidrug-Resistant Cancer Cell Lines," *Cancer Research* 60:1104-1110.

Sharma, S. et al. (2000). "Secondary Lymphoid Tissue Chemokine Mediates T Cell-Dependent Antitumor Responses In Vivo," *J. Immunol.* 164(9):4558-4563.

Sharma, S. et al. (2001). "Secondary Lymphoid Organ Chemokine Reduces Pulmonary Tumor Burden in Spontaneous Murine Bronchoalveolar Cell Carcinoma," *Cancer Research* 61(17):6406-6412.

Sharma, S. et al. (Apr. 15, 2003). "SLC/CCL21-Mediated Anti-Tumor Responses Require IFNγ, MIG/CXCL9 and IP-10/CXCL10," *Molecular Cancer* 2:22, 6 pages.

Sinha, P. et al. (2005). "Reduction of Myeloid-Derived Suppressor Cells and Induction of MI Macrophages Facilitate the Rejection of Established Metastatic Disease," *The Journal of Immunology* 174(2):636-645.

Siva, A.C. et al. (2001). "Up-Regulation of Vaults May Be Necessary But Not Sufficient for Multidrug Resistance," *Int. J. Cancer* 92:195-202.

(56) References Cited

OTHER PUBLICATIONS

Slesina, M. et al. (2005, e-pub. May 18, 2005). "Nuclear Localization of the Major Vault Protein in U373 Cells," *Cell Tissue Res.* 321:97-104.
Slesina, M. et al. (2006, e-pub. Feb. 28, 2006). "Movement of Vault Particles Visualized by GFP-Tagged Major Vault Protein," *Cell Tissue Res.* 324:403-410.
Smith, T.R. et al. (1981). "Comparison of Biosequences," *Advances in Applied Mathematics* 2:482-489.
Smyth, M.J. et al. (2006). "$CD4^+CD25^+$ T Regulatory Cells Suppress NK Cell-Mediated Immunotherapy of Cancer," *The Journal of Immunology* 176(3):1582-1587.
Srivastava, M.K. et al. (Oct. 2008). "Lung Cancer Patients' $CD4^+$ T Cells are Activated in Vitro by MHC II Cell-Based Vaccines Despite the Presence of Myeloid-Derived Suppressor Cells," *Cancer Immunol. Immunother.* 57(10):1493-1504.
Stephen, A.G. et al. (Jun. 29, 2001). "Assembly of Vault-Like Particles in Insect Cells Expressing Only the Major Vault Protein," *J. Biol. Chem.* 276(26):23217-23220.
Subiza, J.L. et al. (1989). "Development of Splenic Natural Suppressor (NS) Cells in Ehrlich Tumor-Bearing Mice," *Int. J. Cancer* 44(2);307-314.
Suprenant, K.A. (Dec. 10, 2002, e-pub. Oct. 23, 2002). "Vault Ribonucleoprotein Particles: Sarcophagi, Gondolas, or Safety Deposit Boxes?" *Biochemistry* 41(49):14447-14454.
Tanaka, H. et al. (Jan. 16, 2009). "The Structure of Rat Liver Vault at 3.5 Angstrom Resolution," *Science* 323:384-388.
Vasu, S.K. et al. (Jul. 25, 1993). "cDNA Cloning and Disruption of the Major Vault Protein α Gene (*mvpA*) in *Dictyostelium discoideum*," *J. Biol. Chem.* 268(21):15356-15360.
Vilalta, A. et al. (Nov. 25, 1994). "The Rat Vault RNA Gene Contains a Unique RNA Polymerase III Promoter Composed of Both External and Internal Elements that Function Synergistically," *J. Biol. Chem.* 269(47):29752-29759.
Walsh, C.E. et al. (1993). "Gene Therapy for Human Hemoglobinopathies," *Exp. Biol. Med.* 204:289-300.
Wang, Q. et al. (1995). "A Packaging Cell Line for Propagation of Recombinant Adenovirus Vectors Containing Two Lethal Gene-Region Deletions," *Gene Therapy* 2:775-783.
Warnock, R.A. et al. (Jan. 3, 2000). "The Role of Chemokines in the Microenvironment Control of T Versus B Cell Arrest in Peyer's Patch High Endothelial Venules," *The Journal of Experimental Medicine* 191(1):77-88.
Willimann, K. et al. (1998). "The Chemokine SLC is Expressed in T Cell Areas of Lymph Nodes and Mucosal Lymphoid Tissues and Attracts Activated T Cells Via CCR7," *Eur. J. Immunol.* 28:2025-2034.
Woo, E.Y. et al. (2002). "Cutting Edge: Regulatory T Cells from Lung Cancer Patients Directly Inhibit Autologous T Cell Proliferation," *The Journal of Immunology* 168:4272-4276.
Wu, S. et al. (2008). "Tumor Transfected with CCL21 Enhanced Reactivity and Apoptosis Resistance of Human Monocyte-Derived Dendritic Cells," *Immunobiology* 213:417-426.
Xia, H. et al. (Oct. 2002, e-pub. Sep. 16, 2002). "siRNA-Mediated Gene Silencing in vitro and in vivo," *Nature Biotechnology* 20:1006-1010.
Xia, T. et al. (Jul. 2008). "Nanobiology: Particles Slip Cell Security," *Nature Materials* 7:519-520.
Xia, Y. et al. (2010, e-pub. Feb. 10, 2010). "Immobilization of Recombinant Vault Nanoparticles on Solid Substrates," *ACS Nano* 4(3):1417-1424.
Yang, J. et al. (2010, e-pub. Dec. 1, 2010). "Vaults Are Dynamically Unconstrained Cytoplasmic Nanoparticles Capable of Half Vault Exchange," *ACS Nano* 4(12):7229-7240.
Yang, S.-C. et al. (Apr. 15, 2004). "Intratumoral Administration of Dendritic Cells Overexpressing CCL21 Generates Systemic Antitumor Responses and Confers Tumor Immunity," *Clinical Cancer Research* 10:2891-2901.
Yang, S.-C. et al. (Mar. 15, 2006). "Intrapulmonary Administration of CCL21 Gene-Modified Dendritic Cells Reduces Tumor Burden in Spontaneous Murine Bronchoalveolar Cell Carcinoma," *Cancer Res* 66(6):3205-3213.
Yannelli, J.R. et al. (2009). "Characteristics of PBMC Obtained from Leukapheresis Products and Tumor Biopsies of Patients with Non-Small Cell Lung Cancer," *Oncology Reports* 22:1459-1471.
Young, M.R. et al. (1987). "Hematopoiesis and Suppressor Bone Marrow Cells in Mice Bearing Large Metastatic Lewis Lung Carcinoma Tumors," *Cancer Research* 47(1):100-105.
Young, M.R. et al. (Jul. 15, 1997). "Myeloid Differentiation Treatment to Diminish the Presence of Immune-Suppressive $CD34^+$ Cells Within Human Head and Neck Squamous Cell Carcinomas," *The Journal of Immunology* 159(2):990-996.
Yousefieh, N. et al. (2009, e-pub. May 6, 2009). "Regulated Expression of CCL21 in the Prostate Tumor Microenvironment Inhibits Tumor Growth and Metastasis in an Orthotopic Model of Prostate Cancer," *Cancer Microenvironment* 2:59-67.
Yu, M. et al. (Oct. 2008, e-pub. Sep. 20, 2008). "Reversible pH Liability of Cross-Linked Vault Nanocapsules," *Nano Letters* 8(10):3510-3515.
Final Office Action mailed on Aug. 6, 2013 for U.S. Appl. No. 13/737,963, filed Jan. 10, 2013, 12 pages.
Non-Final Office Action mailed on Mar. 21, 2013 for U.S. Appl. No. 13/737,963, filed Jan. 10, 2013, 11 pages.
Extended European Search Report for European Application No. 10827661.9-1402/2496607 mailed Nov. 15, 2013.
Communication pursuant to Rules 70(2) and 70a(2) EPC, EP No. 10827661.9-1402/2496607 Dec. 3, 2013.
Seok-Chul Yang, et al., "Intratumoral Administration of Dendritic Cells Overexpressing CCL21 Generates Systemic Antitumor Responses and Confers Tumor Immunity", Clinical Cancer Research, Apr. 15, 2004, pp. 2891-2901, vol. 10.
Chun-Min Liang, et al., "More than chemotaxis: A new anti-tumor DC vaccine modified by rAAV2-SLC", Molecular Immunology, 2007, pp. 3797-3804, vol. 44.
Cheng-Yu Lai, et al. "Vault Nanopartides Containing an Adenovirus-Derived Membrane Lytic Protein Facilitate Toxin and Gene Transfer", American Chemical Society, 2009, pp. 691-699, vol. 3; No. 3.
Cheryl I. Champion, et al., "A Vault Nanopartide Vaccine Induces Protective Mucosal Immunity", PloS ONE, Apr. 2009, 12 pp., vol. 4; Issue 4.
Kickhoefer et al., (ACS Nano. 2009;3(1 ):27-36. Epub Dec. 19, 2008).
Australian Office Action mailed on Feb. 26, 2014 for Australian Patent Application No. 2010313112, filed on Nov. 2, 2010, two pages.
Canadian Office Action mailed on Jul. 30, 2013 for Canadian Patent Application No. 2,779,512, filed on Nov. 2, 2010, three pages.
Chinese Office Action mailed on Jul. 10, 2013 for Chinese Patent Application No. 201080060374.2, filed on Nov. 2, 2010, nine pages.
Chinese Office Action mailed on Mar. 9, 2014 for Chinese Patent Application No. 201080060374.2, filed on Nov. 2, 2010, six pages.
European Communication mailed on Jun. 20, 2012 for EP Patent Application No. 10 827 661.9, filed on Nov. 2, 2010, two pages.
International Preliminary Report on Patentability mailed on May 8, 2012 for PCT Patent Application No. PCT/US2010/055146, filed on Nov. 2, 2010, seven pages.
Xie, F.Q. et al. (May 2008). "Vault and Tum or Multidrug Resistance," *Medical Recapitulate* 14(9):1326-1328.
Written Opinion of the International Searching Authority mailed on Oct. 19, 2011 for PCT Patent Application No. PCT/US2010/055146, filed on Nov. 2, 2010, six pages.
U.S. Appl. No. 14/565,676, filed Dec. 10, 2014, by Rome et al.
U.S. Appl. No. 14/411,982, filed Jul. 9, 2013, by Champion.
Office Action received in JP 2012-537196, mailed Dec. 25, 2014.

* cited by examiner

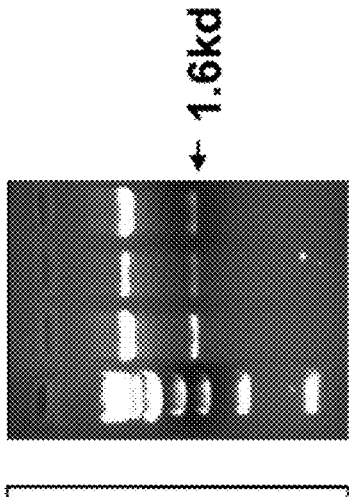

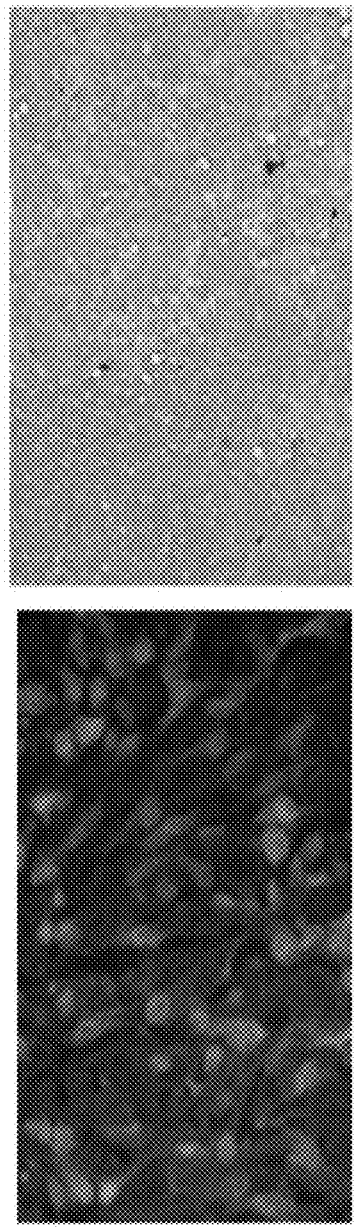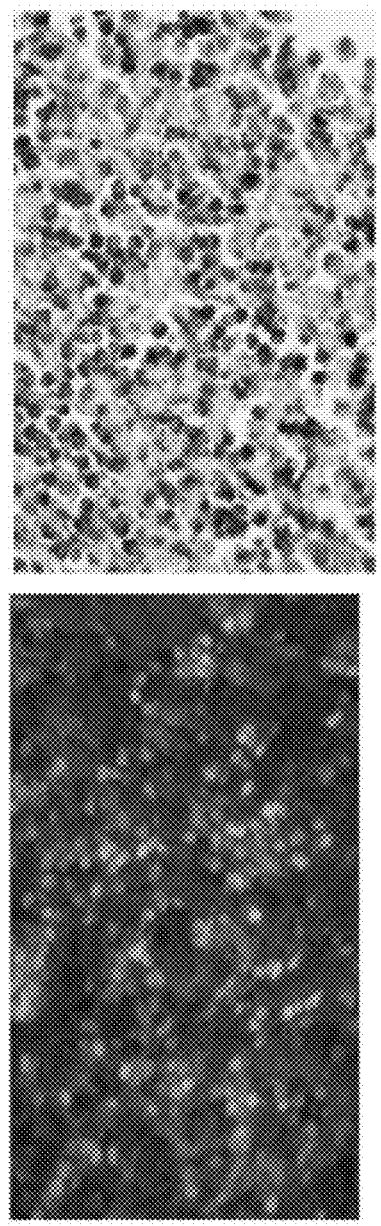
Fig. 4A
Fig. 4B

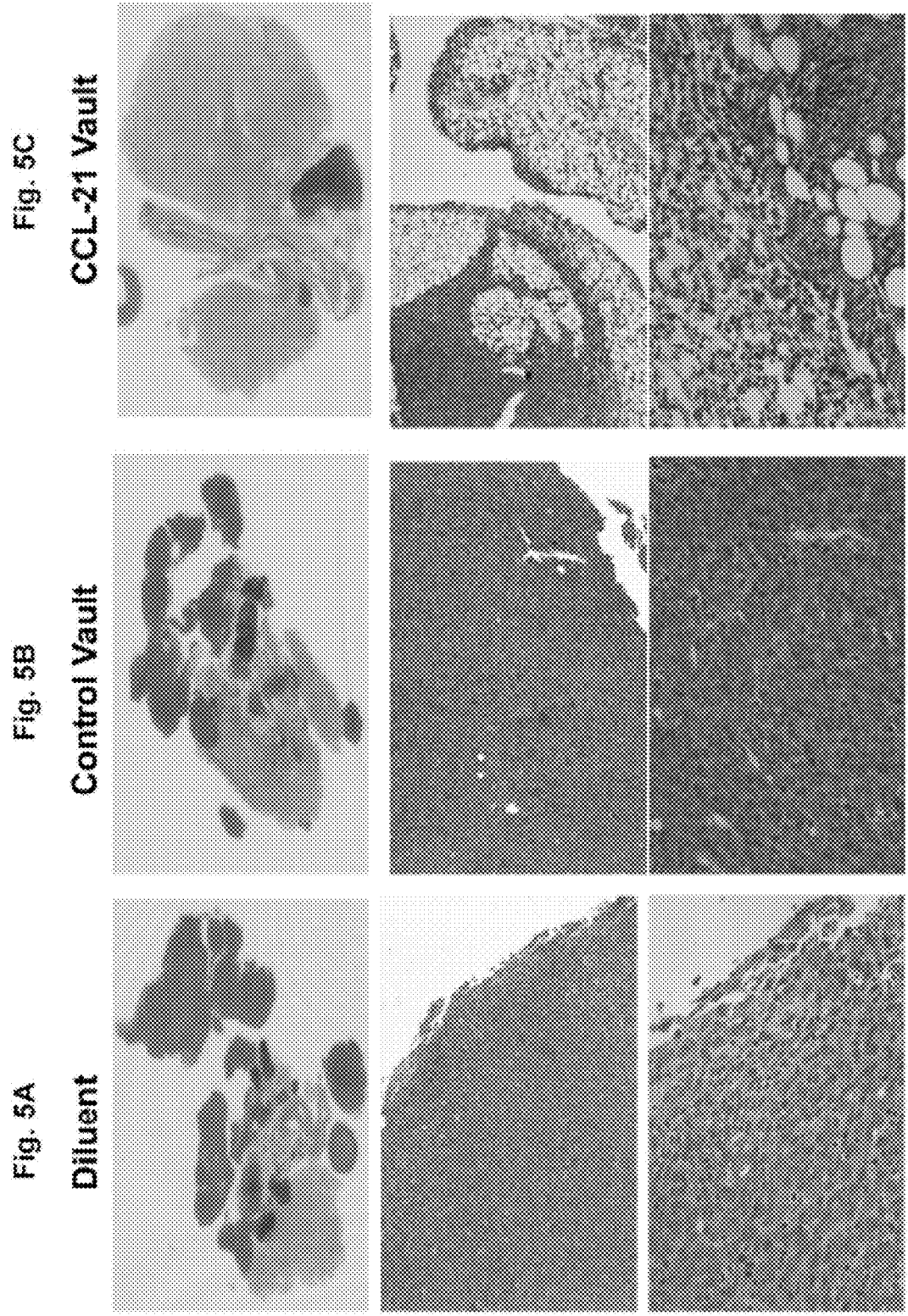

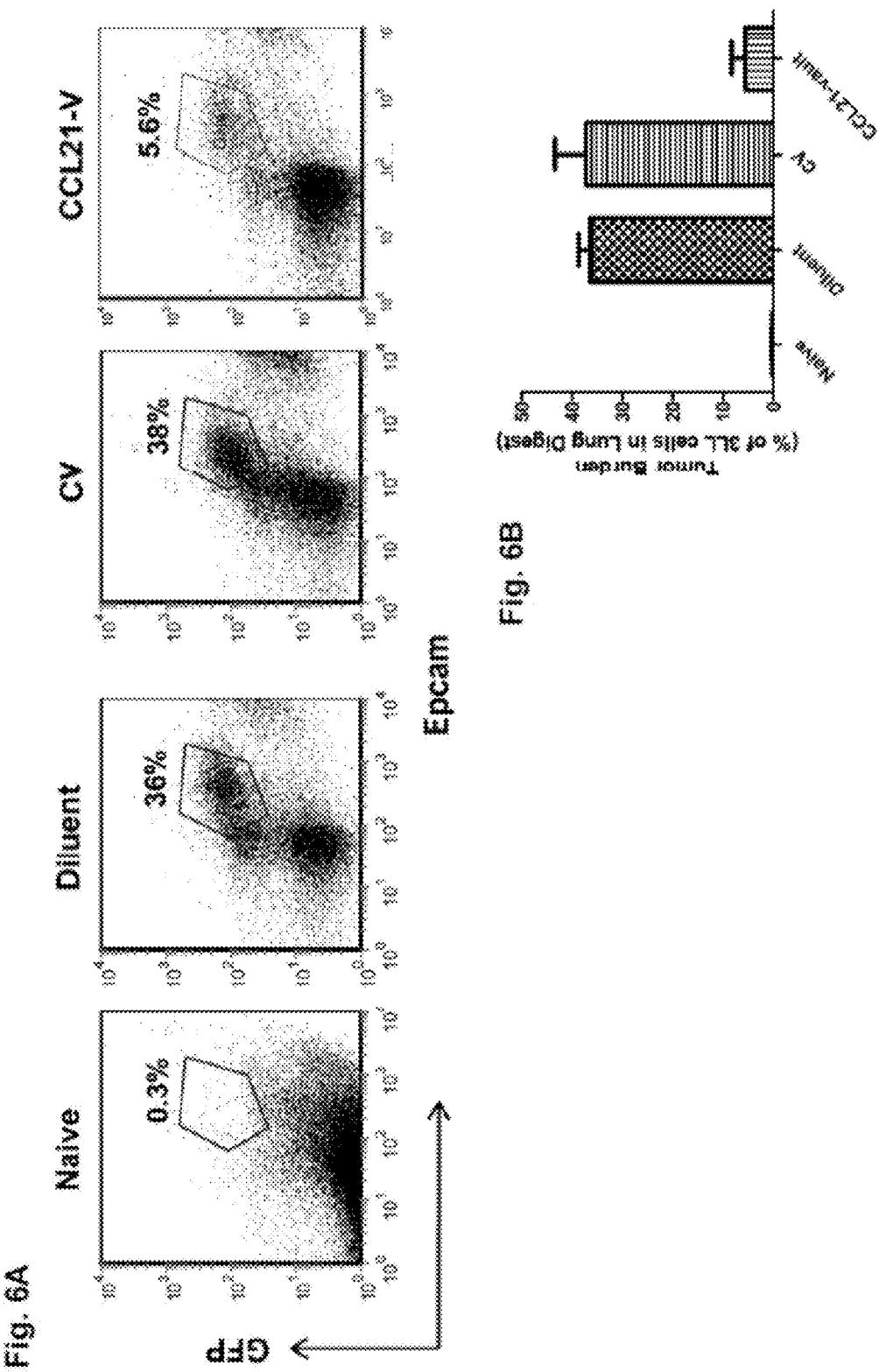

VAULT COMPLEXES FOR CYTOKINE DELIVERY

CROSS REFERENCE TO RELATED APPLICATIONS

This application is a continuation of U.S. application Ser. No. 13/505,420, which is a 371 National Phase entry of PCT/US10/55146, filed Nov. 2, 2010, and claims the benefit of U.S. Provisional Application No. 61/257,358, filed Nov. 2, 2009, which are hereby incorporated by reference in their entirety for all purposes.

STATEMENT REGARDING FEDERALLY SPONSORED RESEARCH OR DEVELOPMENT

This invention was made with Government support under Grant No. CA126944, awarded by the National Institutes of Health. This work was supported by the U.S. Department of Veterans Affairs. The Government has certain rights in the invention.

REFERENCE TO A SEQUENCE LISTING SUBMITTED VIA EFS-WEB

The content of the ASCII text file of the sequence listing named "20141125_034044_137CON1_seq" which is 203 kb in size was created on Nov. 25, 2014 and electronically submitted via EFS-Web herewith the application is incorporated herein by reference in its entirety.

BACKGROUND OF THE INVENTION

Field of the Invention

The invention relates to compositions of vault complexes containing cytokines, such as the chemokine CCL-21, and use of vault complexes for delivering the cytokines to a cell. The vault complexes include a fusion protein of the cytokine of interest fused to major vault interaction domain. Also included in the invention is the use of the compositions as cancer immunotherapy agents for activating an immune response against a tumor and for treating cancers, including lung cancer.

Description of the Related Art

Vaults are cytoplasmic ubiquitous ribonucleoprotein particles first described in 1986 that are found in all eukaryotic cells [1]. Native vaults are 12.9±1 MDa ovoid spheres with overall dimensions of approximately 40 nm in width and 70 nm in length [2,3], present in nearly all-eukaryotic organisms with between $10^4$ and $10^7$ particles per cell [4]. Despite their cellular abundance, vault function remains elusive although they have been linked to many cellular processes, including the innate immune response, multidrug resistance in cancer cells, multifaceted signaling pathways, and intracellular transport [5].

Vaults are highly stable structures in vitro, and a number of studies indicate that the particles are non-immunogenic [6]. Vaults can be engineered and expressed using a baculovirus expression system and heterologous proteins can be encapsulated inside of these recombinant particles using a protein-targeting domain termed INT for vault INTeraction. Several heterologous proteins have been fused to the INT domain (e.g. fluorescent and enzymatic proteins) and these fusion proteins are expressed in the recombinant vaults and retain their native characteristics, thus conferring new properties onto these vaults [7,8].

CCL-21 has been identified as a lymphoid chemokine that is predominantly and constitutively expressed by high endothelial venules in lymph nodes and Peyer's patches and by lymphatic vessels, stromal cells in the spleen and appendix [9]. CCL-21 binds to the chemokine receptor CCR7 and is a chemoattractant for mature DCs, naive and memory T cells [10,11]. This chemokine, along with CCL-19, is required for normal lymphoid tissue organization that is ultimately essential for effective T cell-DC interactions. Natural killer (NK) and natural killer T (NKT) antitumor effectors express the CCR7 receptor and are chemo attracted by CCL-21. The use of chemokines that attract DC, lymphocyte, and NK and NKT effectors into tumors can serve as an effective antitumor strategy. Based on this concept, it has been previously shown that intratumoral administration of recombinant CCL-21 reduces tumor burden in murine lung cancer models [12]. The antitumor responses induced by recombinant CCL-21 however required high and frequent dosing because proteins administered intratumorally are not retained locally for prolonged periods. Although these studies delineated the role of CCL-21 as an effective antitumor agent, frequent high dose intratumoral administration is clinically limiting with the potential of unnecessary systemic toxicity. Based on the limitations of this approach, the use of autologous dendritic cells for intratumoral CCL-21 delivery was examined [13.14]. In preclinical studies, it was demonstrated that intratumoral administration of CCL-21 gene modified dendritic cells led to tumor eradication in murine lung cancer models. Following this initial description of the antitumor properties of CCL-21, several other research groups have reported that CCL-21 has potent antitumor properties in a variety of model systems [15-19]. In all models, CCL-21 demonstrated potent regression of tumors, which was shown to be dependent on host T cell immunity. Based on extensive pre-clinical evaluation, the intratumoral injection of DC transduced with an adenoviral vector expressing the secondary lymphoid chemokine gene (Ad-CCL-21-DC) was assessed in a phase I trial in advanced non-small cell lung cancer (NSCLC).

While clinical studies utilizing intratumoral administration of chemokine gene modified DC show promise as an effective therapy, the preparation of CCL-21 expressing autologous dendritic cells is cumbersome, expensive and time consuming. A reagent that is efficacious and works through a similar therapeutic mechanism is highly desired. Compositions and methods are needed to circumvent autologous DC preparation, minimize batch to batch variability and allow for comparability and standardization. There is a need for cytokine delivery, e.g., a non-DC based approach for intratumoral CCL-21 delivery for the purpose of initiating antitumor immune responses Vaults are generally described in U.S. Pat. No. 7,482,319, filed on Mar. 10, 2004; U.S. application Ser. No. 12/252,200, filed on Oct. 15, 2008; International Application No. PCT/US2004/007434, filed on Mar. 10, 2004; U.S. Provisional Application No. 60/453,800, filed on Mar. 20, 2003; U.S. Pat. No. 6,156,879, filed on Jun. 3, 1998; U.S. Pat. No. 6,555,347, filed on Jun. 28, 2000; U.S. Pat. No. 6,110,740, filed on Mar. 26, 1999; International Application No. PCT/US1999/06683, filed on Mar. 26, 1999; U.S. Provisional App. No. 60/079,634, filed on Mar. 27, 1998; and International Application No. PCT/US1998/011348, filed on Jun. 3, 1998. Vault compositions for immunization against chlamydia genital infection are described in U.S. application Ser. No. 12/467,255, filed on May 15, 2009. The entire contents of these applications are incorporated by reference in their entirety for all purposes.

SUMMARY OF THE INVENTION

Disclosed herein are compositions including a vault complex having a fusion protein of a cytokine and a vault targeting domain, e.g., mINT. In one embodiment, the vault complex includes a chemokine fusion protein having a chemokine (C-C motif) ligand 21 (CCL-21) consisting of SEQ ID NO:1 (mouse CCL21 amino acid sequence) and a major vault protein interaction domain (mINT) consisting of SEQ ID NO:9 (mouse mINT amino acid sequence). In another embodiment, the vault complex includes a chemokine fusion protein having a chemokine (C-C motif) ligand 21 (CCL-21) consisting of SEQ ID NO:2 (human CCL21 amino acid sequence) and a major vault protein interaction domain (mINT) consisting of SEQ ID NO:8 (human mINT amino acid sequence).

Accordingly, in one aspect of the invention, the cytokine is a chemokine. In one aspect, the cytokine is a cysteine-cysteine (CC) chemokine. In another aspect, the cytokine is a CCL-21 chemokine. The chemokine can include all or part of human or mouse CCL-21, e.g, SEQ ID NO:1 or SEQ ID NO:2. In some embodiments, the cytokine fusion protein includes a fluorescent protein, e.g., mCherry fluorescent protein.

In one embodiment, the vault targeting domain is a vault interaction domain from a vault poly ADP-ribose polymerase (VPARP). In one embodiment, the vault targeting domain is a major vault protein interaction (mINT) domain. In another embodiment, the vault targeting domain comprises or consists of SEQ ID NO:8 (a human amino acid sequence). In yet another embodiment, the vault targeting domain comprises SEQ ID NO:9 (a mouse amino acid sequence).

In some embodiments, the vault complex includes a MVP. The MVP can be a human MVP, e.g., SEQ ID NO:16.

Vault complexes of the invention can include a vault poly ADP-ribose polymerase (VPARP), and/or a telomerase vault associated protein 1 (TEP1), and/or an untranslated RNA molecule (vRNA).

In addition, the invention provides an isolated nucleic acid encoding a cytokine fusion protein that includes a cytokine encoding sequence and a mINT encoding sequence. In one embodiment, the mINT encoding sequence is SEQ ID NO:7 (a human sequence) or SEQ ID NO:6 (a mouse sequence). In another embodiment, the cytokine encoding sequence is SEQ ID NO:5 (human) and the mINT encoding sequence consists of SEQ ID NO:7 (human). In one embodiment, the cytokine encoding sequence is SEQ ID NO:3 (a mouse sequence) and the mINT encoding sequence is SEQ ID NO:6 (a mouse sequence).

In some embodiments, the cytokine fusion protein is SEQ ID NO:13 (human). In other embodiments, the cytokine fusion protein is SEQ ID NO:12 (mouse). Also included in the invention are vectors including an isolated nucleic acid described herein, cells having an isolated nucleic acid described herein, and cells having a vector described herein.

The invention also includes a method of delivering a cytokine to a cell, including introducing the vault complexes of the invention to the cell. In some embodiments, the method includes introducing the vault complexes into the extracellular environment surrounding the cell. The invention includes a method for stimulating an immune response in a cell by contacting the cell with the vault complexes of the invention. In some embodiments, the cell is a human cell. In other embodiments, the immune response induces migration of T cells and dendritic cells. In another embodiment, contacting the cell with the vault complexes of the invention increases T cell migration to the cell by at least 5% compared to administration of CCL-21 cytokine alone.

In addition, the invention provides a method for stimulating an immune response in a subject by administering the vault complexes the invention to the subject. In one embodiment, the subject is a human.

In another embodiment, the invention includes a method of treating or managing cancer in a subject in need of treatment or management of cancer including administering to a subject a therapeutically effective amount of the vault complexes described herein. In some embodiments, administering includes intra-tumoral injection of the composition to a tumor in the subject. In one embodiment, the cancer is lung cancer. In another embodiment, administering reduces tumor volume and/or reduces tumor growth. In some embodiments, administering increases interleukin-2 (IL-2) expression. In one embodiment, the method includes a subject that is a mammal or a human.

The invention includes a method of preparing the vault complexes of the invention including a) mixing a fusion protein comprising a cytokine fused to a mINT generated in Sf9 cells with a rat MVP generated in Sf9 cells to generate a mixture; b) incubating the mixture for a sufficient period of time to allow packaging of the fusion protein inside of vault complexes, thereby generating the vault complexes.

In yet another embodiment, the invention also provides method of preparing the vault complexes of the invention including a) mixing a fusion protein comprising a cytokine fused to a mINT generated in insect larvae cells with a rat MVP generated in insect larvae cells to generate a mixture; b) incubating the mixture for a sufficient period of time to allow packaging of the fusion protein inside of vault complexes, thereby generating the vault complexes described herein.

In another embodiment, the invention provides a method of preparing the composition of the invention including a) mixing a fusion protein comprising a cytokine fused to a mINT generated in Sf9 cells or insect larvae cells with a human MVP generated in Sf9 cells or insect larvae cells to generate a mixture; b) incubating the mixture for a sufficient period of time to allow packaging of the fusion protein inside of vault complexes, thereby generating the vault complexes described herein.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1A shows a diagram of the CCL-21 and mCherry-INT constructs that were fused to create the CCL-21 fusion protein.

FIG. 1B shows the incorporation into a pFastBac expression vector by restriction digest and expression of CCL-21 fusion protein as analyzed by gel electrophoresis.

FIG. 1C shows the MVP recombinant vaults containing packaged CCL-21-mCherry-mINT purified on a sucrose gradient. The 40 and 45% fractions were analyzed by SDS-PAGE.

FIG. 1D shows the MVP recombinant vaults containing packaged CCL-21-mCherry-mINT purified on a sucrose gradient and analyzed by staining with Coomassie.

FIG. 1E shows purified vault complexes examined by negative stain transmission electron microscopy.

FIG. 4A shows the leukocytic infiltrates in cells treated with a control vault.

FIG. 4B shows the leukocytic infiltrates in cells treated with CCL-21 vault complexes.

FIG. 5A is a photo showing the effects of treatment of 3LL lung cancer cells with diluent.

FIG. 5B is a photo showing the effects of treatment of 3LL lung cancer cells with control vault.

FIG. 5C is a photo showing the effects of treatment of 3LL lung cancer cells with CCL-21 vault complex.

FIG. 6A is a set of graphs showing the percentage tumor burden in naïve 3LL cells, and 3LL cells treated with diluents, control vault (VC), or CCL-21 vault complexes as measured in a flow cytometry assay. Tumor burden was calculated on total percentage of GFP and Epcam expressing tumor cells in total lung digest.

FIG. 6B is a bar graph showing percentage tumor burden in 3LL cells after treatment with diluents, control vault, or CCL-21 vault complexes.

DETAILED DESCRIPTION OF THE INVENTION

Figure 2B:
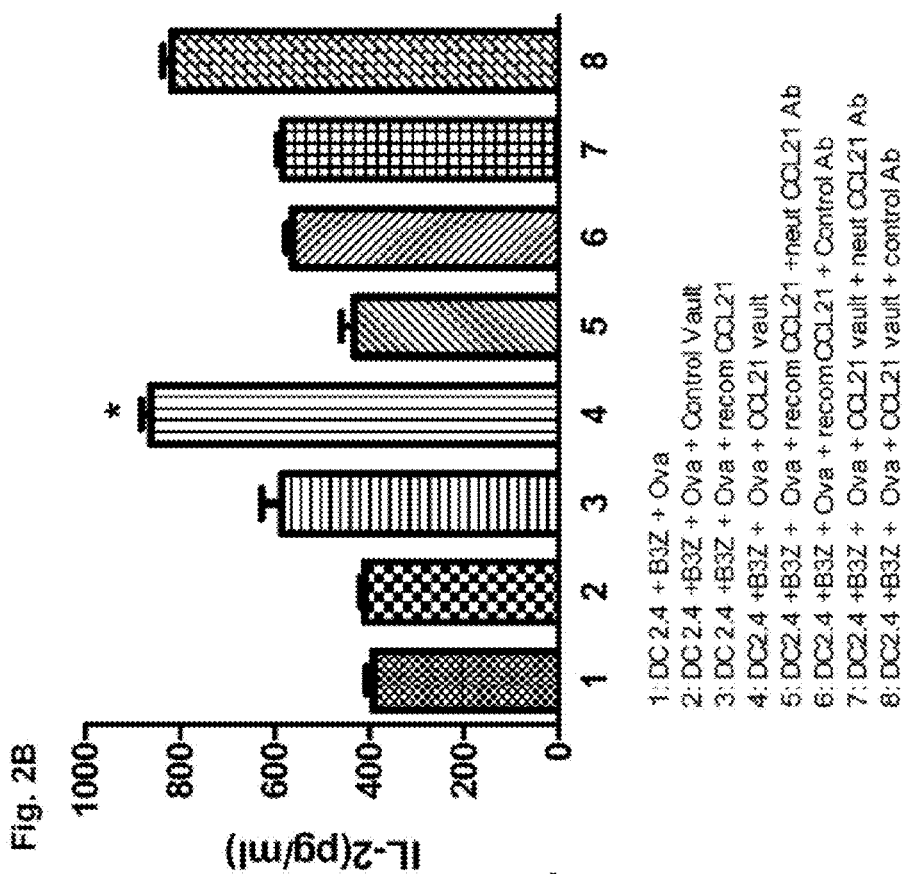
FIG. 2B is a graph showing T cell activation by CCL-21 vault complexes measured by IL-2 production.

The descriptions of various aspects of the invention are presented for purposes of illustration, and are not intended to be exhaustive or to limit the invention to the forms disclosed. Persons skilled in the relevant art can appreciate that many modifications and variations are possible in light of the embodiment teachings.

It should be noted that the language used herein has been principally selected for readability and instructional purposes, and it may not have been selected to delineate or circumscribe the inventive subject matter. Accordingly, the disclosure is intended to be illustrative, but not limiting, of the scope of invention.

It must be noted that, as used in the specification, the singular forms "a", "an", and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of embodiments of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the invention herein.

Briefly, and as described in more detail below, described herein are compositions of vault complexes containing cytokines, such as CCL-21, and their use in delivering the cytokines to a cell. The vault particles include a fusion protein of the cytokine of interest fused to major vault interaction domain. Also included in the invention is the use of the compositions as cancer immunotherapy agents for activating an immune response against a tumor and for treating cancers, including lung cancer.

CCL-21 and other cytokines have been shown to be effective as cancer immunotherapy agents. However, conventional approaches for cancer therapy treatment with cytokines, such as CCL-21, involve use of modified dendritic cells. These preparations and treatments are cumbersome, expensive and time consuming. Difficulties with conventional methods include autologous DC preparation, batch to batch variability and lack of comparability and standardization. More convenient and efficacious options for delivery and treatment with cytokine reagents are required.

The invention supplies the deficiencies of the conventional DC-based methods. Vault complexes provide effective and efficient intratumoral cytokine, e.g., CCL-21 delivery for the purpose of initiating antitumor immune responses.

DEFINITIONS

Terms used in the claims and specification are defined as set forth below unless otherwise specified.

The term "cytokine" is a protein that is a member of a family of secreted cell-signaling proteins involved in immunoregulatory and inflammatory processes. A "chemokine" is a member of a family of cytokines defined by invariant cysteine residues that form disulfide bonds. One example of a chemokine is "CCL-21" referring to a chemokine (C-C motif) ligand 21. A C-C motif is a cysteine-cysteine motif.

As used herein, the term "vault" or "vault particle" refers to a large cytoplasmic ribonucleoprotein (RNP) particle found in eukaryotic cells. The vault or vault particle is composed of MVP, VPARP, and/or TEP1 proteins and one or more untranslated vRNA molecules.

As used herein, the term "vault complex" refers to a recombinant vault that encapsulates a small molecule or protein of interest. A vault complex of the invention includes a fusion protein, e.g., a cytokine fusion protein.

As used herein, the term "cytokine fusion protein" is a recombinant protein expressed from a nucleotide encoding a cytokine fused in frame to a vault targeting domain.

As used herein, the term "vault targeting domain" or "vault interaction domain" is a domain that is responsible for interaction or binding of a heterologous fusion protein with a vault protein, or interaction of a VPARP with a vault protein, such as a MVP. As used herein, the term "mINT domain" is a vault interaction domain from a vault poly ADP-ribose polymerase (VPARP) that is responsible for the interaction of VPARP with a major vault protein (MVP). The term "mINT domain" refers to a major vault protein (MVP) interaction domain.

As used herein, the term "MVP" is major vault protein. The term "cp-MVP" is a cysteine-rich peptide major vault protein.

The term "VPARP" refers to a vault poly ADP-ribose polymerase.

As used herein, the term "TEP-1" is a telomerase/vault associated protein 1.

As used herein, the term "vRNA" is an untranslated RNA molecule found in vaults.

As used herein, the term "fluorescent protein" is a protein that has the property of forming a visible wavelength chromophore from within its polypeptide sequence. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet).

As used herein, the term "vector" is a DNA or RNA molecule used as a vehicle to transfer foreign genetic material into a cell. The four major types of vectors are plasmids, bacteriophages and other viruses, cosmids, and artificial chromosomes. Vectors can include an origin of replication, a multi-cloning site, and a selectable marker.

As used herein, a "cell" includes eukaryotic and prokaryotic cells.

As used herein, the terms "organism", "tissue" and "cell" include naturally occurring organisms, tissues and cells, genetically modified organisms, tissues and cells, and pathological tissues and cells, such as tumor cell lines in vitro and tumors in vivo.

As used herein, the term "T cell" or T lymphocyte is a white blood cell known as a lymphocyte, and plays a central role in cell-mediated immunity.

As used herein, the term "extracellular environment" is the environment external to the cell.

As used herein, the term "in vivo" refers to processes that occur in a living organism.

A "subject" referred to herein can be any animal, including a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species, or a human.

The term "mammal" as used herein includes both humans and non-humans and include but is not limited to, humans, non-human primates, canines, felines, murines, bovines, equines, and porcines.

As used herein, the term "human" refers to "*Homo sapiens.*"

As used herein, the term "sufficient amount" is an amount sufficient to produce a desired effect, e.g., an amount sufficient to modulate protein aggregation in a cell.

As used herein, the term "therapeutically effective amount" is an amount that is effective to ameliorate a symptom of a disease, such as cancer.

A "prophylactically effective amount" refers to an amount that is effective for prophylaxis.

An "immune response" is a response by a host against foreign immunogens or antigens. A "cell-mediated immune response" refers to a helper T cell response which involves the production of interferon-gamma (IFN-γ), leading to cell-mediated immunity.

As used herein, the term "stimulating" refers to activating, increasing, or triggering a molecular, cellular or enzymatic activity or response from within a cell or organism.

As used herein, the term "administering" includes any suitable route of administration, as will be appreciated by one of ordinary skill in the art with reference to this disclosure, including direct injection into a solid organ, direct injection into a cell mass such as a tumor, inhalation, intraperitoneal injection, intravenous injection, topical application on a mucous membrane, or application to or dispersion within an environmental medium, and a combination of the preceding.

As used in this disclosure, the term "modified" and variations of the term, such as "modification," means one or more than one change to the naturally occurring sequence of MVP, VPARP or TEP1 selected from the group consisting of addition of a polypeptide sequence to the C-terminal, addition of a polypeptide sequence to the N-terminal, deletion of between about 1 and 100 amino acid residues from the C-terminal, deletion of between about 1 and 100 amino acid residues from the N-terminal, substitution of one or more than one amino acid residue that does not change the function of the polypeptide, as will be appreciated by one of ordinary skill in the art with reference to this disclosure, such as for example, an alanine to glycine substitution, and a combination of the preceding.

As used herein, the term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

As used in this disclosure, the term "comprise" and variations of the term, such as "comprising" and "comprises," are not intended to exclude other additives, components, integers or steps.

It must be noted that, as used in the specification and the appended claims, the singular forms "a," "an" and "the" include plural referents unless the context clearly dictates otherwise.

Compositions of the Invention

As described in more detail below, the invention includes compositions and methods of using vault particles. The vault particles are recombinant particles having a MVP and a fusion protein and mINT and a protein of interest, e.g., a cytokine, e.g., CCL-21. The vault particle can be used for delivery of the protein of interest, e.g., the cytokine, to a cell or tumor or subject.

Vaults and Vault Complexes

The compositions of the invention comprise a vault complex. A vault complex is a recombinant particle that encapsulates a small molecule (drug, sensor, toxin, etc.), or a protein of interest, e.g., a peptide, or a protein, including an endogenous protein, a heterologous protein, a recombinant protein, or recombinant fusion protein. Vault complexes are of the invention include a cytokine recombinant fusion protein. Vault complexes are derived from vault particles.

Vaults, e.g., vault particles are ubiquitous, highly conserved ribonucleoprotein particles found in nearly all eukaryotic tissues and cells, including dendritic cells (DCs), endometrium, and lung, and in phylogeny as diverse as mammals, avians, amphibians, the slime mold *Dictyostelium discoideum*, and the protozoan *Trypanosoma brucei* (Izquierdo et al., *Am. J. Pathol.*, 148(3):877-87 (1996)). Vaults have a hollow, barrel-like structure with two protruding end caps, an invaginated waist, and regular small openings surround the vault cap. These openings are large enough to allow small molecules and ions to enter the interior of the vault. Vaults have a mass of about 12.9±1 MDa (Kedersha et al., *J. Cell Biol.*, 112(2):225-35 (1991)) and overall dimensions of about 42×42×75 nm (Kong et al., *Structure*, 7(4):371-9 (1999)). The volume of the internal vault cavity is approximately $50 \times 10^3$ nm$^3$, which is large enough to enclose an entire ribosomal protein.

Vaults comprise three different proteins, designated MVP, VPARP and TEP1, and comprise one or more different untranslated RNA molecules, designated vRNAs. The number of vRNA can vary. For example, the rat *Rattus norvegicus* has only one form of vRNA per vault, while humans have three forms of vRNA per vault. The most abundant protein, major vault protein (MVP), is a 95.8 kDa protein in *Rattus norvegicus* and a 99.3 kDa protein in humans which is present in 96 copies per vault and accounts for about 75% of the total protein mass of the vault particle. The two other proteins, the vault poly-ADP ribose polymerase, VPARP, a 193.3 kDa protein in humans, and the telomerase/vault associated protein 1, TEP1, a 292 kDa protein in *Rattus norvegicus* and a 290 kDa protein in humans, are each present in between about 2 and 16 copies per vault.

VPARP, mINT Domain, and mINT Fusion Proteins

A vault poly ADP-ribose polymerase (VPARP) includes a region of about 350 amino acids that shares 28% identity with the catalytic domain of poly ADP-ribosyl polymerase, PARP, a nuclear protein that catalyzes the formation of ADP-ribose polymers in response to DNA damage. VPARP catalyzes an NAD-dependent poly ADP-ribosylation reaction, and purified vaults have poly ADP-ribosylation activity that targets MVP, as well as VPARP itself. VPARP includes a mINT domain (major vault protein (MVP) interaction domain). The mINT domain is responsible for the interaction of VPARP with a major vault protein (MVP).

A vault complex of the invention includes a mINT domain. The mINT domain is responsible for interaction of a protein of interest, e.g., a cytokine, with a vault protein such as a MVP. In general, the mINT domain is expressed as a fusion protein with a protein of interest, e.g., a cytokine. The mINT of the vault complexes of the invention are derived from VPARP sequences. Exemplary VPARP sequences and mINT sequences can be found in Table 1. One of skill in the art understands that the mINT can have the entire naturally occurring sequence or portions of the sequence or fragments thereof. In other embodiments, the mINT has at least 50%, 60%, 70%, 80%, 90%, 95%, 96%, 97%, 98% or 99% sequence identity to any of the VPARP and/or mINT sequences disclosed in Table 1.

In one embodiment, the mINT is derived from a human VPARP, SEQ ID NO:14, GenBank accession number AAD47250, encoded by the cDNA, SEQ ID NO:15, GenBank accession number AF158255. In some embodiments, the vault targeting domain comprises or consists of the INT domain corresponding to residues 1473-1724 (SEQ ID NO:69) of human VPARP protein sequence (full human VPARP amino acid sequence is SEQ ID NO:14). In other embodiments, the vault targeting domain comprises or consists of the mINT domain comprising residues 1563-1724 (SEQ ID NO: 8) of the human VPARP protein sequence. In certain embodiments, the vault targeting domain comprises or consists of a mINT domain (SEQ ID NO: 6) (mouse mINT). In some embodiments, the vault targeting domain comprises or consists of SEQ ID NO: 7 (human mINT). In certain embodiments, the vault targeting domain is at least 90%, 91%, 92%, 93%, 94%, 95%, 96%, 97%, 98%, or 99% identical to SEQ ID NOs: 6 or 7.

In alternative embodiments, the mINT domain is derived from TEP1 sequences. One of skill in the art understands that the mINT can have the entire naturally occurring sequence of the vault interaction domain in TEP1 or portions of the sequence or fragments thereof.

MVP

A vault complex of the invention generally includes an MVP. Exemplary MVP sequences can be found in Table 1. One of skill in the art understands that the MVP can have the entire naturally occurring sequence or portions of the sequence or fragments thereof. In other embodiments, the MVP has at least 50%, 60%, 70%, 80%, 90%, 95%, 96%, 97%, 98% or 99% sequence identity to any of the MVP sequences disclosed in Table 1.

In one embodiment, the MVP is human MVP, SEQ ID NO:16, GenBank accession number CAA56256, encoded by the cDNA, SEQ ID NO:17, GenBank accession number X79882. In another embodiment, the MVP is *Rattus norvegicus* MVP, SEQ ID NO:18, GenBank accession number AAC52161, encoded by the cDNA, SEQ ID NO:19, GenBank accession number U09870. In other embodiments, the MVP is at least 90%, 91%, 92%, 93%, 94%, 95%, 96%, 97%, 98%, or 99% identical to the MVP sequences described herein.

In one embodiment, there is provided a vault complex comprising, consisting essentially of, or consisting of an MVP modified by adding a peptide to the N-terminal to create a one or more than one of heavy metal binding domains. In a preferred embodiment, the heavy metal binding domains bind a heavy metal selected from the group consisting of cadmium, copper, gold and mercury. In a preferred embodiment, the peptide added to the N-terminal is a cysteine-rich peptide (CP), such as for example, SEQ ID NO:20, the MVP is human MVP, SEQ ID NO:16, and the modification results in CP-MVP, SEQ ID NO:21, encoded by the cDNA, SEQ ID NO:22. In another preferred embodiment, the cysteine-rich peptide is SEQ ID NO:20, the MVP is *Rattus norvegicus* MVP, SEQ ID NO:18, and the modification results in CP-MVP, SEQ ID NO:23, encoded by the cDNA, SEQ ID NO:24. These embodiments are particularly useful because vault particles consisting of CP-MVP, SEQ ID NO:21 or SEQ ID NO:23, are stable without the presence of other vault proteins.

Any of the vault complexes described herein can include MVPs or modified MVPs disclosed herein.

TEP1

In some embodiments, a vault particle of the invention includes a TEP1 protein. Exemplary TEP1 sequences can be found in Table 1. One of skill in the art understands that the TEP1 can have the entire naturally occurring sequence or portions of the sequence or fragments thereof. In other embodiments, the TEP1 has at least 50%, 60%, 70%, 80%, 90%, 95%, 96%, 97%, 98% or 99% sequence identity to any of the TEP1 sequences disclosed in Table 1.

The TEP1 can be human TEP1, SEQ ID NO:25, GenBank accession number AAC51107, encoded by the cDNA, SEQ ID NO:26, GenBank accession number U86136. In another embodiment, the TEP1 is *Rattus norvegicus* TEP1, SEQ ID NO:27, GenBank accession number AAB51690, encoded by the cDNA, SEQ ID NO:28, GenBank accession number U89282. Any of the vault complexes described herein can include TEP1 or modifications thereof.

vRNA

A vault complex of the invention can include a vRNA. Exemplary vRNA sequences can be found in Table 1. One of skill in the art understands that the vRNA can have the entire naturally occurring sequence or portions of the sequence or fragments thereof. In other embodiments, the vRNA has at least 50%, 60%, 70%, 80%, 90%, 95%, 96%, 97%, 98% or 99% sequence identity to any of the vRNA sequences disclosed in Table 1.

In one embodiment, the vRNA can be a human vRNA, SEQ ID NO:29, GenBank accession number AF045143, SEQ ID NO:30, GenBank accession number AF045144, or SEQ ID NO:31, GenBank accession number AF045145, or a combination of the preceding. In another embodiment, the vRNA is *Rattus norvegicus* vRNA, SEQ ID NO:32, GenBank accession number Z11711.

As will be appreciated by one of ordinary skill in the art with reference to this disclosure, the actual sequence of any of MVP, VPARP, TEP1 and vRNAs can be from any species suitable for the purposes disclosed in this disclosure, even though reference or examples are made to sequences from specific species. For example, when delivering chemokines or cytokines to human organs or tissues, it is preferred to use human vaults or vault-like particles comprising human sequences for MVP, VPARP, TEP1 and vRNAs. Further, as will be appreciated by one of ordinary skill in the art with reference to this disclosure, there are some intraspecies variations in the sequences of MVP, VPARP, TEP1 and vRNAs that are not relevant to the purposes of the present invention. Therefore, references to MVP, VPARP, TEP1 and vRNAs are intended to include such intraspecies variants.

Cytokines

The compositions of the invention include a vault complex including a cytokine. In general, the vault complex includes a cytokine fusion protein.

Cytokines are a family of secreted cell-signaling proteins involved in immunoregulatory and inflammatory processes, which are secreted by the glial cells of the nervous system and by numerous cells of the immune system. Cytokines can be classified as proteins, peptides or glycoproteins, and encompass a large and diverse family of regulators. Cytokines bind to cell surface receptors to trigger intracellular signaling, which can result in upregulation or downregulation of several genes and their transcription factors, or feedback inhibition.

In certain embodiments, the cytokines of the invention include immunomodulating agents, such as interleukins (IL) and interferons (IFN). Suitable cytokines can include proteins from one or more of the following types: the four α-helix bundle family (which includes the IL-2 subfamily, the IFN subfamily, and the IL-10 subfamily); the IL-1 family (which includes IL-1 and IL-8), and the IL-17 family. Cytokines can also include those classified as type 1 cytokines, which enhance cellular immune responses (e.g., IFN-γ, TGF-β, etc.), or type 2 cytokines, which favor antibody responses (e.g., IL-4, IL-10, IL-13, etc.).

In one embodiment, the cytokine is a chemokine Chemokines are the largest family of cytokines and are defined by four invariant cysteine residues that form disulfide bonds. Chemokines function by activating specific G protein-coupled receptors, which results in the migration of inflammatory and noninflammatory cells to the appropriate tissues or compartments within tissues. The role of chemokines is to act as a chemoattractant to guide the migration of cells and to promote accumulation of cells at the source of chemokine production.

In some embodiments, the cytokines of the invention include homeostatic chemokines, which are constitutively produced and secreted. Homeostatic chemokines direct trafficking of lymphocytes to lymphoid tissues and are involved in immune surveillance and function to localize T cells or B cells with an antigen in the lymphatic system. In other embodiments, the chemokines of the invention include inflammatory chemokines that promote recruitment and localization of dendritic cells to sites of inflammation and infection. Several chemokines are involved in migration of monocytes and immature dendritic cells, which express chemokine receptors such as CCR1, CCR2, CCR5, CCR6, CCR7 and CXCR2. Chemokine receptor expression is regulated on these dendritic cells. Upon exposure to maturation signals, dendritic cells undergo a chemokine receptor switch, with downregulation of inflammatory chemokine receptors followed by induction of CCR7. This allows immature dendritic cells to leave tissues and to localize in lymphoid organs (due to CCR7 agonists), where antigen presentation takes place.

In certain embodiments, the cytokine comprises CC or β-chemokines, which have the first two cysteines adjacent to each other. In other embodiments, the chemokine comprises CXC or α chemokines, which have an intervening amino acid between the first two cysteines. In other embodiments, the chemokine comprises a CX3C or γ-chemokine, which possess only one protein in its category and is defined by three intervening residues between the first two cysteines. One of two exceptions to the four-cysteine paradigm is the C or δ-chemokine, in which the polypeptide has only two of the four cysteines.

In some embodiments, the cytokine comprises a CC chemokine. The CC chemokine is characterized by two adjacent cysteines near the amino terminus and is also called a β-chemokine or 17q chemokine. The CC subfamily includes at least 27 distinct members of the subfamily in mammals. These include, but are not limited to the following CC chemokines: CCL-1, CCL-2, CCL-3, CCL-4, CCL-5, CCL-7, CCL-8, CCL-9/CCL-10, CCL-11, CCL-12, CCL-13, CCL-14, CCL-15, CCL-16, CCL-17, CCL-18, CCL-19, CCL-20, CCL-21, CCL-22, CCL-23, CCL-24, CCL-25, CCL-26, CCL-27 and CCL-28. Chemokines of this subfamily usually contain four cysteines (C4-CC chemokines), but a small number of CC chemokines possess six cysteines (C6-CC chemokines). C6-CC chemokines include CCL1, CCL15, CCL21, CCL23 and CCL28. CC chemokines inhibit haemopoiesis and induce the migration of monocytes and other cell types such as natural killer (NK) cells and dendritic cells. CC Chemokines are chemotactic in vitro for thymocytes and activated T cells, but not for B cells, macrophages, or neutrophils. CC Chemokines may also play a role in mediating homing of lymphocytes to secondary lymphoid organs.

In other embodiments, the cytokine comprises a CXC chemokine CXC chemokines have two N-terminal cysteines separated by an amino acid "X". There are 17 different CXC chemokines in mammals and are separated in two categories, those with a specific amino acid sequence (or motif) of glutamic acid-leucine-arginine (or ELR for short) immediately before the first cysteine of the CXC motif (ELR-positive), and those without an ELR motif (ELR-negative). Other CXC chemokines that lack the ELR motif, such as CXCL13, tend to be chemoattractant for lymphocytes. CXC chemokines bind to CXC chemokine receptors, of which seven have been discovered to date, designated CXCR1-7.

In another embodiment, the cytokine comprises a C chemokine (also called γ chemokine), which has only two cysteines (one N-terminal cysteine and one cysteine downstream). Two chemokines are included in this subgroup (XCL1 (lymphotactin-α) and XCL2 (lymphotactin-β)). These chemokines attract T cell precursors to the thymus.

In yet another embodiment, the cytokine comprises a $CX_3C$ chemokine (or d-chemokines). The $CX_3C$ chemokine has three amino acids between the two cysteines. The only $CX_3C$ chemokine discovered to date is called fractalkine (or $CX_3CL1$).

In some embodiments, the cytokine comprises a CCL-21 protein. CCL-21 stands for chemokine (C-C motif) ligand 21 and is a member of the CC chemokine family. CCL-21 is encoded by the Scya21 gene and is also called secondary lymphoid-tissue chemokine (SLC), 6Ckine, Exodus-2, Ckβ9, and TCA-4. The CCL-21 binds to the CCR7 receptor, a cell surface chemokine receptor. The human CCL-21 gene is found on the p-arm of chromosome 9 and has the Genbank Accession No. NP_002980.

Exemplary cytokine sequences can be found in Table 1. One of skill in the art understands that the cytokine can have the entire naturally occurring sequence or portions of the sequence or fragments thereof. In other embodiments, the cytokine has at least 50%, 60%, 70%, 80%, 90%, 95%, 96%, 97%, 98% or 99% sequence identity to any of the cytokine sequences disclosed in Table 1.

In some embodiments, the cytokine comprises or consists of SEQ ID NO: 1 (mouse CCL-21 protein sequence). In other embodiments, the cytokine comprises or consists of SEQ ID NO:2 (human CCL-21 protein sequence). In other embodiments, the cytokine has at least 50%, 60%, 70%, 80%, 90%, 95%, 96%, 97%, 98% or 99% sequence identity to SEQ ID NOs:1 or 2. In another embodiment, the cytokine of the invention is encoded by a nucleic acid comprising SEQ ID NO:3 (mouse CCL-21 DNA sequence minus 3 amino acids for stop codon) or SEQ ID NO:4 (full mouse CCL-21 DNA sequence). In yet another embodiment, the cytokine of the invention is encoded by a nucleic acid comprising SEQ ID NO:5 (human CCL-21 DNA sequence). In certain embodiments, the cytokine of the invention comprises the entire naturally occurring DNA sequence, portions of the DNA sequence or fragments thereof. In some embodiments, the cytokine of the invention is encoded by a nucleic acid comprising 50%, 60%, 70%, 80%, 85%, 90%, 95%, 96%, 97%, 98%, or 99% sequence identity to SEQ ID NOs:3, 4 or 5.

In yet another embodiment, the cytokine comprises one of any of the sequences of cytokines or chemokines in Table 1, shown below. Suitable cytokines from humans for use in compositions and methods of the invention include, but are not limited to, interleukin-2 (IL-2) (DNA sequence is SEQ ID NO:33 and protein sequence is SEQ ID NO:34), interleukin-7 (IL-7) (DNA sequence is SEQ ID NO:35 and protein sequence is SEQ ID NO:36), interleukin 15 (IL-15) (DNA sequence is SEQ ID NO:37 and protein sequence is SEQ ID NO:38), interleukin 12B (IL-12B) (DNA sequence is SEQ ID NO:39 and protein sequence is SEQ ID NO:40), interleukin 12A (IL-12A) (DNA sequence is SEQ ID NO:41 and protein sequence is SEQ ID NO:42), colony stimulating factor 2 (DNA sequence is SEQ ID NO:43 and protein sequence is SEQ ID NO:44), chemokine (C-X-C motif) ligand 9 (CXCL9) (DNA sequence is SEQ ID NO:45 and protein sequence is SEQ ID NO:46), chemokine (C-X-C motif) ligand 10 (CXCL10) (DNA sequence is SEQ ID NO:47 and protein sequence is SEQ ID NO:48), interferon alpha-d (IFN-alpha) (DNA sequence is SEQ ID NO:49 and protein sequence is SEQ ID NO:50), interferon-gamma IEF SSP 5111 (DNA sequence is SEQ ID NO:51 and protein sequence is SEQ ID NO:52), chemokine (C-C motif) ligand 19 (CCL-19) (DNA sequence is SEQ ID NO:53 and protein sequence is SEQ ID NO:54), chemokine (C-C motif) ligand 21 (CCL-21) (DNA sequence is SEQ ID NO:55 and protein sequence is SEQ ID NO:56), tumor necrosis factor (TNF) (DNA sequence is SEQ ID NO:57 and protein sequence is SEQ ID NO:58), and interleukin 27 (IL-27) (DNA sequence is SEQ ID NO:59 and protein sequence is SEQ ID NO:60).

As will be appreciated by one of ordinary skill in the art with reference to this disclosure, the actual sequence of any of cytokine can be from any species suitable for the purposes disclosed in this disclosure, even though reference or examples are made to sequences from specific species. For example, when delivering chemokines or cytokines to human organs or tissues, it is preferred to use human cytokines. Further, as will be appreciated by one of ordinary skill in the art with reference to this disclosure, there are some intraspecies variations in the sequences of cytokine that are not relevant to the purposes of the present invention. Therefore, references to cytokine are intended to include such intraspecies variants.

Fusion Proteins

In general, the vault complexes of the invention include a fusion protein, e.g., a cytokine fusion protein. The cytokine fusion protein is a recombinant protein expressed from a nucleotide encoding a chemokine or cytokine fused in frame to a vault targeting domain, e.g., mINT. In some embodiments, the cytokine fusion protein comprises a mINT domain fused to a chemokine protein sequence. In other embodiments, the cytokine fusion protein comprises a mINT domain fused to a CCL-21 protein. In another embodiment, the cytokine is fused to the N-terminus of an MVP protein. In one embodiment, the cytokine is fused to the C-terminus of the MVP protein.

Exemplary cytokine fusion sequences can be found in Table 1. One of skill in the art understands that the cytokine fusion sequences can have the entire naturally occurring sequence or portions of the sequence or fragments thereof. In other embodiments, the cytokine fusion sequence has at least 50%, 60%, 70%, 80%, 90%, 95%, 96%, 97%, 98% or 99% sequence identity to any of the cytokine fusion sequences disclosed in Table 1.

In certain embodiments, the cytokine fusion protein is encoded by the nucleic acid sequence of SEQ ID NO: 10 (mouse CCL21-mINT fusion DNA sequence). In other embodiments, the cytokine fusion protein is encoded by the nucleic acid sequence of SEQ ID NO: 11 (human CCL21-mINT fusion DNA sequence). In some embodiments, the cytokine fusion protein comprises or consists of SEQ ID NO:12 (mouse CCL-21-mINT fusion protein sequence). In some embodiments, the cytokine fusion protein comprises or consists of SEQ ID NO: 13 (human CCL-21-mINT fusion protein sequence).

In one embodiment, the cytokine fusion protein includes the entire naturally occurring cytokine protein sequence, a portion of the cytokine protein sequence, or fragments thereof. In other embodiments, the cytokine fusion protein is at least 90%, 91%, 92%, 93%, 94%, 95%, 96%, 97%, 98%, or 99% identical to SEQ ID NOs: 12 or 13. In another embodiment, the cytokine fusion recombinant DNA sequence includes the entire naturally occurring cytokine DNA sequence, a portion of the cytokine DNA sequence, or fragments thereof.

Any of the cytokines described herein can be expressed as a fusion protein with any of the mINT domain disclosed herein.

Fluorescent Proteins

In certain embodiments, the vault complex of the invention includes a fluorescent protein. In some embodiments, the cytokine fusion protein comprises a fluorescent protein. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet). In one embodiment, the cytokine fusion protein comprises a mCherry fluorescent protein or a portion of a mCherry fluorescent protein.

Isolated Nucleic Acids and Vectors

The invention also includes isolated nucleic acid encoding a cytokine fusion protein comprising a cytokine encoding sequence and a vault targeting domain encoding sequence. In one embodiment, the isolated nucleic acid encodes a chemokine fusion protein comprising a CCL-21 encoding sequence and a mINT encoding sequence. In another embodiment, the chemokine encoding sequence comprises or consists of SEQ ID NO:5 (human) and the mINT encoding sequence consists of SEQ ID NO:7 (human). In another embodiment, the chemokine encoding sequence comprises or consists of SEQ ID NO:3 (mouse) and the mINT encoding sequence consists of SEQ ID NO:6 (mouse). In one embodiment, the isolated nucleic acid is a cDNA plasmid construct encoding the full length cytokine protein and a mINT domain comprising or consisting of SEQ ID NO: 6 or 7 (human and mouse mINT). Table 1 lists nucleic acid sequences encoding some exemplary chemokine or cytokine fusion proteins.

The nucleic acid molecules encoding a cytokine fusion protein of the invention can be expressed from a vector, such as a recombinant viral vector. The recombinant viral vectors of the invention comprise sequences encoding the cytokine fusion protein of the invention and any suitable promoter for expressing the cytokine fusion sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the cytokine fusion recombinant genes in a particular tissue or in a particular intracellular environment. In one embodiment, recombinant baculoviruses and promoters can be used from pFastBac plasmid and the Bac-to-Bac protocol (Invitrogen, Gaithersburg, Md., Cat. No. 13459-016 or 10608-016).

Suitable expression vectors generally include DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of expression vectors can be systemic, such as by intravenous or intramuscular administration, by administration to target cells ex-planted from the patient followed by reintroduction into the patient, or by any other means that allows for introduction into a desired target cell.

Plasmids expressing a nucleic acid sequence encoding a cytokine fusion protein can be transfected into target cells as a complex with cationic lipid carriers (e.g., Oligofectamine) or non-cationic lipid-based carriers (e.g., Transit-TKO™). Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g., EPV and EBV vectors. Constructs for the recombinant expression of a nucleic acid encoding a cytokine fusion protein will generally require regulatory elements, e.g., promoters, enhancers, etc., to ensure the expression of the cytokine fusion nucleic acid in target cells. Other aspects to consider for vectors and constructs are further described below.

Vectors useful for the delivery of a cytokine fusion nucleic acid can include regulatory elements (promoter, enhancer, etc.) sufficient for expression of the cytokine fusion nucleic acid in the desired target cell or tissue. The regulatory elements can be chosen to provide either constitutive or regulated/inducible expression. A person skilled in the art would be able to choose the appropriate regulatory/promoter sequence based on the intended use of the transgene.

In a specific embodiment, viral vectors that contain the recombinant gene can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding a cytokine fusion protein are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of isolated nucleic acids encoding cytokine fusion proteins into a cell. Adenoviruses are especially attractive vehicles for delivering genes to respiratory epithelia or for use in adenovirus-based delivery systems such as delivery to the liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing a nucleic acid molecule featured in the invention, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol. 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Examples of additional expression vectors that can be used in the invention include pFASTBAC expression vectors and *E. coli* pET28a expression vectors.

Generally, recombinant vectors capable of expressing genes for recombinant cytokine fusion proteins are delivered into and persist in target cells. The vectors or plasmids can be transfected into target cells by a transfection agent, such as Lipofectamine. Examples of cells useful for expressing the nucleic acids encoding the cytokine fusion proteins of the invention include Sf9 cells or insect larvae cells. Recombinant vaults based on expression of the MVP protein alone can be produced in insect cells. Stephen, A. G. et al. (2001). *J. Biol. Chem.* 276:23217:23220; Poderycki, M. J., et al. (2006). *Biochemistry* (Mosc). 45: 12184-12193.

Pharmaceutical Compositions of the Invention

In one embodiment, the invention provides methods using pharmaceutical compositions comprising the vault complexes of the invention. These compositions can comprise, in addition to one or more of the vault complexes, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

In certain embodiments, the pharmaceutical compositions that are injected intratumorally comprise an isotonic or other suitable carrier fluid or solution.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In other embodiments, pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In some embodiments, administration of the pharmaceutical compositions may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration. Formulations for parenteral administration may include sterile aqueous solutions which may also contain buffers, diluents and other suitable additives. For intravenous use, the total concentration of solutes should be controlled to render the preparation isotonic.

Methods of Use

Vault complexes described herein can be used to deliver a protein of interest, e.g., cytokines, to a cell, a tissue, an environment outside a cell, a tumor, an organism or a subject. In one embodiment, the vault complex comprises a cytokine described herein, e.g., CCL-21, and the vault complex is introduced to the cell, tissue, or tumor. In some embodiments, the vault complex is introduced into the extracellular environment surrounding the cell. In other embodiments, the vault complex is introduced into an organism or subject. Delivery of the vault complex of the invention can include administering the vault complex to a specific tissue, specific cells, an environmental medium, or to the organism. In some embodiments, delivery of the vault complex can be detected by a sensor within the cell, tissue, or organism. For example, detection can be performed using standard techniques, such as fluorometry or spectrophotometry. This method can be used, for example, to determine the pH within cells, where the sensor is a pH dependent fluorescent sensor, as will be appreciated by one of ordinary skill in the art with reference to this disclosure.

The methods of the invention comprise stimulating an immune response to a cell by contacting the cell with any of the vault complexes described herein. Cells of the invention can include, but are not limited to, any eukaryotic cell, mammalian cell, or human cells, including tumor cells. In some embodiments, contacting the cell with a vault complex induces migration of T cells and/or dendritic cells to the cell.

Methods of the invention include delivery of the vault complex to a subject. The delivery of a vault complex to a subject in need thereof can be achieved in a number of different ways. In vivo delivery can be performed directly by administering a vault complex to a subject. Alternatively, delivery can be performed indirectly by administering one or more vectors that encode and direct the expression of the vault complex or components of the vault complex. In one embodiment, the vault complex is administered to a mammal, such as a mouse or rat. In another embodiment, the vault complex is administered to a human.

In one embodiment, the methods of delivery of the invention include systemic injection of vault complexes to tumors, producing the enhanced permeability and retention (EPR) effect. See Maeda et al., *J. of Controlled Release* 2000, 65: 271-284; Griesh, K., *J. of Drug Targeting* 2007, 15(7-8): 457-464; Allen et al., *Science* 2004, 303:1818-1822. Solid tumors possess extensive angiogenesis and hence hypervasculature, defective vascular architecture, impaired lymphatic drainage/recovery systems, and greatly increased production of a number of permeability mediators. Due to the biology of solid tumors, macromolecular anti-cancer drugs and agents, including vault complexes, administered intravenously can accumulate and are retained in the tumor due to the lack of efficient lymphatic drainage in the solid tumor. The invention includes methods of systemic or targeted delivery of vault complexes described herein to solid tumors, such as those found in lung cancer.

Other methods of the invention include stimulating an immune response in a subject. The method comprises administering the vault complex to a subject. Administering can include intra-tumoral injection of the vault complex in a subject, which is described in detail herein.

Methods of Treatment

The invention features a method of treating or managing disease, such as cancer, by administering the vault complex of the invention to a subject (e.g., patient). In some embodiments, the vault complexes of the invention can be used for treating or managing lung cancer. In another embodiment, the method of the invention comprises treating or managing cancer in a subject in need of such treatment or management, comprising administering to the subject a therapeutically effective amount of the vault complexes described herein. In one embodiment, the method involves treating a human by identifying a human diagnosed as having lung cancer or at risk for developing lung cancer and administering to the human a therapeutically or prophylactically effective amount of the CCL-21 vault complex to the human. In another embodiment, the method comprises administering to the human to therapeutically or prophylactically effective amount of the CCL-21 vault complex by intra-tumoral injection.

Vault complexes of the invention can be used to treat any solid cancer, e.g., lung cancer, breast cancer, head and neck cancer, prostate cancer, etc. Advances in mouse genetics have generated a number of mouse models for the study of various human diseases, such as treatment of lung cancer. Such models are used for in vivo testing of vault complexes, as well as for determining a therapeutically effective dose. A suitable mouse model is, for example, a tumor-bearing mouse that is administered an intra-tumoral injection of a CCL-21 vault complex.

The data obtained from cell culture assays and animal studies can be used in formulating a range of dosage for use in humans. For any compound used in the methods featured in the invention, the therapeutically effective dose can be estimated initially from cell culture assays. A dose may be formulated in animal models to achieve a circulating plasma concentration range of the vault complex. Such information can be used to more accurately determine useful doses in humans. Analysis of tumor cell samples of mice administered a vault complex can also indicate a therapeutically effective dose.

The pharmaceutical composition according to the present invention to be given to a subject, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. A composition can be administered alone or in combination with other treatments, either simultaneously or sequentially dependent upon the condition to be treated.

In certain embodiments, the dosage of vault complexes is between about 0.1 and 10,000 micrograms per kilogram of body weight or environmental medium. In another embodiment, the dosage of vault complexes is between about 1 and 1,000 micrograms per kilogram of body weight or environmental medium. In another embodiment, the dosage of vault complexes is between about 10 and 1,000 micrograms per kilogram of body weight or environmental medium. For intravenous injection and intraperitoneal injection, the dosage is preferably administered in a final volume of between about 0.1 and 10 ml. For inhalation the dosage is preferably administered in a final volume of between about 0.01 and 1 ml. As will be appreciated by one of ordinary skill in the art with reference to this disclosure, the dose can be repeated a one or multiple times as needed using the same parameters to effect the purposes disclosed in this disclosure.

For instance, the pharmaceutical composition may be administered once for each tumor in a subject, or the vault complex may be administered as two, three, or more sub-doses or injections at appropriate intervals. In that case, the vault complexes can be injected in sub-doses in order to achieve the total required dosage.

The vault complexes featured in the invention can be administered in combination with other known agents effective in treatment of cancers, including lung cancer. An administering physician can adjust the amount and timing of vault complex administration or injection on the basis of results observed using standard measures of efficacy known in the art or described herein. The skilled artisan will also appreciate that certain factors may influence the dosage and timing required to effectively treat a subject, including but not limited to the severity of the disease or disorder, previous treatments, the general health and/or age of the subject, and other diseases present.

Methods of Preparing Vault Complexes

The methods of the invention include preparing the vault complexes described herein.

In one embodiment, the vault complexes are derived or purified from natural sources, such as mammalian liver or spleen tissue, using methods known to those with skill in the art, such as for example tissue homogenization, differential centrifugation, discontinuous sucrose gradient fractionation and cesium chloride gradient fractionation. In another embodiment, the vault complexes are made using recombinant technology. Details about the methods for recombinant vault complexes are described below.

In some embodiments, a target of interest, i.e., protein of interest, is selected for packaging in the vault complexes. The target of interest may be selected from the group consisting of an enzyme, a pharmaceutical agent, a plasmid, a polynucleotide, a polypeptide, a sensor and a combination of the preceding. In a preferred embodiment, the target of interest is a recombinant protein, e.g., a cytokine fusion protein, e.g., a CCL-21 fusion protein.

Preferably, if the target of interest is a recombinant protein, the polynucleotide sequences encoding the recombinant protein are used to generate a bacmid DNA, which is used to generate a baculovirus comprising the sequence. The baculovirus is then used to infect insect cells for protein production using an in situ assembly system, such as the baculovirus protein expression system, according to standard techniques, as will be appreciated by one of ordinary skill in the art with reference to this disclosure. Advantageously, the baculovirus protein expression system can be used to produce milligram quantities of vault complexes, and this system can be scaled up to allow production of gram quantities of vault complexes according to the present invention.

In another embodiment, the target of interest is incorporated into the provided vaults. In a preferred embodiment, incorporation is accomplished by incubating the vaults with the target of interest at an appropriate temperature and for an appropriate time, as will be appreciated by one of ordinary skill in the art with reference to this disclosure. The vaults containing the protein of interest are then purified, such as, for example sucrose gradient fractionation, as will be appreciated by one of ordinary skill in the art with reference to this disclosure.

In other embodiments, the vaults comprising the target of interest are administered to an organism, to a specific tissue, to specific cells, or to an environmental medium. Administration is accomplished using any suitable route, as will be appreciated by one of ordinary skill in the art with reference to this disclosure.

In one embodiment, the method comprises preparing the composition of the invention by a) mixing a fusion protein comprising a chemokine fused to a mINT generated in Sf9 cells with a rat MVP generated in Sf9 cells to generate a mixture; b) incubating the mixture for a sufficient period of time to allow packaging of the fusion protein inside of vault complexes, thereby generating the composition. Sf9 cells are infected with CCL-21-mCherry-mINT or CP-MVP encoding recombinant baculoviruses. Lysates containing recombinant CCL-21-mINT and rat MVP generated in Sf-9 cells can be mixed to allow the formation of a macromolecular vault complex containing the CCL-21 fusion protein.

In another embodiment, the composition is prepared by a) mixing a fusion protein comprising a chemokine fused to a mINT generated in insect larvae cells with a rat MVP generated in insect larvae cells to generate a mixture; b) incubating the mixture for a sufficient period of time to allow packaging of the fusion protein inside of vault complexes.

Details about methods of preparing vault complexes are further described in the Examples.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B (1992).

Methods

Cloning, Expression, and Purification of Vault Complexes

A cDNA encoding CCL-21 was fused in frame to either mINT or mCherry-mINT [21]. Murine CCL-21 was PCR amplified using the following primers: CCL21-forward GCGCGGATCCCCATGGCTCAGATGATG (SEQ ID NO:63) and CCL-21-reverse GCGCAGATCTTCCTCTT-GAGGGCTGTGTCTG (SEQ ID NO:64). To form mCCL-21-mCherry-mINT in pFastBac, the CCL21 PCR product was purified on a Qiagen column, digested with BamH1 and Bgl I, gel purified, and ligated to BamH1 phosphatase treated mCherry-mINT pFastBac. Human CCL21 was PCR amplified with the following primers: CCL-21 F-SpeI CCCCACTAGTCCAGTTCTCAGTCACTGGCTCTG (SEQ ID NO: 65), CCL-21-NheI CCCCGCTAGCTGGC-CCTTTAGGGGTCTGTG (SEQ ID NO:66), mINT with NheI CCCCGCTAGCTGCACACAACACTGGCAGGA (SEQ ID NO:67), mINT with XhoI GGGGCTCGAGT-TAGCCTTGACTGTAATGGA (SEQ ID NO:68) to form hCCL-21-mINT.

Recombinant baculoviruses were generated using the Bac-to-Bac protocol (Invitrogen, Gaithersburg, Md.). Sf9 cells were infected with CCL-21-mCherry-mINT or CP-MVP encoding recombinant baculoviruses at a multiplicity of infection (MOI) of 0.01 for 65 h. The infected cells were pelleted, and lysed on ice in buffer A [50 mM Tris-HCl (pH 7.4), 75 mM NaCl, and 0.5 mM $MgCl_2$] with 1% Triton X-100, 1 mM dithiothreitol, 0.5 mM PMSF, and protease inhibitor cocktail (Sigma P8849). Lysates containing CP-MVP vaults were mixed with lysates containing mCCL-21-mCherry-mINT, hCCL-21-mINT and were incubated on ice for 30 min to allow the INT fusion proteins to package inside of vaults. Recombinant vault complexes were purified as previously described [7]. Purified recombinant vault complexes were resuspended in 100-200 µl of sterile phosphate buffered saline. Protein concentration was determined using the BCA assay (Bio-Rad Laboratories, Hercules, Calif.) and sample integrity was analyzed by negative stain electron microscopy and SDS-PAGE followed by Coomassie staining and Western blot analysis.

Antibodies

Primary antibodies for Western blot analyses were rabbit anti-MVP polyclonal antibody (1/1000 dilution) or rabbit anti-VPARP polyclonal antibody (1/500 dilution, overnight) and secondary goat anti-rabbit HRP-conjugated antibodies (1:2000 dilution) (Amersham). The anti-CCL-21 antibodies were purchased from R&D Systems, (Minneapolis, Minn.). Primary antibody for immunostaining for CD3 was purchased from DAKO. Fluorescein isothiocyanate-, phycoerythrin-, allophycocyanin-, PerCP- or PerCP-Cy7-conjugated anti-mouse mAbs to CD3 (145-2C11), CD4 (RM4-5), CD8a (53-6.7) and subclass control antibody, were purchased from BD Biosciences (San Diego, Calif.). Anti-mouse mAbs to detect Tregs with cell surface CD4 (GK1.5), CD25 (PC61), intranuclear Foxp3 (FJK-16s) IL-10 (JES5-16E3), and IFNγ (XMG1.2) were purchased from eBioScience (San Diego, Calif.) were purchased from eBioScience (San Diego, Calif.). Antibodies to DEC205 (205yekta), CCR7 (4B12) and EpCam (G8.8) were from eBioScience. Antibody to mouse CD11b (M1/70), Gr1 (RB6-8C5), were purchased from BioLegend (San Diego). Anti-mouse mAb to CXCR3 (220803), was purchased from R&D Systems (Minneapolis, Minn.). Ovalbumin protein and Bradford protein quantification dye was obtained from Sigma (St. Louis, Mo.). Tissue digestion buffer consisted of [0.2 mg/ml of Collagenase A (Boehringer Mannheim/Roche, Indianapolis, Ind.), DNase 25 U/ml (Sigma), and 0.3 U/ml of Dispase (Invitrogen, Carlsbad, Ca)] in RPMI.

Chemotaxis Assay

Dual-chamber chemotaxis assays were performed using 24-well plates with 3 µm pore size inserts (Costar/Corning, Corning, N.Y., United States) according to the manufacturer's instructions. Briefly, $2.0×10^5$ T2 cells were resuspended in serum-free medium and loaded in the upper chamber. 200 ng/ml of CCL-21-mcherry-vault, 600 ng/ml recombinant CCL-21 (R&D Systems), 200 ng/ml CCL-21-mcherry-vault with neutralizing anti-CCL-21 recombinant antibody (5 µg/ml), 600 ng/ml CCL-21 with neutralizing anti-CCL-21 antibody (5 µg/ml) were added to the lower chamber of the wells (in triplicate). The neutralizing concentration of anti-CCL-21 antibody (R&D) used in these studies (5 µg/ml) was based on the ND50 (50% maximum inhibition of cytokine activity when CCL-21 is present at a concentration high enough to elicit maximum response). After 2 hours incubation at 37° C., migrated cells were recovered from the lower chamber and the inserts according to the manufacturer's instructions. Migrated T2 cells were resuspended in FACS buffer and evaluated by counting the number of lymphocytes.

Antigen Processing and Presentation Assay

Cells (DC2.4 ($5×10^4$ c/well)) were plated in triplicates in 96-well plates with OVA protein (350 µg/ml), MHC Class I restricted CD8 T cell line B3Z ($10^5$ c/well), in the presence of control vaults (200 ng/ml), or CCL-21 vault complex (200 ng/ml) or rCCL-21 (200 ng/ml) for 24 hrs. To determine the impact of CCL-21 on APC activity, CCL-21 was neutralized with anti-CCL-21 Ab (5 µg/ml) (R&D). IL-2 secreted by the activated CD8 T cells in the supernatant was quantified by ELISA (eBioScience).

Cell Culture

The murine Lewis lung carcinoma cell line (3LL, $H2^b$) was obtained from American Type Culture Collection (ATCC, Manassas, Va.). The cells were routinely cultured as monolayers in 25-$cm^2$ tissue culture flasks containing RPMI 1640 medium (Irvine Scientific, Santa Ana, Calif.) supplemented with 10% FBS (Gemini Bioproducts, Calabasas, Calif.), penicillin (100 U/ml), streptomycin (0.1 mg/ml), and 2 mM glutamine (JRH Biosciences, Lenexa, Kans.), and maintained at 37° C. in humidified atmosphere containing 5% $CO_2$ in air. The cell line was mycoplasma free, and cells were utilized before the tenth passage.

Tumorigenesis Model

Pathogen-free C57BL/6 mice and UBC-GFP/BL6 (6-8 wk old; Jackson Laboratory) were maintained in the West Los Angeles Veterans Affairs Animal Research vivarium. For tumorigenesis experiments, $1.5×10^5$ 3 LL tumor cells were injected s.c. in the right suprascapular area of C57BL/6 mice. Mice bearing 9-day-old established tumors were treated with a single intratumoral injection of mCCL-21-mCherry-CP-MVP vaults (200 ng), CP-MVP vaults (200 ng) in 200 µl or normal saline diluents. Tumor volumes were monitored by measuring two bisecting diameters of each tumor with calipers. Tumor volumes were calculated using the formula: $V=0.4ab^2$, with "a" as the larger diameter and "b" as the smaller diameter. To determine the extent of lymphocytes infiltrating the tumors, UBC-GFP/BL6 mice bearing 9-day tumors were treated as described and 7 days post treatment, non-necrotic tumors were isolated and frozen in OCT. The frozen tissue was sectioned to 5-µm thickness, fixed onto slides, and counterstained with 4',6-diamidino-2-phenylindole (DAPI) fixative. The slides were observed under a 1×71 Olympus fluorescence microscope attached to a charge-coupled device camera. The images were acquired under ×10 and ×40 objectives using the Image Pro software.

Orthotopic Model

Implantation of the tumors in the lung was performed as previously described in Andersson, A. et al. *J Immunol* 2009, 182(11):6951-6958 [24]. Briefly, $5×10^3$ 3 LL-GFP cells in 25 µl NS diluent were injected by the transthoracic route of C57BL/6 mice utilizing a tuberculin syringe with a 30-gauge needle in the left lung under ketamine/xylazine anesthesia. One week following tumor inoculation, mice were treated with diluent, control vault or CCL-21 vault complex via transthoracic injection. Four weeks after tumor implantation, lungs were harvested for evaluation of tumor burden and leukocytic infiltrates. Tumor burden was quantified by gating on the GFP and EpCam expressing 3LL tumor cells in single cell suspension of lung-tumor digests.

Immunostaining

Immunohistochemical staining was performed to determine and characterize the infiltrating cells. Specifically, paraffin sections of 5 µm were deparaffinized in xylene and rehydrated in decreasing concentrations of ethanol according to standard protocol [25]. Heat-induced antigen retrieval in citrate buffer (3 min in a steamer) was followed by blockade of endogenous peroxidase activity with 3% hydrogen peroxide in TBS for 10 min. All tissue was blocked (4% BSA, 10% sucrose, 1% normal swine serum in TBS) for 20 min at room temperature (RT). Primary antibody (DAKO, Cytomation, Carpinteria, Calif., USA) was diluted in the blocking solution to the following concentrations: CD3 1:200. Sections were incubated with the antibodies overnight at 4° C. On the second day, the slides were washed with Tris-buffered saline containing 0.02% Tween. This was followed by incubation with secondary biotinylated goat anti-mouse antibody at room temperature, streptavidin-conjugated alkaline phosphatase (Vectastain ABC-AP kit; Vector Laboratories, Burlingame, Calif.), and chromagen development with Vector Red substrate solution (Vector Laboratories). Slides were counterstained with hematoxylin, dehydrated, and mounted for analysis and photography.

Flow Cytometry

Flow cytometry was performed for the following leukocytic markers CD3, CD4, CD8, CCR7, CD11b, Gr1, DEC205, CD25, FOXP3 and CXCR3 on single cell suspension of tumors following treatment as described above. T cells were stained for intracytoplasmic IFNγ and IL-10. For analyses in the tumor tissue, tumors were mechanically dissociated on a wire mesh by crushing with a 10 ml syringe and incubated in tissue digestion buffer at 37° C. for 25 min. The cells were filtered through 70 μm nylon strainers (BD Biosciences, Bedford, Mass.) and stained with specific markers and analyzed by flow cytometry. Samples were acquired on a FACSCanto (BD Biosciences/FACSCalibur flow cytometer (Becton Dickinson, San Jose, Calif.) in the University of California, Los Angeles, Jonsson Cancer Center Flow Cytometry Core Facility. A total of 10,000 to 25,000 gated events were analyzed using FCS Express 3 (De Novo Software, Canada). Cells incubated with irrelevant isotype-matched antibodies and unstained cells served as controls. The cutoffs were set according to control staining.

T Cell Cytolysis

T lymphocyte lytic responses were evaluated following therapy. T cells were purified from spleens by negative selection using Miltenyi Biotec beads, and cytolytic activities were evaluated against autologous 3LL tumor cell line and the syngeneic control B16 melanoma tumor cell line. The T cell effectors were co-cultured with tumor cell targets (E:T of 20:1 and 40:1) in quadruplet wells in a 96-well plate, and 20 μl alamar blue was added to each well after 18 hours of incubation. Three hours after alamar blue addition, the plate was read with the Wallac 1420 fluorescence plate reader (Perkin-Elmer Life Science, Turku, Finland) with the excitation/emission set at 530/590 nm.

Example 1

Packaging CCL-21 into the Recombinant Vaults

A mouse chemokine CCL-21 was fused to a mouse mINT to create a CCL-21 fusion protein that was packaged into vault complexes. FIG. 1A shows a diagram of the CCL-21 and mCherry-INT constructs (SEQ ID NO:60) that were fused to create the mouse CCL-21-mCherry-mINT fusion protein (SEQ ID NO: 61). Mixing of lysates containing recombinant CCL-21-mINT and rat MVP generated in Sf-9 cells allowed the formation of a macromolecular vault complex containing the CCL-21 fusion protein that could be isolated by density gradient ultracentrifugation. The purified vault complexes contained both MVP as well as CCL-21-mINT (henceforth referred to as CCL-21 vault complex). FIG. 1B shows the incorporation of the recombinant CCL-21-mINT into a pFastBac expression vector by restriction digest and expression of CCL-21 fusion protein as analyzed on an electrophoresis gel. The MVP recombinant vaults containing packaged CCL-21-mCherry-mINT were purified on a sucrose gradient and the 40 and 45% fractions were analyzed by SDS-PAGE (FIG. 1C) and followed by staining with Coomassie (FIG. 1D). FIG. 1E shows a negative stain TEM image of vaults containing CCL-21-mCherry-mINT.

There was an estimated 20-30 molecules of the CCL-21-mINT protein in each vault complex is based on extrapolation from densitometric analysis of the Coomassie stained SDS-PAGE gels. This is consistent with previous studies in packaging multiple copies of other mINT fusion proteins into recombinant vault complexes [21]. With an estimate of 20-30 CCL-21-mINT proteins per vault, it is likely that this is at or near a saturating level for the packaging of this size protein. The CCL-21 vault complex also exhibited a very similar sedimentation profile on sucrose gradients as vault particles containing the INT domain fused to luciferase [6, 8, 21], suggesting that incorporation of CCL-21-mINT did not impact the normal structure of recombinant vault complexes. FIG. 1E shows purified vault complexes examined by negative stain transmission electron microscopy.

These results demonstrate that CCL-21 vaults complexes exhibit the characteristic barrel shaped morphology of vaults, consistent with the previously established morphology of vaults containing recombinant-INT fusion proteins [8, 26].

Example 2

CCL-21-Vault Complexes are Biologically Active and Induce the Migration of T2 Cells In Vitro To determine whether CCL-21 retains its biological function when packaged inside the vault, a chemotaxis assay was used. The chemotactic activity of CCL-21 is mediated through its receptor CCR7 to induce the migration of T cells and dendritic cells. To evaluate the biological activity of CCL-21 in the vault, T2 hybridoma cells were used that constitutively express CCR7. Two different concentrations of CCL-21 vault complexes (200 ng and 600 ng), empty vaults (600 ng), and recombinant CCL-21 (600 ng) were placed in the bottom chamber of a 24-well transwell plates and $2 \times 10^5$ T2 cells were loaded in the upper chamber.

Figure 2A:
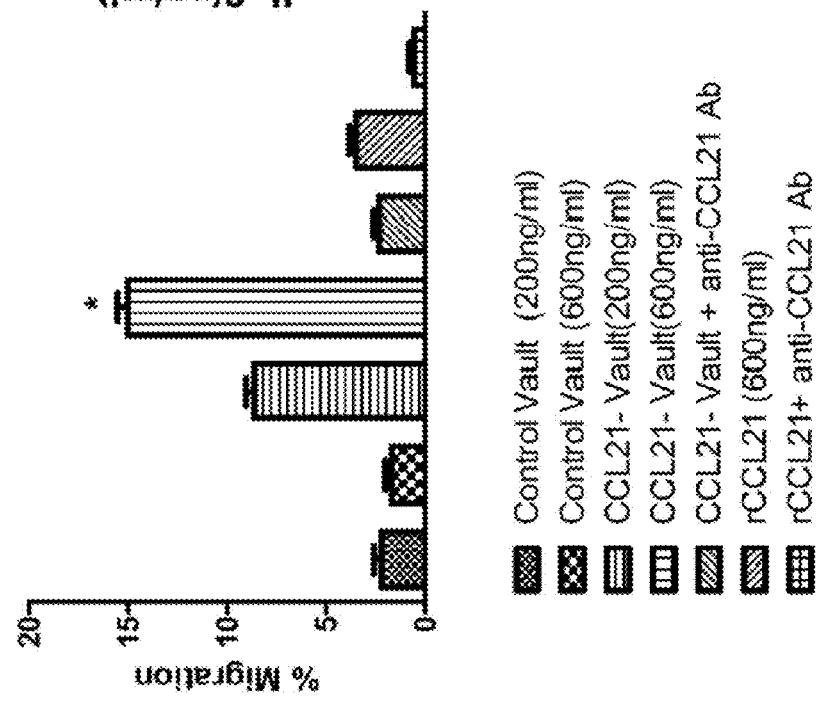
FIG. 2A is a graph that shows CCL-21 vault complexes increases the migration of T2 cells.

In FIG. 2A, the number of cells that migrated to the lower chamber following incubation was determined by flow cytometry and represented as the % migration. $2.0 \times 10^5$ T2 cells were plated in serum-free medium in the upper chamber. CCL-21-mCherry-vault complexes (200 ng/ml or 600 ng/ml), recombinant CCL-21 (600 ng/ml), control vaults (600 ng/ml) or neutralizing anti-CCL-21 recombinant antibody (5 μg/ml) were added to the lower chamber of the wells. Following a two hour incubation, migration of T2 cells were analyzed by flow cytometry. CCL-21 vault complexes effectively increased the T2 migration as compared with control, and anti-CCL-21 neutralizing Ab. abrogated the increase in migration suggesting that CCL-21 vault complexes are biological active and can mediate the chemotactic migration of T cells. Data in the panel are representative of 2 independent experiments. (Bars; Mean±SEM, *$p<0.05$ between the CCL-21 vault complexes and control vault or anti-CCL-21 antibody treatment groups.)

More than 7.5% of the T2 cells responded to 200 ng of CCL-21 vault complexes compared with ≤2.5% of the T2 cells incubated with 600 ng of recombinant CCL-21. This is a phenomenal response considering that the given concentration is of CCL-vault complexes and the actual concentration of CCL-21 inside of the vaults would be estimated to be ≤20 ng. It is possible that the increased bioactivity of CCL-21 vault complexes results from increased stabilization of CCL-21 resulting from packaging of the protein into the protective environment of the vault lumen. As the fusion protein non-covalently associates within vaults, it is plausible that vault breathing in solution releases CCL-21 in a gradient fashion and the number of cells migrated was higher than the recombinant CCL-21 because a steeper gradient is formed. To demonstrate that the migration of T2 cells was CCL-21 dependent, a neutralizing antibody (against CCL-21) was shown to efficiently block the chemotactic activity of both recombinant CCL-21 and CCL-21 vault complexes. This led to the conclusion that CCL-21 vault complexes were functionally active at inducing the migration of T2 cells in vitro.

These results demonstrate that CCL-21 cytokines retain their biological function when packaged inside the vault complex.

Example 3

CCL-21 Vault Complexes Enhance DC APC Activity

In order to determine the effect of CCL-21 vault complexes on dendritic cell (DC) antigen presenting cell (APC) activity, the impact of CCL-21-vault complexes on DC APC activity was studied in vitro. In comparison to control vaults, CCL-21-vault complexes augmented DC capacity to process and present ovalbumin and activate CD8 T cells to secrete IL-2 (FIG. 2B).

FIG. 2B shows CCL-21 vault complexes enhanced DC APC activity, and blocking CCL-21 reversed the increase in APC activity. B3Z cells ($1\times10^5$ cells/200 ul/well) were co-cultured with DC 2.4 ($5\times10^4$ cells/200 ul/well) and ovalbumin (350 ug/ml) in the presence or absence of CCL21 vaults (200 ng/ml) and anti-CCL-21 antibody (5 ug/ml) or control antibody (5 ug/ml goat IgG) for 24 hrs. Control vaults were used at concentration of 200 ng/ml. T cell activation was analyzed by measuring IL-2 production by ELISA. Data are representative of 2 independent experiments. (Bars; Mean±SEM, *p<0.05 between the CCL21 vault and control vault or anti-CCL21 antibody treatment groups.) Neutralization of CCL-21 abrogated the increase in DC APC activity to control levels.

These results demonstrate that CCL-21 vault complexes enhance DC APC activity in vitro.

Example 4

CCL-21 Vault Complexes Enhance the Recruitment of Antitumor Leukocytic Infiltrates and Reduce 3LL Tumor Burden In Vivo To determine the anti-tumor activity of CCL-21 vault complexes in vivo, CCL-21 vault complexes were tested for effects on established tumor burden in 3LL tumor-bearing mice.

Figure 3:
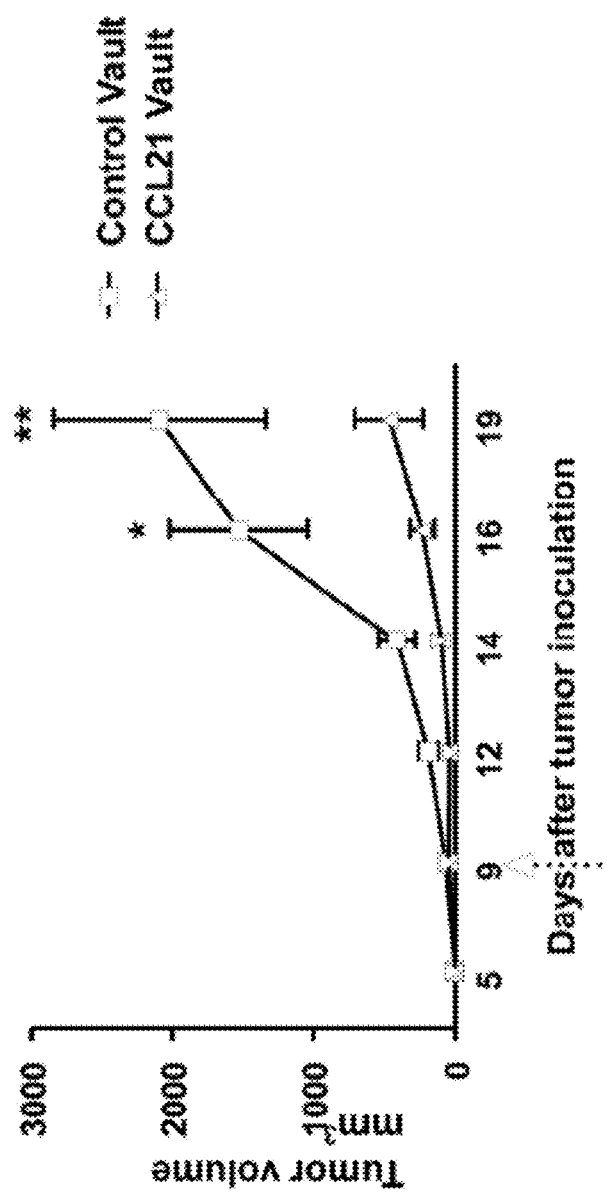
FIG. 3 is a graph showing a decrease in tumor burden by intratumoral injection of CCL-21 vault complexes (200 ng) compared to empty vaults.

As shown in FIG. 3, a single intratumoral injection of CCL-21 vault complexes (200 ng) led to significant decrease in tumor burden compared to empty vaults. C57BL/6 mice (n=5) were injected s.c. with $1.5\times10^5$ 3 LL tumor cells and tumor growth was monitored daily. After 5 days following tumor implantation, mice were treated with vaults containing CCL-21-mCherry-mINT (200 ng), vaults alone (200 ng) or normal saline (diluent) via intra tumoral injection and tumor growth was monitored for the duration of the experiment. Tumor size was measured and tumor volume calculated as described herein. Bisecting tumor diameters were measured with calipers. Intra-tumoral administration of vaults containing CCL-21-mCherry-mINT led to significant reduction in tumor volume compared with untreated tumor bearing mice (p<0.001).

FIGS. 4A-4B show that the CCL-21-vault complex treatment group (FIG. 4B) had enhanced leukocytic infiltrates compared to control vault (FIG. 4A), and immune staining showed that the infiltrates were mostly CD3 expressing T cells (FIG. 4B, bottom right panel). Sections from paraffin-embedded tissue were stained by hematoxylin-eosin (H&E) and CD3, CD4, CD8 and S-100 by immunohistochemistry using commercially available antibodies. Each panel of FIGS. 4A and 4B show photographs taken at 400× of representative areas within distinct primary tumors and Lymph nodes. Thus, CCL-21 vaults reduced tumor burden and increased the influx of CD3 expressing T cells in the tumor as compared to control vaults. (Data; Mean±SEM, *p<0.05 between CCL-21 vaults and control group, n=8 mice/group.)

In additional experiments, the antitumor efficacy of CCL-21-vault complexes was determined in a 7-day established orthotopic 3LL lung cancer model. CCL-21-vault complexes reduced tumor burden by 7-fold compared to controls. In FIGS. 5A-5C, H&E staining of lung tumor sections from diluent or control vaults showed increased tumor masses as compared to reduced tumor mass in the CCL-21 vault complex treatment group. FIG. 5A illustrates the effects of treatment of 3LL lung cancer cells with diluents only. FIG. 5B shows treatment with control vault, and FIG. 5C shows treatment with CCL-21 vault.

FIG. 6A shows the percentage tumor burden in naïve cells, and 3LL cells treated with diluents, control vault (CV), or CCL-21 vault complexes in a flow cytometry assay. Tumor burden was calculated on total percentage of GFP and Epcam expressing tumor cells in total lung digest. Naïve lung was used as control to set up the gate. CCL-21 vault complex treatment reduced tumor burden. FIG. 6B is a graph illustrating the percentage tumor burden in 3LL cells after treatment with diluents, control vault, or CCL-21 vault complexes.

Example 5

CCL-21-Vault Complexes Induce Tumor Infiltrating T Cell IFNγ but Reduce IL-10 and Augment Systemic T Cell Cytolytic Activity The effect of CCL-21 vault complexes on inducing tumor infiltrates and IL-10 expression was studied in vivo.

Figure 7A:
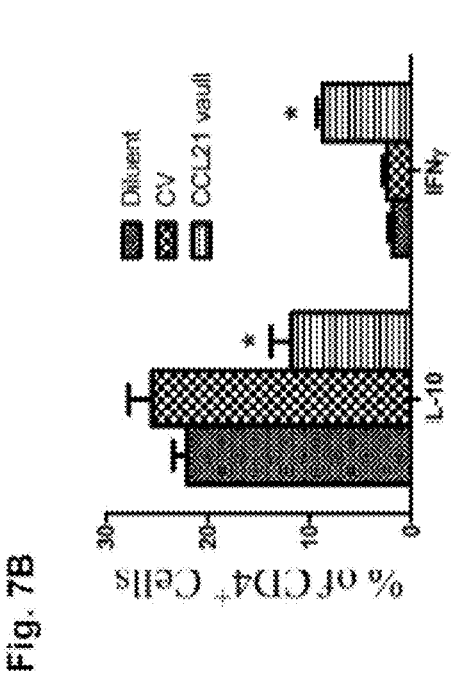
FIG. 7A is a graph showing percentage of intratumoral leukocytic populations (CD4, CD8, CD3 CXCR3, CD3 CCR7, DEC205, MDSC and Tregs) at the tumor site after injection with diluent, control vault, or CCL-21 vault complexes. CCL-21 vault complex augmented CD4, CD8, CXCR3$^+$CD3$^+$T, CCR7$^+$CD3$^+$T and DEC205$^+$DC infiltrates and reduced MDSC and Tregs.
Figure 7B:
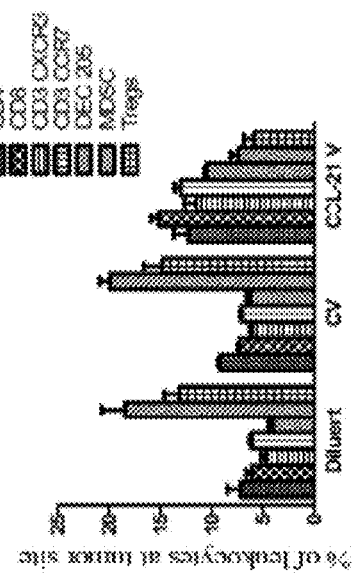
FIG. 7B is a graph of the percentage of CD4+ cells with IFNγ and IL-10 expression after treatment with diluent, control vault, or CCL-21 vault complexes. Tumor T lymphocytic infiltrates from CCL-21 vault complex treated mice had increased intracytoplasmic IFNγ and reduced IL-10 expression.
Figure 7C:
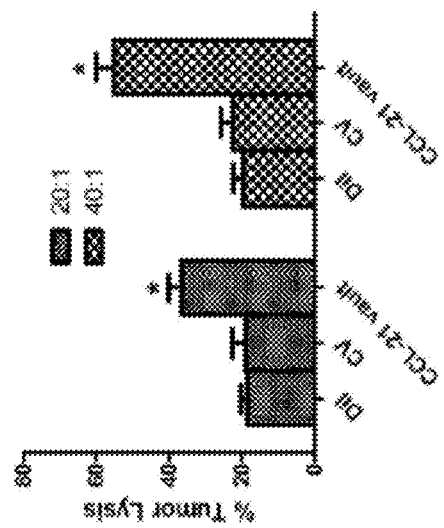
FIG. 7C is a graph of the percentage of CD8+ cells with IFNγ and IL-10 expression after treatment with diluent, control vault, or CCL-21 vault complexes.
Figure 7D:
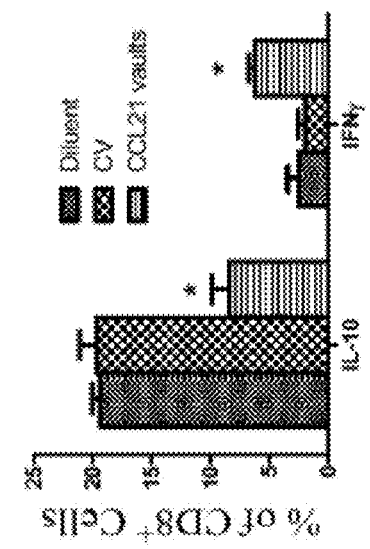
FIG. 7D is a graph of percentage tumor lysis of splenic T cells after intratumoral injection with diluent, control vault, or CCL-21 vault complexes.

Accompanying the reduced tumor burden, an evaluation of intratumoral leukocytic populations showed enhanced frequency of CD4, CD8, CD3 CXCR3, CD3 CCR7 and DEC205 but reduced levels of MDSC and Tregs (FIG. 7A-7D). In FIG. 7A, CCL-21 vault complexes augmented CD4, CD8, CXCR3$^+$CD3$^+$T, CCR7$^+$CD3$^+$T and DEC205$^+$ DC infiltrates and reduced MDSC and Tregs compared with treatment with diluents or control vault alone. FIGS. 7B and 7C show T cell infiltrates of CCL-21 vault complex treatment mice increased IFNγ and reduced IL-10 expression compared to controls. FIG. 7D illustrates that CCL-21 vault treatment enhanced the cytolytic activity of purified splenic T cells against parental 3LL tumors in vitro (E:T of 20:1 and 40:1).

FIGS. 6A-7D demonstrate that CCL-21 vaults reduced tumor burden and immune suppressors, increased T and DC infiltrates and induced systemic T cell antitumor activity.

Specifically, CCL-21 vaults reduced tumor burden and immune suppressors (MDSC and Tregs) and enhanced intra-tumoral immune cell infiltrates in a 3LL orthotopic lung cancer model. For experiments shown in FIGS. 6A-7D, $5 \times 10^3$ 3 LL-GFP tumor cells were injected in the left lung via transthoracic route. One week after tumor injections, mice were treated with diluent (NS), control vaults (2 ug) or CCL-21 vaults (2 ug) via transthoracic route in the left lung. Day 28 post tumor implantation, lung tumors were harvested for the analysis of tumor burden and tumor leukocytic infiltrates. (Data bars, mean±SEM, *p<0.05 between CCL-21 vaults and control vault groups, n=8 mice/group.).

These results demonstrate that CCL-21 vault complexes induce tumor infiltrating T cell IFNγ but reduce IL-10 and augment systemic T cell cytolytic activity.

Example 6

Use of CCL-21 Vault Complexes for Treatment of Cancer in Humans

For treatment of cancer in humans, the pharmaceutical compositions used in the present invention may be administered in a number of ways depending upon the invasiveness of treatment and based on whether local or systemic treatment is desired. The preferred initial treatment may be performed by intra-tumoral injection of the CCL-21 vault complex into a tumor of the patient. In some embodiments, intra-tumoral injection of a CCL-21 vault complex is performed on a tumor in the lung of the patient in need of treatment of lung cancer.

In certain embodiments, various dosages of the pharmaceutical composition comprising CCL-21 vault complexes can be administered to the patient.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 1

| Sequences | |
| --- | --- |
| SEQ ID NO: 1 | Mouse CCL-21 Protein sequence |
| MAQMMTLSLLSLVLALCIPWTQGSDGGGQDCCLKYSQKKIPYSIVRGYRKQEPSLGCPIP | |
| AILFSPRKHSKPELCANPEEGWVQNLMRRLDQFPAPGKQSPGCRKNRGTSKSGKKGKGSK | |
| GCKRTEQTQPSRG | |
| SEQ ID NO: 2 | Human CCL-21 Protein sequence |
| MAQSLALSLLILVLAFGIPRTQGSDGGAQDCCLKYSQRKIPAKVVRSYRKQEPSLGCSIP | |
| AILFLPRKRSQAELCADPKELWVQQLMQHLDKTPSPQKPAQGCRKDRGASKTGKKGKGSK | |
| GCKRTERSQTPKGP | |
| SEQ ID NO: 3 | Mouse CCL-21 DNA cloned sequence |
| ATGGCTCAGATGATGACTCTGAGCCTCCTTAGCCTGGTCCTGGCTCTCTGCATCCCCTGGACCCAAGGCA | |
| GTGATGGAGGGGGTCAGGACTGCTGCCTTAAGTACAGCCAGAAGAAAATTCCCTACAGTATTGTCCGAGG | |
| CTATAGGAAGCAAGAACCAAGTTTAGGCTGTCCCATCCCGGCAATCCTGTTCTCACCCCGGAAGCACTCT | |
| AAGCCTGAGCTATGTGCAAACCCTGAGGAAGGCTGGGTGCAGAACCTGATGCGCCGCCTGGACCAGCCTC | |
| CAGCCCCAGGGAAACAAAGCCCCGGCTGCAGGAAGAACCGGGGAACCTCTAAGTCTGGAAAGAAAGGAAA | |
| GGGCTCCAAGGGCTGCAAGAGAACTGAACAGACACAGCCCTCAAGAGGA | |
| SEQ ID NO: 4 | Mouse CCL-21 DNA full sequence |
| ATGGCTCAGATGATGACTCTGAGCCTCCTTAGCCTGGTCCTGGCTCTCTGCATCCCCTGGACCCAAGGCA | |
| GTGATGGAGGGGGTCAGGACTGCTGCCTTAAGTACAGCCAGAAGAAAATTCCCTACAGTATTGTCCGAGG | |
| CTATAGGAAGCAAGAACCAAGTTTAGGCTGTCCCATCCCGGCAATCCTGTTCTCACCCCGGAAGCACTCT | |
| AAGCCTGAGCTATGTGCAAACCCTGAGGAAGGCTGGGTGCAGAACCTGATGCGCCGCCTGGACCAGCCTC | |
| CAGCCCCAGGGAAACAAAGCCCCGGCTGCAGGAAGAACCGGGGAACCTCTAAGTCTGGAAAGAAAGGAAA | |
| GGGCTCCAAGGGCTGCAAGAGAACTGAACAGACACAGCCCTCAAGAGGATAG | |
| SEQ ID NO: 5 | Human CCL-21 DNA sequence, Genbank #NP_002980 |
| ATGGCTCAGTCACTGGCTCTGAGCCTCCTTATCCTGGTTCTGGCCTTTGGCATCCCCAGGACCCAAGGCA | |
| GTGATGGAGGGGCTCAGGACTGTTGCCTCAAGTACAGCCAAAGGAAGATTCCCGCCAAGGTTGTCCGCAG | |

TABLE 1-continued

Sequences

CTACCGGAAGCAGGAACCAAGCTTAGGCTGCTCCATCCCAGCTATCCTGTTCTTGCCCCGCAAGCGCTCT

CAGGCAGAGCTATGTGCAGACCCAAAGGAGCTCTGGGTGCAGCAGCTGATGCAGCATCTGGACAAGACAC

CATCCCCACAGAAACCAGCCCAGGGCTGCAGGAAGGACAGGGGGGCCTCCAAGACTGGCAAGAAAGGAAA

GGGCTCCAAAGGCTGCAAGAGGACTGAGCGGTCACAGACCCCTAAAGGGCCATAG

| SEQ ID NO: 6 | Mouse mINT DNA sequence |
|---|---|

TGC ACA CAA CAC TGG CAG GAT GCT GTG CCT TGG ACA GAA CTC CTC AGT CTA CAG ACA GAG GAT

GGC TTC TGG AAA CTT ACA CCA GAA CTG GGA CTT ATA TTA AAT CTT AAT ACA AAT GGT TTG CAC

AGC TTT CTT AAA CAA AAA GGC ATT CAA TCT CTA GGT GTA AAA GGA AGA GAA TGT CTC CTG GAC

CTA ATT GCC ACA ATG CTG GTA CTA CAG TTT ATT CGC ACC AGG TTG GAA AAA GAG GGA ATA GTG

TTC AAA TCA CTG ATG AAA ATG GAT GAC CCT TCT ATT TCC AGG AAT ATT CCC TGG GCT TTT GAG

GCA ATA AAG CAA GCA AGT GAA TGG GTA AGA AGA ACT GAA GGA CAG TAC CCA TCT ATC TGC CCA

CGG CTT GAA CTG GGG AAC GAC TGG GAC TCT GCC ACC AAG CAG TTG CTG GGA CTC CAG CCC ATA

AGC ACT GTG TCC CCT CTT CAT AGA GTC CTC CAT TAC AGT CAA GGC TAA

| SEQ ID NO: 7 | Human mINT DNA sequence |
|---|---|

TGC ACA CAA CAC TGG CAG GAT GCT GTG CCT TGG ACA GAA CTC CTC AGT CTA CAG ACA GAG GAT

GGC TTC TGG AAA CTT ACA CCA GAA CTG GGA CTT ATA TTA AAT CTT AAT ACA AAT GGT TTG CAC

AGC TTT CTT AAA CAA AAA GGC ATT CAA TCT CTA GGT GTA AAA GGA AGA GAA TGT CTC CTG GAC

CTA ATT GCC ACA ATG CTG GTA CTA CAG TTT ATT CGC ACC AGG TTG GAA AAA GAG GGA ATA GTG

TTC AAA TCA CTG ATG AAA ATG GAT GAC CCT TCT ATT TCC AGG AAT ATT CCC TGG GCT TTT GAG

GCA ATA AAG CAA GCA AGT GAA TGG GTA AGA AGA ACT GAA GGA CAG TAC CCA TCT ATC TGC CCA

CGG CTT GAA CTG GGG AAC GAC TGG GAC TCT GCC ACC AAG CAG TTG CTG GGA CTC CAG CCC ATA

AGC ACT GTG TCC CCT CTT CAT AGA GTC CTC CAT TAC AGT CAA GGC TAA

| SEQ ID NO: 8 | Human mINT protein sequence (residues 1563-1724 of the human VPARP protein sequence) |
|---|---| ctqhwqdavpwtellslqtedgfwkltpelglilnlntnglhsflkqkgiqslgvkgreclldliatmlvlqfirtrlekegi vfkslmkmddpsisrnipwafealkqasewvrrtegqypsicprlelgndwdsatkqllglqpistvsplhrvlhysqg

| SEQ ID NO: 9 | Mouse mINT protein sequence |
|---|---|

CTQHWQDAVPWTELLSLQTEDGFWKLTPELGLILNLNTNGLHSFLKQKGIQSLGVKGRECLLDLIATMLVLQFIRTRLEKEGI

VFKSLMKMDDPSISRNIPWAFEAIKQASEWVRRTEGQYPSICPRLELGNDWDSATKQLLGLQPISTVSPLHRVLHYSQG

| SEQ ID NO: 10 | Mouse CCL-21-mINT fusion DNA sequence |
|---|---|

ATGGCTCAGATGATGACTCTGAGCCTCCTTAGCCTGGTCCTGGCTCTCTGCATCCCCTGGACCCAAGGCA

GTGATGGAGGGGGTCAGGACTGCTGCCTTAAGTACAGCCAGAAGAAAATTCCCTACAGTATTGTCCGAGG

CTATAGGAAGCAAGAACCAAGTTTAGGCTGTCCCATCCCGGCAATCCTGTTCTCACCCCGGAAGCACTCT

AAGCCTGAGCTATGTGCAAACCCTGAGGAAGGCTGGGTGCAGAACCTGATGCGCCGCCTGGACCAGCCTC

CAGCCCCAGGGAAACAAAGCCCCGGCTGCAGGAAGAACCGGGGAACCTCTAAGTCTGGAAAGAAAGGAAA

GGGCTCCAAGGGCTGCAAGAGAACTGAACAGACACAGCCCTCAAGAGGA TGC ACA CAA CAC TGG CAG GAT GCT

GTG CCT TGG ACA GAA CTC CTC AGT CTA CAG ACA GAG GAT GGC TTC TGG AAA CTT ACA CCA GAA

CTG GGA CTT ATA TTA AAT CTT AAT ACA AAT GGT TTG CAC AGC TTT CTT AAA CAA AAA GGC ATT

CAA TCT CTA GGT GTA AAA GGA AGA GAA TGT CTC CTG GAC CTA ATT GCC ACA ATG CTG GTA CTA

TABLE 1-continued

Sequences

CAG TTT ATT CGC ACC AGG TTG GAA AAA GAG GGA ATA GTG TTC AAA TCA CTG ATG AAA ATG GAT
GAC CCT TCT ATT TCC AGG AAT ATT CCC TGG GCT TTT GAG GCA ATA AAG CAA GCA AGT GAA TGG
GTA AGA AGA ACT GAA GGA CAG TAC CCA TCT ATC TGC CCA CGG CTT GAA CTG GGG AAC GAC TGG
GAC TCT GCC ACC AAG CAG TTG CTG GGA CTC CAG CCC ATA AGC ACT GTG TCC CCT CTT CAT AGA
GTC CTC CAT TAC AGT CAA GGC TAA

| SEQ ID NO: 11 | Human CCL-21-mINT fusion DNA sequence |
| --- | --- |

ATGGCTCAGTCACTGGCTCTGAGCCTCCTTATCCTGGTTCTGGCCTTTGGCATCCCCAGGACCCAAGGCA
GTGATGGAGGGGCTCAGGACTGTTGCCTCAAGTACAGCCAAAGGAAGATTCCCGCCAAGGTTGTCCGCAG
CTACCGGAAGCAGGAACCAAGCTTAGGCTGCTCCATCCCAGCTATCCTGTTCTTGCCCCGCAAGCGCTCT
CAGGCAGAGCTATGTGCAGACCCAAAGGAGCTCTGGGTGCAGCAGCTGATGCAGCATCTGGACAAGACAC
CATCCCCACAGAAACCAGCCCAGGGCTGCAGGAAGGACAGGGGGGCCTCCAAGACTGGCAAGAAAGGAAA
GGGCTCCAAAGGCTGCAAGAGGACTGAGCGGTCACAGACCCCTAAAGGGCCAGCTAGCTGC ACA CAA CAC TGG CAG
GAT GCT GTG CCT TGG ACA GAA CTC CTC AGT CTA CAG ACA GAG GAT GGC TTC TGG AAA CTT ACA
CCA GAA CTG GGA CTT ATA TTA AAT CTT AAT ACA AAT GGT TTG CAC AGC TTT CTT AAA CAA AAA
GGC ATT CAA TCT CTA GGT GTA AAA GGA AGA GAA TGT CTC CTG GAC CTA ATT GCC ACA ATG CTG
GTA CTA CAG TTT ATT CGC ACC AGG TTG GAA AAA GAG GGA ATA GTG TTC AAA TCA CTG ATG AAA
ATG GAT GAC CCT TCT ATT TCC AGG AAT ATT CCC TGG GCT TTT GAG GCA ATA AAG CAA GCA AGT
GAA TGG GTA AGA AGA ACT GAA GGA CAG TAC CCA TCT ATC TGC CCA CGG CTT GAA CTG GGG AAC
GAC TGG GAC TCT GCC ACC AAG CAG TTG CTG GGA CTC CAG CCC ATA AGC ACT GTG TCC CCT CTT
CAT AGA GTC CTC CAT TAC AGT CAA GGC TAA

| SEQ ID NO: 12 | Mouse CCL-21-INT fusion Protein Sequence |
| --- | --- |

MAQMMTLSLLSLVLALCIPWTQGSDGGGQDCCLKYSQKKIPYSIVRGYRKQEPSLGCPIPAILFSPRKHSKPELCANPEEGWV
QNLMRRLDQFPAPGKQSPGCRKNRGTSKSGKKGKGSKGCKRTEQTQFSRGCTQHWQDAVPWTELLSLQTEDGFWKLTPELGLI
LNLNTNGLHSFLKQKGIQSLGVKGRECLLDLIATMLVLQFIRTRLEKEGIVFKSLMKMDDPSISRNIPWAFEAIKQASEWVRR
TEGQYPSICPRLELGNDWDSATKQLLGLQPISTVSPLHRVLHYSQG

| SEQ ID NO: 13 | Human CCL-21-INT fusion Protein Sequence |
| --- | --- |

MAQSLALSLLILVLAFGIPRTQGSDGGAQDCCLKYSQRKIPAKVVRSYRKQEPSLGCSIPAILFLPRKRSQAELCADPKELWV
QQLMQHLDKTPSPQKPAQGCRKDRGASKTGKKGKGSKGCKRTERSQTPKGPASCTQHWQDAVPWTELLSLQTEDGFWKLTPEL
GLILNLNTNGLHSFLKQKGIQSLGVKGRECLLDLIATMLVLQFIRTRLEKEGIVFKSLMKMDDPSISRNIPWAFEAIKQASEW
VRRTEGQYPSICPRLELGNDWDSATKQLLGLQPISTVSPLHRVLHYSQG

| SEQ ID NO: 14 | Human VPARP protein sequence Genbank #AAD47250 |
| --- | --- |

Met Val Met Gly Ile Phe Ala Asn Cys Ile Phe Cys Leu Lys Val Lys
Tyr Leu Pro Gln Gln Gln Lys Lys Lys Leu Gln Thr Asp Ile Lys Glu
Asn Gly Gly Lys Phe Ser Phe Ser Leu Asn Pro Gln Cys Thr His Ile
Ile Leu Asp Asn Ala Asp Val Leu Ser Gln Tyr Gln Leu Asn Ser Ile
Gln Lys Asn His Val His Ile Ala Asn Pro Asp Phe Ile Trp Lys Ser
Ile Arg Glu Lys Arg Leu Leu Asp Val Lys Asn Tyr Asp Pro Tyr Lys
Pro Leu Asp Ile Thr Pro Pro Asp Gln Lys Ala Ser Ser Ser Glu
Val Lys Thr Glu Gly Leu Cys Pro Asp Ser Ala Thr Glu Glu Glu Asp

TABLE 1-continued

Sequences

Thr Val Glu Leu Thr Glu Phe Gly Met Gln Asn Val Glu Ile Pro His
Leu Pro Gln Asp Phe Glu Val Ala Lys Tyr Asn Thr Leu Glu Lys Val
Gly Met Glu Gly Gly Gln Glu Ala Val Val Glu Leu Gln Cys Ser
Arg Asp Ser Arg Asp Cys Pro Phe Leu Ile Ser Ser His Phe Leu Leu
Asp Asp Gly Met Glu Thr Arg Arg Gln Phe Ala Ile Lys Lys Thr Ser
Glu Asp Ala Ser Glu Tyr Phe Glu Asn Tyr Ile Glu Glu Leu Lys Lys
Gln Gly Phe Leu Leu Arg Glu His Phe Thr Pro Glu Ala Thr Gln Leu
Ala Ser Glu Gln Leu Gln Ala Leu Leu Leu Glu Glu Val Met Asn Ser
Ser Thr Leu Ser Gln Glu Val Ser Asp Leu Val Glu Met Ile Trp Ala
Glu Ala Leu Gly His Leu Glu His Met Leu Leu Lys Pro Val Asn Arg
Ile Ser Leu Asn Asp Val Ser Lys Ala Glu Gly Ile Leu Leu Leu Val
Lys Ala Ala Leu Lys Asn Gly Glu Thr Ala Glu Gln Leu Gln Lys Met
Met Thr Glu Phe Tyr Arg Leu Ile Pro His Lys Gly Thr Met Pro Lys
Glu Val Asn Leu Gly Leu Leu Ala Lys Lys Ala Asp Leu Cys Gln Leu
Ile Arg Asp Met Val Asn Val Cys Glu Thr Asn Leu Ser Lys Pro Asn
Pro Pro Ser Leu Ala Lys Tyr Arg Ala Leu Arg Cys Lys Ile Glu His
Val Glu Gln Asn Thr Glu Glu Phe Leu Arg Val Arg Lys Glu Val Leu
Gln Asn His His Ser Lys Ser Pro Val Asp Val Leu Gln Ile Phe Arg
Val Gly Arg Val Asn Glu Thr Thr Glu Phe Leu Ser Lys Leu Gly Asn
Val Arg Pro Leu Leu His Gly Ser Pro Val Gln Asn Ile Val Gly Ile
Leu Cys Arg Gly Leu Leu Leu Pro Lys Val Val Glu Asp Arg Gly Val
Gln Arg Thr Asp Val Gly Asn Leu Gly Ser Gly Ile Tyr Phe Ser Asp
Ser Leu Ser Thr Ser Ile Lys Tyr Ser His Pro Gly Glu Thr Asp Gly
Thr Arg Leu Leu Leu Ile Cys Asp Val Ala Leu Gly Lys Cys Met Asp
Leu His Glu Lys Asp Phe Pro Leu Thr Glu Ala Pro Pro Gly Tyr Asp
Ser Val His Gly Val Ser Gln Thr Ala Ser Val Thr Thr Asp Phe Glu
Asp Asp Glu Phe Val Val Tyr Lys Thr Asn Gln Val Lys Met Lys Tyr
Ile Ile Lys Phe Ser Met Pro Gly Asp Gln Ile Lys Asp Phe His Pro
Ser Asp His Thr Glu Leu Glu Glu Tyr Arg Pro Glu Phe Ser Asn Phe
Ser Lys Val Glu Asp Tyr Gln Leu Pro Asp Ala Lys Thr Ser Ser Ser
Thr Lys Ala Gly Leu Gln Asp Ala Ser Gly Asn Leu Val Pro Leu Glu
Asp Val His Ile Lys Gly Arg Ile Ile Asp Thr Val Ala Gln Val Ile
Val Phe Gln Thr Tyr Thr Asn Lys Ser His Val Pro Ile Glu Ala Lys
Tyr Ile Phe Pro Leu Asp Asp Lys Ala Ala Val Cys Gly Phe Glu Ala
Phe Ile Asn Gly Lys His Ile Val Gly Glu Ile Lys Glu Lys Glu Glu
Ala Gln Gln Glu Tyr Leu Glu Ala Val Thr Gln Gly His Gly Ala Tyr
Leu Met Ser Gln Asp Ala Pro Asp Val Phe Thr Val Ser Val Gly Asn
Leu Pro Pro Lys Ala Lys Val Leu Ile Lys Ile Thr Tyr Ile Thr Glu
Leu Ser Ile Leu Gly Thr Val Gly Val Phe Phe Met Pro Ala Thr Val

TABLE 1-continued

Sequences

Ala Pro Trp Gln Gln Asp Lys Ala Leu Asn Glu Asn Leu Gln Asp Thr

Val Glu Lys Ile Cys Ile Lys Glu Ile Gly Thr Lys Gln Ser Phe Ser

Leu Thr Met Ser Ile Glu Met Pro Tyr Val Ile Glu Phe Ile Phe Ser

Asp Thr His Glu Leu Lys Gln Lys Arg Thr Asp Cys Lys Ala Val Ile

Ser Thr Met Glu Gly Ser Ser Leu Asp Ser Ser Gly Phe Ser Leu His

Ile Gly Leu Ser Ala Ala Tyr Leu Pro Arg Met Trp Val Glu Lys His

Pro Glu Lys Glu Ser Glu Ala Cys Met Leu Val Phe Gln Pro Asp Leu

Asp Val Asp Leu Pro Asp Leu Ala Ser Glu Ser Glu Val Ile Ile Cys

Leu Asp Cys Ser Ser Ser Met Glu Gly Val Thr Phe Leu Gln Ala Lys

Gln Ile Thr Leu His Ala Leu Ser Leu Val Gly Glu Lys Gln Lys Val

Asn Ile Ile Gln Phe Gly Thr Gly Tyr Lys Glu Leu Phe Ser Tyr Pro

Lys His Ile Thr Ser Asn Thr Thr Ala Ala Glu Phe Ile Met Ser Ala

Thr Pro Thr Met Gly Asn Thr Asp Phe Trp Lys Thr Leu Arg Tyr Leu

Ser Leu Leu Tyr Pro Ala Arg Gly Ser Arg Asn Ile Leu Leu Val Ser

Asp Gly His Leu Gln Asp Glu Ser Leu Thr Leu Gln Leu Val Lys Arg

Ser Arg Pro His Thr Arg Leu Phe Ala Cys Gly Ile Gly Ser Thr Ala

Asn Arg His Val Leu Arg Ile Leu Ser Gln Cys Gly Ala Gly Val

Phe Glu Tyr Phe Asn Ala Lys Ser Lys His Ser Trp Arg Lys Gln

Ile Glu Asp Gln Met Thr Arg Leu Cys Ser Pro Ser Cys His Ser

Val Ser Val Lys Trp Gln Gln Leu Asn Pro Asp Ala Pro Glu Ala

Leu Gln Ala Pro Ala Gln Val Pro Ser Leu Phe Arg Asn Asp Arg

Leu Leu Val Tyr Gly Phe Ile Pro His Cys Thr Gln Ala Thr Leu

Cys Ala Leu Ile Gln Glu Lys Glu Phe Cys Thr Met Val Ser Thr

Thr Glu Leu Gln Lys Thr Thr Gly Thr Met Ile His Lys Leu Ala

Ala Arg Ala Leu Ile Arg Asp Tyr Glu Asp Gly Ile Leu His Glu

Asn Glu Thr Ser His Glu Met Lys Lys Gln Thr Leu Lys Ser Leu

Ile Ile Lys Leu Ser Lys Glu Asn Ser Leu Ile Thr Gln Phe Thr

Ser Phe Val Ala Val Glu Lys Arg Asp Glu Asn Glu Ser Pro Phe

Pro Asp Ile Pro Lys Val Ser Glu Leu Ile Ala Lys Glu Asp Val

Asp Phe Leu Pro Tyr Met Ser Trp Gln Gly Glu Pro Gln Glu Ala

Val Arg Asn Gln Ser Leu Leu Ala Ser Ser Glu Trp Pro Glu Leu

Arg Leu Ser Lys Arg Lys His Arg Lys Ile Pro Phe Ser Lys Arg

Lys Met Glu Leu Ser Gln Pro Glu Val Ser Glu Asp Phe Glu Glu

Asp Gly Leu Gly Val Leu Pro Ala Phe Thr Ser Asn Leu Glu Arg

Gly Gly Val Glu Lys Leu Leu Asp Leu Ser Trp Thr Glu Ser Cys

Lys Pro Thr Ala Thr Glu Pro Leu Phe Lys Lys Val Ser Pro Trp

Glu Thr Ser Thr Ser Ser Phe Phe Pro Ile Leu Ala Pro Ala Val

Gly Ser Tyr Leu Thr Pro Thr Thr Arg Ala His Ser Pro Ala Ser

Leu Ser Phe Ala Ser Tyr Arg Gln Val Ala Ser Phe Gly Ser Ala

TABLE 1-continued

Sequences

Ala Pro Pro Arg Gln Phe Asp Ala Ser Gln Phe Ser Gln Gly Pro
Val Pro Gly Thr Cys Ala Asp Trp Ile Pro Gln Ser Ala Ser Cys
Pro Thr Gly Pro Pro Gln Asn Pro Pro Ser Ala Pro Tyr Cys Gly
Ile Val Phe Ser Gly Ser Ser Leu Ser Ser Ala Gln Ser Ala Pro
Leu Gln His Pro Gly Gly Phe Thr Thr Arg Pro Ser Ala Gly Thr
Phe Pro Glu Leu Asp Ser Pro Gln Leu His Phe Ser Leu Pro Thr
Asp Pro Asp Pro Ile Arg Gly Phe Gly Ser Tyr His Pro Ser Ala
Tyr Ser Pro Phe His Phe Gln Pro Ser Ala Ala Ser Leu Thr Ala
Asn Leu Arg Leu Pro Met Ala Ser Ala Leu Pro Glu Ala Leu Cys
Ser Gln Ser Arg Thr Thr Pro Val Asp Leu Cys Leu Leu Glu Glu
Ser Val Gly Ser Leu Glu Gly Ser Arg Cys Pro Val Phe Ala Phe
Gln Ser Ser Asp Thr Glu Ser Asp Glu Leu Ser Glu Val Leu Gln
Asp Ser Cys Phe Leu Gln Ile Lys Cys Asp Thr Lys Asp Asp Ser
Ile Pro Cys Phe Leu Glu Leu Lys Glu Glu Asp Glu Ile Val Cys
Thr Gln His Trp Gln Asp Ala Val Pro Trp Thr Glu Leu Leu Ser
Leu Gln Thr Glu Asp Gly Phe Trp Lys Leu Thr Pro Glu Leu Gly
Leu Ile Leu Asn Leu Asn Thr Asn Gly Leu His Ser Phe Leu Lys
Gln Lys Gly Ile Gln Ser Leu Gly Val Lys Gly Arg Glu Cys Leu
Leu Asp Leu Ile Ala Thr Met Leu Val Leu Gln Phe Ile Arg Thr
Arg Leu Glu Lys Glu Gly Ile Val Phe Lys Ser Leu Met Lys Met
Asp Asp Pro Ser Ile Ser Arg Asn Ile Pro Trp Ala Phe Glu Ala
Ile Lys Gln Ala Ser Glu Trp Val Arg Arg Thr Glu Gly Gln Tyr
Pro Ser Ile Cys Pro Arg Leu Glu Leu Gly Asn Asp Trp Asp Ser
Ala Thr Lys Gln Leu Leu Gly Leu Gln Pro Ile Ser Thr Val Ser
Pro Leu His Arg Val Leu His Tyr Ser Gln Gly

| SEQ ID NO: 15 | Human VPARP cDNA, Genbank #AF158255 |
|---|---| atggtgatgg gaatctttgc aaattgtatc ttctgtttga aagtgaagta cttacctcag
cagcagaaga aaaagctaca aactgacatt aaggaaaatg gcggaaagtt ttccttttcg
ttaaatcctc agtgcacaca tataatctta gataatgctg atgttctgag tcagtaccaa
ctgaattcta tccaaaagaa ccacgttcat attgcaaacc cagattttat atggaaatct
atcagagaaa agagactctt ggatgtaaag aattatgatc cttataagcc cctggacatc
acaccacctc ctgatcagaa ggcgagcagt tctgaagtga aaacagaagg tctatgcccg
gacagtgcca cagaggagga agacactgtg gaactcactg agtttggtat gcagaatgtt
gaaattcctc atcttcctca agattttgaa gttgcaaaat ataacacctt ggagaaagtg
ggaatggagg gaggccagga agctgtggtg gtggagcttc agtgttcgcg ggactccagg
gactgtcctt tcctgatatc ctcacacttc ctcctggatg atggcatgga gactagaaga
cagtttgcta taagaaaaac ctctgaagat gcaagtgaat actttgaaaa ttacattgaa
gaactgaaga acaaggatt tctactaaga gaacatttca cacctgaagc aacccaatta
gcatctgaac aattgcaagc attgcttttg gaggaagtca tgaattcaag cactctgagc TABLE 1-continued Sequences

```
caagaggtga gcgatttagt agagatgatt tgggcagagg ccctgggcca cctggaacac atgcttctca agccagtgaa caggattagc ctcaacgatg tgagcaaggc agagggatt ctccttctag taaaggcagc actgaaaaat ggagaaacag cagagcaatt gcaaaagatg atgacagagt tttacagact gatacctcac aaaggcacaa tgcccaaaga agtgaacctg ggactattgg ctaagaaagc agacctctgc cagctaataa gagacatggt taatgtctgt gaaactaatt tgtccaaacc caacccacca tccctggcca ataccgagc tttgaggtgc aaaattgagc atgttgaaca gaatactgaa gaatttctca gggttagaaa agaggttttg cagaatcatc acagtaagag cccagtggat gtcttgcaga tatttagagt tggcagagtg aatgaaacca cagagttttt gagcaaactt ggtaatgtga ggcccttgtt gcatggttct cctgtacaaa acatcgtggg aatcttgtgt cgagggttgc ttttacccaa agtagtggaa gatcgtggtg tgcaaagaac agacgtcgga aaccttggaa gtgggattta tttcagtgat tcgctcagta caagtatcaa gtactcacac ccgggagaga cagatggcac cagactcctg ctcatttgtg acgtagccct cggaaagtgt atggacttac atgagaagga cttcccctta actgaagcac caccaggcta cgacagtgtg catggagttt cacaaacagc ctctgtcacc acagactttg aggatgatga atttgttgtc tataaaacca atcaggttaa aatgaaatat attattaaat tttccatgcc tggagatcag ataaaggact ttcatcctag tgatcatact gaattagagg aatacagacc tgagttttca aatttttcaa aggttgaaga ttaccagtta ccagatgcca aaacttccag cagcaccaag gccggcctcc aggatgcctc tgggaacttg gttcctctgg aggatgtcca catcaaaggg agaatcatag acactgtagc ccaggtcatt gttttcaga catacacaaa taaaagtcac gtgcccattg aggcaaaata tatctttcct ttggatgaca aggccgctgt gtgtggcttc gaagccttca tcaatgggaa gcacatagtt ggagagatta agagaagga agaagcccag caagagtacc tagaagccgt gacccagggc catggcgctt acctgatgag tcaggatgct ccggacgttt ttactgtaag tgttggaaac ttaccccta aggctaaggt tcttataaaa attacctaca tcacagaact cagcatcctg ggcactgttg gtgtcttttt catgcccgcc accgtagcac cctggcaaca ggacaaggct ttgaatgaaa accttcagga tacagtagag aagatttgta taaaagaaat aggaacaaag caaagcttct cttgactat gtctattgag atgccgtatg tgattgaatt cattttcagt gatacacatg aactgaaaca aaagcgcaca gactgcaaag ctgtcattag caccatggaa ggcagctcct tagacagcag tggatttct ctccacatcg gtttgtctgc tgcctatctc ccaagaatgt gggttgaaaa acatccagaa aaagaaagcg aggcttgcat gcttgtcttt caacccgatc tcgatgtcga cctccctgac ctagccagtg agagcgaagt gattatttgt cttgactgct ccagttccat ggagggtgtg acattcttgc aagccaagca aatcaccttg catgcgctgt ccttggtggg tgagaagcag aaagtaaata ttatccagtt cggcacaggt tacaaggagc tattttcgta tcctaagcat atcacaagca ataccacggc agcagagttc atcatgtctg ccacacctac catggggaac acagacttct ggaaaacact ccgatatctt agcttattgt accctgctcg agggtcacgg aacatcctcc tggtgtctga tgggcacctc caggatgaga gcctgacatt acagctcgtg aagaggagcc gcccgcacac caggttattc gcctgcggta tcggttctac agcaaatcgt cacgtcttaa ggattttgtc ccagtgtggt gccggagtat ttgaatattt taatgcaaaa tccaagcata gttggagaaa acagatagaa
```

TABLE 1-continued

Sequences gaccaaatga ccaggctatg ttctccgagt tgccactctg tctccgtcaa atggcagcaa
ctcaatccag atgcgcccga ggccctgcag gccccagccc aggtgccatc cttgtttcgc
aatgatcgac tccttgtcta tggattcatt cctcactgca cacaagcaac tctgtgtgca
ctaattcaag agaaagaatt tgtacaatg gtgtcgacta ctgagcttca gaagacaact
ggaactatga tccacaagct ggcagcccga gctctaatca gagattatga agatggcatt
cttcacgaaa atgaaaccag tcatgagatg aaaaaacaaa ccttgaaatc tctgattatt
aaactcagta agaaaactc tctcataaca caatttacaa gctttgtggc agttgagaaa
agggatgaga atgagtcgcc ttttcctgat attccaaaag tttctgaact tattgccaaa
gaagatgtag acttcctgcc ctacatgagc tggcaggggg agcccaaga agccgtcagg
aaccagtctc ttttagcatc ctctgagtgg ccagaattac gtttatccaa acgaaaacat
aggaaaattc cattttccaa aagaaaaatg gaattatctc agccagaagt ttctgaagat
tttgaagagg atggcttagg tgtactacca gctttcacat caaatttgga acgtggaggt
gtggaaaagc tattggattt aagttggaca gagtcatgta aaccaacagc aactgaacca
ctatttaaga aagtcagtcc atgggaaaca tctacttcta gctttttttcc tattttggct
ccggccgttg gttcctatct taccccgact acccgcgctc acagtcctgc ttccttgtct
tttgcctcat atcgtcaggt agctagtttc ggttcagctg ctcctcccag acagtttgat
gcatctcaat tcagccaagg ccctgtgcct ggcacttgtg ctgactggat cccacagtcg
gcgtcttgtc ccacaggacc tccccagaac ccaccttctg cacccctattg tggcattgtt
ttttcaggga gctcattaag ctctgcacag tctgctccac tgcaacatcc tggaggcttt
actaccaggc cttctgctgg caccttccct gagctggatt ctccccagct tcatttctct
cttcctacag accctgatcc catcagaggt tttgggtctt atcatccctc tgcttactct
ccttttcatt ttcaaccttc cgcagcctct ttgactgcca accttaggct gccaatggcc
tctgctttac ctgaggctct ttgcagtcag tcccggacta cccagtaga tctctgtctt
ctagaagaat cagtaggcag tctcgaagga agtcgatgtc ctgtctttgc ttttcaaagt
tctgacacaa aaagtgatga gctatcagaa gtacttcaag acagctgctt tttacaaata
aagtgtgata caaaagatga cagtatcccg tgctttctgg aattaaaaga agaggatgaa
atagtgtgca cacaacactg gcaggatgct gtgccttgga cagaactcct cagtctacag
acagaggatg gcttctggaa acttacacca gaactgggac ttatattaaa tcttaataca
aatggtttgc acagctttct taaacaaaaa ggcattcaat ctctaggtgt aaaaggaaga
gaatgtctcc tggacctaat tgccacaatg ctggtactac agtttattcg caccaggttg
gaaaaagagg aatagtgtt caaatcactg atgaaaatgg atgacccttc tatttccagg
aatattccct gggcttttga ggcaataaag caagcaagtg aatgggtaag aagaactgaa
ggacagtacc catctatctg cccacggctt gaactgggga acgactggga ctctgccacc
aagcagttgc tgggactcca gcccataagc actgtgtccc ctcttcatag agtcctccat
tacagtcaag gctaa

| SEQ ID NO: 16 | Human MVP, Genbank #CAA56256 |
|---|---|

Met Ala Thr Glu Glu Phe Ile Ile Arg Ile Pro Pro Tyr His Tyr Ile
His Val Leu Asp Gln Asn Ser Asn Val Ser Arg Val Glu Val Gly Pro
Lys Thr Tyr Ile Arg Gln Asp Asn Glu Arg Val Leu Phe Ala Pro Met

TABLE 1-continued

Sequences

Arg Met Val Thr Val Pro Pro Arg His Tyr Cys Thr Val Ala Asn Pro
Val Ser Arg Asp Ala Gln Gly Leu Val Leu Phe Asp Val Thr Gly Gln
Val Arg Leu Arg His Ala Asp Leu Glu Ile Arg Leu Ala Gln Asp Pro
Phe Pro Leu Tyr Pro Gly Glu Val Leu Glu Lys Asp Ile Thr Pro Leu
Gln Val Val Leu Pro Asn Thr Ala Leu His Leu Lys Ala Leu Leu Asp
Phe Glu Asp Lys Asp Gly Asp Lys Val Val Ala Gly Asp Glu Trp Leu
Phe Glu Gly Pro Gly Thr Tyr Ile Pro Arg Lys Glu Val Glu Val Val
Glu Ile Ile Gln Ala Thr Ile Ile Arg Gln Asn Gln Ala Leu Arg Leu
Arg Ala Arg Lys Glu Cys Trp Asp Arg Asp Gly Lys Glu Arg Val Thr
Gly Glu Glu Trp Leu Val Thr Thr Val Gly Ala Tyr Leu Pro Ala Val
Phe Glu Glu Val Leu Asp Leu Val Asp Ala Val Ile Leu Thr Glu Lys
Thr Ala Leu His Leu Arg Ala Arg Arg Asn Phe Arg Asp Phe Arg Gly
Val Ser Arg Arg Thr Gly Glu Glu Trp Leu Val Thr Val Gln Asp Thr
Glu Ala His Val Pro Asp Val His Glu Glu Val Leu Gly Val Val Pro
Ile Thr Thr Leu Gly Pro His Asn Tyr Cys Val Ile Leu Asp Pro Val
Gly Pro Asp Gly Lys Asn Gln Leu Gly Gln Lys Arg Val Val Lys Gly
Glu Lys Ser Phe Phe Leu Gln Pro Gly Glu Gln Leu Glu Gln Gly Ile
Gln Asp Val Tyr Val Leu Ser Glu Gln Gln Gly Leu Leu Leu Arg Ala
Leu Gln Pro Leu Glu Glu Gly Glu Asp Glu Glu Lys Val Ser His Gln
Ala Gly Asp His Trp Leu Ile Arg Gly Pro Leu Glu Tyr Val Pro Ser
Ala Lys Val Glu Val Val Glu Glu Arg Gln Ala Ile Pro Leu Asp Glu
Asn Glu Gly Ile Tyr Val Gln Asp Val Lys Thr Gly Lys Val Arg Ala
Val Ile Gly Ser Thr Tyr Met Leu Thr Gln Asp Glu Val Leu Trp Glu
Lys Glu Leu Pro Pro Gly Val Glu Glu Leu Leu Asn Lys Gly Gln Asp
Pro Leu Ala Asp Arg Gly Glu Lys Asp Thr Ala Lys Ser Leu Gln Pro
Leu Ala Pro Arg Asn Lys Thr Arg Val Val Ser Tyr Arg Val Pro His
Asn Ala Ala Val Gln Val Tyr Asp Tyr Arg Glu Lys Arg Ala Arg Val
Val Phe Gly Pro Glu Leu Val Ser Leu Gly Pro Glu Glu Gln Phe Thr
Val Leu Ser Leu Ser Ala Gly Arg Pro Lys Arg Pro His Ala Arg Arg
Ala Leu Cys Leu Leu Leu Gly Pro Asp Phe Phe Thr Asp Val Ile Thr
Ile Glu Thr Ala Asp His Ala Arg Leu Gln Leu Gln Leu Ala Tyr Asn
Trp His Phe Glu Val Asn Asp Arg Lys Asp Pro Gln Glu Thr Ala Lys
Leu Phe Ser Val Pro Asp Phe Val Gly Asp Ala Cys Lys Ala Ile Ala
Ser Arg Val Arg Gly Ala Val Ala Ser Val Thr Phe Asp Asp Phe His
Lys Asn Ser Ala Arg Ile Ile Arg Thr Ala Val Phe Gly Phe Glu Thr
Ser Glu Ala Lys Gly Pro Asp Gly Met Ala Leu Pro Arg Pro Arg Asp
Gln Ala Val Phe Pro Gln Asn Gly Leu Val Val Ser Ser Val Asp Val
Gln Ser Val Glu Pro Val Asp Gln Arg Thr Arg Asp Ala Leu Gln Arg
Ser Val Gln Leu Ala Ile Glu Ile Thr Thr Asn Ser Gln Glu Ala Ala

TABLE 1-continued

Sequences

Ala Lys His Glu Ala Gln Arg Leu Glu Gln Glu Ala Arg Gly Arg Leu
Glu Arg Gln Lys Ile Leu Asp Gln Ser Glu Ala Glu Lys Ala Arg Lys
Glu Leu Leu Glu Leu Glu Ala Leu Ser Met Ala Val Glu Ser Thr Gly
Thr Ala Lys Ala Glu Ala Glu Ser Arg Ala Glu Ala Ala Arg Ile Glu
Gly Glu Gly Ser Val Leu Gln Ala Lys Leu Lys Ala Gln Ala Leu Ala
Ile Glu Thr Glu Ala Glu Leu Gln Arg Val Gln Lys Val Arg Glu Leu
Glu Leu Val Tyr Ala Arg Ala Gln Leu Glu Leu Glu Val Ser Lys Ala
Gln Gln Leu Ala Glu Val Glu Val Lys Lys Phe Lys Gln Met Thr Glu
Ala Ile Gly Pro Ser Thr Ile Arg Asp Leu Ala Val Ala Gly Pro Glu
Met Gln Val Lys Leu Leu Gln Ser Leu Gly Leu Lys Ser Thr Leu Ile
Thr Asp Gly Ser Thr Pro Ile Asn Leu Phe Asn Thr Ala Phe Gly Leu
Leu Gly Met Gly Pro Glu Gly Gln Pro Leu Gly Arg Arg Val Ala Ser
Gly Pro Ser Pro Gly Glu Gly Ile Ser Pro Gln Ser Ala Gln Ala Pro
Gln Ala Pro Gly Asp Asn His Val Val Pro Val Leu Arg

| SEQ ID NO: 17 | Human MVP cDNA, Genbank #X79882 |
|---|---| atggcaactg aagagttcat catccgcatc cccccatacc actatatcca tgtgctggac
cagaacagca acgtgtcccg tgtggaggtc gggccaaaga cctacatccg gcaggacaat
gagagggtac tgtttgcccc catgcgcatg gtgaccgtcc cccacgtca ctactgcaca
gtggccaacc ctgtgtctcg ggatgcccag ggcttggtgc tgtttgatgt cacagggcaa
gttcggcttc gccacgctga cctcgagatc cggctggccc aggacccctt cccctgtac
ccaggggagg tgctggaaaa ggacatcaca cccctgcagg tggttctgcc caacactgcc
ctccatctaa aggcgctgct tgattttgag gataaagatg agacaaggt ggtggcagga
gatgagtggc ttttcgaggg acctggcacg tacatccccc ggaaggaagt ggaggtcgtg
gagatcattc aggccaccat catcaggcag aaccaggctc tgcggctcag ggcccgcaag
gagtgctggg accgggacgg caaggagagg gtgacagggg aagaatggct ggtcaccaca
gtagggggcgt acctcccagc ggtgtttgag gaggttctgg atttggtgga cgccgtcatc
cttacgaaaa agacagccct gcacctccgg gctcggcgga acttccggga cttcagggga
gtgtcccgcc gcactgggga ggagtggctg gtaacagtgc aggacacaga ggcccacgtg
ccagatgtcc acgaggaggt gctgggggtt gtgcccatca ccaccctggg cccccacaac
tactgcgtga ttctcgaccc tgtcggaccg gatggcaaga tcagctggg gcagaagcgc
gtggtcaagg gagagaagtc tttttttcctc cagccaggag agcagctgga caaggcatc
caggatgtgt atgtgctgtc ggagcagcag ggctgctgc tgagggccct gcagcccctg
gaggaggggg aggatgagga gaaggtctca caccaggctg ggaccactg gctcatccgc
ggaccectgg agtatgtgcc atctgccaaa gtggaggtgg tggaggagcg ccaggccatc
cctctagacg agaacgaggg catctatgtg caggatgtca agaccggaaa ggtgcgcgct
gtgattggaa gcacctacat gctgacccag gacgaagtcc tgtgggagaa agagctgcct
cccggggtgg aggagctgct gaacaagggg caggaccctc tggcagacag ggtgagaag
gacacagcta gagcctcca gcccttggcg ccccggaaca agacccgtgt ggtcagctac
cgcgtgcccc acaacgctgc ggtgcaggtg tacgactacc gagagaagcg agcccgcgtg TABLE 1-continued

| Sequences |
|---|
| gtcttcgggc ctgagctggt gtcgctgggt cctgaggagc agttcacagt gttgtccctc |
| tcagctgggc ggcccaagcg tccccatgcc cgccgtgcgc tctgcctgct gctggggcct |
| gacttcttca cagacgtcat caccatcgaa acggcggatc atgccaggct gcaactgcag |
| ctggcctaca actggcactt tgaggtgaat gaccggaagg accccaaga dacggccaag |
| ctcttttcag tgccagactt tgtaggtgat gcctgcaaag ccatcgcatc ccgggtgcgg |
| ggggccgtgg cctctgtcac tttcgatgac ttccataaga actcagcccg catcattcgc |
| actgctgtct ttggctttga gacctcggaa gcgaagggcc ccgatggcat ggccctgccc |
| aggcccgggg accaggctgt cttcccccaa aacgggctgg tggtcagcag tgtggacgtg |
| cagtcagtgg agcctgtgga tcagaggacc cgggacgccc tgcaacgcag cgtccagctg |
| gccatcgaga tcaccaccaa ctcccaggaa gcggcggcca agcatgaggc tcagagactg |
| gagcaggaag cccgcggccg gcttgagcgg cagaagatcc tggaccagtc agaagccgag |
| aaagctcgca aggaactttt ggagctggag gctctgagca tggccgtgga gagcaccggg |
| actgccaagg cggaggccga gtcccgtgcg gaggcagccc ggattgaggg agaagggtcc |
| gtgctgcagg ccaagctaaa agcacaggcc ttggccattg aaacggaggc tgagctccag |
| agggtccaga aggtccgaga gctggaactg gtctatgccc gggcccagct ggagctggag |
| gtgagcaagg ctcagcagct ggctgaggtg gaggtgaaga agttcaagca gatgacagag |
| gccataggcc ccagcaccat cagggacctt gctgtggctg ggcctgagat gcaggtaaaa |
| ctgctccagt ccctgggcct gaaatcaacc ctcatcaccg atggctccac tcccatcaac |
| ctcttcaaca cagcctttgg gctgctgggg atggggcccg agggtcagcc cctgggcaga |
| agggtggcca gtgggcccag ccctggggag gggatatccc cccagtctgc tcaggcccct |
| caagctcctg gagacaacca cgtggtgcct gtactgcgct aa |

| SEQ ID NO: 18 | Rat MVP, Genbank #AAC52161 |
|---|---|
| Met Ala Thr Glu Glu Ala Ile Ile Arg Ile Pro Pro Tyr His Tyr Ile |
| His Val Leu Asp Gln Asn Ser Asn Val Ser Arg Val Glu Val Gly Pro |
| Lys Thr Tyr Ile Arg Gln Asp Asn Glu Arg Val Leu Phe Ala Pro Val |
| Arg Met Val Thr Val Pro Pro Arg His Tyr Cys Ile Val Ala Asn Pro |
| Val Ser Arg Asp Thr Gln Ser Ser Val Leu Phe Asp Ile Thr Gly Gln |
| Val Arg Leu Arg His Ala Asp Gln Glu Ile Arg Leu Ala Gln Asp Pro |
| Phe Pro Leu Tyr Pro Gly Glu Val Leu Glu Lys Asp Ile Thr Pro Leu |
| Gln Val Val Leu Pro Asn Thr Ala Leu His Leu Lys Ala Leu Leu Asp |
| Phe Glu Asp Lys Asn Gly Asp Lys Val Met Ala Gly Asp Glu Trp Leu |
| Phe Glu Gly Pro Gly Thr Tyr Ile Pro Gln Lys Glu Val Glu Val Val |
| Glu Ile Ile Gln Ala Thr Val Ile Lys Gln Asn Gln Ala Leu Arg Leu |
| Arg Ala Arg Lys Glu Cys Phe Asp Arg Glu Gly Lys Gly Arg Val Thr |
| Gly Glu Glu Trp Leu Val Arg Ser Val Gly Ala Tyr Leu Pro Ala Val |
| Phe Glu Glu Val Leu Asp Leu Val Asp Ala Val Ile Leu Thr Glu Lys |
| Thr Ala Leu His Leu Arg Ala Leu Gln Asn Phe Arg Asp Leu Arg Gly |
| Val Leu His Arg Thr Gly Glu Glu Trp Leu Val Thr Val Gln Asp Thr |
| Glu Ala His Val Pro Asp Val Tyr Glu Glu Val Leu Gly Val Val Pro |

TABLE 1-continued

Sequences

Ile Thr Thr Leu Gly Pro Arg His Tyr Cys Val Ile Leu Asp Pro Met

Gly Pro Asp Gly Lys Asn Gln Leu Gly Gln Lys Arg Val Val Lys Gly

Glu Lys Ser Phe Phe Leu Gln Pro Gly Glu Arg Leu Glu Arg Gly Ile

Gln Asp Val Tyr Val Leu Ser Glu Gln Gln Gly Leu Leu Leu Lys Ala

Leu Gln Pro Leu Glu Glu Gly Glu Ser Glu Glu Lys Val Ser His Gln

Ala Gly Asp Cys Trp Leu Ile Arg Gly Pro Leu Glu Tyr Val Pro Ser

Ala Lys Val Glu Val Val Glu Glu Arg Gln Ala Ile Pro Leu Asp Gln

Asn Glu Gly Ile Tyr Val Gln Asp Val Lys Thr Gly Lys Val Arg Ala

Val Ile Gly Ser Thr Tyr Met Leu Thr Gln Asp Glu Val Leu Trp Glu

Lys Glu Leu Pro Ser Gly Val Glu Glu Leu Leu Asn Leu Gly His Asp

Pro Leu Ala Asp Arg Gly Gln Lys Gly Thr Ala Lys Pro Leu Gln Pro

Ser Ala Pro Arg Asn Lys Thr Arg Val Val Ser Tyr Arg Val Pro His

Asn Ala Ala Val Gln Val Tyr Asp Tyr Arg Ala Lys Arg Ala Arg Val

Val Phe Gly Pro Glu Leu Val Thr Leu Asp Pro Glu Glu Gln Phe Thr

Val Leu Ser Leu Ser Ala Gly Arg Pro Lys Arg Pro His Ala Arg Arg

Ala Leu Cys Leu Leu Leu Gly Pro Asp Phe Phe Thr Asp Val Ile Thr

Ile Glu Thr Ala Asp His Ala Arg Leu Gln Leu Gln Leu Ala Tyr Asn

Trp His Phe Glu Leu Lys Asn Arg Asn Asp Pro Ala Glu Ala Ala Lys

Leu Phe Ser Val Pro Asp Phe Val Gly Asp Ala Cys Lys Ala Ile Ala

Ser Arg Val Arg Gly Ala Val Ala Ser Val Thr Phe Asp Asp Phe His

Lys Asn Ser Ala Arg Ile Ile Arg Met Ala Val Phe Gly Phe Glu Met

Ser Glu Asp Thr Gly Pro Asp Gly Thr Leu Leu Pro Lys Ala Arg Asp

Gln Ala Val Phe Pro Gln Asn Gly Leu Val Val Ser Ser Val Asp Val

Gln Ser Val Glu Pro Val Asp Gln Arg Thr Arg Asp Ala Leu Gln Arg

Ser Val Gln Leu Ala Ile Glu Ile Thr Thr Asn Ser Gln Glu Ala Ala

Ala Lys His Glu Ala Gln Arg Leu Glu Gln Glu Ala Arg Gly Arg Leu

Glu Arg Gln Lys Ile Leu Asp Gln Ser Glu Ala Glu Lys Ala Arg Lys

Glu Leu Leu Glu Leu Glu Ala Met Ser Met Ala Val Glu Ser Thr Gly

Asn Ala Lys Ala Glu Ala Glu Ser Arg Ala Glu Ala Ala Arg Ile Glu

Gly Glu Gly Ser Val Leu Gln Ala Lys Leu Lys Ala Gln Ala Leu Ala

Ile Glu Thr Glu Ala Glu Leu Glu Arg Val Lys Lys Val Arg Glu Met

Glu Leu Ile Tyr Ala Arg Ala Gln Leu Glu Leu Glu Val Ser Lys Ala

Gln Gln Leu Ala Asn Val Glu Ala Lys Lys Phe Lys Glu Met Thr Glu

Ala Leu Gly Pro Gly Thr Ile Arg Asp Leu Ala Val Ala Gly Pro Glu

Met Gln Val Lys Leu Leu Gln Ser Leu Gly Leu Lys Ser Thr Leu Ile

Thr Asp Gly Ser Ser Pro Ile Asn Leu Phe Ser Thr Ala Phe Gly Leu

Leu Gly Leu Gly Ser Asp Gly Gln Pro Pro Ala Gln Lys

TABLE 1-continued

Sequences

SEQ ID NO: 19    Rat MVP cDNA, Genbank #U09870 atggcaactg aagaggccat catccgcatc cccccatacc actacatcca tgtgctggac cagaacagta atgtgtcccg tgtggaggtt ggaccaaaga cctacatccg gcaggacaat gagagggtac tgtttgcccc agttcgcatg gtgaccgtcc ccccacgcca ctactgcata gtggccaacc ctgtgtcccg ggacacccag agttctgtgt tatttgacat cacaggacaa gtccgactcc ggcacgctga ccaggagatc cgactagccc aggacccctt cccctgtat ccaggggagg tgctggaaaa ggacatcacc ccactgcagg tggttctgcc caacacagca ctgcatctta aggcgttgct ggactttgag ataagaatg gagacaaggt catggcagga gacgagtggc tatttgaggg acctggcacc tacatcccac agaaggaagt ggaagtcgtg gagatcattc aggccacagt catcaaacag aaccaagcac tgcggctaag ggcccgaaag gagtgctttg accgggaggg caaggggcgc gtgacaggtg aggagtggct ggtccgatcc gtgggggctt acctcccagc tgtctttgaa gaggtgctgg atctggtgga tgctgtgatc cttacagaaa agactgccct gcacctccgg gctctgcaga acttcaggga ccttcgggga gtgctccacc gcaccgggga ggaatggtta gtgacagtgc aggacacaga agcccatgtt ccagatgtct atgaggaggt gcttggggta gtacccatca ccaccctggg acctcgacac tactgtgtca ttcttgaccc aatgggacca gacggcaaga accagctggg acaaaagcgt gttgtcaagg gagagaagtc ctttttcctc cagccaggag agaggctgga gcgaggcatc caggatgtgt atgtgctgtc agagcagcag gggctgctac tgaaggcact gcagcccctg gaggagggag agagcgagga gaaggtctcc catcaggccg gagactgctg gctcatccgt gggcccctgg agtatgtgcc atctgcaaaa gtggaggtgg tggaggagcg tcaggctatc cctctggacc aaaatgaggg catctatgtg caggatgtca agacggggaa ggtgcgggct gtgattggaa gcacctacat gctgactcag gatgaagtcc tgtgggaaaa ggagctgcct tctggggtgg aggagctgct gaacttgggg catgaccctc tggcagacag gggtcagaag ggcacagcca agccccttca gccctcagct ccaaggaaca agacccgagt ggtcagctac cgtgtcccgc acaatgcagc ggtgcaggtc tatgactaca gagccaagag agcccgtgtg gtctttgggc ccgagctagt gacactggat cctgaggagc agttcacagt attgtccctt tctgccgggc gacccaagcg tcctcatgcc cgccgtgcac tctgcctact gctgggacct gatttctttta ctgatgtcat caccatcgaa actgcagatc atgccaggtt gcagctgcag cttgcctaca actggcactt tgaactgaag aaccggaatg accctgcaga ggcagccaag cttttctccg tgcctgactt cgtgggtgac gcctgcaagg ccattgcatc ccgagtccgg ggggctgtag cctctgtcac ctttgatgac ttccataaaa actcagcccg gatcattcga atggctgttt ttggctttga gatgtctgaa gacacaggtc ctgatggcac actcctgccc aaggctcgag accaggcagt cttttcccca aacgggctgg tagtcagcag tgtggatgtg cagtcagtgg agcccgtgga ccagaggacc cgggatgccc ttcagcgcag cgttcagctg gccatcgaaa ttaccaccaa ctcccaggag gcagcagcca agcacgaggc tcagagactg gaacaggaag cccgtggtcg gcttgagagg cagaagatct tggaccagtc agaagctgaa aaagcccgca aggaactctt ggagcttgag gctatgagca tggctgtgga gagcacgggt aatgccaaag cagaggctga gtcccgtgca gaggcagcga ggatcgaagg agaaggctct gtgctgcagg ccaagctcaa ggcacaggcg ctagccattg agacggaggc tgagttggag TABLE 1-continued

| Sequences |
|---|
| cgagtaaaga aagtacgaga gatggaactg atctatgccc gggcccagtt ggagctggag |
| gtgagcaagg cgcagcagct tgccaatgtg gaggcaaaga agttcaagga gatgacagag |
| gcactgggcc ccggcaccat cagggacctg gctgtggccg ggccagagat gcaggtgaaa |
| cttctccagt ccctgggcct gaaatccact ctcatcaccg atggctcgtc tcccatcaac |
| ctcttcagca cagccttcgg gttgctgggg ctggggtctg atggtcagcc gccagcacag |
| aagtga |

| SEQ ID NO: 20 | CP Peptide |
|---|---|
| Met Ala Gly Cys Gly Cys Pro Cys Gly Cys Gly Ala | |

| SEQ ID NO: 21 | Human CP-MVP |
|---|---|

Met Ala Gly Cys Gly Cys Pro Cys Gly Cys Gly Ala Met Ala Thr Glu
Glu Phe Ile Ile Arg Ile Pro Pro Tyr His Tyr Ile His Val Leu Asp
Gln Asn Ser Asn Val Ser Arg Val Glu Val Gly Pro Lys Thr Tyr Ile
Arg Gln Asp Asn Glu Arg Val Leu Phe Ala Pro Met Arg Met Val Thr
Val Pro Pro Arg His Tyr Cys Thr Val Ala Asn Pro Val Ser Arg Asp
Ala Gln Gly Leu Val Leu Phe Asp Val Thr Gly Gln Val Arg Leu Arg
His Ala Asp Leu Glu Ile Arg Leu Ala Gln Asp Pro Phe Pro Leu Tyr
Pro Gly Glu Val Leu Glu Lys Asp Ile Thr Pro Leu Gln Val Val Leu
Pro Asn Thr Ala Leu His Leu Lys Ala Leu Leu Asp Phe Glu Asp Lys
Asp Gly Asp Lys Val Val Ala Gly Asp Glu Trp Leu Phe Glu Gly Pro
Gly Thr Tyr Ile Pro Arg Lys Glu Val Glu Val Val Glu Ile Ile Gln
Ala Thr Ile Ile Arg Gln Asn Gln Ala Leu Arg Leu Arg Ala Arg Lys
Glu Cys Trp Asp Arg Asp Gly Lys Glu Arg Val Thr Gly Glu Glu Trp
Leu Val Thr Thr Val Gly Ala Tyr Leu Pro Ala Val Phe Glu Glu Val
Leu Asp Leu Val Asp Ala Val Ile Leu Thr Glu Lys Thr Ala Leu His
Leu Arg Ala Arg Arg Asn Phe Arg Asp Phe Arg Gly Val Ser Arg Arg
Thr Gly Glu Glu Trp Leu Val Thr Val Gln Asp Thr Glu Ala His Val
Pro Asp Val His Glu Glu Val Leu Gly Val Val Pro Ile Thr Thr Leu
Gly Pro His Asn Tyr Cys Val Ile Leu Asp Pro Val Gly Pro Asp Gly
Lys Asn Gln Leu Gly Gln Lys Arg Val Val Lys Gly Glu Lys Ser Phe
Phe Leu Gln Pro Gly Glu Gln Leu Glu Gln Gly Ile Gln Asp Val Tyr
Val Leu Ser Glu Gln Gln Gly Leu Leu Leu Arg Ala Leu Gln Pro Leu
Glu Glu Gly Glu Asp Glu Glu Lys Val Ser His Gln Ala Gly Asp His
Trp Leu Ile Arg Gly Pro Leu Glu Tyr Val Pro Ser Ala Lys Val Glu
Val Val Glu Glu Arg Gln Ala Ile Pro Leu Asp Glu Asn Glu Gly Ile
Tyr Val Gln Asp Val Lys Thr Gly Lys Val Arg Ala Val Ile Gly Ser
Thr Tyr Met Leu Thr Gln Asp Glu Val Leu Trp Glu Lys Glu Leu Pro
Pro Gly Val Glu Glu Leu Leu Asn Lys Gly Gln Asp Pro Leu Ala Asp
Arg Gly Glu Lys Asp Thr Ala Lys Ser Leu Gln Pro Leu Ala Pro Arg
Asn Lys Thr Arg Val Val Ser Tyr Arg Val Pro His Asn Ala Ala Val

TABLE 1-continued

| Sequences |
|---|
| Gln Val Tyr Asp Tyr Arg Glu Lys Arg Ala Arg Val Val Phe Gly Pro |
| Glu Leu Val Ser Leu Gly Pro Glu Glu Gln Phe Thr Val Leu Ser Leu |
| Ser Ala Gly Arg Pro Lys Arg Pro His Ala Arg Arg Ala Leu Cys Leu |
| Leu Leu Gly Pro Asp Phe Phe Thr Asp Val Ile Thr Ile Glu Thr Ala |
| Asp His Ala Arg Leu Gln Leu Gln Leu Ala Tyr Asn Trp His Phe Glu |
| Val Asn Asp Arg Lys Asp Pro Gln Glu Thr Ala Lys Leu Phe Ser Val |
| Pro Asp Phe Val Gly Asp Ala Cys Lys Ala Ile Ala Ser Arg Val Arg |
| Gly Ala Val Ala Ser Val Thr Phe Asp Asp Phe His Lys Asn Ser Ala |
| Arg Ile Ile Arg Thr Ala Val Phe Gly Phe Glu Thr Ser Glu Ala Lys |
| Gly Pro Asp Gly Met Ala Leu Pro Arg Pro Arg Asp Gln Ala Val Phe |
| Pro Gln Asn Gly Leu Val Val Ser Ser Val Asp Val Gln Ser Val Glu |
| Pro Val Asp Gln Arg Thr Arg Asp Ala Leu Gln Arg Ser Val Gln Leu |
| Ala Ile Glu Ile Thr Thr Asn Ser Gln Glu Ala Ala Ala Lys His Glu |
| Ala Gln Arg Leu Glu Gln Glu Ala Arg Gly Arg Leu Glu Arg Gln Lys |
| Ile Leu Asp Gln Ser Glu Ala Glu Lys Ala Arg Lys Glu Leu Leu Glu |
| Leu Glu Ala Leu Ser Met Ala Val Glu Ser Thr Gly Thr Ala Lys Ala |
| Glu Ala Glu Ser Arg Ala Glu Ala Ala Arg Ile Glu Gly Glu Gly Ser |
| Val Leu Gln Ala Lys Leu Lys Ala Gln Ala Leu Ala Ile Glu Thr Glu |
| Ala Glu Leu Gln Arg Val Gln Lys Val Arg Glu Leu Glu Leu Val Tyr |
| Ala Arg Ala Gln Leu Glu Leu Glu Val Ser Lys Ala Gln Gln Leu Ala |
| Glu Val Glu Val Lys Lys Phe Lys Gln Met Thr Glu Ala Ile Gly Pro |
| Ser Thr Ile Arg Asp Leu Ala Val Ala Gly Pro Glu Met Gln Val Lys |
| Leu Leu Gln Ser Leu Gly Leu Lys Ser Thr Leu Ile Thr Asp Gly Ser |
| Thr Pro Ile Asn Leu Phe Asn Thr Ala Phe Gly Leu Leu Gly Met Gly |
| Pro Glu Gly Gln Pro Leu Gly Arg Arg Val Ala Ser Gly Pro Ser Pro |
| Gly Glu Gly Ile Ser Pro Gln Ser Ala Gln Ala Pro Gln Ala Pro Gly |
| Asp Asn His Val Val Pro Val Leu Arg |
| SEQ ID NO: 22    Human CP-MVP cDNA |
| atggcaggct gcggttgtcc atgcggttgt ggcgccatgg caactgaaga gttcatcatc |
| cgcatccccc cataccacta tatccatgtg ctggaccaga acagcaacgt gtcccgtgtg |
| gaggtcgggc caaagaccta catccggcag acaatgaga gggtactgtt tgcccccatg |
| cgcatggtga ccgtcccccc acgtcactac tgcacagtgg ccaaccctgt gtctcgggat |
| gcccagggct tggtgctgtt tgatgtcaca gggcaagttc ggcttcgcca cgctgacctc |
| gagatccggc tggcccagga cccttcccc ctgtacccag gggaggtgct ggaaaaggac |
| atcacacccc tgcaggtggt tctgcccaac actgccctcc atctaaaggc gctgcttgat |
| tttgaggata aagatggaga caaggtggtg gcaggagatg agtggctttt cgagggacct |
| ggcacgtaca tccccggaa ggaagtggag gtcgtggaga tcattcaggc caccatcatc |
| aggcagaacc aggctctgcg gctcagggcc gcaaggagt gctgggaccg ggacggcaag |
| gagagggtga caggggaaga atggctggtc accacagtag gggcgtacct cccagcggtg |

TABLE 1-continued

Sequences tttgaggagg ttctggattt ggtggacgcc gtcatcctta cggaaaagac agccctgcac ctccgggctc ggcggaactt ccgggacttc aggggagtgt cccgccgcac tggggaggag tggctggtaa cagtgcagga cacagaggcc cacgtgccag atgtccacga ggaggtgctg ggggttgtgc ccatcaccac cctgggcccc acaactact gcgtgattct cgaccctgtc ggaccggatg caagaatca gctggggcag aagcgcgtgg tcaagggaga gaagtctttt ttcctccagc caggagagca gctggaacaa ggcatccagg atgtgtatgt gctgtcggag cagcaggggc tgctgctgag ggccctgcag cccctggagg aggggagga tgaggagaag gtctcacacc aggctgggga ccactggctc atccgcggac ccctggagta tgtgccatct gccaaagtgg aggtggtgga ggagcgccag gccatccctc tagacgagaa cgagggcatc tatgtgcagg atgtcaagac cggaaaggtg cgcgctgtga ttggaagcac ctacatgctg acccaggacg aagtcctgtg ggagaaagag ctgcctcccg gggtggagga gctgctgaac aaggggcagg accctctggc agacaggggt gagaaggaca cagctaagag cctccagccc ttggcgcccc ggaacaagac ccgtgtggtc agctaccgcg tgccccacaa cgctgcggtg caggtgtacg actaccgaga gaagcgagcc cgcgtggtct cgggcctga gctggtgtcg ctgggtcctg aggagcagtt cacagtgttg tccctctcag ctgggcggcc caagcgtccc catgcccgcc gtgcgctctg cctgctgctg gggcctgact tcttcacaga cgtcatcacc atcgaaacgg cggatcatgc caggctgcaa ctgcagctgg cctacaactg cactttgag gtgaatgacc ggaaggaccc ccaagagacg gccaagctct tttcagtgcc agactttgta ggtgatgcct gcaaagccat cgcatcccgg gtgcgggggg ccgtggcctc tgtcactttc gatgacttcc ataagaactc agcccgcatc attcgcactg ctgtctttgg ctttgagacc tcggaagcga agggccccga tggcatggcc ctgcccaggc cccgggacca ggctgtcttc ccccaaaacg ggctggtggt cagcagtgtg gacgtgcagt cagtggagcc tgtggatcag aggacccggg acgccctgca acgcagcgtc cagctggcca tcgagatcac caccaactcc caggaagcgg cggccaagca tgaggctcag agactgagc aggaagcccg cggccggctt gagcggcaga agatcctgga ccagtcagaa gccgagaaag ctcgcaagga acttttggag ctggaggctc tgagcatggc cgtggagagc accgggactg ccaaggcgga ggccgagtcc cgtgcggagg cagcccggat tgagggagaa gggtccgtgc tgcaggccaa gctaaaagca caggcctggg ccattgaaac ggaggctgag ctccagaggg tccagaaggt ccgagagctg gaactggtct atgcccgggc ccagctggag ctggaggtga gcaaggctca gcagctggct gaggtggagg tgaagaagtt caagcagatg acagaggcca taggccccag caccatcagg gaccttgctg tggctgggcc tgagatgcag gtaaaactgc tccagtccct gggcctgaaa tcaaccctca tcaccgatgg ctccactccc atcaacctct tcaacacagc ctttgggctg ctggggatgg ggcccgaggg tcagcccctg gcagaaggg tggccagtgg gcccagccct ggggagggga tatccccca gtctgctcag gcccctcaag ctcctggaga caaccacgtg SEQ ID NO: 23    Rat CP-MVP Met Ala Gly Cys Gly Cys Pro Cys Gly Cys Gly Ala Met Ala Thr Glu Glu Ala Ile Ile Arg Ile Pro Pro Tyr His Tyr Ile His Val Leu Asp Gln Asn Ser Asn Val Ser Arg Val Glu Val Gly Pro Lys Thr Tyr Ile Arg Gln Asp Asn Glu Arg Val Leu Phe Ala Pro Val Arg Met Val Thr TABLE 1-continued Sequences Val Pro Pro Arg His Tyr Cys Ile Val Ala Asn Pro Val Ser Arg Asp Thr Gln Ser Ser Val Leu Phe Asp Ile Thr Gly Gln Val Arg Leu Arg His Ala Asp Gln Glu Ile Arg Leu Ala Gln Asp Pro Phe Pro Leu Tyr Pro Gly Glu Val Leu Glu Lys Asp Ile Thr Pro Leu Gln Val Val Leu Pro Asn Thr Ala Leu His Leu Lys Ala Leu Leu Asp Phe Glu Asp Lys Asn Gly Asp Lys Val Met Ala Gly Asp Glu Trp Leu Phe Glu Gly Pro Gly Thr Tyr Ile Pro Gln Lys Glu Val Glu Val Val Glu Ile Ile Gln Ala Thr Val Ile Lys Gln Asn Gln Ala Leu Arg Leu Arg Ala Arg Lys Glu Cys Phe Asp Arg Glu Gly Lys Gly Arg Val Thr Gly Glu Glu Trp Leu Val Arg Ser Val Gly Ala Tyr Leu Pro Ala Val Phe Glu Glu Val Leu Asp Leu Val Asp Ala Val Ile Leu Thr Glu Lys Thr Ala Leu His Leu Arg Ala Leu Gln Asn Phe Arg Asp Leu Arg Gly Val Leu His Arg Thr Gly Glu Glu Trp Leu Val Thr Val Gln Asp Thr Glu Ala His Val Pro Asp Val Tyr Glu Glu Val Leu Gly Val Val Pro Ile Thr Thr Leu Gly Pro Arg His Tyr Cys Val Ile Leu Asp Pro Met Gly Pro Asp Gly Lys Asn Gln Leu Gly Gln Lys Arg Val Val Lys Gly Glu Lys Ser Phe Phe Leu Gln Pro Gly Glu Arg Leu Glu Arg Gly Ile Gln Asp Val Tyr Val Leu Ser Glu Gln Gln Gly Leu Leu Leu Lys Ala Leu Gln Pro Leu Glu Glu Gly Glu Ser Glu Glu Lys Val Ser His Gln Ala Gly Asp Cys Trp Leu Ile Arg Gly Pro Leu Glu Tyr Val Pro Ser Ala Lys Val Glu Val Val Glu Glu Arg Gln Ala Ile Pro Leu Asp Gln Asn Glu Gly Ile Tyr Val Gln Asp Val Lys Thr Gly Lys Val Arg Ala Val Ile Gly Ser Thr Tyr Met Leu Thr Gln Asp Glu Val Leu Trp Glu Lys Glu Leu Pro Ser Gly Val Glu Glu Leu Leu Asn Leu Gly His Asp Pro Leu Ala Asp Arg Gly Gln Lys Gly Thr Ala Lys Pro Leu Gln Pro Ser Ala Pro Arg Asn Lys Thr Arg Val Val Ser Tyr Arg Val Pro His Asn Ala Ala Val Gln Val Tyr Asp Tyr Arg Ala Lys Arg Ala Arg Val Val Phe Gly Pro Glu Leu Val Thr Leu Asp Pro Glu Glu Gln Phe Thr Val Leu Ser Leu Ser Ala Gly Arg Pro Lys Arg Pro His Ala Arg Arg Ala Leu Cys Leu Leu Leu Gly Pro Asp Phe Phe Thr Asp Val Ile Thr Ile Glu Thr Ala Asp His Ala Arg Leu Gln Leu Gln Leu Ala Tyr Asn Trp His Phe Glu Leu Lys Asn Arg Asn Asp Pro Ala Glu Ala Ala Lys Leu Phe Ser Val Pro Asp Phe Val Gly Asp Ala Cys Lys Ala Ile Ala Ser Arg Val Arg Gly Ala Val Ala Ser Val Thr Phe Asp Asp Phe His Lys Asn Ser Ala Arg Ile Ile Arg Met Ala Val Phe Gly Phe Glu Met Ser Glu Asp Thr Gly Pro Asp Gly Thr Leu Leu Pro Lys Ala Arg Asp Gln Ala Val Phe Pro Gln Asn Gly Leu Val Val Ser Ser Val Asp Val Gln Ser Val Glu Pro Val Asp Gln Arg Thr Arg Asp Ala Leu Gly Arg Ser Val Gln Leu Ala Ile Glu Ile Thr Thr Asn Ser Gln Glu Ala Ala Ala Lys His Glu TABLE 1-continued Sequences Ala Gln Arg Leu Glu Gln Glu Ala Arg Gly Arg Leu Glu Arg Gln Lys Ile Leu Asp Gln Ser Glu Ala Glu Lys Ala Arg Lys Glu Leu Leu Glu Leu Glu Ala Met Ser Met Ala Val Glu Ser Thr Gly Asn Ala Lys Ala Glu Ala Glu Ser Arg Ala Glu Ala Ala Arg Ile Glu Gly Glu Gly Ser Val Leu Gln Ala Lys Leu Lys Ala Gln Ala Leu Ala Ile Glu Thr Glu Ala Glu Leu Glu Arg Val Lys Lys Val Arg Glu Met Glu Leu Ile Tyr Ala Arg Ala Gln Leu Glu Leu Glu Val Ser Lys Ala Gln Gln Leu Ala Asn Val Glu Ala Lys Lys Phe Lys Glu Met Thr Glu Ala Leu Gly Pro Gly Thr Ile Arg Asp Leu Ala Val Ala Gly Pro Glu Met Gln Val Lys Leu Leu Gln Ser Leu Gly Leu Lys Ser Thr Leu Ile Thr Asp Gly Ser Ser Pro Ile Asn Leu Phe Ser Thr Ala Phe Gly Leu Leu Gly Leu Gly Ser Asp Gly Gln Pro Pro Ala Gln Lys

| SEQ ID NO: 24 | Rat CP-MVP cDNA |
|---|---| atggcaggct gcggttgtcc atgcggttgt ggcgccatgg caactgaaga ggccatcatc cgcatccccc cataccacta catccatgtg ctggaccaga acagtaatgt gtcccgtgtg gaggttggac caaagaccta catccggcag acaatgaga gggtactgtt tgccccagtt cgcatggtga ccgtcccccc acgccactac tgcatagtgg ccaaccctgt gtcccgggac acccagagtt ctgtgttatt tgacatcaca ggacaagtcc gactccggca cgctgaccag gagatccgac tagcccagga cccctccc ctgtatccag gggaggtgct ggaaaaggac atcaccccac tgcaggtggt tctgcccaac acagcactgc atcttaaggc gttgctggac tttgaggata agaatggaga caaggtcatg gcaggagacg agtggctatt tgagggacct ggcacctaca tcccacagaa ggaagtggaa gtcgtggaga tcattcaggc acagtcatc aaacagaacc aagcactgcg gctaagggcc cgaaaggagt gctttgaccg ggagggcaag gggcgcgtga caggtgagga gtggctggtc cgatccgtgg gggcttacct cccagctgtc tttgaagagg tgctggatct ggtggatgct gtgatcctta cagaaaagac tgccctgcac ctccgggctc tgcagaactt cagggacctt cggggagtgc tccaccgcac cggggaggaa tggttagtga cagtgcagga cacagaagcc catgttccag atgtctatga ggaggtgctt ggggtagtac ccatcaccac cctgggacct cgacactact gtgtcattct tgacccaatg ggaccagacg gcaagaacca gctgggacaa aagcgtgttg tcaagggaga aagtcctttt ttcctccagc caggagagag gctggagcga ggcatccagg atgtgtatgt gctgtcagag cagcaggggc tgctactgaa ggcactgcag cccctggagg agggagagag cgaggagaag gtctcccatc aggccggaga ctgctggctc atccgtgggc ccctggagta tgtgccatct gcaaaagtgg aggtggtgga ggagcgtcag gctatccctc tggaccaaaa tgagggcatc tatgtgcaga tgtcaagac ggggaaggtg cgggctgtga ttggaagcac ctacatgctg actcaggatg aagtcctgtg ggaaaaggag ctgccttctg gggtggagga gctgctgaac ttggggcatg accctctggc agacagggt cagaagggca cagccaagcc ccttcagccc tcagctccaa ggaacaagac ccgagtggtc agctaccgtg tcccgcacaa tgcagcggtg caggtctatg actacagagc caagagagcc cgtgtggtct ttgggcccga gctagtgaca ctggatcctg aggagcagtt cacagtattg tccctttctg ccgggcgacc caagcgtcct TABLE 1-continued

| Sequences |
|---|
| catgcccgcc gtgcactctg cctactgctg ggacctgatt tctttactga tgtcatcacc<br>atcgaaactg cagatcatgc caggttgcag ctgcagcttg cctacaactg cactttgaa<br>ctgaagaacc ggaatgaccc tgcagaggca gccaagcttt tctccgtgcc tgacttcgtg<br>ggtgacgcct gcaaggccat tgcatcccga gtccggggg ctgtagcctc tgtcaccttt<br>gatgacttcc ataaaaactc agcccggatc attcgaatgg ctgtttttgg ctttgagatg<br>tctgaagaca caggtcctga tggcacactc ctgcccaagg ctcgagacca ggcagtcttt<br>ccccaaaacg ggctggtagt cagcagtgtg gatgtgcagt cagtggagcc cgtggaccag<br>aggacccggg atgcccttca gcgcagcgtt cagctggcca tcgaaattac caccaactcc<br>caggaggcag cagccaagca cgaggctcag agactggaac aggaagcccg tggtcggctt<br>gagaggcaga agatcttgga ccagtcagaa gctgaaaaag cccgcaagga actcttggag<br>cttgaggcta tgagcatggc tgtggagagc acgggtaatg ccaaagcaga ggctgagtcc<br>cgtgcagagg cagcgaggat cgaaggagaa ggctctgtgc tgcaggccaa gctcaaggca<br>caggcgctag ccattgagac ggaggctgag ttggagcgag taaagaaagt acgagagatg<br>gaactgatct atgcccgggc ccagttggag ctggaggtga gcaaggcgca gcagcttgcc<br>aatgtggagg caaagaagtt caaggagatg acagaggcac tgggccccgg caccatcagg<br>gacctggctg tggccgggcc agagatgcag gtgaaacttc tccagtccct gggcctgaaa<br>tccactctca tcaccgatgg ctcgtctccc atcaacctct tcagcacagc cttcgggttg<br>ctggggctgg ggtctgatgg tcagccgcca gcacagaagt ga |
| SEQ ID NO: 25          Human TEP1, Genbank #AAC51107 |
| Met Glu Lys Leu His Gly His Val Ser Ala His Pro Asp Ile Leu Ser<br>Leu Glu Asn Arg Cys Leu Ala Met Leu Pro Asp Leu Gln Pro Leu Glu<br>Lys Leu His Gln His Val Ser Thr His Ser Asp Ile Leu Ser Leu Lys<br>Asn Gln Cys Leu Ala Thr Leu Pro Asp Leu Lys Thr Met Glu Lys Pro<br>His Gly Tyr Val Ser Ala His Pro Asp Ile Leu Ser Leu Glu Asn Gln<br>Cys Leu Ala Thr Leu Ser Asp Leu Lys Thr Met Glu Lys Pro His Gly<br>His Val Ser Ala His Pro Asp Ile Leu Ser Leu Glu Asn Arg Cys Leu<br>Ala Thr Leu Pro Ser Leu Lys Ser Thr Val Ser Ala Ser Pro Leu Phe<br>Gln Ser Leu Gln Ile Ser His Met Thr Gln Ala Asp Leu Tyr Arg Val<br>Asn Asn Ser Asn Cys Leu Leu Ser Glu Pro Pro Ser Trp Arg Ala Gln<br>His Phe Ser Lys Gly Leu Asp Leu Ser Thr Cys Pro Ile Ala Leu Lys<br>Ser Ile Ser Ala Thr Glu Thr Ala Gln Glu Ala Thr Leu Gly Arg Trp<br>Phe Asp Ser Glu Glu Lys Lys Gly Ala Glu Thr Gln Met Pro Ser Tyr<br>Ser Leu Ser Leu Gly Glu Glu Glu Val Glu Asp Leu Ala Val Lys<br>Leu Thr Ser Gly Asp Ser Glu Ser His Pro Glu Pro Thr Asp His Val<br>Leu Gln Glu Lys Lys Met Ala Leu Leu Ser Leu Leu Cys Ser Thr Leu<br>Val Ser Glu Val Asn Met Asn Asn Thr Ser Asp Pro Thr Leu Ala Ala<br>Ile Phe Glu Ile Cys Arg Glu Leu Ala Leu Leu Glu Pro Glu Phe Ile<br>Leu Lys Ala Ser Leu Tyr Ala Arg Gln Gln Leu Asn Val Arg Asn Val<br>Ala Asn Asn Ile Leu Ala Ile Ala Ala Phe Leu Pro Ala Cys Arg Pro |

TABLE 1-continued

Sequences

His Leu Arg Arg Tyr Phe Cys Ala Ile Val Gln Leu Pro Ser Asp Trp
Ile Gln Val Ala Glu Leu Tyr Gln Ser Leu Ala Glu Gly Asp Lys Asn
Lys Leu Val Pro Leu Pro Ala Cys Leu Arg Thr Ala Met Thr Asp Lys
Phe Ala Gln Phe Asp Glu Tyr Gln Leu Ala Lys Tyr Asn Pro Arg Lys
His Arg Ala Lys Arg His Pro Arg Arg Pro Pro Arg Ser Pro Gly Met
Glu Pro Pro Phe Ser His Arg Cys Phe Pro Arg Tyr Ile Gly Phe Leu
Arg Glu Glu Gln Arg Lys Phe Glu Lys Ala Gly Asp Thr Val Ser Glu
Lys Lys Asn Pro Pro Arg Phe Thr Leu Lys Lys Leu Val Gln Arg Leu
His Ile His Lys Pro Ala Gln His Val Gln Ala Leu Leu Gly Tyr Arg
Tyr Pro Ser Asn Leu Gln Leu Phe Ser Arg Ser Arg Leu Pro Gly Pro
Trp Asp Ser Ser Arg Ala Gly Lys Arg Met Lys Leu Ser Arg Pro Glu
Thr Trp Glu Arg Glu Leu Ser Leu Arg Gly Asn Lys Ala Ser Val Trp
Glu Glu Leu Ile Glu Asn Gly Lys Leu Pro Phe Met Ala Met Leu Arg
Asn Leu Cys Asn Leu Leu Arg Val Gly Ile Ser Ser Arg His His Glu
Leu Ile Leu Gln Arg Leu Gln His Gly Lys Ser Val Ile His Ser Arg
Gln Phe Pro Phe Arg Phe Leu Asn Ala His Asp Ala Ile Asp Ala Leu
Glu Ala Gln Leu Arg Asn Gln Ala Leu Pro Phe Pro Ser Asn Ile Thr
Leu Met Arg Arg Ile Leu Thr Arg Asn Glu Lys Asn Arg Pro Arg Arg
Arg Phe Leu Cys His Leu Ser Arg Gln Gln Leu Arg Met Ala Met Arg
Ile Pro Val Leu Tyr Glu Gln Leu Lys Arg Glu Lys Leu Arg Val His
Lys Ala Arg Gln Trp Lys Tyr Asp Gly Glu Met Leu Asn Arg Tyr Arg
Gln Ala Leu Glu Thr Ala Val Asn Leu Ser Val Lys His Ser Leu Pro
Leu Leu Pro Gly Arg Thr Val Leu Val Tyr Leu Thr Asp Ala Asn Ala
Asp Arg Leu Cys Pro Lys Ser Asn Pro Gln Gly Pro Pro Leu Asn Tyr
Ala Leu Leu Leu Ile Gly Met Met Ile Thr Arg Ala Glu Gln Val Asp
Val Val Leu Cys Gly Gly Asp Thr Leu Lys Thr Ala Val Leu Lys Ala
Glu Glu Gly Ile Leu Lys Thr Ala Ile Lys Leu Gln Ala Gln Val Gln
Glu Phe Asp Glu Asn Asp Gly Trp Ser Leu Asn Thr Phe Gly Lys Tyr
Leu Leu Ser Leu Ala Gly Gln Arg Val Pro Val Asp Arg Val Ile Leu
Leu Gly Gln Ser Met Asp Asp Gly Met Ile Asn Val Ala Lys Gln Leu
Tyr Trp Gln Arg Val Asn Ser Lys Cys Leu Phe Val Gly Ile Leu Leu
Arg Arg Val Gln Tyr Leu Ser Thr Asp Leu Asn Pro Asn Asp Val Thr
Leu Ser Gly Cys Thr Asp Ala Ile Leu Lys Phe Ile Ala Glu His Gly
Ala Ser His Leu Leu Glu His Val Gly Gln Met Asp Lys Ile Phe Lys
Ile Pro Pro Pro Gly Lys Thr Gly Val Gln Ser Leu Arg Pro Leu
Glu Glu Asp Thr Pro Ser Pro Leu Ala Pro Val Ser Gln Gln Gly Trp
Arg Ser Ile Arg Leu Phe Ile Ser Ser Thr Phe Arg Asp Met His Gly
Glu Arg Asp Leu Leu Leu Arg Ser Val Leu Pro Ala Leu Gln Ala Arg
Ala Ala Pro His Arg Ile Ser Leu His Gly Ile Asp Leu Arg Trp Gly

TABLE 1-continued

Sequences

Val Thr Glu Glu Glu Thr Arg Arg Asn Arg Gln Leu Glu Val Cys Leu

Gly Glu Val Glu Asn Ala Gln Leu Phe Val Gly Ile Leu Gly Ser Arg

Tyr Gly Tyr Ile Pro Pro Ser Tyr Asn Leu Pro Asp His Pro His Phe

His Trp Ala Gln Gln Tyr Pro Ser Gly Arg Ser Val Thr Glu Met Glu

Val Met Gln Phe Leu Asn Arg Asn Gln Arg Leu Gln Pro Ser Ala

Gln Ala Leu Ile Tyr Phe Arg Asp Ser Ser Phe Leu Ser Ser Val

Pro Asp Ala Trp Lys Ser Asp Phe Val Ser Glu Ser Glu Glu Ala

Ala Cys Arg Ile Ser Glu Leu Lys Ser Tyr Leu Ser Arg Gln Lys

Gly Ile Thr Cys Arg Arg Tyr Pro Cys Glu Trp Gly Gly Val Ala

Ala Gly Arg Pro Tyr Val Gly Gly Leu Glu Glu Phe Gly Gln Leu

Val Leu Gln Asp Val Trp Asn Met Ile Gln Lys Leu Tyr Leu Gln

Pro Gly Ala Leu Leu Glu Gln Pro Val Ser Ile Pro Asp Asp Asp

Leu Val Gln Ala Thr Phe Gln Gln Leu Gln Lys Pro Pro Ser Pro

Ala Arg Pro Arg Leu Leu Gln Asp Thr Val Gln Leu Met Leu

Pro His Gly Arg Leu Ser Leu Val Thr Gly Gln Ser Gly Gln Gly

Lys Thr Ala Phe Leu Ala Ser Leu Val Ser Ala Leu Gln Ala Pro

Asp Gly Ala Lys Val Ala Pro Leu Val Phe Phe His Phe Ser Gly

Ala Arg Pro Asp Gln Gly Leu Ala Leu Thr Leu Leu Arg Arg Leu

Cys Thr Tyr Leu Arg Gly Gln Leu Lys Glu Pro Gly Ala Leu Pro

Ser Thr Tyr Arg Ser Leu Val Trp Glu Leu Gln Gln Arg Leu Leu

Pro Lys Ser Ala Glu Ser Leu His Pro Gly Gln Thr Gln Val Leu

Ile Ile Asp Gly Ala Asp Arg Leu Val Asp Gln Asn Gly Gln Leu

Ile Ser Asp Trp Ile Pro Lys Lys Leu Pro Arg Cys Val His Leu

Val Leu Ser Val Ser Ser Asp Ala Gly Leu Gly Glu Thr Leu Glu

Gln Ser Gln Gly Ala His Val Leu Ala Leu Gly Pro Leu Glu Ala

Ser Ala Arg Ala Arg Leu Val Arg Glu Glu Leu Ala Leu Tyr Gly

Lys Arg Leu Glu Glu Ser Pro Phe Asn Asn Gln Met Arg Leu Leu

Leu Val Lys Arg Glu Ser Gly Arg Pro Leu Tyr Leu Arg Leu Val

Thr Asp His Leu Arg Leu Phe Thr Leu Tyr Glu Gln Val Ser Glu

Arg Leu Arg Thr Leu Pro Ala Thr Val Pro Leu Leu Leu Gln His

Ile Leu Ser Thr Leu Glu Lys Glu His Gly Pro Asp Val Leu Pro

Gln Ala Leu Thr Ala Leu Glu Val Thr Arg Ser Gly Leu Thr Val

Asp Gln Leu His Gly Val Leu Ser Val Trp Arg Thr Leu Pro Lys

Gly Thr Lys Ser Trp Glu Glu Ala Val Ala Ala Gly Asn Ser Gly

Asp Pro Tyr Pro Met Gly Pro Phe Ala Cys Leu Val Gln Ser Leu

Arg Ser Leu Leu Gly Glu Gly Pro Leu Glu Arg Pro Gly Ala Arg

Leu Cys Leu Pro Asp Gly Pro Leu Arg Thr Ala Ala Lys Arg Cys

Tyr Gly Lys Arg Pro Gly Leu Glu Asp Thr Ala His Ile Leu Ile

Ala Ala Gln Leu Trp Lys Thr Cys Asp Ala Asp Ala Ser Gly Thr

TABLE 1-continued

Sequences

Phe Arg Ser Cys Pro Pro Glu Ala Leu Gly Asp Leu Pro Tyr His
Leu Leu Gln Ser Gly Asn Arg Gly Leu Leu Ser Lys Phe Leu Thr
Asn Leu His Val Val Ala Ala His Leu Glu Leu Gly Leu Val Ser
Arg Leu Leu Glu Ala His Ala Leu Tyr Ala Ser Ser Val Pro Lys
Glu Glu Gln Lys Leu Pro Glu Ala Asp Val Ala Val Phe Arg Thr
Phe Leu Arg Gln Gln Ala Ser Ile Leu Ser Gln Tyr Pro Arg Leu
Leu Pro Gln Gln Ala Ala Asn Gln Pro Leu Asp Ser Pro Leu Cys
His Gln Ala Ser Leu Leu Ser Arg Arg Trp His Leu Gln His Thr
Leu Arg Trp Leu Asn Lys Pro Arg Thr Met Lys Asn Gln Gln Ser
Ser Ser Leu Ser Leu Ala Val Ser Ser Pro Thr Ala Val Ala
Phe Ser Thr Asn Gly Gln Arg Ala Ala Val Gly Thr Ala Asn Gly
Thr Val Tyr Leu Leu Asp Leu Arg Thr Trp Gln Glu Glu Lys Ser
Val Val Ser Gly Cys Asp Gly Ile Ser Ala Cys Leu Phe Leu Ser
Asp Asp Thr Leu Phe Leu Thr Ala Phe Asp Gly Leu Leu Glu Leu
Trp Asp Leu Gln His Gly Cys Arg Val Leu Gln Thr Lys Ala His
Gln Tyr Gln Ile Thr Gly Cys Cys Leu Ser Pro Asp Cys Arg Leu
Leu Ala Thr Val Cys Leu Gly Gly Cys Leu Lys Leu Trp Asp Thr
Val Arg Gly Gln Leu Ala Phe Gln His Thr Tyr Pro Lys Ser Leu
Asn Cys Val Ala Phe His Pro Glu Gly Gln Val Ile Ala Thr Gly
Ser Trp Ala Gly Ser Ile Ser Phe Phe Gln Val Asp Gly Leu Lys
Val Thr Lys Asp Leu Gly Ala Pro Gly Ala Ser Ile Arg Thr Leu
Ala Phe Asn Val Pro Gly Gly Val Val Ala Val Gly Arg Leu Asp
Ser Met Val Glu Leu Trp Ala Trp Arg Glu Gly Ala Arg Leu Ala
Ala Phe Pro Ala His His Gly Phe Val Ala Ala Leu Phe Leu
His Ala Gly Cys Gln Leu Leu Thr Ala Gly Glu Asp Gly Lys Val
Gln Val Trp Ser Gly Ser Leu Gly Arg Pro Arg Gly His Leu Gly
Ser Leu Ser Leu Ser Pro Ala Leu Ser Val Ala Leu Ser Pro Asp
Gly Asp Arg Val Ala Val Gly Tyr Arg Ala Asp Gly Ile Arg Ile
Tyr Lys Ile Ser Ser Gly Ser Gln Gly Ala Gln Gly Gln Ala Leu
Asp Val Ala Val Ser Ala Leu Ala Trp Leu Ser Pro Lys Val Leu
Val Ser Gly Ala Glu Asp Gly Ser Leu Gln Gly Trp Ala Leu Lys
Glu Cys Ser Leu Gln Ser Leu Trp Leu Leu Ser Arg Phe Gln Lys
Pro Val Leu Gly Leu Ala Thr Ser Gln Glu Leu Leu Ala Ser Ala
Ser Glu Asp Phe Thr Val Gln Leu Trp Pro Arg Gln Leu Leu Thr
Arg Pro His Lys Ala Glu Asp Phe Pro Cys Gly Thr Glu Leu Arg
Gly His Glu Gly Pro Val Ser Cys Cys Ser Phe Ser Thr Asp Gly
Gly Ser Leu Ala Thr Gly Gly Arg Asp Arg Ser Leu Leu Cys Trp
Asp Val Arg Thr Pro Lys Thr Pro Val Leu Ile His Ser Phe Pro
Ala Cys His Arg Asp Trp Val Thr Gly Cys Ala Trp Thr Lys Asp

TABLE 1-continued

Sequences

Asn Leu Leu Ile Ser Cys Ser Ser Asp Gly Ser Val Gly Leu Trp
Asp Pro Glu Ser Gly Gln Arg Leu Gly Gln Phe Leu Gly His Gln
Ser Ala Val Ser Ala Val Ala Ala Val Glu Glu His Val Val Ser
Val Ser Arg Asp Gly Thr Leu Lys Val Trp Asp His Gln Gly Val
Glu Leu Thr Ser Ile Pro Ala His Ser Gly Pro Ile Ser His Cys
Ala Ala Ala Met Glu Pro Arg Ala Ala Gly Gln Pro Gly Ser Glu
Leu Leu Val Val Thr Val Gly Leu Asp Gly Ala Thr Arg Leu Trp
His Pro Leu Leu Val Cys Gln Thr His Thr Leu Leu Gly His Ser
Gly Pro Val Arg Ala Ala Ala Val Ser Glu Thr Ser Gly Leu Met
Leu Thr Ala Ser Glu Asp Gly Ser Val Arg Leu Trp Gln Val Pro
Lys Glu Ala Asp Asp Thr Cys Ile Pro Arg Ser Ser Ala Ala Val
Thr Ala Val Ala Trp Ala Pro Asp Gly Ser Met Ala Val Ser Gly
Asn Gln Ala Gly Glu Leu Ile Leu Trp Gln Glu Ala Lys Ala Val
Ala Thr Ala Gln Ala Pro Gly His Ile Gly Ala Leu Ile Trp Ser
Ser Ala His Thr Phe Phe Val Leu Ser Ala Asp Glu Lys Ile Ser
Glu Trp Gln Val Lys Leu Arg Lys Gly Ser Ala Pro Gly Asn Leu
Ser Leu His Leu Asn Arg Ile Leu Gln Glu Asp Leu Gly Val Leu
Thr Ser Leu Asp Trp Ala Pro Asp Gly His Phe Leu Ile Leu Ala
Lys Ala Asp Leu Lys Leu Leu Cys Met Lys Pro Gly Asp Ala Pro
Ser Glu Ile Trp Ser Ser Tyr Thr Glu Asn Pro Met Ile Leu Ser
Thr His Lys Glu Tyr Gly Ile Phe Val Leu Gln Pro Lys Asp Pro
Gly Val Leu Ser Phe Leu Arg Gln Lys Glu Ser Gly Glu Phe Glu
Glu Arg Leu Asn Phe Asp Ile Asn Leu Glu Asn Pro Ser Arg Thr
Leu Ile Ser Ile Thr Gln Ala Lys Pro Glu Ser Glu Ser Ser Phe
Leu Cys Ala Ser Ser Asp Gly Ile Leu Trp Asn Leu Ala Lys Cys
Ser Pro Glu Gly Glu Trp Thr Thr Gly Asn Met Trp Gln Lys Lys
Ala Asn Thr Pro Glu Thr Gln Thr Pro Gly Thr Asp Pro Ser Thr
Cys Arg Glu Ser Asp Ala Ser Met Asp Ser Asp Ala Ser Met Asp
Ser Glu Pro Thr Pro His Leu Lys Thr Arg Gln Arg Arg Lys Ile
His Ser Gly Ser Val Thr Ala Leu His Val Leu Pro Glu Leu Leu
Val Thr Ala Ser Lys Asp Arg Asp Val Lys Leu Trp Glu Arg Pro
Ser Met Gln Leu Leu Gly Leu Phe Arg Cys Glu Gly Ser Val Ser
Cys Leu Glu Pro Trp Leu Gly Ala Asn Ser Thr Leu Gln Leu Ala
Val Gly Asp Val Gln Gly Asn Val Tyr Phe Leu Asn Trp Glu

| SEQ ID NO: 26 | Human TEP1 cDNA, Genbank #U86136 |
|---|---| atggaaaaac tccatgggca tgtgtctgcc catccagaca tcctctcctt ggagaaccgg tgcctggcta tgctccctga cttacagccc ttggagaaac tacatcagca tgtatctacc cactcagata tcctctcctt gaagaaccag tgcctagcca cgcttcctga cctgaagacc atggaaaaac acacatggata tgtgtctgcc cacccagaca tcctctcctt ggagaaccag TABLE 1-continued Sequences

```
tgcctggcca cactttctga cctgaagacc atggagaaac cacatggaca tgtttctgcc
cacccagaca tcctctcctt ggagaaccgg tgcctggcca ccctccctag tctaaagagc
actgtgtctg ccagcccctt gttccagagt ctacagatat ctcacatgac gcaagctgat
ttgtaccgtg tgaacaacag caattgcctg ctctctgagc ctccaagttg gagggctcag
catttctcta agggactaga cctttcaacc tgccctatag ccctgaaatc catctctgcc
acagagacag ctcaggaagc aactttgggt cgttggtttg attcagaaga gaagaaggg
gcagagaccc aaatgccttc ttatagtctg agcttgggag aggaggagga ggtgaggat
ctggccgtga agctcacctc tggagactct gaatctcatc cagagcctac tgaccatgtc
cttcaggaaa agaagatggc tctactgagc ttgctgtgct ctactctggt ctcagaagta
aacatgaaca atacatctga ccccaccctg gctgccattt ttgaaatctg tcgtgaactt
gccctcctgg agcctgagtt tatcctcaag gcatctttgt atgccaggca gcagctgaac
gtccggaatg tggccaataa catcttggcc attgctgctt tcttgccggc gtgtcgcccc
cacctgcgac gatatttctg tgccattgtc cagctgcctt ctgactggat ccaggtggct
gagctttacc agagcctggc tgagggagat aagaataagc tggtgcccct gcccgcctgt
ctccgtactg ccatgacgga caaatttgcc cagtttgacg agtaccagct ggctaagtac
aaccctcgga agcaccgggc caagagacac ccccgccggc caccccgctc tccagggatg
gagcctccat tttctcacag atgttttcca aggtacatag ggtttctcag agaagagcag
agaaagtttg agaaggccgg tgatacagtg tcagagaaaa agaatcctcc aaggttcacc
ctgaagaagc tggttcagcg actgcacatc cacaagcctg cccagcacgt tcaagccctg
ctgggttaca gatacccctc caacctacag ctctttttctc gaagtcgcct tcctgggcct
tgggattcta gcagagctgg gaagaggatg aagctgtcta ggccagagac ctggagcgg
gagctgagcc tacgggggaa caaagcgtcg gtctgggagg aactcattga aaatgggaag
cttcccttca tggccatgct tcggaacctg tgcaacctgc tgcgggttgg aatcagttcc
cgccaccatg agctcattct ccagagactc cagcatggga agtcggtgat ccacagtcgg
cagtttccat tcagatttct taacgcccat gatgccattg atgccctcga ggctcaactc
agaaatcaag cattgccctt tccttcgaat ataacactga tgaggcggat actaactaga
aatgaaaaga accgtcccag gcggaggttt cttttgccacc taagccgtca gcagcttcgt
atggcaatga ggatacctgt gttgtatgag cagctcaaga gggagaagct gagagtacac
aaggccagac agtggaaata tgatggtgag atgctgaaca ggtaccgaca ggccctagag
acagctgtga acctctctgt gaagcacagc ctgcccctgc tgccaggccg cactgtcttg
gtctatctga cagatgctaa tgcagacagg ctctgtccaa agagcaaccc acaagggccc
ccgctgaact atgcactgct gttgattggg atgatgatca cgagggcgga gcaggtggac
gtcgtgctgt gtggaggtga cactctgaag actgcagtgc ttaaggcaga agaaggcatc
ctgaagactg ccatcaagct ccaggctcaa gtccaggagt ttgatgaaaa tgatggatgg
tccctgaata cttttgggaa atacctgctg tctctggctg gccaaagggt tcctgtggac
agggtcatcc tccttggcca aagcatggat gatggaatga taaatgtggc caaacagctt
tactggcagc gtgtgaattc caagtgcctc tttgttggta tcctcctaag aagggtacaa
tacctgtcaa cagatttgaa tcccaatgat gtgacactct caggctgtac tgatgcgata
ctgaagttca ttgcagagca tggggcctcc catcttctgg aacatgtggg ccaaatggac
```

TABLE 1-continued

Sequences aaaatattca agattccacc accccagga aagacagggg tccagtctct ccggccactg gaagaggaca ctccaagccc cttggctcct gtttcccagc aaggatggcg cagcatccgg cttttcattt catccacttt ccgagacatg cacggggagc gggacctgct gctgaggtct gtgctgccag cactgcaggc ccgagcggcc cctcaccgta tcagccttca cggaatcgac ctccgctggg gcgtcactga ggaggagacc cgtaggaaca gacaactgga agtgtgcctt ggggaggtgg agaacgcaca gctgtttgtg gggattctgg gctcccgtta tggatacatt cccccagct acaaccttcc tgaccatcca cacttccact gggcccagca gtacccttca gggcgctctg tgacagagat ggaggtgatg cagttcctga accggaacca acgtctgcag ccctctgccc aagctctcat ctacttccgg gattccagct tcctcagctc tgtgccagat gcctggaaat ctgactttgt ttctgagtct gaagaggccg catgtcggat ctcagaactg aagagctacc taagcagaca gaaagggata acctgccgca gatacccctg tgagtggggg ggtgtggcag ctggccggcc ctatgttggc gggctggagg agtttgggca gttggttctg caggatgtat ggaatatgat ccagaagctc tacctgcagc ctggggccct gctggagcag ccagtgtcca tcccagacga tgacttggtc caggccacct tccagcagct gcagaagcca ccgagtcctg cccggccacg ccttcttcag gacacagtgc aacagctgat gctgccccac ggaaggctga gcctggtgac ggggcagtca ggacagggca agacagcctt cctggcatct cttgtgtcag ccctgcaggc tcctgatggg gccaaggtgg caccattagt cttcttccac ttttctgggg ctcgtcctga ccagggtctt gccctcactc tgctcagacg cctctgtacc tatctgcgtg gccaactaaa agagccaggt gccctcccca gcacctaccg aagcctggtg tgggagctgc agcagaggct gctgcccaag tctgctgagt ccctgcatcc tggccagacc caggtcctga tcatcgatgg ggctgatagg ttagtggacc agaatgggca gctgatttca gactggatcc caaagaagct tccccggtgt gtacacctgg tgctgagtgt gtctagtgat gcaggcctag gggagaccct tgagcagagc cagggtgccc acgtgctggc cttggggcct ctggaggcct ctgctcgggc ccggctggtg agagaggagc tggccctgta cgggaagcgg ctggaggagt caccatttaa caaccagatg cgactgctgc tggtgaagcg ggaatcaggc cggccgctct acctgcgctt ggtcaccgat cacctgaggc tcttcacgct gtatgagcag gtgtctgaga gactccggac cctgcctgcc actgtccccc tgctgctgca gcacatcctg agcacactgg agaaggagca cgggcctgat gtccttcccc aggccttgac tgccctagaa gtcacacgga gtggtttgac tgtggaccag ctgcacggag tgctgagtgt gtggcggaca ctaccgaagg ggactaagag ctgggaagaa gcagtggctg ctggtaacag tggagacccc taccccatgg gcccgtttgc ctgcctcgtc cagagtctgc gcagtttgct aggggagggc cctctggagc gccctggtgc ccggctgtgc ctccctgatg ggcccctgag aacagcagct aaacgttgct atgggaagag gccagggcta gaggacacgg cacacatcct cattgcagct cagctctgga agacatgtga cgctgatgcc tcaggcacct tccgaagttg ccctcctgag gctctgggag acctgcctta ccacctgctc cagagcggga accgtggact tctttcgaag ttccttacca acctccatgt ggtggctgca cacttggaat tgggtctggt ctctcggctc ttggaggccc atgccctcta tgcttcttca gtccccaaag aggaacaaaa gctccccgag gctgacgttg cagtgtttcg caccttcctg aggcagcagg cttcaatcct cagccagtac ccccggctcc tgccccagca ggcagccaac cagcccctgg actcacctct ttgccaccaa TABLE 1-continued Sequences gcctcgctgc tctcccggag atggcacctc caacacacac tacgatggct taataaaccc cggaccatga aaaatcagca aagctccagc ctgtctctgg cagtttcctc atcccctact gctgtggcct tctccaccaa tgggcaaaga gcagctgtgg gcactgccaa tgggacagtt tacctgttgg acctgagaac ttggcaggag agaagtctg tggtgagtgg ctgtgatgga atctctgctt gtttgttcct ctccgatgat acactctttc ttactgcctt cgacgggctc ctggagctct gggacctgca gcatggttgt cgggtgctgc agactaaggc tcaccagtac caaatcactg gctgctgcct gagcccagac tgccggctgc tagccaccgt gtgcttggga ggatgcctaa agctgtggga cacagtccgt gggcagctgg ccttccagca cacctacccc aagtccctga actgtgttgc cttccaccca gaggggcagg taatagccac aggcagctgg gctggcagca tcagcttctt ccaggtggat gggctcaaag tcaccaagga cctggggca cccggagcct ctatccgtac cttggccttc aatgtgcctg gggggttgt ggctgtgggc cggctggaca gtatggtgga gctgtgggcc tggcgagaag gggcacggct ggctgccttc cctgcccacc atggctttgt tgctgctgcg cttttcctgc atgcgggttg ccagttactg acggctggag aggatggcaa ggttcaggtg tggtcagggt ctctgggtcg gccccgtggg cacctgggtt ccctttctct ctctcctgcc ctctctgtgg cactcagccc agatggtgat cgggtggctg ttggatatcg agcggatggc attaggatct acaaaatctc ttcaggttcc caggggctc agggtcaggc actggatgtg gcagtgtccg ccctggcctg gctaagcccc aaggtattgg tgagtggtgc agaagatggg tccttgcagg gctgggcact caaggaatgc tcccttcagt ccctctggct cctgtccaga ttccagaagc ctgtgctagg actggccact tcccaggagc tcttggcttc tgcctcagag gatttcacag tgcagctgtg gccaaggcag ctgctgacgc ggccacacaa ggcagaagac tttccctgtg gcactgagct gcggggacat gagggccctg tgagctgctg tagtttcagc actgatggag gcagcctggc caccggggc cgggatcgga gtctcctctg ctgggacgtg aggacaccca aaaccctgt tttgatccac tccttccctg cctgtcaccg tgactgggtc actggctgtg cctggaccaa agataaccta ctgatatcct gctccagtga tggctctgtg gggctctggg acccagagtc aggacagcgg cttggtcagt tcctgggtca tcagagtgct gtgagcgctg tggcagctgt ggaggagcac gtggtgtctg tgagccggga tgggaccttg aaagtgtggg accatcaagg cgtggagctg accagcatcc ctgctcactc aggacccatt agccactgtg cagctgccat ggagccccgt gcagctggac agcctgggtc agagcttctg gtggtaaccg tcgggctaga tggggccaca cggttatggc atccactctt ggtgtgccaa acccacaccc tcctgggaca cagcggccca gtccgtgctg ctgctgtttc agaaacctca ggcctcatgc tgaccgcctc tgaggatggt tctgtacggc tctggcaggt tcctaaggaa gcagatgaca catgtatacc aaggagttct gcagccgtca ctgctgtggc ttgggcacca gatggttcca tggcagtatc tggaaatcaa gctggggaac taatcttgtg gcaggaagct aaggctgtgg ccacagcaca ggctccaggc cacattggtg ctctgatctg gtcctcggca cacaccttt ttgtcctcag tgctgatgag aaaatcagcg agtggcaagt gaaactgcgg aagggttcgg cacccggaaa tttgagtctt caactgaacc gaattctaca ggaggactta ggggtgctga caagtctgga ttgggctcct gatggtcact ttctcatctt ggccaaagca gatttgaagt tactttgcat gaagccaggg gatgctccat ctgaaatctg gagcagctat acagaaaatc ctatgatatt gtccacccac TABLE 1-continued

| Sequences |
|---|
| aaggagtatg gcatatttgt cctgcagccc aaggatcctg gagttctttc tttcttgagg |
| caaaaggaat caggagagtt tgaagagagg ctgaactttg atataaactt agagaatcct |
| agtaggaccc taatatcgat aactcaagcc aaacctgaat ctgagtcctc atttttgtgt |
| gccagctctg atgggatcct atggaacctg gccaaatgca gcccagaagg agaatggacc |
| acaggtaaca tgtggcagaa aaaagcaaac actccagaaa cccaaactcc agggacagac |
| ccatctacct gcagggaatc tgatgccagc atggatagtg atgccagcat ggatagtgag |
| ccaacaccac atctaaagac acggcagcgt agaaagattc actcgggctc tgtcacagcc |
| ctccatgtgc tacctgagtt gctggtgaca gcttcgaagg acagagatgt taagctatgg |
| gagagaccca gtatgcagct gctgggcctg ttccgatgcg aagggtcagt gagctgcctg |
| gaaccttggc tgggcgctaa ctccaccctg cagcttgccg tgggagacgt gcagggcaat |
| gtgtactttc tgaattggga atga |

| SEQ ID NO: 27      Rat TEP1, Genbank #AAB51690 |
|---|
| Met Glu Lys Leu Cys Gly Tyr Val Pro Val His Pro Asp Ile Leu Ser |
| Leu Lys Asn Arg Cys Leu Thr Met Leu Ser Asp Ile Gln Pro Leu Glu |
| Lys Ile His Gly Gln Arg Ser Val Asn Pro Asp Ile Leu Ser Leu Glu |
| Asn Arg Cys Leu Thr Leu Leu Pro Asp Leu Gln Pro Met Glu Lys Ile |
| His Gly Gln Arg Ser Val His Pro Asp Ile Leu Ser Ser Glu Asn Arg |
| Cys Leu Thr Leu Leu Pro Asp Leu Gln Ser Leu Glu Lys Leu Cys Gly |
| His Met Ser Ser His Pro Asp Val Leu Ser Leu Glu Asn Arg Cys Leu |
| Ala Thr Leu Pro Thr Val Lys Arg Thr Val Ser Ser Gly Pro Leu Leu |
| Gln Cys Leu His Arg Ser His Thr Ala Gln Ala Asp Leu Arg Asp Pro |
| Asn Phe Arg Asn Cys Leu Phe Pro Glu Pro Pro Thr Ile Glu Ala Pro |
| Cys Phe Leu Lys Glu Leu Asp Leu Pro Thr Gly Pro Arg Ala Leu Lys |
| Ser Met Ser Ala Thr Ala Arg Val Gln Glu Val Ala Leu Gly Gln Arg |
| Cys Val Ser Glu Gly Lys Glu Leu Gln Glu Glu Lys Glu Ser Ala Glu |
| Val Pro Met Pro Leu Tyr Ser Leu Ser Leu Gly Gly Glu Glu Glu Glu |
| Val Val Gly Ala Pro Val Leu Lys Leu Thr Ser Gly Asp Ser Asp Ser |
| His Pro Glu Thr Thr Asp Gln Ile Leu Gln Glu Lys Lys Met Ala Leu |
| Leu Thr Leu Leu Cys Ser Ala Met Ala Ser Ser Val Asn Val Lys Asp |
| Ala Ser Asp Pro Thr Arg Ala Ser Ile His Glu Val Cys Ser Ala Leu |
| Ala Pro Leu Glu Pro Glu Phe Ile Leu Lys Ala Ser Leu Tyr Ala Arg |
| Gln Gln Leu Asn Leu Arg Asp Ile Ala Asn Ile Val Leu Ala Val Ala |
| Ala Leu Leu Pro Ala Cys Arg Pro His Val Arg Arg Tyr Tyr Ser Ala |
| Ile Val His Leu Pro Ser Asp Trp Ile Gln Val Ala Glu Phe Tyr Gln |
| Ser Leu Ala Glu Gly Asp Glu Lys Lys Leu Val Pro Leu Pro Ala Cys |
| Leu Arg Ala Ala Met Thr Asp Lys Phe Ala Gln Phe Asp Glu Tyr Gln |
| Leu Ala Lys Tyr Asn Pro Arg Lys His Arg Ser Lys Thr Arg Ser Arg |
| Gln Pro Pro Arg Pro Gln Arg Thr Lys Pro Pro Phe Ser Glu Ser Gly |
| Lys Cys Phe Pro Lys Ser Val Trp Pro Leu Lys Asn Glu Gln Ile Ser |

TABLE 1-continued

Sequences

Phe Glu Ala Ala Tyr Asn Ala Val Ser Glu Lys Lys Arg Leu Pro Arg

Phe Thr Leu Lys Lys Leu Val Glu Gln Leu His Ile His Glu Pro Ala

Gln His Val Gln Ala Leu Leu Gly Tyr Arg Tyr Pro Ser Thr Leu Glu

Leu Phe Ser Arg Ser His Leu Pro Gly Pro Trp Asp Ser Ser Arg Ala

Gly Gln Arg Met Lys Leu Gln Arg Pro Glu Thr Trp Glu Arg Glu Leu

Ser Leu Arg Gly Asn Arg Ala Ser Val Trp Glu Glu Leu Ile Asp Asn

Gly Lys Leu Pro Phe Met Ala Met Leu Arg Asn Leu Cys Asn Leu Leu

Arg Thr Gly Ile Ser Ala His His His Glu Leu Val Leu Gln Arg Leu

Gln His Glu Lys Ser Val Ile His Ser Arg Gln Phe Pro Phe Arg Phe

Leu Asn Ala His Asp Ser Leu Asp Arg Leu Glu Ala Gln Leu Arg Ser

Lys Ala Ser Pro Phe Pro Ser Asn Thr Thr Leu Met Lys Arg Ile Met

Ile Arg Asn Ser Lys Lys Ile Lys Arg Pro Ala Asn Pro Arg Tyr Leu

Cys Thr Leu Thr Gln Arg Gln Leu Arg Ala Ala Met Ala Ile Pro Val

Met Tyr Glu His Leu Lys Arg Glu Lys Leu Arg Leu His Lys Ala Arg

Gln Trp Thr Cys Asp Leu Glu Leu Leu Glu Arg Tyr Arg Gln Ala Leu

Glu Thr Ala Val Asn Ile Ser Val Lys His Asn Leu Pro Pro Leu Pro

Gly Arg Thr Leu Leu Val Tyr Leu Thr Asp Ala Asn Ala Asn Arg Leu

Cys Pro Lys Ser His Leu Gln Gly Pro Pro Leu Asn Tyr Val Leu Leu

Leu Ile Gly Met Met Met Ala Arg Ala Glu Gln Thr Thr Val Trp Leu

Cys Gly Thr Gly Thr Val Lys Thr Pro Val Leu Thr Ala Asp Glu Gly

Ile Leu Lys Thr Ala Ile Lys Leu Gln Ala Gln Val Gln Glu Leu Glu

Glu Asn Asp Glu Trp Pro Leu Gly Thr Phe Glu Lys Tyr Leu Leu Ser

Leu Ala Val Arg Arg Thr Pro Ile Asp Arg Val Ile Leu Phe Gly Gln

Arg Met Asp Thr Glu Leu Leu Asn Val Ala Lys Gln Ile Ile Trp Gln

His Val Asn Ser Lys Cys Leu Phe Val Ser Val Leu Leu Arg Lys Met

Gln Tyr Met Ser Pro Asn Leu Asn Pro Asn Asp Val Thr Leu Ser Gly

Cys Thr Asp Gly Ile Leu Lys Phe Ile Ala Glu His Gly Ala Ser Arg

Leu Leu Glu His Val Gly Gln Leu Asp Lys Ile Phe Lys Ile Pro Pro

Pro Pro Gly Lys Thr Lys Val Ser Pro Leu Arg Pro Leu Glu Glu Asn

Asn Pro Gly Pro Phe Val Pro Ile Ser Gln His Gly Trp Arg Asn Ile

Arg Leu Phe Ile Ser Ser Thr Phe Arg Asp Met His Gly Glu Arg Asp

Leu Leu Met Arg Ser Val Leu Pro Ala Leu Gln Ala Arg Ala Phe Pro

His Arg Ile Ser Leu His Ala Ile Asp Leu Arg Trp Gly Ile Thr Glu

Glu Glu Thr Arg Arg Asn Arg Gln Leu Glu Val Cys Leu Gly Glu Val

Glu Asn Ser Gln Leu Phe Val Gly Ile Leu Gly Ser Arg Tyr Gly Tyr

Thr Pro Pro Ser Tyr Asp Leu Pro Asp His Pro His Phe His Trp Thr

Gln Arg Tyr Pro Ser Gly Arg Ser Val Thr Glu Met Glu Val Met

Gln Phe Leu Asn Arg Gly Gln Arg Ser Glu Pro Ser Asp Gln Ala

Leu Ile Tyr Phe Arg Asp Pro Gly Phe Leu Ser Ser Val Pro Asp

TABLE 1-continued

Sequences

Val Trp Lys Pro Asp Phe Ile Ser Glu Ser Glu Glu Ala Ala His

Arg Val Ser Glu Leu Lys Arg Phe Leu Gln Glu Gln Lys Glu Val

Thr Cys Arg Arg Tyr Ser Cys Glu Trp Gly Gly Val Ala Ala Gly

Arg Pro Tyr Thr Gly Gly Leu Glu Glu Phe Gly Gln Leu Val Leu

Gln Asp Val Trp Ser Val Ile Gln Lys Arg Tyr Leu Gln Pro Gly

Ala Gln Leu Glu Gln Pro Gly Ser Ile Ser Glu Glu Asp Leu Ile

Gln Ala Ser Phe Gln Gln Leu Lys Ser Pro Pro Ser Pro Ala Arg

Pro Arg Leu Leu Gln Asp Thr Val Gln Gln Leu Met Leu Pro His

Gly Arg Leu Ser Leu Val Ile Gly Gln Ala Gly Gln Gly Lys Thr

Ala Phe Leu Ala Ser Leu Val Ser Ala Leu Lys Val Pro Asp Gln

Pro Asn Val Ala Pro Phe Val Phe His Phe Ser Ala Ala Arg

Pro Asp Gln Cys Leu Ala Phe Asn Leu Leu Arg Arg Leu Cys Thr

His Leu His Gln Lys Leu Gly Glu Pro Ser Ala Leu Pro Ser Thr

Tyr Arg Gly Leu Val Trp Glu Leu Gln Gln Lys Leu Leu Leu Lys

Ser Ala Gln Trp Leu Gln Pro Gly Gln Thr Leu Val Leu Ile Ile

Asp Gly Ala Asp Lys Leu Val Asp His Asn Gly Gln Leu Ile Ser

Asp Trp Ile Pro Lys Ser Leu Pro Arg Arg Val His Leu Val Leu

Ser Val Ser Ser Asp Ser Gly Leu Gly Glu Thr Leu Gln Gln Ser

Gln Ser Ala Tyr Val Val Ala Leu Gly Ser Leu Val Pro Ser Ser

Arg Ala Gln Leu Val Arg Glu Glu Leu Ala Leu Tyr Gly Lys Arg

Leu Glu Glu Ser Pro Phe Asn Asn Gln Met Arg Leu Leu Leu Ala

Lys Gln Gly Ser Ser Leu Pro Leu Tyr Leu His Leu Val Thr Asp

Tyr Leu Arg Leu Phe Thr Leu Tyr Glu Gln Val Ser Glu Arg Leu

Arg Thr Leu Pro Ala Thr Leu Pro Leu Leu Leu Gln His Ile Leu

Ser Thr Leu Glu Gln Glu His Gly His Asn Val Leu Pro Gln Ala

Leu Thr Ala Leu Glu Val Thr His Ser Gly Leu Thr Val Asp Gln

Leu His Ala Val Leu Ser Thr Trp Leu Thr Leu Pro Lys Glu Thr

Lys Ser Trp Glu Glu Ala Val Ala Ala Ser His Ser Gly Asn Leu

Tyr Pro Leu Ala Pro Phe Ala Tyr Leu Val Gln Ser Leu Arg Ser

Leu Leu Gly Glu Gly Pro Val Glu Arg Pro Gly Ala Arg Leu Cys

Leu Ser Asp Gly Pro Leu Arg Thr Ala Val Lys Arg Arg Tyr Gly

Lys Arg Leu Gly Leu Glu Lys Thr Ala His Val Leu Ile Ala Ala

His Leu Trp Lys Met Cys Asp Pro Asp Ala Ser Gly Thr Phe Arg

Ser Cys Pro Pro Glu Ala Leu Lys Asp Leu Pro Tyr His Leu Leu

Gln Ser Gly Asn His Gly Leu Leu Ala Lys Phe Leu Thr Asn Leu

His Val Val Ala Ala Tyr Leu Glu Val Gly Leu Val Pro Asp Leu

Leu Glu Ala Tyr Glu Leu Tyr Ala Ser Ser Lys Pro Glu Val Asn

Gln Lys Leu Pro Glu Ala Asp Val Ala Val Phe His Asn Phe Leu

Lys Gln Gln Ala Ser Leu Leu Thr Gln Tyr Pro Leu Leu Leu Leu

TABLE 1-continued

Sequences

Gln Gln Ala Ala Ser Gln Pro Glu Glu Ser Pro Val Cys Cys Gln
Ala Pro Leu Leu Thr Gln Arg Trp His Asn Gln Cys Ile Leu Lys
Trp Ile Asn Lys Pro Gln Thr Leu Lys Gly Gln Gln Ser Leu Ser
Leu Pro Ile Ser Ser Ser Pro Thr Ala Val Ala Phe Ser Pro Asn
Gly Gln Arg Ala Ala Val Gly Thr Ala Gly Gly Thr Ile Tyr Leu
Leu Asn Leu Arg Thr Trp Gln Glu Glu Lys Ala Leu Val Ser Gly
Cys Asp Gly Ile Ser Ser Phe Ala Phe Leu Ser Asp Thr Ala Leu
Phe Leu Thr Thr Phe Asp Gly Leu Leu Glu Leu Trp Asp Leu Gln
His Gly Cys Trp Val Phe Gln Thr Lys Ala His Gln Tyr Gln Ile
Thr Gly Cys Cys Leu Ser Pro Asp Arg Arg Leu Leu Ala Thr Val
Cys Leu Gly Gly Tyr Val Lys Leu Trp Asp Thr Val Gln Gly Gln
Leu Ala Phe Gln Tyr Thr His Pro Lys Ser Leu Asn Cys Ile Thr
Phe His Pro Glu Gly Gln Val Val Ala Thr Gly Asn Trp Ser Gly
Ile Val Thr Phe Phe Gln Ala Asp Gly Leu Lys Val Thr Lys Glu
Leu Gly Gly Pro Gly Pro Ser Val Arg Thr Leu Ala Phe Ser Ala
Pro Gly Lys Val Val Ala Leu Gly Arg Ile Asp Gly Thr Val Glu
Leu Trp Ala Trp Gln Glu Gly Thr Arg Leu Ala Ala Phe Pro Ala
Gln Cys Gly Gly Val Ser Thr Val Leu Phe Leu His Ala Gly Gly
Arg Phe Leu Thr Ala Gly Glu Asp Gly Lys Ala Gln Leu Trp Ser
Gly Phe Leu Gly Arg Pro Arg Gly Cys Leu Gly Ser Leu Tyr Leu
Ser Pro Ala Leu Ser Val Ala Leu Asn Pro Asp Gly Asp Gln Val
Ala Val Gly Tyr Arg Gly Asp Gly Ile Lys Ile Tyr Arg Ile Ser
Ser Gly Pro Gln Glu Ala Gln Cys Gln Glu Leu Asn Val Ala Val
Ser Ala Leu Val Trp Leu Ser Pro Ser Val Leu Val Ser Gly Ala
Glu Asp Gly Ser Leu His Gly Trp Met Leu Arg Arg Asn Ser Leu
Gln Ser Leu Trp Leu Ser Ser Val Cys Gln Lys Pro Val Leu Gly
Leu Ala Ala Ser Gln Glu Phe Leu Ala Ser Ala Ser Glu Asp Phe
Thr Val Arg Leu Trp Pro Arg Gln Leu Leu Thr Gln Pro His Ala
Val Glu Glu Leu Pro Cys Ala Ala Glu Leu Arg Gly His Glu Gly
Pro Val Cys Cys Cys Ser Phe Ser Pro Asp Gly Arg Ile Leu Ala
Thr Ala Gly Arg Asp Arg Asn Leu Leu Cys Trp Asp Val Lys Val
Ala Gln Ala Pro Leu Leu Ile His Thr Phe Ser Ser Cys His Arg
Asp Trp Ile Thr Gly Cys Thr Trp Thr Lys Asp Asn Ile Leu Ile
Ser Cys Ser Ser Asp Gly Ser Val Gly Leu Trp Asn Pro Glu Ala
Gly Gln Gln Leu Gly Gln Phe Pro Gly His Gln Ser Ala Val Ser
Ala Val Val Ala Val Glu Glu His Ile Val Ser Val Ser Arg Asp
Gly Thr Leu Lys Val Trp Asp Arg Gln Gly Val Glu Leu Thr Ser
Ile Pro Ala His Ser Gly Pro Ile Ser Gln Cys Ala Ala Ala Leu
Glu Pro Arg Pro Ala Gly Gln Pro Gly Ser Glu Leu Met Val Val

TABLE 1-continued

Sequences

Thr Val Gly Leu Asp Gly Ala Thr Lys Leu Trp His Pro Leu Leu
Val Cys Gln Ile His Thr Leu Gln Gly His Ser Gly Pro Val Thr
Ala Ala Ala Ala Ser Glu Ala Ser Gly Leu Leu Leu Thr Ser Asp
Asn Ser Ser Val Arg Leu Trp Gln Ile Pro Lys Glu Ala Asp Asp
Thr Cys Lys Pro Arg Ser Ser Ala Val Ile Thr Ala Val Ala Trp
Ala Pro Asp Gly Ser Leu Val Val Ser Gly Asn Glu Ala Gly Glu
Leu Thr Leu Trp Gln Lys Ala Gln Ala Val Ala Thr Ala Arg Ala
Pro Gly Arg Val Ser Asp Leu Ile Trp Cys Ser Ala Asn Ala Phe
Phe Val Leu Ser Ala Asn Glu Asn Val Ser Glu Trp Gln Val Glu
Leu Arg Lys Gly Ser Thr Cys Thr Asn Phe Arg Leu Tyr Leu Lys
Arg Val Leu Gln Glu Asp Leu Gly Val Leu Thr Gly Met Ala Leu
Ala Pro Asp Gly Gln Ser Leu Ile Leu Met Lys Glu Asp Val Glu
Leu Leu Gln Met Lys Pro Gly Ser Thr Pro Ser Ser Ile Cys Arg
Arg Tyr Ala Val His Ser Ser Ile Leu Cys Thr Ser Lys Asp Tyr
Gly Leu Phe Tyr Leu Gln Gln Gly Asn Ser Gly Ser Leu Ser Ile
Leu Glu Gln Glu Glu Ser Gly Lys Phe Glu Lys Thr Leu Asp Phe
Asn Leu Asn Leu Asn Asn Pro Asn Gly Ser Pro Val Ser Ile Thr
Gln Ala Glu Pro Glu Ser Gly Ser Ser Leu Leu Cys Ala Thr Ser
Asp Gly Met Leu Trp Asn Leu Ser Glu Cys Thr Pro Glu Gly Glu
Trp Val Val Asp Asn Ile Trp Gln Lys Lys Ser Arg Asn Pro Lys
Ser Arg Thr Pro Gly Thr Asp Ser Ser Pro Gly Leu Phe Cys Met
Asp Ser Trp Val Glu Pro Thr His Leu Lys Ala Arg Gln Cys Lys
Lys Ile His Leu Gly Ser Val Thr Ala Leu His Val Leu Pro Gly
Leu Leu Val Thr Ala Ser Glu Asp Arg Asp Val Lys Leu Trp Glu
Arg Pro Ser Met Gln Leu Leu Gly Leu Phe Arg Cys Glu Gly Pro
Val Ser Cys Leu Glu Pro Trp Met Glu Pro Ser Ser Pro Leu Gln
Leu Ala Val Gly Asp Ala Gln Gly Asn Leu Tyr Phe Leu Ser Trp
Glu

SEQ ID NO: 28    Rat TEP1 cDNA, Genbank #U89282 atggagaaac tctgtggtta tgtgcctgtc cacccagaca tcctctcctt gaagaatcgg
tgcctgacca tgctctctga catccaaccc ctggagaaaa tacatggaca gagatctgtc
aacccagaca tcctgtcctt ggagaaccgg tgcctgacct tgctccctga tctccagccc
atggagaaaa tacatggaca gagatctgtc cacccagaca tcctctcctc agagaaccgg
tgtctgacct tgctccctga cctccagtcc ctggagaagc tatgtggaca tatgtctagt
cacccagacg tcctctcttt ggagaaccga tgtcttgcta ccctcccgac tgtaaagaga
actgtttcga gtggcccctt gctccagtgt cttcacagat ctcatacggc acaagctgat
ctgcgtgacc cgaactttcg caactgcctg ttccctgagc ctcctaccat agaggctcca
tgtttcttga aggaactaga ccttccaact ggacccaggg ccctgaaatc catgtctgct
acagctcgag ttcaggaagt agctttgggt cagcggtgcg tctcagaagg aaaggaattg TABLE 1-continued Sequences caggaagaaa aagaaagcgc agaagtcccg atgcctttgt acagtctaag cttgggggga gaagaagaag aagtggtggg ggcaccggtc ctaaaactca catctggaga ctctgactct caccctgaaa ccactgacca gatcctgcag gagaagaaga tggctctctt gaccttgctg tgctcagcta tggcctcaag tgtgaatgtg aaagatgcct ccgatcctac ccgggcatct atccatgaag tctgcagtgc gctggccccc ttggaacctg agttcatcct taaggcatct ttgtatgcta ggcagcagct taacctccgg gacatagcca atatagtgtt ggccgtggct gccctcttgc cagcctgccg cccccatgta cgacggtatt actctgccat tgttcacctg ccttcagact ggatccaggt agccgagttc taccagagcc tggcagaagg ggatgagaag aagttggtgc ccctgcctgc ctgcctccgt gctgccatga ctgacaaatt tgcccagttt gatgagtacc agctagcgaa gtacaaccca cggaaacacc gatccaagac acgttcccgc cagccacccc gccctcaaag gacaaaacct ccattttcag agagtgggaa atgttttcca aagagcgttt ggccccttaa aaacgaacag atttcgttcg aagcagctta taatgcagtg tcagagaaga aaaggctacc aaggttcact ctgaagaagt tggtagagca actgcatatc catgagcctg cgcagcatgt ccaggccctg ctgggctaca ggtacccatc caccctagag ctcttttctc ggagtcatct ccctgggcca tgggactcta gcagggctgg gcaacggatg aagctccaaa ggccagagac ctgggagcgg gagctgagct tacgtggaaa cagagcttct gtgtgggagg aactcataga caatgggaaa ctcccccttca tggccatgct ccggaacctg tgtaacctgc tgcggactgg gatcagtgcc caccaccatg aactcgttct ccagagactc cagcatgaga aatctgtgat tcacagtcgg cagtttccat tcagattcct taatgctcac gactctctcg atagactcga ggctcagctc agaagtaaag catcgccctt cccttccaat acaacattga tgaagcggat aatgattaga aactcaaaaa aaatcaagag acctgccaac ccgaggtacc tgtgcaccct gacgcagcgg cagcttcggg cggcaatggc tatcccggtg atgtatgagc atctcaagcg ggagaaactg aggctgcaca aggccagaca gtggacctgt gaccttgagt tgctggagcg gtatcgccag gccctgaaaa cggccgtgaa catctctgta aagcacaacc tacccccgct gccaggccga accctcttgg tctatctcac agatgcaaat gccaacagac tttgtcccaa gagtcacttg caagggcctc ccctgaacta tgtgctgctg ttgatcggga tgatgatggc tcgggcggag cagacgacag tttggctgtg tgggacagga actgtgaaga caccagtact tacagccgac gaaggtatcc tgaagactgc catcaaactt caggctcaag tccaggagtt agaagaaaat gatgagtggc ccctggaaac ttttgagaag tacctgctat ctctggctgt gcgaaggacc cctattgaca gggtcatcct gttcggccaa aggatggata cggagctgct gaatgtagcc aaacagatta tctggcagca tgtgaattcc aagtgcctct tcgtcagtgt cctcctacgg aaaatgcagt acatgtcacc aaatttgaat cccaatgatg tgacgctctc gggctgcact gacgggatcc tgaagttcat tgcggagcat ggagcctctc gtcttctgga acatgtgggc caactagata agatattcaa gatccctcca ccccaggaa agacaaaggt ctcacctctc cggccgctgg aggagaacaa ccctggtccc ttcgttccta tttcccagca tggatggcgc aacatccggc ttttcatttc gtccactttc cgagacatgc atggggaacg agacttgctg atgcgatctg ttctgccagc gctgcaggcc cgagcgttcc cccaccgcat cagccttcac gccattgacc tgcgctgggg aatcacggag gaagagaccc gcaggaacag acaactggaa gtgtgccttg gggaggtgga gaactctcag TABLE 1-continued Sequences

```
ctgttcgtgg ggatcctggg ctcccgctat ggctatactc cccccagcta tgatctgcct gaccacccccc actttcactg gacccagcga taccccttcgg ggcgctctgt aacagagatg gaggtgatgc agttcctgaa ccgtggccaa cgctcggaac cctctgacca agctctcatc tacttccgag atcctggttt ccttagctct gtgccagatg tctggaaacc tgactttatt tccgagtcag aagaggctgc acatcgggtc tcagaactga agagattcct acaggaacag aaagaggtta cctgccgcag gtactcctgt gaatggggag gcgtagcagc cggccggccc tatactgggg gcctggagga gtttggacag ttggttctcc aagatgtgtg gagcgtgatc cagaagcgtt acctgcagcc tggggcccag ttggagcagc caggatccat ctcagaagag gatttgatcc aggccagctt tcagcagctg aagagcccac cgagtcccgc acggccacgc cttcttcagg ataccgtgca acagctgatg ctgccccacg ggaggctgag cctagtgatt gggcaggcag gacagggaaa gactgccttc ctggcatccc ttgtgtcggc cctgaaggtt cccgaccagc ccaatgtggc cccgttcgtt ttcttccact tttcagcagc ccgccctgac cagtgtcttg ctttcaacct cctcagacgc ctctgtaccc atctgcatca aaaactggga gagccgagcg ctctccccag cacttacaga ggcctggtgt gggaactgca gcagaagctg ctcctcaaat ctgcccagtg gctgcaacca ggccagactt tggtccttat tatcgacggg gcagataagt tggtggacca taatggacag ctgatttcag actggatccc caagtctctt ccgcggcgag tacacctggt gctgagtgtg tctagtgact caggcctggg agagacccctt cagcaaagtc agagtgctta tgtggtggcc ttggggtctt tggtcccgtc ttcaagggct cagcttgtga gagaagagct agcactgtat gggaaacggc tggaggagtc acctttaac aaccagatgc ggctgctgct ggcaaagcag gggtcaagcc tgccactgta cctgcacctc gtcactgact acctgaggct tttcacactg tacgaacagg tgtctgagag acttcgaacc ctgcccgcca ctctcccact gctgctgcag cacatcctga gcaccttgga gcaagagcat ggccataacg tccttcctca agctttgact gcccttgagg tcacgcacag tggtctgact gtggaccagc tgcatgcagt cctgagcacg tggttgactt tgcccaagga gactaagagc tgggaagagg cagtggctgc cagtcacagt ggaaacctct accccttggc tccatttgcc taccttgtcc agagtctacg cagtttacta ggcgagggcc ccgtggagcg ccctggcgcc cgtctctgcc tctctgatgg gcctctgagg acagcagtta aacgtcgcta tgggaaaagg ctggggctag agaagactgc gcatgtcctc attgcagctc acctctggaa gatgtgtgac cctgatgcct caggcaccctt ccgaagttgc cctcccgagg ctctgaaaga tttaccttac cacctgctcc agagcgggaa ccatggtctc cttgcaaagt tccttaccaa cctccatgtg gtggctgcat atctggaagt gggtctagtc ccggacctct tggaggctta cgagctctat gcttcttcaa agcctgaagt gaaccagaag ctcccggagg cagatgttgc tgtattccac aacttcctga acaacaggc ttcactcctt acccagtatc ctttgctcct gctccagcag gcagctagcc agcctgaaga gtcacctgtt tgctgccagg ccccccctgct cacccagcgg tggcacaacc agtgcatact gaaatggatt aataaaccccc agaccttgaa gggtcagcaa agcttgtctc tgccaatttc ctcatcccca actgctgtgg ccttctctcc taatgggcaa agagcagctg tggggactgc tggtgggaca atttacctgt tgaacttgag aacctggcag gaggagaagg ctctggtgag tggctgtgat gggatttcct cttttcgcgtt cctgtcagac actgctctttt tccttaccac cttcgatggg ctcctggagc tttgggacct gcaacatggt
```

TABLE 1-continued

Sequences

```
tgttgggtgt tccagaccaa ggcccaccag taccaaatca ctggctgctg cctgagccca
gaccgccgcc tgctggccac cgtgtgtttg ggaggatacg taaagctgtg ggacacagtc
cagggccagc tggctttcca gtacacccat cccaagtctc taaactgcat caccttccac
ccagaggggc aggtggtagc cacaggcaac tggtctggca tcgtgacctt cttccaggca
gatggactca aagtcaccaa ggaactaggg gcccaggac cctctgttcg tacgctggca
ttcagtgcac ccgggaaggt tgtggctcta ggccggatag atgggacagt ggagctgtgg
gcctggcaag agggcacacg gctggcagcc ttccctgcac agtgtggcgg tgtctccacc
gttcttttct tgcatgctgg aggccggttc ctgacggctg ggaagatgg caaggctcag
ttatggtcag gatttcttgg ccggcccagg ggttgcctgg gctctcttta tctttctcct
gcgctctctg tggctctcaa cccagacggt gaccaggtgg ctgttgggta ccgaggagat
ggcattaaaa tctacagaat ttcttcaggt ccccaggagg ctcaatgcca agagctaaat
gtggcggtgt ctgcactggt ctggctgagt cccagcgtct tggtgagtgg tgcagaagat
ggctccctgc atggctggat gctcaggaga aactcccttc agtccctgtg gctgtcatcc
gtgtgccaga agcctgtgct ggggctggct gcctcccagg agttcttggc ttctgcctca
gaggacttca cggtgcgact gtggccaaga cagctgctga cacagccaca tgcagtagaa
gagttgccct gtgcggctga actccgggga cacgaggggc cggtgtgctg ctgtagcttc
agcccggatg gacgcatctt ggccacagcg ggcagggatc ggaatctcct ctgctgggac
gtcaaggtag cccaagcccc tctcctgatt cacacgttct cgtcctgtca tcgagactgg
atcactggct gtacgtggac caaagacaac atcctgatct cctgctctag tgatggctct
gtgggactct ggaacccaga ggcaggacag caacttggcc agttcccagg tcaccagagt
gccgtgagcg ctgtggttgc tgtggaggaa cacattgtat ctgtgagtcg ggatgggacc
ttgaaagtgt gggaccgtca gggtgtggag ctgaccagca tccctgccca ttccggaccc
attagccagt gtgcggctgc tctggaaccc cgtccagctg gacagcctgg atcagagctt
atggtggtga ctgttggact ggatgggggcc acaaagctgt ggcatcccct gttggtgtgc
caaatacata ccctgcaggg acacagtggt ccagtcacag ctgctgctgc ttcagaggcc
tcaggcctcc tgctgacctc agacaatagc tctgtacgac tctggcagat ccctaaggaa
gcagatgata cctgcaaacc taggagttct gcggtcatca ccgctgtggc gtgggcacca
gatggttctc tggtggtgtc tggaaatgaa gctggggaac taacgctgtg gcagaaagcg
caggctgtgg ctacggcacg ggctccaggc cgcgtcagtg acctgatctg gtgctccgca
aatgcattct ttgttctcag tgctaatgaa aatgtcagtg agtggcaagt ggaactgagg
aaaggttcaa catgcaccaa tttcagactt tatctgaaga gagttctgca ggaggacttg
ggagtcttga caggtatggc cctggcgcct gacggccagt ctctcatttt gatgaaagag
gatgtagaat tgctacagat gaagcccggg tctactccat cttcgatctg caggaggtat
gcagtgcatt cttctatact gtgcaccagc aaagactatg cctgttttta cctgcagcag
ggaaactctg gatctctttc tatcttggag caggaggagt cagggaagtt tgaaaagacc
ctggacttca atctgaactt aaataatcct aatgggtccc cagtatcaat cactcaggct
gaacctgagt ctgggtcctc gcttttgtgt gctacctctg atgggatgct gtggaactta
tctgagtgta cccagaagg agagtgggtc gtagataaca tctggcagaa aaaatcaaga
aaccctaaaa gtcgaactcc ggggacagat tcgtccccag gcttattctg catggatagc
```

TABLE 1-continued

Sequences tgggtagaac ccacacattt aaaggcacgg cagtgtaaaa agattcactt gggctctgtc acggccctcc atgtgctgcc cggattgctg gtgactgctt cagaggacag agatgttaag ctgtgggaga gacccagtat gcagctgctc ggcttgttcc gatgtgaagg gccggtgagc tgtctggaac cttggatgga gcccagctct cccctgcagc ttgctgtggg agatgcacaa ggaaacttgt attttctatc ttgggaatga

| SEQ ID NO: 29 | Human vRNA, Genbank #AF045143 | ggcuggcuuu agcucagcgg uuacuucgac aguucuuuaa uugaaacaag caaccugucu ggguuguucg agacccgcgg gcgcucucca guccuuuu

| SEQ ID NO: 30 | Human vRNA, Genbank #AF045144 | ggcuggcuuu agcucagcgg uuacuucgag uacauuguaa ccaccucucu gggugguucg agacccgcgg gugcuuucca gcucuuuu

| SEQ ID NO: 31 | Human vRNA, Genbank #AF045145 | ggcuggcuuu agcucagcgg uuacuucgcg ugucaucaaa ccaccucucu ggguuguucg agacccgcgg gcgcucucca gcccucuu

| SEQ ID NO: 32 | Rat vRNA, Genbank #Z1171 | ggccagcuuu agcucagcgg uuacuucgac gugcuccagu uugagcaggc uauguaacgu ggucgguucg agcaacacaa ccagccgcuu gccuaucugg ugaguggung guucgagacc cgcgggcgcu cucuggcccu uuu

| SEQ ID NO: 33 | Human IL-2 cDNA Sequence, Genbank # BC070338.1, coding sequence: 48-509 |

1   atcactctct ttaatcacta ctcacagtaa cctcaactcc tgccacaatg tacaggatgc
   61   aactcctgtc ttgcattgca ctaagtcttg cacttgtcac aaacagtgca cctacttcaa
  121   gttctacaaa gaaaacacag ctacaactgg agcatttact gctggattta cagatgattt
  181   tgaatggaat taataattac aagaatccca aactcaccag gatgctcaca tttaagtttt
  241   acatgcccaa gaaggccaca gaactgaaac atcttcagtg tctagaagaa gaactcaaac
  301   ctctggagga agtgctaaat ttagctcaaa gcaaaaactt tcacttaaga cccagggact
  361   taatcagcaa tatcaacgta atagttctgg aactaaaggg atctgaaaca acattcatgt
  421   gtgaatatgc tgatgagaca gcaaccattg tagaatttct gaacagatgg attaccttt
  481   gtcaaagcat catctcaaca ctgacttgat aattaagtgc ttcccactta aaacgtatca
  541   ggccttctat ttatttaaat atttaaattt tatatttatt gttgaatgta tggtttgcta
  601   cctattgtaa ctattattct taatcttaaa actataaata tggatctttt atgattcttt
  661   ttgtaagccc taggggctct aaaatgattt cacttatta tcccaaaata tttattatta
  721   tgttgaatgt taaatatagt atctatgtag attggttagt aaaactattt aataaatttg
  781   ataaatataa aaaaaaaaaa aaaaaaaaaa aaaa

| SEQ ID NO: 34 | Human IL-2 Protein sequence, Genbank # AAH70338.1 |

MYRMQLLSCIALSLALVTNSAFTSSSTKKTQLQLEHLLLDLQMILNGINNYKNFKLTRMLTFKFYMFKKA

TELKHLQCLEEELKFLEEVLNLAQSKNFHLRFRDLISNINVIVLELKGSETTFMCEYADETATIVEFLNR

WITFCQSIISTLT

TABLE 1-continued

Sequences

| SEQ ID NO: 35 | Human IL-7 cDNA sequence, Genbank # J04156.1; coding sequence: 385-918 |

```
   1  gaattcctct ggtcctcatc caggtgcgcg ggaagcaggt gcccaggaga gaggggataa
  61  tgaagattcc atgctgatga tcccaaagat tgaacctgca gaccaagcgc aaagtagaaa
 121  ctgaaagtac actgctggcg gatcctacgg aagttatgga aaaggcaaag cgcagagcca
 181  cgccgtagtg tgtgccgccc ccttgggat ggatgaaact gcagtcgcgg cgtgggtaag
 241  aggaaccagc tgcagagatc accctgccca acacagactc ggcaactccg cggaagacca
 301  gggtcctggg agtgactatg ggcggtgaga gcttgctcct gctccagttg cggtcatcat
 361  gactacgccc gcctcccgca gaccatgttc catgtttctt ttaggtatat cttttggactt
 421  cctcccctga tccttgttct gttgccagta gcatcatctg attgtgatat tgaaggtaaa
 481  gatggcaaac aatatgagag tgttctaatg gtcagcatcg atcaattatt ggacagcatg
 541  aaagaaattg gtagcaattg cctgaataat gaatttaact ttttaaaag acatatctgt
 601  gatgctaata aggaaggtat gttttattc cgtgctgctc gcaagttgag gcaatttctt
 661  aaaatgaata gcactggtga ttttgatctc cacttattaa aagtttcaga aggcacaaca
 721  atactgttga actgcactgg ccaggttaaa ggaagaaaac cagctgccct gggtgaagcc
 781  caaccaacaa agagtttgga agaaaataaa tctttaaagg aacagaaaaa actgaatgac
 841  ttgtgtttcc taaagagact attacaagag ataaaaactt gttggaataa aattttgatg
 901  ggcactaaag aacactgaaa aatatggagt ggcaatatag aaacacgaac tttagctgca
 961  tcctccaaga atctatctgc ttatgcagtt tttcagagtg gaatgcttcc tagaagttac
1021  tgaatgcacc atggtcaaaa cggattaggg catttgagaa atgcatattg tattactaga
1081  agatgaatac aaacaatgga aactgaatgc tccagtcaac aaactatttc ttatatatgt
1141  gaacatttat caatcagtat aattctgtac tgattttgt aagacaatcc atgtaaggta
1201  tcagttgcaa taatacttct caaacctgtt taaatatttc aagacattaa atctatgaag
1261  tatataatgg tttcaaagat tcaaaattga cattgcttta ctgtcaaaat aatttatgg
1321  ctcactatga atctattata ctgtattaag agtgaaaatt gtcttcttct gtgctggaga
1381  tgttttagag ttaacaatga tatatggata atgccggtga gaataagaga gtcataaacc
1441  ttaagtaagc aacagcataa caaggtccaa gatacctaaa agagatttca agagatttaa
1501  ttaatcatga atgtgtaaca cagtgccttc aataaatggt atagcaaatg ttttgacatg
1561  aaaaaggac aatttcaaaa aaataaaat
```

| SEQ ID NO: 36 | Human IL-7 Protein sequence, Genbank # AAA59156.1 |

MFHVSFRYIFGLFFLILVLLFVASSDCDIEGKDGKQYESVLMVSIDQLLDSMKEIGSNCLNNEFNFFKRH

ICDANKEGMFLFRAARKLRQFLKMNSTGDFDLHLLKVSEGTTILLNCTGQVKGRKFAALGEAQFTKSLEE

NKSLKEQKKLNDLCFLKRLLQEIKTCWNKILMGTKEH

| SEQ ID NO: 37 | Human IL-15 cDNA sequence, Genbank #BC018149.2; coding sequence: 845-1333 |

```
   1  actccgggtg gcaggcgccc gggggaatcc cagctgactc gctcactgcc ttcgaagtcc
  61  ggcgcccccc gggagggaac tgggtggccg caccctcccg gctgcggtgg ctgtcgcccc
 121  ccaccctgca gccaggactc gatggaggta cagagctcgg cttctttgcc ttgggagggg
 181  agtggtggtg gttgaaaggg cgatggaatt tccccgaaa gctacgccc agggcccctc
 241  ccagctccag cgttaccctc cggtctatcc tactggccga gctgccccgc cttctcatgg
```

TABLE 1-continued

Sequences

| | |
|---|---|
| 301 | ggaaaactta gccgcaactt caattttttgg tttttccttt aatgacactt ctgaggctct |
| 361 | cctagccatc ctcccgcttc cggaggagcg cagatcgcag gtccctttgc ccctggcgtg |
| 421 | cgactcccta ctgcgctgcg ctcttacggc gttccaggct gctggctagc gcaaggcggg |
| 481 | ccgggcaccc cgcgctccgc tgggagggtg agggacgcgc gtctggcggc cccagccaag |
| 541 | ctgcgggttt ctgagaagac gctgtcccgc agccctgagg ctgagttct gcacccagtc |
| 601 | aagctcagga aggccaagaa aagaatccat tccaatatat ggccatgtgg ctctttggag |
| 661 | caatgttcca tcatgttcca tgctgctgac gtcacatgga gcacagaaat caatgttagc |
| 721 | agatagccag cccatacaag atcgtattgt attgtaggag catcgtgga tggatggctg |
| 781 | ctggaaaccc cttgccatag ccagctcttc ttcaatactt aaggatttac cgtggctttg |
| 841 | agtaatgaga atttcgaaac cacatttgag aagtatttcc atccagtgct acttgtgttt |
| 901 | acttctaaac agtcattttc taactgaagc tggcattcat gtcttcattt gggctgttt |
| 961 | cagtgcaggg cttcctaaaa cagaagccaa ctgggtgaat gtaataagtg atttgaaaaa |
| 1021 | aattgaagat cttattcaat ctatgcatat tgatgctact ttatatacgg aaagtgatgt |
| 1081 | tcaccccagt tgcaaagtaa cagcaatgaa gtgctttctc ttggagttac aagttatttc |
| 1141 | acttgagtcc ggagatgcaa gtattcatga tacagtagaa aatctgatca tcctagcaaa |
| 1201 | caacagtttg tcttctaatg gaatgtaac agaatctgga tgcaaagaat gtgaggaact |
| 1261 | ggaggaaaaa aatattaaag aattttttgca gagttttgta catattgtcc aaatgttcat |
| 1321 | caacacttct tgattgcaat tgattctttt taaagtgttt ctgttattaa caaacatcac |
| 1381 | tctgctgctt agacataaca aaacactcgg catttcaaat gtgctgtcaa acaagttttt |
| 1441 | tctgtcaaga agatgatcag accttggatc agatgaactc ttagaaatga aggcagaaaa |
| 1501 | atgtcattga gtaatatagt gactatgaac ttctctcaga cttactttac tcatttttttt |
| 1561 | aatttattat tgaaattgta catatttgtg gaataatgta aaatgttgaa taaaaatatg |
| 1621 | tacaagtgtt gtttttttaag ttgcactgat attttacctc ttattgcaaa atagcatttg |
| 1681 | tttaagggtg atagtcaaat tatgtattgg tggggctggg taccaatgct gcaggtcaac |
| 1741 | agctatgctg gtaggctcct gcctgtgtgg aaccactgac tactggctct cattgacttc |
| 1801 | cttactaagc atagcaaaca gaggaagaat tgttatcag taagaaaaag aagaactata |
| 1861 | tgtgaatcct cttcttaca ctgtaattta gttattgatg tataaagcaa ctgttatgaa |
| 1921 | ataagaaat tgcaataact ggcaaaaaaa aaaaaaaaaa aaaaaaaa |

| SEQ ID NO: 38 | Human IL-15 protein sequence, Genbank #AAH18149.1 |
|---|---|

MRISKPHLRSISIQCYLCLLLNSHFLTEAGIHVFILGCFSAGLPKTEANWVNVISDLKKIEDLIQSMHIDATLYTESDVHPSC
KVTAMKCFLLELQVISLESGDASIHDTVENLIILANNSLSSNGNVTESGCKECEELEEKNIKEFLQSFVHIVQMFIN

| SEQ ID NO: 39 | Human IL-12B cDNA Sequence, Genbank #NM_002187.2; coding sequence: 43-1029 |
|---|---|

| | |
|---|---|
| 1 | ctgtttcagg gccattggac tctccgtcct gcccagagca agatgtgtca ccagcagttg |
| 61 | gtcatctctt ggtttttccct ggttttttctg gcatctcccc tcgtggccat atgggaactg |
| 121 | aagaaagatg tttatgtcgt agaattggat tggtatccgg atgcccctgg agaaatggtg |
| 181 | gtcctcacct gtgacacccc tgaagaagat ggtatcacct ggaccttgga ccagagcagt |
| 241 | gaggtcttag ctctggcaa aacctgacc atccaagtca agagtttgg agatgctggc |

TABLE 1-continued

Sequences

```
 301  cagtacacct gtcacaaagg aggcgaggtt ctaagccatt cgctcctgct gcttcacaaa
 361  aaggaagatg gaatttggtc cactgatatt ttaaaggacc agaaagaacc caaaaataag
 421  acctttctaa gatgcgaggc caagaattat tctggacgtt tcacctgctg gtggctgacg
 481  acaatcagta ctgatttgac attcagtgtc aaaagcagca gaggctcttc tgaccccaa
 541  ggggtgacgt gcggagctgc tacactctct gcagagagag tcagagggga caacaaggag
 601  tatgagtact cagtggagtg ccaggaggac agtgcctgcc cagctgctga ggagagtctg
 661  cccattgagg tcatggtgga tgccgttcac aagctcaagt atgaaaacta caccagcagc
 721  ttcttcatca gggacatcat caaacctgac ccacccaaga acttgcagct gaagccatta
 781  aagaattctc ggcaggtgga ggtcagctgg gagtaccctg acacctggag tactccacat
 841  tcctacttct ccctgacatt ctgcgttcag gtccagggca gagcaagag agaaaagaaa
 901  gatagagtct tcacggacaa gacctcagcc acggtcatct gccgcaaaaa tgccagcatt
 961  agcgtgcggg cccaggaccg ctactatagc tcatcttgga gcgaatgggc atctgtgccc
1021  tgcagttagg ttctgatcca ggatgaaaat ttggaggaaa agtggaagat attaagcaaa
1081  atgtttaaag acacaacgga atagacccaa aaagataatt tctatctgat ttgctttaaa
1141  acgttttttt aggatcacaa tgtatatctt tgctgtatttg tatagttaga tgctaaatgc
1201  tcattgaaac aatcagctaa tttatgtata gattttccag ctctcaagtt gccatgggcc
1261  ttcatgctat ttaaatattt aagtaattta tgtatttatt agtatattac tgttatttaa
1321  cgtttgtctg ccaggatgta tggaatgttt catactctta tgacctgatc catcaggatc
1381  agtccctatt atgcaaaatg tgaatttaat tttatttgta ctgacaactt tcaagcaag
1441  gctgcaagta catcagtttt atgacaatca ggaagaatgc agtgttctga taccagtgcc
1501  atcatacact tgtgatggat gggaacgcaa gagatactta catggaaacc tgacaatgca
1561  aacctgttga gaagatccag gagaacaaga tgctagttcc catgtctgtg aagacttcct
1621  ggagatggtg ttgataaagc aatttagggc cacttacact tctaagcaag tttaatcttt
1681  ggatgcctga attttaaaag ggctagaaaa aaatgattga ccagcctggg aaacataaca
1741  agaccccgtc tctacaaaaa aaatttaaaa ttagccaggc gtggtggctc atgcttgtgg
1801  tcccagctgt tcaggaggat gaggcaggag gatctcttga gcccaggagg tcaaggctat
1861  ggtgagccgt gattgtgcca ctgcatacca gcctaggtga cagaatgaga ccctgtctca
1921  aaaaaaaaaa tgattgaaat taaaattcag ctttagcttc catggcagtc ctcaccccca
1981  cctctctaaa agacacagga ggatgacaca gaaacaccgt aagtgtctgg aagcaaaaa
2041  gatcttaaga ttcaagagag aggacaagta gttatggcta aggacatgaa attgtcagaa
2101  tggcaggtgg cttcttaaca gccctgtgag aagcagacag atgcaaagaa aatctggaat
2161  ccctttctca ttagcatgaa tgaacctgat acacaattat gaccagaaaa tatggctcca
2221  tgaaggtgct acttttaagt aatgtatgtg cgctctgtaa agtgattaca tttgtttcct
2281  gtttgtttat ttatttattt atttttgcat tctgaggctg aactaataaa aactcttctt
2341  tgtaatc
```

| SEQ ID NO: 40 | Human IL-12B Protein Sequence, Genbank # NP_002178.2 |
| --- | --- |

MCHQQLVISWFSLVFLASPLVAIWELKKDVYVVELDWYPDAPGEMVVLTCDTPEEDGITWTLDQSSEVLGSGKT

LTIQVKEFGDAGQYTCHKGGEVLSHSLLLLHKKEDGIWSTDILKDQKEPKNKTFLRCEAKNYSGRFTCWWLTTI

STDLTFSVKSSRGSSDPQGVTCGAATLSAERVRGDNKEYEYSVECQEDSACPAAEESLPIEVMVDAVHKLKYEN

TABLE 1-continued

Sequences

YTSSFFIRDIIKPDPPKNLQLKPLKNSRQVEVSWEYPDTWSTPHSYFSLTFCVQVQGKSKREKKDRVFTDKTSA

TVICRKNASISVRAQDRYYSSSWSEWASVPCS

| SEQ ID NO: 41 | Human IL-12A cDNA sequence, Genbank # NM_000882.2; coding sequence: 216-977 |
|---|---|

```
   1 tttcattttg ggccgagctg gaggcggcgg ggccgtcccg gaacggctgc ggccgggcac
  61 cccgggagtt aatccgaaag cgccgcaagc cccgcgggcc ggccgcaccg cacgtgtcac
 121 cgagaagctg atgtagagag agacacagaa ggagacagaa agcaagagac cagagtcccg
 181 ggaaagtcct gccgcgcctc gggacaatta taaaaatgtg gcccctggg tcagcctccc
 241 agccaccgcc ctcacctgcc gcgccacag gtctgcatcc agcggctcgc cctgtgtccc
 301 tgcagtgccg gctcagcatg tgtccagcgc gcagcctcct ccttgtggct accctggtcc
 361 tcctggacca cctcagtttg ccagaaacc tccccgtggc cactccagac caggaatgt
 421 tcccatgcct tcaccactcc caaaacctgc tgagggccgt cagcaacatg ctccagaagg
 481 ccagacaaac tctagaattt tacccttgca cttctgaaga gattgatcat gaagatatca
 541 caaaagataa aaccagcaca gtggaggcct gtttaccatt ggaattaacc aagaatgaga
 601 gttgcctaaa ttccagagag acctctttca taactaatgg agttgcctg cctccagaa
 661 agacctcttt tatgatggcc ctgtgcctta gtagtattta tgaagacttg aagatgtacc
 721 aggtggagtt caagaccatg aatgcaaagc ttctgatgga tcctaagagg cagatctttc
 781 tagatcaaaa catgctggca gttattgatg agctgatgca ggccctgaat ttcaacagtg
 841 agactgtgcc acaaaaatcc tcccttgaag aaccggattt ttataaaact aaaatcaagc
 901 tctgcatact tcttcatgct ttcagaattc gggcagtgac tattgataga gtgatgagct
 961 atctgaatgc ttcctaaaaa gcgaggtccc tccaaaccgt tgtcattttt ataaaacttt
1021 gaaatgagga aactttgata ggatgtggat taagaactag ggaggggaa agaaggatgg
1081 gactattaca tccacatgat acctctgatc aagtattttt gacatttact gtggataaat
1141 tgtttttaag ttttcatgaa tgaattgcta agaagggaaa atatccatcc tgaaggtgtt
1201 tttcattcac tttaatagaa gggcaaatat ttataagcta tttctgtacc aaagtgtttg
1261 tggaaacaaa catgtaagca taacttattt taaaatattt atttatataa cttggtaatc
1321 atgaaagcat ctgagctaac ttatatttat ttatgttata tttattaaat tatttatcaa
1381 gtgtatttga aaaatatttt taagtgttct aaaaataaaa gtattgaatt aaagtgaaaa
1441 aaaa
```

| SEQ ID NO: 42 | Human IL-12A Protein sequence, Genbank #NP_000873.2 |
|---|---|

MWPPGSASQPPPSPAAATGLHPAARPVSLQCRLSMCPARSLLLVATLVLLDHLSLARNLPVATPDPGMFPCLHH

SQNLLRAVSNMLQKARQTLEFYPCTSEEIDHEDITKDKTSTVEACLPLELTKNESCLNSRETSFITNGSCLASR

KTSFMMALCLSSIYEDLKMYQVEFKTMNAKLLMDPKRQIFLDQNMLAVIDELMQALNFNSETVPQKSSLEEPDF

YKTKIKLCILLHAFRIRAVTIDRVMSYLNAS

| SEQ ID NO: 43 | Human CSF2 cDNA Sequence, Genbank #BC108724.1; coding sequence: 20-454 |
|---|---|

```
   1 ggctaaagtt ctctggagga tgtggctgca gagcctgctg ctcttgggca ctgtggcctg
  61 cagcatctct gcacccgccc gctcgcccag ccccagcacg cagccctggg agcatgtgaa
 121 tgccatccag gaggcccggc gtcctcctgaa cctgagtaga cactgctg ctgagatgaa
 181 tgaaacagta gaagtcatct cagaaatgtt tgacctccag gagccgacct gcctacagac
```

TABLE 1-continued

Sequences

| | |
|---|---|
| 241 | ccgcctggag ctgtacaagc agggcctgcg gggcagcctc accaagctca agggcccctt |
| 301 | gaccatgatg gccagccact acaagcagca ctgcccctcca acccggaaaa cttcctgtgc |
| 361 | aacccagatt atcacctttg aaagtttcaa agagaacctg aaggactttc tgcttgtcat |
| 421 | ccccttttgac tgctgggagc cagtccagga gtgagaccgg ccagatgagg ctggccaagc |
| 481 | cggggagctg ctctctcatg aaacaagagc tagaaactca ggatggtcat cttggaggga |
| 541 | ccaagggtg gccacagcc atggtgggag tggcctggac ctgccctggg ccacactgac |
| 601 | cctgatacag gcatggcaga agaatgggaa tattttatac tgacagaaat cagtaatatt |
| 661 | tatatattta tatttttaaa atatttattt atttatttat ttaagttcat attccatatt |
| 721 | tattcaagat gttttaccgt aataattatt attaaaaata tgcttctact tgaaaaaaaa |
| 781 | aaaaaaa |

| SEQ ID NO: 44 | Human CSF2 Protein Sequence, Genbank #AAI08725.1 |
|---|---|

MWLQSLLLLGTVACSISAPARSPSPSTQPWEHVNAIQEARRLLNLSRDTAAEMNETVEVISEMFDLQEPTCLQT
RLELYKQGLRGSLTKLKGPLTMMASHYKQHCPPTPETSCATQIITFESFKENLKDFLLVIPFDCWEPVQE

| SEQ ID NO: 45 | Human CXCL9 cDNA Sequence, Genbank #NM_002416.1; coding sequence: 40-417 |
|---|---|

| | |
|---|---|
| 1 | atccaataca ggagtgactt ggaactccat tctatcacta tgaagaaaag tggtgttctt |
| 61 | ttcctcttgg gcatcatctt gctggttctg attggagtgc aaggaacccc agtagtgaga |
| 121 | aagggtcgct gttcctgcat cagcaccaac caagggacta tccacctaca atccttgaaa |
| 181 | gaccttaaac aatttgcccc aagcccttcc tgcgagaaaa ttgaaatcat tgctacactg |
| 241 | aagaatggag ttcaaacatg tctaaaccca gattcagcag atgtgaagga actgattaaa |
| 301 | aagtgggaga acaggtcag ccaaaagaaa aagcaaaaga tgggaaaaa acatcaaaaa |
| 361 | aagaaagttc tgaaagttcg aaaatctcaa cgttctcgtc aaaagaagac tacataagag |
| 421 | accacttcac caataagtat tctgtgttaa aaatgttcta ttttaattat accgctatca |
| 481 | ttccaaagga ggatggcata taatacaaag gcttattaat ttgactagaa aatttaaaac |
| 541 | attactctga aattgtaact aaagttagaa agttgatttt aagaatccaa acgttaagaa |
| 601 | ttgttaaagg ctatgattgt ctttgttctt ctaccaccca ccagttgaat tcatcatgc |
| 661 | ttaaggccat gattttagca atacccatgt ctacacagat gttcacccaa ccacatccca |
| 721 | ctcacaacag ctgcctggaa gagcagccct aggcttccac gtactgcagc tccagagag |
| 781 | tatctgaggc acatgtcagc aagtcctaag cctgttagca tgctggtgag ccaagcagtt |
| 841 | tgaaattgag ctggacctca ccaagctgct gtggccatca acctctgtat ttgaatcagc |
| 901 | ctacaggcct cacacacaat gtgtctgaga gattcatgct gattgttatt gggtatcacc |
| 961 | actggagatc accagtgtgt ggctttcaga gcctcctttc tggctttgga agccatgtga |
| 1021 | ttccatcttg cccgctcagg ctgaccactt tatttctttt tgttcccctt tgcttcattc |
| 1081 | aagtcagctc ttctccatcc taccacaatg cagtgccttt cttctctcca gtgcacctgt |
| 1141 | catatgctct gatttatctg agtcaactcc tttctcatct tgtccccaac accccacaga |
| 1201 | agtgctttct tctcccaatt catcctcact cagtccagct tagttcaagt cctgcctctt |
| 1261 | aaataaacct ttttggacac acaaattatc ttaaaactcc tgtttcactt ggttcagtac |
| 1321 | cacatggggtg aacactcaat ggttaactaa ttcttgggtg tttatcctat ctctccaacc |
| 1381 | agattgtcag ctccttgagg gcaagagcca cagtatattt ccctgttttct tccacagtgc |

TABLE 1-continued

Sequences

```
1441  ctaataatac tgtggaacta ggttttaata attttttaat tgatgttgtt atgggcagga
1501  tggcaaccag accattgtct cagagcaggt gctggctctt tcctggctac tccatgttgg
1561  ctagcctctg gtaacctctt acttattatc ttcaggacac tcactacagg gaccagggat
1621  gatgcaacat ccttgtcttt ttatgacagg atgtttgctc agcttctcca acaataagaa
1681  gcacgtggta aaacacttgc ggatattctg gactgttttt aaaaaatata cagtttaccg
1741  aaaatcatat aatcttacaa tgaaaaggac tttatagatc agccagtgac caaccttttc
1801  ccaaccatac aaaaattcct tttcccgaag gaaaagggct ttctcaataa gcctcagctt
1861  tctaagatct aacaagatag ccaccgagat ccttatcgaa actcatttta ggcaaatatg
1921  agttttattg tccgtttact tgtttcagag tttgtattgt gattatcaat taccacacca
1981  tctcccatga agaaagggaa cggtgaagta ctaagcgcta gaggaagcag ccaagtcggt
2041  tagtggaagc atgattggtg cccagttagc ctctgcagga tgtggaaacc tccttccagg
2101  ggaggttcag tgaattgtgt aggagaggtt gtctgtggcc agaatttaaa cctatactca
2161  ctttcccaaa ttgaatcact gctcacactg ctgatgattt agagtgctgt ccggtggaga
2221  tcccacccga acgtcttatc taatcatgaa actccctagt tccttcatgt aacttccctg
2281  aaaaatctaa gtgtttcata aatttgagag tctgtgaccc acttaccttg catctcacag
2341  gtagacagta tataactaac aaccaaagac tacatattgt cactgacaca cacgttataa
2401  tcatttatca tatatataca tacatgcata cactctcaaa gcaaataatt tttcacttca
2461  aaacagtatt gacttgtata ccttgtaatt tgaaatattt tctttgttaa aatagaatgg
2521  tatcaataaa tagaccatta atcag
```

| SEQ ID NO: 46 | Human CXCL9 Protein Sequence, Genbank #NP_002407.1 |
|---|---|

MKKSGVLFLLGIILLVLIGVQGTPVVRKGRCSCISTNQGTIHLQSLKDLKQFAPSPSCEKIEIIATLKNGVQTCLNPDSADVK

ELIKKWEKQVSQKKKQKNGKKHQKKKVLKVRKSQRSRQKKTT

| SEQ ID NO: 47 | Human CXCL10 cDNA Sequence, Genbank #NM_001565.2; coding sequence: 71-367 |
|---|---|

```
  1  gggggagaca ttcctcaatt gcttagacat attctgagcc tacagcagag gaacctccag
 61  tctcagcacc atgaatcaaa ctgccattct gatttgctgc cttatctttc tgactctaag
121  tggcattcaa ggagtacctc tctctagaac tgtacgctgt acctgcatca gcattagtaa
181  tcaacctgtt aatccaaggt ctttagaaaa acttgaaatt attcctgcaa gccaattttg
241  tccacgtgtt gagatcattg ctacaatgaa aaagaagggt gagaagagat gtctgaatcc
301  agaatcgaag gccatcaaga atttactgaa agcagttagc aaggaaggt ctaaaagatc
361  tccttaaaac cagaggggag caaaatcgat gcagtgcttc caaggatgga ccacacagag
421  gctgcctctc ccatcacttc cctacatgga gtatatgtca agccataatt gttcttagtt
481  tgcagttaca ctaaaaggtg accaatgatg gtcaccaaat cagctgctac tactcctgta
541  ggaaggttaa tgttcatcat cctaagctat tcagtaataa ctctaccctg cactataat
601  gtaagctcta ctgaggtgct atgttcttag tggatgttct gaccctgctt caaatatttc
661  cctcaccttt cccatcttcc aagggtacta aggaatcttt ctgctttggg gtttatcaga
721  attctcagaa tctcaaataa ctaaaggta tgcaatcaaa tctgctttt aaagaatgct
781  cttacttca tggacttcca ctgccatcct cccaagggc ccaaattctt tcagtggcta
841  cctacataca attccaaaca catacaggaa ggtagaaata tctgaaaatg tatgtgtaag
901  tattcttatt taatgaaaga ctgtacaaag tagaagtctt agatgtatat atttcctata
```

TABLE 1-continued

Sequences

| | |
|---|---|
| 961 | ttgttttcag tgtacatgga ataacatgta attaagtact atgtatcaat gagtaacagg |
| 1021 | aaaatttaa aatacagat agatatatgc tctgcatgtt acataagata aatgtgctga |
| 1081 | atggttttca aaataaaaat gaggtactct cctggaaata ttaagaaaga ctatctaaat |
| 1141 | gttgaaagat caaaaggtta ataaagtaat tataactaaa aaaa |

| SEQ ID NO: 48 | Human CXCL10 Protein Sequence, Genbank #NP_001556.2 |
|---|---|

MNQTAILICCLIFLTLSGIQGVPLSRTVRCTCISISNQPVNPRSLEKLEIIPASQFCPRVEIIATMKKKGEKRCLNPESKAIK

NLLKAVSKERSKRSP

| SEQ ID NO: 49 | Human IFN-alpha cDNA Sequence, Genbank #J00210.1; coding sequence: 221-790 |
|---|---|

| | |
|---|---|
| 1 | aaaacaaaac atttgagaaa cacggctcta aactcatgta aagagtgcat gaaggaaagc |
| 61 | aaaaacagaa atggaaagtg gcccagaagc attaagaaag tggaaatcag tatgttccct |
| 121 | atttaaggca tttgcaggaa gcaaggcctt cagagaacct agagcccaag gttcagagtc |
| 181 | acccatctca gcaagcccag aagtatctgc aatatctacg atggcctcgc cctttgcttt |
| 241 | actgatggtc ctggtggtgc tcagctgcaa gtcaagctgc tctctgggct gtgatctccc |
| 301 | tgagacccac agcctggata acaggaggac cttgatgctc ctggcacaaa tgagcagaat |
| 361 | ctctccttcc tcctgtctga tggacagaca tgactttgga tttccccagg aggagtttga |
| 421 | tggcaaccag ttccagaagg ctccagccat ctctgtcctc catgagctga tccagcagat |
| 481 | cttcaacctc tttaccacaa aagattcatc tgctgcttgg gatgaggacc tcctagacaa |
| 541 | attctgcacc gaactctacc agcagctgaa tgacttggaa gcctgtgtga tgcaggagga |
| 601 | gagggtggga gaaactcccc tgatgaatgc ggactccatc ttggctgtga agaaatactt |
| 661 | ccgaagaatc actctctatc tgacagagaa gaaatacagc ccttgtgcct gggaggttgt |
| 721 | cagagcagaa atcatgagat ccctctcttt atcaacaaac ttgcaagaaa gattaaggag |
| 781 | gaaggaataa catctggtcc aacatgaaaa caattcttat tgactcatac accaggtcac |
| 841 | gctttcatga attctgtcat ttcaaagact ctcaccctg ctataactat gaccatgctg |
| 901 | ataaactgat ttatctattt aaatatttat ttaactattc ataagattta aattattttt |
| 961 | gttcatataa cgtcatgtgc acctttacac tgtggttagt gtaataaaac atgttcctta |
| 1021 | tatttactca atccattatt ttgtgttgtt cattaaactt ttactatagg aacttcctgt |
| 1081 | atgtgttcat tctttaatat gaaattccta gcctgactgt gcaacctgat tagagaataa |
| 1141 | agggtatatt ttatttgctt atcattatta tatgtaaga |

| SEQ ID NO: 50 | Human IFN-alpha Protein Sequence, Genbank # AAB59403.1 |
|---|---|

MASPFALLMVLVVLSCKSSCSLGCDLPETHSLDNRRTLMLLAQMSRISPSSCLMDRHDFGFPQEEFDGNQFQKAPAISVLHEL

IQQIFNLFTTKDSSAAWDEDLLDKFCTELYQQLNDLEACVMQEERVGETPLMNADSILAVKKYFRRITLYLTEKKYSPCAWEV

VRAEIMRSLSLSTNLQERLRRKE

| SEQ ID NO: 51 | Human IFN-gamma IEF SSP 5111 cDNA Sequence, Genbank # L07633.1; coding sequence: 93-842 |
|---|---|

| | |
|---|---|
| 1 | gcggagctgg gtgcgagcgc cctaccgctt tcgctttccc ttcgcggtgc ccactccact |
| 61 | ccttgtgcgg cgctaggccc cccgtcccgg tcatggccat gctcagggtc cagcccgagg |
| 121 | cccaagccaa ggtggatgtg tttcgtgaag acctctgtac caagacagaa aacctgctcg |
| 181 | ggagctattt ccccaagaag atttctgagc tggatgcatt tttaaaggag ccagctctca |

TABLE 1-continued

Sequences

```
241  atgaagccaa cttgagcaat ctgaaggccc cattggacat cccagtgcct gatccagtca
301  aggagaaaga gaaagaggag cggaagaaac agcaggagaa ggaagacaag gatgaaaaga
361  agaaggggga ggatgaagac aaaggtcctc cctgtggccc agtgaactgc aatgaaaaga
421  tcgtggtcct tctgcagcgc ttgaagcctg agatcaagga tgtcattgag cagctcaacc
481  tggtcaccac ctggttgcag ctgcagatac tcggattga ggatggtaac aattttggag
541  tggctgtcca ggagaaggtg tttgagctga tgaccagcct ccacaccaag ctagaaggct
601  tccacactca aatctctaag tatttctctg agcgtggtga tgcagtgact aaagcagcca
661  agcagcccca tgtgggtgat tatcggcagc tggtgcacga gctggatgag gcagagtacc
721  gggacatccg gctgatggtc atggagatcc gcaatgctta tgctgtgtta tatgacatca
781  tcctgaagaa cttcgagaag ctcaagaagc caggggaga acaaaggga atgatctatt
841  gagagccctc tctcccattc tgtgatgagt acagcagaga ccttcctgct ttttactggg
901  gactccagat ttttccccaaa cttgcttctg ttgagatttt ccctcacct tgcctctcag
961  gcacaataaa tatagttata ccact
```

| SEQ ID NO: 52 | Human IFN-gamma IEF SSP 5111 Protein Sequence, Genbank # AAA16521.1 |
|---|---|

MAMLRVQPEAQAKVDVFREDLCTKTENLLGSYFPKKISELDAFLKEPALNEANLSNLKAPLDIPVPDPVKEKEK
EERKKQQEKEDKDEKKKGEDEDKGPPCGPVNCNEKIVVLLQRLKPEIKDVIEQLNLVTTWLQLQIPRIEDGNNF
GVAVQEKVFELMTSLHTKLEGFHTQISKYFSERGDAVTKAAKQPHVGDYRQLVHELDEAEYRDIRLMVMEIRNA
YAVLYDIILKNFEKLKKPRGETKGMIY

| SEQ ID NO: 53 | Human CCL-19 cDNA Sequence, Genbank #BC027968.1; coding sequence: 125-421 |
|---|---|

```
  1  catcactcac accttgcatt tcaccctgc atcccagtcg ccctgcagcc tcacacagat
 61  cctgcacaca cccagacagc tggcgctcac acattcaccg ttggcctgcc tctgttcacc
121  ctccatggcc ctgctactgg ccctcagcct gctggttctc tggacttccc cagccccaac
181  tctgagtggc accaatgatg ctgaagactg ctgcctgtct gtgacccaga acccatccc
241  tgggtacatc gtgaggaact ccactacct tctcatcaag gatggctgca gggtgcctgc
301  tgtagtgttc accacactga ggggccgcca gctctgtgca ccccagacc agccctgggt
361  agaacgcatc atccagagac tgcagaggac ctcagccaag atgaagcgcc gcagcagtta
421  acctatgacc gtgcagaggg agcccggagt ccgagtcaag cattgtgaat tattacctaa
481  cctggggaac cgaggaccag aaggaaggac caggcttcca gctcctctgc accagacctg
541  accagccagg acagggcctg gggtgtgtgt gagtgtgagt gtgagcgaga gggtgagtgt
601  ggtcagagta aagctgctcc acccccagat tgcaatgcta ccaataaagc cgcctggtgt
661  ttacaactaa aaaaaaaaaa aaaaaaaaa aaaa
```

| SEQ ID NO: 54 | Human CCL-19 Protein Sequence, Genbank #AAH27968.1 |
|---|---|

ALLLALSLLVLWTSPAPTLSGTNDAEDCCLSVTQKPIPGYIVRNFHYLLIKDGCRVPAVVFTTLRGRQLCAPPDQPWVERIIQ
RLQRTSAKMKRRSS

| SEQ ID NO: 55 | Human CCL-21 cDNA Sequence, Genbank #BC027918.1; coding sequence: 8-412 |
|---|---|

```
  1  cacagacatg gctcagtcac tggctctgag cctccttatc ctggttctgg cctttggcat
 61  ccccaggacc caaggcagtg atgggggc tcaggactgt tgcctcaagt acagccaaag
```

TABLE 1-continued

Sequences

```
 121   gaagattccc gccaaggttg tccgcagcta ccggaagcag gaaccaagct taggctgctc
 181   catcccagct atcctgttct tgccccgcaa gcgctctcag gcagagctat gtgcagaccc
 241   aaaggagctc tgggtgcagc agctgatgca gcatctggac aagacaccat ccccacagaa
 301   accagcccag ggctgcagga aggacagggg ggcctccaag actggcaaga aaggaaaggg
 361   ctccaaaggc tgcaagagga ctgagcggtc acagacccct aaagggccat agcccagtga
 421   gcagcctgga gccctggaga ccccaccagc ctcaccagcg cttgaagcct gaacccaaga
 481   tgcaagaagg aggctatgct caggggccct ggagcagcca ccccatgctg gccttgccac
 541   actctttctc ctgctttaac caccccatct gcattcccag ctctaccctg catggctgag
 601   ctgcccacag caggccaggt ccagagagac cgaggaggga gagtctccca gggagcatga
 661   gaggaggcag caggactgtc cccttgaagg agaatcatca ggaccctgga cctgatacgg
 721   ctccccagta cacccccacct cttccttgta aatatgattt atacctaact gaataaaaag
 781   ctgttctgtc ttcccaccca aaaaaaaaaa aaaaaaaaaa aaaaaaaaaa aaaaaaaaaa
 841   aaaaaaaaaa aaaaaa
```

| SEQ ID NO: 56 | Human CCL-21 Protein Sequence, Genbank #AAH27918.1 |
|---|---|

MAQSLALSLLILVLAFGIPRTQGSDGGAQDCCLKYSQRKIPAKVVRSYRKQEPSLGCSIPAILFLPRKRSQAELCADP

KELWVQQLMQHLDKTPSPQKPAQGCRKDRGASKTGKKGKGSKGCKRTERSQTPKGP

| SEQ ID NO: 57 | Human TNF DNA Sequence, Genbank #NM_000594.2; coding sequence: 170-871 |
|---|---|

```
   1   ctccctcagc aaggacagca gaggaccagc taagagggag agaagcaact acagacccccc
  61   cctgaaaaca accctcagac gccacatccc ctgacaagct gccaggcagg ttctcttcct
 121   ctcacatact gacccacggc tccaccctct ctccctgga aaggacacca tgagcactga
 181   aagcatgatc cgggacgtgg agctggccga ggaggcgctc cccaagaaga caggggggcc
 241   ccagggctcc aggcggtgct tgttcctcag cctcttctcc ttcctgatcg tggcaggcgc
 301   caccacgctc ttctgcctgc tgcactttgg agtgatcggc cccagaggg aagagttccc
 361   cagggacctc tctctaatca gccctctggc ccaggcagtc agatcatctt ctcgaacccc
 421   gagtgacaag cctgtagccc atgttgtagc aaaccctcaa gctgaggggc agctccagtg
 481   gctgaaccgc cgggccaatg ccctcctggc caatggcgtg gagctgagag ataaccagct
 541   ggtggtgcca tcagagggcc tgtacctcat ctactcccag gtcctcttca agggccaagg
 601   ctgcccctcc acccatgtgc tcctcaccca ccaccatcagc cgcatcgccg tctcctacca
 661   gaccaaggtc aacctcctct ctgccatcaa gagccctgc cagagggaga ccccagaggg
 721   ggctgaggcc aagccctggt atgagcccat ctatctggga ggggtcttcc agctggagaa
 781   gggtgaccga ctcagcgctg agatcaatcg gcccgactat ctcgactttg ccgagtctgg
 841   gcaggtctac tttgggatca ttgccctgtg aggaggacga acatccaacc ttcccaaacg
 901   cctccctgc cccaatccct ttattacccc ctccttcaga caccctcaac ctcttctggc
 961   tcaaaagag aattgggggc ttagggtcgg aacccaagct tagaacttta agcaacaaga
1021   ccaccacttc gaaacctggg attcaggaat gtgtggcctg cacagtgaag tgctggcaac
1081   cactaagaat tcaaactggg gcctccagaa ctcactgggg cctacagctt tgatccctga
1141   catctggaat ctggagacca gggagccttt ggttctggcc agaatgctgc aggacttgag
1201   aagacctcac ctagaaattg acacaagtgg acctaggcc ttcctctctc cagatgtttc
1261   cagacttcct tgagacacgg agcccagccc tccccatgga gccagctccc tctatttatg
```

TABLE 1-continued

Sequences

```
1321  tttgcacttg tgattattta ttatttattt attatttatt tatttacaga tgaatgtatt
1381  tatttgggag accggggtat cctgggggac caatgtagg agctgccttg gctcagacat
1441  gttttccgtg aaaacggagc tgaacaatag gctgttccca tgtagccccc tggcctctgt
1501  gccttctttt gattatgttt tttaaaatat ttatctgatt aagttgtcta acaatgctg
1561  atttggtgac caactgtcac tcattgctga gcctctgctc cccaggggag ttgtgtctgt
1621  aatcgcccta ctattcagtg gcgagaaata agtttgctt agaaaagaa
```

| SEQ ID NO: 58 | Human TNF Protein Sequence, Genbank #NP_000585.2 |
|---|---|

MSTESMIRDVELAEEALPKKTGGPQGSRRCLFLSLFSFLIVAGATTLFCLLHFGVIGPQREEFPRDLSLISPLAQAVRSSSRT
PSDKPVAHVVANPQAEGQLQWLNRRANALLANGVELRDNQLVVPSEGLYLIYSQVLFKGQGCPSTHVLLTHTISRIAVSYQTK
VNLLSAIKSPCQRETPEGAEAKPWYEPIYLGGVFQLEKGDRLSAEINRPDYLDFAESGQVYFGIIAL

| SEQ ID NO: 59 | Human IL-27 cDNA Sequence, Genbank #BC062422.1; coding sequence: 27-758 |
|---|---|

```
   1  ggggaccaaa gaggctgggc cccgccatgg gccagacggc aggcgacctt ggctggcggc
  61  tcagcctgtt gctgcttccc ttgctcctgg ttcaagctgg tgtctgggga ttcccaaggc
 121  ccccaggag gccccagctg agcctgcagg agctgcggag ggagttcaca gtcagcctgc
 181  atctcgccag gaagctgctc gccgaggttc ggggccaggc ccaccgcttt gcggaatctc
 241  acctgccagg agtgaacctg tacctcctgc cctgggaga gcagctccct gatgtttccc
 301  tgaccttcca ggcctggcgc cgcctctctg acccggagcg tctctgcttc atctccacca
 361  cgcttcagcc cttccatgcc ctgctgggag ggctggggac ccagggccgc tggaccaaca
 421  tggagaggat gcagctgtgg gccatgaggc tggacctccg cgatctgcag cggcacctcc
 481  gcttccaggt gctggctgca ggattcaacc tcccggagga ggaggaggag gaagaggagg
 541  aggaggagga ggagaggaag gggctgctcc cagggcact gggcagcgcc ttacagggcc
 601  cggcccaggt gtcctggccc cagctcctct ccacctaccg cctgctgcac tccttggagc
 661  tcgtcttatc tcgggccgtg cgggagttgc tgctgctgtc caaggctggg cactcagtct
 721  ggcccttggg gttcccaaca ttgagcccc agccctgatc ggtggcttct tagcccctg
 781  cccccaccc tttagaactt taggactgga gtcttggcat cagggcagcc ttcgcatcat
 841  cagccttgga caagggaggg ctcttccagc ccctgcccc aggccctacc cagtaactga
 901  aagcccctct ggtcctcgcc agctatttat ttcttggata tttatttatt gtttagggag
 961  atgatggttt atttattgtc ttggggcccg atggtcctcc tcgggccaag ccccatgct
1021  gggtgcccaa taaagcactc tcatccataa aaaaaaaaaa aaaaaaaaa aaaaaaa
```

| SEQ ID NO: 60 | Human IL-27 Protein Sequence, Genbank #AAH62422.1 |
|---|---|

MGQTAGDLGWRLSLLLLPLLLVQAGVWGFPRPPGRPQLSLQELRREFTVSLHLARKLLAEVRGQAHRFAESHLPGVNLYLLPL
GEQLPDVSLTFQAWRRLSDPERLCFISTTLQPFHALLGGLGTQGRWTNMERMQLWAMRLDLRDLQRHLRFQVLAAGFNLPEEE
EEEEEEEEERKGLLPGALGSALQGPAQVSWPQLLSTYRLLHSLELVLSRAVRELLLLSKAGHSVWFLGFPTLSPQP

| SEQ ID NO: 61 | mCherry sequence |
|---|---|

```
ATGGTGAGCA AGGGCGAGGA GGATAACATG GCCATCATCA AGGAGTTCAT GCGCTTCAAG GTGCACATGG
AGGGCTCCGT GAACGGCCAC GAGTTCGAGA TCGAGGGCGA GGGCGAGGGC CGCCCCTACG AGGGCACCCA
GACCGCCAAG CTGAAGGTGA CCAAGGGTGG CCCCCTGCCC TTCGCCTGGG ACATCCTGTC CCCTCAGTTC
ATGTACGGCT CCAAGGCCTA CGTGAAGCAC CCCGCCGACA TCCCCGACTA CTTGAAGCTG TCCTTCCCCG
```

TABLE 1-continued

Sequences

AGGGCTTCAA GTGGGAGCGC GTGATGAACT TCGAGGACGG CGGCGTGGTG ACCGTGACCC AGGACTCCTC

CCTGCAGGAC GGCGAGTTCA TCTACAAGGT GAAGCTGCGC GGCACCAACT TCCCCTCCGA CGGCCCCGTA

ATGCAGAAGA AGACCATGGG CTGGGAGGCC TCCTCCGAGC GGATGTACCC CGAGGACGGC GCCCTGAAGG

GCGAGATCAA GCAGAGGCTG AAGCTGAAGG ACGGCGGCCA CTACGACGCT GAGGTCAAGA CCACCTACAA

GGCCAAGAAG CCCGTGCAGC TGCCCGGCGC CTACAACGTC AACATCAAGT TGGACATCAC CTCCCACAAC

GAGGACTACA CCATCGTGGA ACAGTACGAA CGCGCCGAGG GCCGCCACTC CACCGGCGGC ATGGACGAGC

TGTACAAGTA A

| SEQ ID NO: 62 | Mouse CCL-21-mCherry-mINT fusion DNA sequence |

ATGGCTCAGATGATGACTCTGAGCCTCCTTAGCCTGGTCCTGGCTCTCTGCATCCCCTGGACCCAAGGCAGTGATGGAGGGGG

TCAGGACTGCTGCCTTAAGTACAGCCAGAAGAAAATTCCCTACAGTATTGTCCGAGGCTATAGGAAGCAAGAACCAAGTTTAG

GCTGTCCCATCCCGGCAATCCTGTTCTCACCCCGGAAGCACTCTAAGCCTGAGCTATGTGCAAACCCTGAGGAAGGCTGGGTG

CAGAACCTGATGCGCCGCCTGGACCAGCCTCCAGCCCCAGGGAAACAAAGCCCCGGCTGCAGGAAGAACCGGGGAACCTCTAA

GTCTGGAAAGAAAGGAAAGGGCTCCAAGGGCTGCAAGAGAACTGAACAGACACAGCCCTCAAGAGGAAGATCC

ATGGTGAGCA AGGGCGAGGA GGATAACATG GCCATCATCA AGGAGTTCAT GCGCTTCAAG GTGCACATGG

AGGGCTCCGT GAACGCCAC GAGTTCGAGA TCGAGGGCGA GGGCGAGGGC CGCCCCTACG AGGGCACCCA

GACCGCCAAG CTGAAGGTGA CCAAGGGTGG CCCCCTGCCC TTCGCCTGGG ACATCCTGTC CCCTCAGTTC

ATGTACGGCT CCAAGGCCTA CGTGAAGCAC CCCGCCGACA TCCCCGACTA CTTGAAGCTG TCCTTCCCCG

AGGGCTTCAA GTGGGAGCGC GTGATGAACT TCGAGGACGG CGGCGTGGTG ACCGTGACCC AGGACTCCTC

CCTGCAGGAC GGCGAGTTCA TCTACAAGGT GAAGCTGCGC GGCACCAACT TCCCCTCCGA CGGCCCCGTA

ATGCAGAAGA AGACCATGGG CTGGGAGGCC TCCTCCGAGC GGATGTACCC CGAGGACGGC GCCCTGAAGG

GCGAGATCAA GCAGAGGCTG AAGCTGAAGG ACGGCGGCCA CTACGACGCT GAGGTCAAGA CCACCTACAA

GGCCAAGAAG CCCGTGCAGC TGCCCGGCGC CTACAACGTC AACATCAAGT TGGACATCAC CTCCCACAAC

GAGGACTACA CCATCGTGGA ACAGTACGAA CGCGCCGAGG GCCGCCACTC CACCGGCGGC ATGGACGAGC

TGTACAAGTA Atgcacacaacactg gcaggatgct gtgccttgga cagaactcct cagtctacag acagaggatg gcttctggaa acttacacca gaactgggac ttatattaaa tcttaataca aatggtttgc acagctttct taaacaaaaa ggcattcaat ctctaggtgt aaaaggaaga gaatgtctcc tggacctaat tgccacaatg ctggtactac agtttattcg caccaggttg gaaaagagg gaatagtgtt caaatcactg atgaaaatgg atgacccttc tatttccagg aatattccct gggcttttga ggcaataaag caagcaagtg aatgggtaag aagaactgaaggacagtacc catctatctg cccacggctt gaactgggga acgactggga ctctgccacc aagcagttgc tgggactcca gcccataagc actgtgtccc ctcttcatag agtcctccat tacagtcaag gctaa

| SEQ ID NO: 63 | Mouse CCL21-forward primer |

GCGCGGATCCCCATGGCTCAGATGATG

| SEQ ID NO: 64 | Mouse CCL-21-reverse primer |

GCGCAGATCTTCCTCTTGAGGGCTGTGTCTG

| SEQ ID NO: 65 | Human CCL21 primer |

CCCCACTAGTCCAGTTCTCAGTCACTGGCTCTG

| SEQ ID NO: 66 | Human CCL21 primer |

CCCCGCTAGCTGGCCCTTTAGGGGTCTGTG

TABLE 1-continued

Sequences

SEQ ID NO: 67    Human CCL21 primer

CCCCGCTAGCTGCACACAACACTGGCAGGA

SEQ ID NO: 68    Human CCL21 primer

GGGGCTCGAGTTAGCCTTGACTGTAATGGA

SEQ ID NO: 69    Human mINT protein sequence (residues 1473-1724 of human VPARP protein sequence)

Ala Asn Leu Arg Leu Pro Met Ala Ser Ala Leu Pro Glu Ala Leu Cys

Ser Gln Ser Arg Thr Thr Pro Val Asp Leu Cys Leu Leu Glu Glu

Ser Val Gly Ser Leu Glu Gly Ser Arg Cys Pro Val Phe Ala Phe

Gln Ser Ser Asp Thr Glu Ser Asp Glu Leu Ser Glu Val Leu Gln

Asp Ser Cys Phe Leu Gln Ile Lys Cys Asp Thr Lys Asp Asp Ser

Ile Pro Cys Phe Leu Glu Leu Lys Glu Glu Asp Glu Ile Val Cys

Thr Gln His Trp Gln Asp Ala Val Pro Trp Thr Glu Leu Leu Ser

Leu Gln Thr Glu Asp Gly Phe Trp Lys Leu Thr Pro Glu Leu Gly

Leu Ile Leu Asn Leu Asn Thr Asn Gly Leu His Ser Phe Leu Lys

Gln Lys Gly Ile Gln Ser Leu Gly Val Lys Gly Arg Glu Cys Leu

Leu Asp Leu Ile Ala Thr Met Leu Val Leu Gln Phe Ile Arg Thr

Arg Leu Glu Lys Glu Gly Ile Val Phe Lys Ser Leu Met Lys Met

Asp Asp Pro Ser Ile Ser Arg Asn Ile Pro Trp Ala Phe Glu Ala

Ile Lys Gln Ala Ser Glu Trp Val Arg Arg Thr Glu Gly Gln Tyr

Pro Ser Ile Cys Pro Arg Leu Glu Leu Gly Asn Asp Trp Asp Ser

Ala Thr Lys Gln Leu Leu Gly Leu Gln Pro Ile Ser Thr Val Ser

Pro Leu His Arg Val Leu His Tyr Ser Gln Gly

REFERENCES CITED

1. Kedersha N L, Rome L H: *Isolation and characterization of a novel ribonucleoprotein particle: large structures contain a single species of small RNA. J Cell Biol* 1986, 103(3):699-709.
2. Kong L B, Siva A C, Rome L H, Stewart P L: *Structure of the vault, a ubiquitous celular component. Structure* 1999, 7(4):371-379.
3. Kedersha N L, Heuser J E, Chugani D C, Rome L H: Vaults. III. *Vault ribonucleoprotein particles open into flower-like structures with octagonal symmetry. J Cell Biol* 1991, 112(2):225-235.
4. Suprenant K A: *Vault ribonucleoprotein particles: sarcophagi, gondolas, or safety deposit boxes? Biochemistry* 2002, 41(49):14447-14454.
5. Berger W, Steiner E, Grusch M, Elbling L, Micksche M: *Vaults and the major vault protein: novel roles in signal pathway regulation and immunity. Cell Mol Life Sci* 2009, 66(1):43-61.
6. Champion C I, Kickhoefer V A, Liu G, Moniz R J, Freed A S, Bergmann L L, Vaccari D, Raval-Fernandes S, Chan A M, Rome L H et al: *A vault nanoparticle vaccine induces protective mucosal immunity. PLoS One* 2009, 4(4):e5409. Epub 209 April 5430.
7. Stephen A G, Raval-Fernandes S, Huynh T, Tones M, Kickhoefer V A, Rome L H: *Assembly of vault-like particles in insect cells expressing only the major vault protein. J Biol Chem* 2001, 276(26):23217-23220. Epub 22001 May 23210.
8. Kickhoefer V A, Garcia Y, Mikyas Y, Johansson E, Zhou J C, Raval-Fernandes S, Minoofar P, Zink J I, Dunn B, Stewart P L et al: *Engineering of vault nanocapsules with enzymatic and fluorescent properties. Proc Natl Acad Sci USA* 2005, 102(12):4348-4352. Epub 205 March 4347.
9. Gunn M, Tangemann K, Tam C, Cyster J, Rosen S, Williams L: *A chemokine expressed in lymphoid high endothelial venules promotes the adhesion and chemotaxis of naive T lymphocytes. Proceedings of the National Academy of Sciences of the United States of America* 1998, 695(1):259-263.
10. Warnock R A, Campbell J J, Dorf M E, Matsuzawa A, McEvoy L M, Butcher E C: *The role of chemokines in the microenvironmental control of T versus B cell arrest in Peyer's patch high endothelial venules. J Exp Med* 2000, 191(1):77-88.
11. Willimann K, Legler D F, Loetscher M, Roos R S, Delgado M B, Clark-Lewis I, Baggiolini M, Moser B: *The chemokine SLC is expressed in T cell areas of lymph nodes and mucosal lymphoid tissues and attracts activated T cells via CCR7. Eur J Immunol* 1998, 28(6):2025-2034.

12. Sharma S, Stolina M, Luo J, Strieter R M, Burdick M, Zhu L X, Batra R K, Dubinett S M: *Secondary lymphoid tissue chemokine mediates T cell-dependent antitumor responses in vivo.* J Immunol 2000, 164(9):4558-4563.
13. Yang S C, Hillinger S, Riedl K, Zhang L, Zhu L, Huang M, Atianzar K, Kuo B Y, Gardner B, Batra R K et al: *Intratumoral administration of dendritic cells overexpressing CCL21 generates systemic antitumor responses and confers tumor immunity.* Clin Cancer Res 2004, 10(8):2891-2901.
14. Yang S C, Batra R K, Hillinger S, Reckamp K L, Strieter R M, Dubinett S M, Sharma S: *Intrapulmonary administration of CCL21 gene-modified dendritic cells reduces tumor burden in spontaneous murine bronchoalveolar cell carcinoma.* Cancer Res 2006, 66(6):3205-3213.
15. Kirk C J, Hartigan-O'Connor D, Mule J J: *The dynamics of the T-cell antitumor response: chemokine-secreting dendritic cells can prime tumor-reactive T cells extranodally.* Cancer Res 2001, 61(24):8794-8802.
16. Novak L, Igoucheva O, Cho S, Alexeev V: *Characterization of the CCL21-mediated melanoma-specific immune responses and in situ melanoma eradication.* Mol Cancer Ther 2007, 6(6):1755-1764.
17. Liang C M, Zhong C P, Sun R X, Liu B B, Huang C, Qin J, Zhou S, Shan J, Liu Y K, Ye S L: *Local expression of secondary lymphoid tissue chemokine delivered by adeno-associated virus within the tumor bed stimulates strong anti-liver tumor immunity.* J Virol 2007, 81(17):9502-9511. Epub 207 June 9513.
18. Wu S, Xing W, Peng J, Yuan X, Zhao X, Lei P, Li W, Wang M, Zhu H, Huang B et al: *Tumor transfected with CCL21 enhanced reactivity and apoptosis resistance of human monocyte-derived dendritic cells.* Immunobiology 2008, 213(5):417-426. Epub 207 November 2028.
19. Yousefieh N, Hahto S M, Stephens A L, Ciavarra R P: *Regulated Expression of CCL21 in the Prostate Tumor Microenvironment Inhibits Tumor Growth and Metastasis in an Orthotopic Model of Prostate Cancer.* Cancer Microenviron 2009, 6:6.
20. Baratelli F, Takedatsu H, Hazra S, Peebles K, Luo J, Kurimoto P S, Zeng G, Batra R K, Sharma S, Dubinett S M et al: *Pre-clinical characterization of GMP grade CCL21-gene modified dendritic cells for application in a phase I trial in Non-Small Cell Lung Cancer.* J Transl Med 2008, 6(1):38.
21. Lai C Y, Wiethoff C M, Kickhoefer V A, Rome L H, Nemerow G R: *Vault nanoparticles containing an adenovirus-derived membrane lytic protein facilitate toxin and gene transfer.* ACS Nano 2009, 3(3):691-699.
22. Siva A C, Raval-Fernandes S, Stephen A G, LaFemina M J, Scheper R J, Kickhoefer V A, Rome L H: *Up-regulation of vaults may be necessary but not sufficient for multidrug resistance.* Int J Cancer 2001, 92(2):195-202.
23. Kickhoefer V A, Siva A C, Kedersha N L, Inman E M, Ruland C, Streuli M, Rome L H: *The 193-kD vault protein, VPARP, is a novel poly(ADP-ribose) polymerase.* J Cell Blot 1999, 146(5):917-928.
24. Andersson A, Yang S C, Huang M, Zhu L, Kar U K, Batra R K, Elashoff D, Strieter R M, Dubinett S M, Sharma S: *IL-7 promotes CXCR3 ligand-dependent T cell antitumor reactivity in lung cancer.* J Immunol 2009, 182(11):6951-6958.
25. Chen H, Liakou C I, Kamat A, Pettaway C, Ward J F, Tang D N, Sun J, Jungbluth A A, Troncoso P, Logothetis C et al: *Anti-CTLA-4 therapy results in higher CD4+ ICOShi T cell frequency and IFN-gamma levels in both nonmalignant and malignant prostate tissues.* Proc Natl Acad Sci USA 2009, 106(8):2729-2734. Epub 209 February 2726.
26. Mikyas Y, Makabi M, Raval-Fernandes S, Harrington L, Kickhoefer V A, Rome L H, Stewart P L: *Cryoelectron microscopy imaging of recombinant and tissue derived vaults: localization of the MVP N termini and VPARP.* J Mol Biol 2004, 344(1):91-105.
27. Sharma S, Stolina M, Zhu L, Lin Y, Batra R, Huang M, Strieter R, Dubinett S M: *Secondary lymphoid organ chemokine reduces pulmonary tumor burden in spontaneous murine bronchoalveolar cell carcinoma.* Cancer research 2001, 61(17):6406-6412.
28. Sharma S, Yang S C, Hillinger S, Zhu L X, Huang M, Batra R K, Lin J F, Burdick M D, Strieter R M, Dubinett S M: *SLC/CCL21-mediated anti-tumor responses require IFNgamma, MIG/CXCL9 and IP-10/CXCL10.* Molecular cancer 2003, 2(1):22.
29. Kickhoefer V A, Han M, Raval-Fernandes S, Poderycki M J, Moniz R J, Vaccari D, Silvestry M, Stewart P L, Kelly K A, Rome L H: *Targeting vault nanoparticles to specific cell surface receptors.* ACS Nano 2009, 3(1):27-36.
30. Johnson S K, Kerr K M, Chapman A D, Kennedy M M, King G, Cockburn J S, Jeffrey R R: *Immune cell infiltrates and prognosis in primary carcinoma of the lung.* Lung Cancer 2000, 27(1):27-35.
31. Hiraoka K, Miyamoto M, Cho Y, Suzuoki M, Oshikiri T, Nakakubo Y, Itoh T, Ohbuchi T, Kondo S, Katoh H: *Concurrent infiltration by CD8+ T cells and CD4+ T cells is a favourable prognostic factor in non-small-cell lung carcinoma.* Br J Cancer 2006, 94(2):275-280.
32. Dieu-Nosjean M C, Antoine M, Danel C, Heudes D, Wislez M, Poulot V, Rabbe N, Laurans L, Tartour E, de Chaisemartin L et al: *Long-term survival for patients with non-small-cell lung cancer with intratumoral lymphoid structures.* J Clin Oncol 2008, 26(27):4410-4417.
33. Woo E Y, Yeh H, Chu C S, Schlienger K, Carroll R G, Riley J L, Kaiser L R, June C H: *Cutting edge: Regulatory T cells from lung cancer patients directly inhibit autologous T cell proliferation.* J Immunol 2002, 168(9):4272-4276.
34. Yannelli J R, Tucker J A, Hidalgo G, Perkins S, Kryscio R, Hirschowitz E A: *Characteristics of PBMC obtained from leukapheresis products and tumor biopsies of patients with non-small cell lung cancer.* Oncol Rep 2009, 22(6):1459-1471.
35. Li L, Chao Q G, Ping L Z, Xue C, Xia Z Y, Qian D, Shi-ang H: *The prevalence of FOXP3+ regulatory T-cells in peripheral blood of patients with NSCLC.* Cancer Biother Radiopharm 2009, 24(3):357-367.
36. Ju S, Qiu H, Zhou X, Zhu B, Lv X, Huang X, Li J, Zhang Y, Liu L, Ge Y et al: *CD13+CD4+CD25hi regulatory T cells exhibit higher suppressive function and increase with tumor stage in non-small cell lung cancer patients.* Cell cycle (Georgetown, Tex. 2009, 8(16):2578-2585.
37. Sakaguchi S: *Regulatory T cells: key controllers of immunologic self-tolerance.* Cell 2000, 101(5):455-458.
38. Boon T, Cerottini J-C, Van den Eynde B, van der Bruggen P, Van Pel A: *Tumor antigens recognized by T lymphocytes.* Annu Rev Immunol 1994, 12:337-365.
39. Li C, Heidt D G, Dalerba P, Burant C F, Zhang L, Adsay V, Wicha M, Clarke M F, Simeone D M: Identification of pancreatic cancer stem cells. Cancer research 2007, 67(3): 1030-1037.
40. Smyth M J, Teng M W, Swann J, Kyparissoudis K, Godfrey D I, Hayakawa Y: *CD4+CD25+ T regulatory* cells suppress NK cell-mediated immunotherapy of cancer. *J Immunol* 2006, 176(3):1582-1587.
41. Young M R, Wright M A, Pandit R: *Myeloid differentiation treatment to diminish the presence of immune-suppressive CD34+ cells within human head and neck squamous cell carcinomas. J Immunol* 1997, 159(2):990-996.
42. Kusmartsev S A, Kusmartseva I N, Afanasyev S G, Cherdyntseva N V: *Immunosuppressive cells in bone marrow of patients with stomach cancer. Adv Exp Med Biol* 1998, 451:189-194.
43. Almand B, Clark J I, Nikitina E, van Beynen J, English N R, Knight S C, Carbone D P, Gabrilovich D I: *Increased production of immature myeloid cells in cancer patients: a mechanism of immunosuppression in cancer. J Immunol* 2001, 166(1):678-689.
44. Diaz-Montero C M, Salem M L, Nishimura M I, Garrett-Mayer E, Cole D J, Montero A J: *Increased circulating myeloid-derived suppressor cells correlate with clinical cancer stage, metastatic tumor burden, and doxorubicin-cyclophosphamide chemotherapy. Cancer Immunol Immunother* 2009, 58(1):49-59.
45. Liu C Y, Wang Y M, Wang C L, Feng P H, Ko H W, Liu Y H, Wu Y C, Chu Y, Chung F T, Kuo C H et al: *Population alterations of L: -arginase- and inducible nitric oxide synthase-expressed CD11b(+)/CD14(-)/CD15 (+)/CD33 (+) myeloid-derived suppressor cells and CD8 (+) T lymphocytes in patients with advanced-stage non-small cell lung cancer. J Cancer Res Clin Oncol* 2009.
46. Srivastava M K, Bosch J J, Thompson J A, Ksander B R, Edelman M J, Ostrand-Rosenberg S: *Lung cancer patients' CD4(+) T cells are activated in vitro by MHC II cell-based vaccines despite the presence of myeloid-derived suppressor cells. Cancer Immunol Immunother* 2008, 57(10):1493-1504.
47. Young M R, Newby M, Wepsic H T: *Hematopoiesis and suppressor bone marrow cells in mice bearing large metastatic Lewis lung carcinoma tumors. Cancer Res* 1987, 47(1):100-105.
48. Subiza J L, Vinuela J E, Rodriguez R, Gil J, Figueredo M A, De La Concha E G: *Development of splenic natural suppressor (NS) cells in Ehrlich tumor-bearing mice. Int J Cancer* 1989, 44(2):307-314.
49. Kusmartsev S A, Ogreba V I: [*Suppressor activity of bone marrow and spleen cells in C57Bl/6 mice during carcinogenesis induced by 7,12-dimethylbenz(a)anthracene*]. *Eksp Onkol* 1989, 11(5):23-26.
50. Kusmartsev S A, Li Y, Chen S H: *Gr-1+ myeloid cells derived from tumor-bearing mice inhibit primary T cell activation induced through CD3/CD28 costimulation. J Immunol* 2000, 165(2):779-785.
51. Sinha P, Clements V K, Ostrand-Rosenberg S: *Reduction of Myeloid-Derived Suppressor Cells and Induction of M1 Macrophages Facilitate the Rejection of Established Metastatic Disease. J Immunol* 2005, 174(2):636-645.
52. Liu C, Yu S, Kappes J, Wang J, Grizzle W E, Zinn K R, Zhang H G: *Expansion of spleen myeloid suppressor cells represses NK cell cytotoxicity in tumor-bearing host. Blood* 2007, 109(10):4336-4342.
53. Maeda et al., *Tumor Vascular* permeability and the EPR effect in macromolecular therapeutics: a review. *J. of Controlled Release* 2000, 65: 271-284.
54. Griesh, K., *Enhanced permeability and retention of macromolecular drugs in solid tumors: A royal gate for targeted anticancer nanomedicines. J. of Drug Targeting* 2007, 15(7-8): 457-464
55. Allen et al., *Drug Delivery Systems: Entering the Mainstream. Science* 2004, 303:1818-1822.

The invention claimed is:

1. A method of preparing a composition comprising a vault complex, said vault complex comprising a vault particle and a cytokine fusion protein, the method comprising a) mixing the cytokine fusion protein with the vault particle to generate a mixture, wherein the cytokine fusion protein comprises a cytokine and a vault targeting domain, which said vault targeting domain is a vault poly ADP-ribose polymerase (VPARP) sequence or a portion thereof that interacts with the major vault protein, or a telomerase/vault associated protein 1 (TEP 1) sequence or a portion thereof that interacts with the major vault protein, and wherein the vault particle comprises a major vault protein (MVP); and b) incubating the mixture for a sufficient period of time to allow non-covalent association of the cytokine fusion protein with the vault particle, thereby generating the vault complex.

2. The method of claim 1, wherein the MVP is human MVP.

3. The method of claim 1, wherein the cytokine fusion protein and the MVP are generated in Sf9 or insect larvae cells.

4. The method of claim 1, wherein the vault targeting domain is a) a vault poly-ADP ribose polymerase (VPARP) sequence or a portion thereof that interacts with the MVP; or b) a telomerase/vault associated protein 1 (TEP 1) sequence or a portion thereof that interacts with the MVP.

5. The method of claim 1, wherein the cytokine fusion protein is non-covalently associated with the vault particle.

6. The method of claim 1, wherein the cytokine is a chemokine.

7. The method of claim 6, wherein the chemokine is a cysteine-cysteine (CC) chemokine.

8. The method of claim 7, wherein the CC chemokine is a CCL-21 chemokine.

9. The method of claim 1, wherein the cytokine comprises the amino acid sequence of SEQ ID NO: 2.

10. The method of claim 4, wherein the vault targeting domain is the portion of the VPARP that is a major vault protein interaction (mINT) domain.

11. The method of claim 10, wherein the mINT domain comprises the amino acid sequence of SEQ ID NO: 8.

12. The method of claim 1, wherein the cytokine fusion protein comprises the amino acid sequence of SEQ ID NO: 13.

* * * * *

SEQUENCE LISTING

```
<160> NUMBER OF SEQ ID NOS: 69

<210> SEQ ID NO 1
<211> LENGTH: 133
<212> TYPE: PRT
<213> ORGANISM: Mus sp.

<400> SEQUENCE: 1

Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gln Asp Cys Cys
            20                  25                  30

Leu Lys Tyr Ser Gln Lys Lys Ile Pro Tyr Ser Ile Val Arg Gly Tyr
            35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
                100                 105                 110

Gly Lys Lys Gly Lys Gly Ser Lys Gly Cys Lys Arg Thr Glu Gln Thr
            115                 120                 125

Gln Pro Ser Arg Gly
```

-continued

```
                130

<210> SEQ ID NO 2
<211> LENGTH: 134
<212> TYPE: PRT
<213> ORGANISM: Homo sapiens

<400> SEQUENCE: 2

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 3
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggctcaga tgatgactct gagcctcctt agcctggtcc tggctctctg catcccctgg      60
acccaaggca gtgatggagg gggtcaggac tgctgcctta agtacagcca agagaaaatt     120
ccctacagta ttgtccgagg ctataggaag caagaaccaa gtttaggctg tcccatcccg     180
gcaatcctgt tctcaccccg gaagcactct aagcctgagc tatgtgcaaa ccctgaggaa     240
ggctgggtgc agaacctgat gcgccgcctg gaccagcctc agcccccagg gaaacaaagc     300
cccggctgca ggaagaaccg ggaaccctct aagtctggaa agaaaggaaa gggctccaag     360
ggctgcaaga gaactgaaca gacacagccc tcaagagga                            399

<210> SEQ ID NO 4
<211> LENGTH: 402
<212> TYPE: DNA
<213> ORGANISM: Mus sp.

<400> SEQUENCE: 4
atggctcaga tgatgactct gagcctcctt agcctggtcc tggctctctg catcccctgg      60
acccaaggca gtgatggagg gggtcaggac tgctgcctta agtacagcca agagaaaatt     120
ccctacagta ttgtccgagg ctataggaag caagaaccaa gtttaggctg tcccatcccg     180
gcaatcctgt tctcaccccg gaagcactct aagcctgagc tatgtgcaaa ccctgaggaa     240
ggctgggtgc agaacctgat gcgccgcctg gaccagcctc agcccccagg gaaacaaagc     300
```

```
cccggctgca ggaagaaccg gggaacctct aagtctggaa agaaaggaaa gggctccaag    360
ggctgcaaga gaactgaaca gacacagccc tcaagaggat ag                      402
```

<210> SEQ ID NO 5
<211> LENGTH: 405
<212> TYPE: DNA
<213> ORGANISM: Homo sapiens

<400> SEQUENCE: 5

```
atggctcagt cactggctct gagcctcctt atcctggttc tggcctttgg catcccagg     60 acccaaggca gtgatggagg ggctcaggac tgttgcctca agtacagcca aaggaagatt   120
cccgccaagg ttgtccgcag ctaccggaag caggaaccaa gcttaggctg ctccatccca   180
gctatcctgt tcttgccccg caagcgctct caggcagagc tatgtgcaga cccaaaggag   240
ctctgggtgc agcagctgat gcagcatctg acaagacac catccccaca gaaaccagcc   300
cagggctgca ggaaggacag gggggcctcc aagactggca agaaggaaa gggctccaaa   360 ggctgcaaga ggactgagcg gtcacagacc cctaaagggc catag                   405
```

<210> SEQ ID NO 6
<211> LENGTH: 489
<212> TYPE: DNA
<213> ORGANISM: Mus sp.

<400> SEQUENCE: 6

```
tgcacacaac actggcagga tgctgtgcct tggacagaac tcctcagtct acagacagag    60
gatggcttct ggaaacttac accagaactg ggacttatat taaatcttaa tacaaatggt   120
ttgcacagct ttcttaaaca aaaaggcatt caatctctag gtgtaaaagg aagagaatgt   180
ctcctggacc taattgccac aatgctggta ctacagttta ttcgcaccag gttggaaaaa   240
gagggaatag tgttcaaatc actgatgaaa atggatgacc cttctatttc caggaatatt   300
ccctgggctt ttgaggcaat aaagcaagca agtgaatggg taagaagaac tgaaggacag   360
tacccatcta tctgcccacg gcttgaactg gggaacgact gggactctgc caccaagcag   420
ttgctgggac tccagcccat aagcactgtg tccctcttc atagagtcct ccattacagt   480
caaggctaa                                                           489
```

<210> SEQ ID NO 7
<211> LENGTH: 489
<212> TYPE: DNA
<213> ORGANISM: Homo sapiens

<400> SEQUENCE: 7

```
tgcacacaac actggcagga tgctgtgcct tggacagaac tcctcagtct acagacagag    60
gatggcttct ggaaacttac accagaactg ggacttatat taaatcttaa tacaaatggt   120
ttgcacagct ttcttaaaca aaaaggcatt caatctctag gtgtaaaagg aagagaatgt   180
ctcctggacc taattgccac aatgctggta ctacagttta ttcgcaccag gttggaaaaa   240
gagggaatag tgttcaaatc actgatgaaa atggatgacc cttctatttc caggaatatt   300
ccctgggctt ttgaggcaat aaagcaagca agtgaatggg taagaagaac tgaaggacag   360
tacccatcta tctgcccacg gcttgaactg gggaacgact gggactctgc caccaagcag   420
ttgctgggac tccagcccat aagcactgtg tccctcttc atagagtcct ccattacagt   480
caaggctaa                                                           489
```

<210> SEQ ID NO 8
<211> LENGTH: 162
<212> TYPE: PRT
<213> ORGANISM: Homo sapiens

<400> SEQUENCE: 8

```
Cys Thr Gln His Trp Gln Asp Ala Val Pro Trp Thr Glu Leu Leu Ser
1               5                   10                  15

Leu Gln Thr Glu Asp Gly Phe Trp Lys Leu Thr Pro Glu Leu Gly Leu
            20                  25                  30

Ile Leu Asn Leu Asn Thr Asn Gly Leu His Ser Phe Leu Lys Gln Lys
        35                  40                  45

Gly Ile Gln Ser Leu Gly Val Lys Gly Arg Glu Cys Leu Leu Asp Leu
    50                  55                  60

Ile Ala Thr Met Leu Val Leu Gln Phe Ile Arg Thr Arg Leu Glu Lys
65                  70                  75                  80

Glu Gly Ile Val Phe Lys Ser Leu Met Lys Met Asp Asp Pro Ser Ile
                85                  90                  95

Ser Arg Asn Ile Pro Trp Ala Phe Glu Ala Ile Lys Gln Ala Ser Glu
            100                 105                 110

Trp Val Arg Arg Thr Glu Gly Gln Tyr Pro Ser Ile Cys Pro Arg Leu
        115                 120                 125

Glu Leu Gly Asn Asp Trp Asp Ser Ala Thr Lys Gln Leu Leu Gly Leu
    130                 135                 140

Gln Pro Ile Ser Thr Val Ser Pro Leu His Arg Val Leu His Tyr Ser
145                 150                 155                 160

Gln Gly
```

<210> SEQ ID NO 9
<211> LENGTH: 162
<212> TYPE: PRT
<213> ORGANISM: Mus sp.

<400> SEQUENCE: 9

```
Cys Thr Gln His Trp Gln Asp Ala Val Pro Trp Thr Glu Leu Leu Ser
1               5                   10                  15

Leu Gln Thr Glu Asp Gly Phe Trp Lys Leu Thr Pro Glu Leu Gly Leu
            20                  25                  30

Ile Leu Asn Leu Asn Thr Asn Gly Leu His Ser Phe Leu Lys Gln Lys
        35                  40                  45

Gly Ile Gln Ser Leu Gly Val Lys Gly Arg Glu Cys Leu Leu Asp Leu
    50                  55                  60

Ile Ala Thr Met Leu Val Leu Gln Phe Ile Arg Thr Arg Leu Glu Lys
65                  70                  75                  80

Glu Gly Ile Val Phe Lys Ser Leu Met Lys Met Asp Asp Pro Ser Ile
                85                  90                  95

Ser Arg Asn Ile Pro Trp Ala Phe Glu Ala Ile Lys Gln Ala Ser Glu
            100                 105                 110

Trp Val Arg Arg Thr Glu Gly Gln Tyr Pro Ser Ile Cys Pro Arg Leu
        115                 120                 125

Glu Leu Gly Asn Asp Trp Asp Ser Ala Thr Lys Gln Leu Leu Gly Leu
    130                 135                 140

Gln Pro Ile Ser Thr Val Ser Pro Leu His Arg Val Leu His Tyr Ser
145                 150                 155                 160

Gln Gly
```

<210> SEQ ID NO 10
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggctcaga tgatgactct gagcctcctt agcctggtcc tggctctctg catcccctgg      60
acccaaggca gtgatggagg gggtcaggac tgctgcctta agtacagcca gaagaaaatt    120
ccctacagta ttgtccgagg ctataggaag caagaaccaa gtttaggctg tcccatcccg    180
gcaatcctgt tctcacccg gaagcactct aagcctgagc tatgtgcaaa ccctgaggaa      240
ggctgggtgc agaacctgat gcgccgcctg accagcctc cagccccagg gaaacaaagc      300
cccggctgca ggaagaaccg ggaacctct aagtctggaa agaaaggaaa gggctccaag      360
ggctgcaaga gaactgaaca gacacagccc tcaagaggat gcacacaaca ctggcaggat    420
gctgtgcctt ggacagaact cctcagtcta cagacagagg atggcttctg gaaacttaca    480
ccagaactgg gacttatatt aaatcttaat acaaatggtt tgcacagctt tcttaaacaa    540
aaaggcattc aatctctagg tgtaaaagga agagaatgtc tcctggacct aattgccaca    600
atgctggtac tacagtttat tcgcaccagg ttggaaaaag agggaatagt gttcaaatca    660
ctgatgaaaa tggatgaccc ttctatttcc aggaatattc cctgggcttt tgaggcaata    720
aagcaagcaa gtgaatgggt aagaagaact gaaggacagt acccatctat ctgcccacgg    780
cttgaactgg ggaacgactg ggactctgcc accaagcagt tgctgggact ccagcccata    840
agcactgtgt cccctcttca tagagtcctc cattacagtc aaggctaa                 888

<210> SEQ ID NO 11
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atggctcagt cactggctct gagcctcctt atcctggttc tggcctttgg catccccagg      60
acccaaggca gtgatggagg ggctcaggac tgttgcctca agtacagcca aggaagatt     120 cccgccaagt tgtccgcag ctaccggaag caggaaccaa gcttaggctg ctccatccca     180
gctatcctgt tcttgccccg caagcgctct caggcagagc tatgtgcaga cccaaaggag    240
ctctgggtgc agcagctgat gcagcatctg gacaagacac atccccaca gaaaccagcc      300 cagggctgca ggaaggacag gggggcctcc aagactggca agaaaggaaa gggctccaaa    360
ggctgcaaga gactgagcg gtcacagacc cctaaaggc cagctagctg cacacaacac      420
tggcaggatg ctgtgccttg gacagaactc ctcagtctac agacagagga tggcttctgg    480
aaacttacac cagaactggg acttatatta aatcttaata caaatggttt gcacagcttt    540
cttaaacaaa aaggcattca atctctaggt gtaaaaggaa gagaatgtct cctggaccta    600
attgccacaa tgctggtact acagtttatt cgcaccaggt tggaaaaaga gggaatagtg    660
ttcaaatcac tgatgaaaat ggatgaccct tctatttcca ggaatattcc ctgggctttt    720
gaggcaataa agcaagcaag tgaatgggta agaagaactg aaggacagta cccatctatc    780

```
tgcccacggc ttgaactggg gaacgactgg gactctgcca ccaagcagtt gctgggactc      840
cagcccataa gcactgtgtc ccctcttcat agagtcctcc attacagtca aggctaa        897
```

```
<210> SEQ ID NO 12
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

| | | | | | | | | | | | | | | |
|---|---|---|---|---|---|---|---|---|---|---|---|---|---|---|
| Met | Ala | Gln | Met | Met | Thr | Leu | Ser | Leu | Leu | Ser | Leu | Val | Leu | Ala | Leu |
| 1 | | | | 5 | | | | | 10 | | | | | 15 | |

Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly Cys Thr Gln His Trp Gln Asp Ala Val Pro Trp
    130                 135                 140

Thr Glu Leu Leu Ser Leu Gln Thr Glu Asp Gly Phe Trp Lys Leu Thr
145                 150                 155                 160

Pro Glu Leu Gly Leu Ile Leu Asn Leu Asn Thr Asn Gly Leu His Ser
                165                 170                 175

Phe Leu Lys Gln Lys Gly Ile Gln Ser Leu Gly Val Lys Gly Arg Glu
            180                 185                 190

Cys Leu Leu Asp Leu Ile Ala Thr Met Leu Val Leu Gln Phe Ile Arg
        195                 200                 205

Thr Arg Leu Glu Lys Glu Gly Ile Val Phe Lys Ser Leu Met Lys Met
    210                 215                 220

Asp Asp Pro Ser Ile Ser Arg Asn Ile Pro Trp Ala Phe Glu Ala Ile
225                 230                 235                 240

Lys Gln Ala Ser Glu Trp Val Arg Arg Thr Glu Gly Gln Tyr Pro Ser
                245                 250                 255

Ile Cys Pro Arg Leu Glu Leu Gly Asn Asp Trp Asp Ser Ala Thr Lys
            260                 265                 270

Gln Leu Leu Gly Leu Gln Pro Ile Ser Thr Val Ser Pro Leu His Arg
        275                 280                 285

Val Leu His Tyr Ser Gln Gly
    290                 295

<210> SEQ ID NO 13
<211> LENGTH: 298
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 13

Met Ala Gln Ser Leu Ala Leu Ser Leu Leu Ile Leu Val Leu Ala Phe
1               5                   10                  15

Gly Ile Pro Arg Thr Gln Gly Ser Asp Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro Ala Ser Cys Thr Gln His Trp Gln Asp Ala
    130                 135                 140

Val Pro Trp Thr Glu Leu Leu Ser Leu Gln Thr Glu Asp Gly Phe Trp
145                 150                 155                 160

Lys Leu Thr Pro Glu Leu Gly Leu Ile Leu Asn Leu Asn Thr Asn Gly
                165                 170                 175

Leu His Ser Phe Leu Lys Gln Lys Gly Ile Gln Ser Leu Gly Val Lys
            180                 185                 190

Gly Arg Glu Cys Leu Leu Asp Leu Ile Ala Thr Met Leu Val Leu Gln
        195                 200                 205

Phe Ile Arg Thr Arg Leu Glu Lys Glu Gly Ile Val Phe Lys Ser Leu
    210                 215                 220

Met Lys Met Asp Asp Pro Ser Ile Ser Arg Asn Ile Pro Trp Ala Phe
225                 230                 235                 240

Glu Ala Ile Lys Gln Ala Ser Glu Trp Val Arg Arg Thr Glu Gly Gln
                245                 250                 255

Tyr Pro Ser Ile Cys Pro Arg Leu Glu Leu Gly Asn Asp Trp Asp Ser
            260                 265                 270

Ala Thr Lys Gln Leu Leu Gly Leu Gln Pro Ile Ser Thr Val Ser Pro
        275                 280                 285

Leu His Arg Val Leu His Tyr Ser Gln Gly
    290                 295

<210> SEQ ID NO 14
<211> LENGTH: 1724
<212> TYPE: PRT
<213> ORGANISM: Homo sapiens

<400> SEQUENCE: 14

Met Val Met Gly Ile Phe Ala Asn Cys Ile Phe Cys Leu Lys Val Lys
1               5                   10                  15

Tyr Leu Pro Gln Gln Lys Lys Leu Gln Thr Asp Ile Lys Glu
            20                  25                  30

Asn Gly Gly Lys Phe Ser Phe Ser Leu Asn Pro Gln Cys Thr His Ile
        35                  40                  45

Ile Leu Asp Asn Ala Asp Val Leu Ser Gln Tyr Gln Leu Asn Ser Ile

```
                50              55              60
Gln Lys Asn His Val His Ile Ala Asn Pro Asp Phe Ile Trp Lys Ser
 65                  70                  75                  80

Ile Arg Glu Lys Arg Leu Leu Asp Val Lys Asn Tyr Asp Pro Tyr Lys
                     85                  90                  95

Pro Leu Asp Ile Thr Pro Pro Asp Gln Lys Ala Ser Ser Ser Glu
                100                 105                 110

Val Lys Thr Glu Gly Leu Cys Pro Asp Ser Ala Thr Glu Glu Glu Asp
            115                 120                 125

Thr Val Glu Leu Thr Glu Phe Gly Met Gln Asn Val Glu Ile Pro His
        130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Glu Leu Gln Cys Ser
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
            195                 200                 205

Glu Asp Ala Ser Glu Tyr Phe Glu Asn Tyr Ile Glu Glu Leu Lys Lys
    210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Leu Glu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
            275                 280                 285

Ile Ser Leu Asn Asp Val Ser Lys Ala Glu Gly Ile Leu Leu Leu Val
    290                 295                 300

Lys Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
                325                 330                 335

Glu Val Asn Leu Gly Leu Leu Ala Lys Lys Ala Asp Leu Cys Gln Leu
            340                 345                 350

Ile Arg Asp Met Val Asn Val Cys Glu Thr Asn Leu Ser Lys Pro Asn
            355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                405                 410                 415

Val Gly Arg Val Asn Glu Thr Thr Glu Phe Leu Ser Lys Leu Gly Asn
            420                 425                 430

Val Arg Pro Leu Leu His Gly Ser Pro Val Gln Asn Ile Val Gly Ile
            435                 440                 445

Leu Cys Arg Gly Leu Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480
```

```
Ser Leu Ser Thr Ser Ile Lys Tyr Ser His Pro Gly Glu Thr Asp Gly
            485                 490                 495

Thr Arg Leu Leu Leu Ile Cys Asp Val Ala Leu Gly Lys Cys Met Asp
            500                 505                 510

Leu His Glu Lys Asp Phe Pro Leu Thr Glu Ala Pro Pro Gly Tyr Asp
            515                 520                 525

Ser Val His Gly Val Ser Gln Thr Ala Ser Val Thr Thr Asp Phe Glu
            530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                565                 570                 575

Ser Asp His Thr Glu Leu Glu Glu Tyr Arg Pro Glu Phe Ser Asn Phe
            580                 585                 590

Ser Lys Val Glu Asp Tyr Gln Leu Pro Asp Ala Lys Thr Ser Ser Ser
            595                 600                 605

Thr Lys Ala Gly Leu Gln Asp Ala Ser Gly Asn Leu Val Pro Leu Glu
            610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                645                 650                 655

Tyr Ile Phe Pro Leu Asp Asp Lys Ala Ala Val Cys Gly Phe Glu Ala
                660                 665                 670

Phe Ile Asn Gly Lys His Ile Val Gly Glu Ile Lys Glu Lys Glu Glu
            675                 680                 685

Ala Gln Gln Glu Tyr Leu Glu Ala Val Thr Gln Gly His Gly Ala Tyr
            690                 695                 700

Leu Met Ser Gln Asp Ala Pro Asp Val Phe Thr Val Ser Val Gly Asn
705                 710                 715                 720

Leu Pro Pro Lys Ala Lys Val Leu Ile Lys Ile Thr Tyr Ile Thr Glu
                725                 730                 735

Leu Ser Ile Leu Gly Thr Val Gly Val Phe Phe Met Pro Ala Thr Val
            740                 745                 750

Ala Pro Trp Gln Gln Asp Lys Ala Leu Asn Glu Asn Leu Gln Asp Thr
            755                 760                 765

Val Glu Lys Ile Cys Ile Lys Glu Ile Gly Thr Lys Gln Ser Phe Ser
770                 775                 780

Leu Thr Met Ser Ile Glu Met Pro Tyr Val Ile Glu Phe Ile Phe Ser
785                 790                 795                 800

Asp Thr His Glu Leu Lys Gln Lys Arg Thr Asp Cys Lys Ala Val Ile
                805                 810                 815

Ser Thr Met Glu Gly Ser Ser Leu Asp Ser Ser Gly Phe Ser Leu His
            820                 825                 830

Ile Gly Leu Ser Ala Ala Tyr Leu Pro Arg Met Trp Val Glu Lys His
            835                 840                 845

Pro Glu Lys Glu Ser Glu Ala Cys Met Leu Val Phe Gln Pro Asp Leu
850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
                885                 890                 895
```

-continued

```
Gln Ile Thr Leu His Ala Leu Ser Leu Val Gly Glu Lys Gln Lys Val
                900                 905                 910

Asn Ile Ile Gln Phe Gly Thr Gly Tyr Lys Glu Leu Phe Ser Tyr Pro
            915                 920                 925

Lys His Ile Thr Ser Asn Thr Thr Ala Ala Glu Phe Ile Met Ser Ala
        930                 935                 940

Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
                965                 970                 975

Asp Gly His Leu Gln Asp Glu Ser Leu Thr Leu Gln Leu Val Lys Arg
            980                 985                 990

Ser Arg Pro His Thr Arg Leu Phe Ala Cys Gly Ile Gly Ser Thr Ala
        995                 1000                1005

Asn Arg His Val Leu Arg Ile Leu Ser Gln Cys Gly Ala Gly Val
        1010                1015                1020

Phe Glu Tyr Phe Asn Ala Lys Ser Lys His Ser Trp Arg Lys Gln
        1025                1030                1035

Ile Glu Asp Gln Met Thr Arg Leu Cys Ser Pro Ser Cys His Ser
        1040                1045                1050

Val Ser Val Lys Trp Gln Gln Leu Asn Pro Asp Ala Pro Glu Ala
        1055                1060                1065

Leu Gln Ala Pro Ala Gln Val Pro Ser Leu Phe Arg Asn Asp Arg
        1070                1075                1080

Leu Leu Val Tyr Gly Phe Ile Pro His Cys Thr Gln Ala Thr Leu
        1085                1090                1095

Cys Ala Leu Ile Gln Glu Lys Glu Phe Cys Thr Met Val Ser Thr
        1100                1105                1110

Thr Glu Leu Gln Lys Thr Thr Gly Thr Met Ile His Lys Leu Ala
        1115                1120                1125

Ala Arg Ala Leu Ile Arg Asp Tyr Glu Asp Gly Ile Leu His Glu
        1130                1135                1140

Asn Glu Thr Ser His Glu Met Lys Lys Gln Thr Leu Lys Ser Leu
        1145                1150                1155

Ile Ile Lys Leu Ser Lys Glu Asn Ser Leu Ile Thr Gln Phe Thr
        1160                1165                1170

Ser Phe Val Ala Val Glu Lys Arg Asp Glu Asn Glu Ser Pro Phe
        1175                1180                1185

Pro Asp Ile Pro Lys Val Ser Glu Leu Ile Ala Lys Glu Asp Val
        1190                1195                1200

Asp Phe Leu Pro Tyr Met Ser Trp Gln Gly Glu Pro Gln Glu Ala
        1205                1210                1215

Val Arg Asn Gln Ser Leu Leu Ala Ser Ser Glu Trp Pro Glu Leu
        1220                1225                1230

Arg Leu Ser Lys Arg Lys His Arg Lys Ile Pro Phe Ser Lys Arg
        1235                1240                1245

Ser Met Glu Leu Ser Gln Pro Glu Val Ser Glu Asp Phe Glu Glu
        1250                1255                1260

Asp Gly Leu Gly Val Leu Pro Ala Phe Thr Ser Asn Leu Glu Arg
        1265                1270                1275

Gly Gly Val Glu Lys Leu Leu Asp Leu Ser Trp Thr Glu Ser Cys
        1280                1285                1290

Lys Pro Thr Ala Thr Glu Pro Leu Phe Lys Lys Val Ser Pro Trp
```

```
                   1295                1300               1305

Glu  Thr  Ser  Thr  Ser  Ser  Phe  Phe  Pro  Ile  Leu  Ala  Pro  Ala  Val
     1310                1315                1320

Gly  Ser  Tyr  Leu  Thr  Pro  Thr  Thr  Arg  Ala  His  Ser  Pro  Ala  Ser
     1325                1330                1335

Leu  Ser  Phe  Ala  Ser  Tyr  Arg  Gln  Val  Ala  Ser  Phe  Gly  Ser  Ala
     1340                1345                1350

Ala  Pro  Pro  Arg  Gln  Phe  Asp  Ala  Ser  Gln  Phe  Ser  Gln  Gly  Pro
     1355                1360                1365

Val  Pro  Gly  Thr  Cys  Ala  Asp  Trp  Ile  Pro  Gln  Ser  Ala  Ser  Cys
     1370                1375                1380

Pro  Thr  Gly  Pro  Pro  Gln  Asn  Pro  Pro  Ser  Ala  Pro  Tyr  Cys  Gly
     1385                1390                1395

Ile  Val  Phe  Ser  Gly  Ser  Ser  Leu  Ser  Ser  Ala  Gln  Ser  Ala  Pro
     1400                1405                1410

Leu  Gln  His  Pro  Gly  Gly  Phe  Thr  Thr  Arg  Pro  Ser  Ala  Gly  Thr
     1415                1420                1425

Phe  Pro  Glu  Leu  Asp  Ser  Pro  Gln  Leu  His  Phe  Ser  Leu  Pro  Thr
     1430                1435                1440

Asp  Pro  Asp  Pro  Ile  Arg  Gly  Phe  Gly  Ser  Tyr  His  Pro  Ser  Ala
     1445                1450                1455

Tyr  Ser  Pro  Phe  His  Phe  Gln  Pro  Ser  Ala  Ala  Ser  Leu  Thr  Ala
     1460                1465                1470

Asn  Leu  Arg  Leu  Pro  Met  Ala  Ser  Ala  Leu  Pro  Glu  Ala  Leu  Cys
     1475                1480                1485

Ser  Gln  Ser  Arg  Thr  Thr  Pro  Val  Asp  Leu  Cys  Leu  Leu  Glu  Glu
     1490                1495                1500

Ser  Val  Gly  Ser  Leu  Glu  Gly  Ser  Arg  Cys  Pro  Val  Phe  Ala  Phe
     1505                1510                1515

Gln  Ser  Ser  Asp  Thr  Glu  Ser  Asp  Glu  Leu  Ser  Glu  Val  Leu  Gln
     1520                1525                1530

Asp  Ser  Cys  Phe  Leu  Gln  Ile  Lys  Cys  Asp  Thr  Lys  Asp  Asp  Ser
     1535                1540                1545

Ile  Pro  Cys  Phe  Leu  Glu  Leu  Lys  Glu  Glu  Asp  Glu  Ile  Val  Cys
     1550                1555                1560

Thr  Gln  His  Trp  Gln  Asp  Ala  Val  Pro  Trp  Thr  Glu  Leu  Leu  Ser
     1565                1570                1575

Leu  Gln  Thr  Glu  Asp  Gly  Phe  Trp  Lys  Leu  Thr  Pro  Glu  Leu  Gly
     1580                1585                1590

Leu  Ile  Leu  Asn  Leu  Asn  Thr  Asn  Gly  Leu  His  Ser  Phe  Leu  Lys
     1595                1600                1605

Gln  Lys  Gly  Ile  Gln  Ser  Leu  Gly  Val  Lys  Gly  Arg  Glu  Cys  Leu
     1610                1615                1620

Leu  Asp  Leu  Ile  Ala  Thr  Met  Leu  Val  Leu  Gln  Phe  Ile  Arg  Thr
     1625                1630                1635

Arg  Leu  Glu  Lys  Glu  Gly  Ile  Val  Phe  Lys  Ser  Leu  Met  Lys  Met
     1640                1645                1650

Asp  Asp  Pro  Ser  Ile  Ser  Arg  Asn  Ile  Pro  Trp  Ala  Phe  Glu  Ala
     1655                1660                1665

Ile  Lys  Gln  Ala  Ser  Glu  Trp  Val  Arg  Arg  Thr  Glu  Gly  Gln  Tyr
     1670                1675                1680

Pro  Ser  Ile  Cys  Pro  Arg  Leu  Glu  Leu  Gly  Asn  Asp  Trp  Asp  Ser
     1685                1690                1695
```

Ala Thr Lys Gln Leu Leu Gly Leu Gln Pro Ile Ser Thr Val Ser
    1700            1705                1710

Pro Leu His Arg Val Leu His Tyr Ser Gln Gly
    1715                1720

<210> SEQ ID NO 15
<211> LENGTH: 5175
<212> TYPE: DNA
<213> ORGANISM: Homo sapiens

<400> SEQUENCE: 15

| | | | | | |
|---|---|---|---|---|---|
| atggtgatgg | gaatctttgc | aaattgtatc | ttctgtttga | aagtgaagta | cttacctcag | 60 |
| cagcagaaga | aaaagctaca | aactgacatt | aaggaaaatg | gcggaaagtt | ttccttttcg | 120 |
| ttaaatcctc | agtgcacaca | tataatctta | gataatgctg | atgttctgag | tcagtaccaa | 180 |
| ctgaattcta | tccaaaagaa | ccacgttcat | attgcaaacc | cagattttat | atggaaatct | 240 |
| atcagagaaa | agagactctt | ggatgtaaag | aattatgatc | cttataagcc | cctggacatc | 300 |
| acaccacctc | ctgatcagaa | ggcgagcagt | tctgaagtga | aaacagaagg | tctatgcccg | 360 |
| gacagtgcca | cagaggagga | agacactgtg | gaactcactg | agtttggtat | gcagaatgtt | 420 |
| gaaattcctc | atcttcctca | agattttgaa | gttgcaaaat | ataacacctt | ggagaaagtg | 480 |
| ggaatggagg | gaggccagga | agctgtggtg | gtggagcttc | agtgttcgcg | ggactccagg | 540 |
| gactgtcctt | tcctgatatc | ctcacacttc | ctcctggatg | atggcatgga | gactagaaga | 600 |
| cagtttgcta | taaagaaaac | ctctgaagat | gcaagtgaat | actttgaaaa | ttacattgaa | 660 |
| gaactgaaga | aacaaggatt | tctactaaga | gaacatttca | cacctgaagc | aacccaatta | 720 |
| gcatctgaac | aattgcaagc | attgcttttg | gaggaagtca | tgaattcaag | cactctgagc | 780 |
| caagaggtga | gcgatttagt | agagatgatt | tgggcagagg | ccctgggcca | cctggaacac | 840 |
| atgcttctca | agccagtgaa | caggattagc | ctcaacgatg | tgagcaaggc | agagggatt | 900 |
| ctccttctag | taaaggcagc | actgaaaaat | ggagaaacag | cagagcaatt | gcaaaagatg | 960 |
| atgacagagt | tttacagact | gatacctcac | aaaggcacaa | tgcccaaaga | agtgaacctg | 1020 |
| ggactattgg | ctaagaaagc | agacctctgc | cagctaataa | gagacatggt | taatgtctgt | 1080 |
| gaaactaatt | tgtccaaacc | caacccacca | tccctggcca | aataccgagc | tttgaggtgc | 1140 |
| aaaattgagc | atgttgaaca | gaatactgaa | gaatttctca | gggttagaaa | agaggttttg | 1200 |
| cagaatcatc | acagtaagag | cccagtggat | gtcttgcaga | tatttagagt | tggcagagtg | 1260 |
| aatgaaacca | cagagttttt | gagcaaactt | ggtaatgtga | ggcccttgtt | gcatggttct | 1320 |
| cctgtacaaa | acatcgtggg | aatcttgtgt | cgagggttgc | ttttacccaa | agtagtggaa | 1380 |
| gatcgtggtg | tgcaaagaac | agacgtcgga | aaccttggaa | gtgggattta | tttcagtgat | 1440 |
| tcgctcagta | caagtatcaa | gtactcacac | ccgggagaga | cagatggcac | cagactcctg | 1500 |
| ctcatttgtg | acgtagccct | cggaaagtgt | atggacttac | atgagaagga | ctttccctta | 1560 |
| actgaagcac | caccaggcta | cgacagtgtg | catggagttt | cacaaacagc | ctctgtcacc | 1620 |
| acagactttg | aggatgatga | atttgttgtc | tataaaacca | atcaggttaa | aatgaaatat | 1680 |
| attattaaat | tttccatgcc | tggagatcag | ataaggact | ttcatcctag | tgatcatact | 1740 |
| gaattagagg | aatacagacc | tgagttttca | aattttcaa | aggttgaaga | ttaccagtta | 1800 |
| ccagatgcca | aaacttccag | cagcaccaag | gccggcctcc | aggatgcctc | tgggaacttg | 1860 |
| gttcctctgg | aggatgtcca | catcaaaggg | agaatccatag | acactgtagc | ccaggtcatt | 1920 |

```
gtttttcaga catacacaaa taaaagtcac gtgcccattg aggcaaaata tatctttcct   1980
ttggatgaca aggccgctgt gtgtggcttc gaagccttca tcaatgggaa gcacatagtt   2040
ggagagatta aagagaagga agaagcccag caagagtacc tagaagccgt gacccagggc   2100
catggcgctt acctgatgag tcaggatgct ccggacgttt ttactgtaag tgttggaaac   2160
ttaccccta aggctaaggt tcttataaaa attacctaca tcacagaact cagcatcctg   2220
ggcactgttg gtgtcttttt catgcccgcc accgtagcac cctggcaaca ggacaaggct   2280
ttgaatgaaa accttcagga tacagtagag aagatttgta taaagaaat aggaacaaag    2340
caaagcttct ctttgactat gtctattgag atgccgtatg tgattgaatt cattttcagt   2400
gatacacatg aactgaaaca aaagcgcaca gactgcaaag ctgtcattag caccatggaa   2460
ggcagctcct tagacagcag tggatttttct ctccacatcg gtttgtctgc tgcctatctc   2520
ccaagaatgt gggttgaaaa acatccagaa aaagaaagcg aggcttgcat gcttgtcttt   2580
caacccgatc tcgatgtcga cctccctgac ctagccagtg agagcgaagt gattatttgt   2640
cttgactgct ccagttccat ggagggtgtg acattcttgc aagccaagca aatcaccttg   2700
catgcgctgt ccttggtggg tgagaagcag aaagtaaata ttatccagtt cggcacaggt   2760
tacaaggagc tattttcgta tcctaagcat atcacaagca ataccacggc agcagagttc   2820
atcatgtctg ccacacctac catggggaac acagacttct ggaaaacact ccgatatctt   2880
agcttattgt accctgctcg agggtcacgg aacatcctcc tggtgtctga tgggcacctc   2940
caggatgaga gcctgacatt acagctcgtg aagaggagcc gcccgcacac caggttattc   3000
gcctgcggta tcggttctac agcaaatcgt cacgtcttaa ggattttgtc ccagtgtggt   3060
gccggagtat ttgaatattt taatgcaaaa tccaagcata gttggagaaa acagatagaa   3120
gaccaaatga ccaggctatg ttctccgagt tgccactctg tctccgtcaa atggcagcaa   3180
ctcaatccag atgcgcccga ggccctgcag gccccagccc aggtgccatc cttgtttcgc   3240
aatgatcgac tccttgtcta tggattcatt cctcactgca cacaagcaac tctgtgtgca   3300
ctaattcaag agaaagaatt ttgtacaatg gtgtcgacta ctgagcttca gaagacaact   3360
ggaactatga tccacaagct ggcagcccga gctctaatca gagattatga agatggcatt   3420
cttcacgaaa atgaaaccag tcatgagatg aaaaaaacaaa ccttgaaatc tctgattatt   3480
aaactcagta agaaaactc tctcataaca caatttacaa gctttgtggc agttgagaaa   3540
agggatgaga atgagtcgcc ttttcctgat attccaaaag tttctgaact tattgccaaa   3600
gaagatgtag acttcctgcc ctacatgagc tggcagggg agcccaaga gccgtcagg    3660
aaccagtctc ttttagcatc ctctgagtgg ccagaattac gtttatccaa acgaaaacat   3720
aggaaaattc cattttccaa aagaaaaatg gaattatctc agccagaagt ttctgaagat   3780
tttgaagagg atggcttagg tgtactacca gctttcacat caaatttgga acgtggaggt   3840
gtggaaaagc tattggattt aagttggaca gagtcatgta aaccaacagc aactgaacca   3900
ctatttaaga aagtcagtcc atgggaaaca tctacttcta gctttttcc tattttggct    3960
ccggccgttg gttcctatct tacccgact acccgcgctc acagtcctgc ttccttgtct   4020
tttgcctcat atcgtcaggt agctagtttc ggttcagctg ctcctcccag acagtttgat   4080
gcatctcaat tcagccaagg ccctgtgcct ggcacttgtg ctgactggat ccacagtcg    4140
gcgtcttgtc ccacaggacc tccccagaac ccaccttctg caccctattg tggcattgtt   4200
ttttcaggga gctcattaag ctctgcacag tctgctccac tgcaacatcc tggaggcttt   4260
actaccaggc cttctgctgg caccttccct gagctggatt ctccccagct tcatttctct   4320
```

-continued

```
cttcctacag accctgatcc catcagaggt tttgggtctt atcatccctc tgcttactct     4380 cctttcatt ttcaaccttc cgcagcctct ttgactgcca accttaggct gccaatggcc      4440
tctgctttac ctgaggctct ttgcagtcag tcccggacta ccccagtaga tctctgtctt     4500
ctagaagaat cagtaggcag tctcgaagga agtcgatgtc ctgtctttgc ttttcaaagt     4560
tctgacacag aaagtgatga gctatcagaa gtacttcaag acagctgctt tttacaaata     4620
aagtgtgata caaaagatga cagtatcccg tgctttctgg aattaaaaga agaggatgaa     4680
atagtgtgca cacaacactg gcaggatgct gtgccttgga cagaactcct cagtctacag     4740
acagaggatg gcttctggaa acttacacca gaactgggac ttatattaaa tcttaataca     4800
aatggtttgc acagctttct taaacaaaaa ggcattcaat ctctaggtgt aaaaggaaga     4860
gaatgtctcc tggacctaat tgccacaatg ctggtactac agtttattcg caccaggttg     4920 gaaaagagg gaatagtgtt caaatcactg atgaaaatgg atgacccttc tatttccagg      4980
aatattccct gggcttttga ggcaataaag caagcaagtg aatgggtaag aagaactgaa     5040
ggacagtacc catctatctg cccacggctt gaactgggga cgactggga ctctgccacc      5100 aagcagttgc tgggactcca gcccataagc actgtgtccc ctcttcatag agtcctccat     5160
tacagtcaag gctaa                                                      5175
```

<210> SEQ ID NO 16
<211> LENGTH: 893
<212> TYPE: PRT
<213> ORGANISM: Homo sapiens

<400> SEQUENCE: 16

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Met
        35                  40                  45

Arg Met Val Thr Val Pro Pro Arg His Tyr Cys Thr Val Ala Asn Pro
    50                  55                  60

Val Ser Arg Asp Ala Gln Gly Leu Val Leu Phe Asp Val Thr Gly Gln
65                  70                  75                  80

Val Arg Leu Arg His Ala Asp Leu Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asp Gly Asp Lys Val Val Ala Gly Asp Glu Trp Leu
    130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                165                 170                 175

Arg Ala Arg Lys Glu Cys Trp Asp Arg Asp Gly Lys Glu Arg Val Thr
            180                 185                 190

Gly Glu Glu Trp Leu Val Thr Thr Val Gly Ala Tyr Leu Pro Ala Val
        195                 200                 205

Phe Glu Glu Val Leu Asp Leu Val Asp Ala Val Ile Leu Thr Glu Lys

-continued

```
            210                 215                 220
Thr Ala Leu His Leu Arg Ala Arg Arg Asn Phe Arg Asp Phe Arg Gly
225                 230                 235                 240

Val Ser Arg Arg Thr Gly Glu Glu Trp Leu Val Thr Val Gln Asp Thr
                245                 250                 255

Glu Ala His Val Pro Asp Val His Glu Val Leu Gly Val Val Pro
                    260                 265                 270

Ile Thr Thr Leu Gly Pro His Asn Tyr Cys Val Ile Leu Asp Pro Val
                275                 280                 285

Gly Pro Asp Gly Lys Asn Gln Leu Gly Gln Lys Arg Val Val Lys Gly
            290                 295                 300

Glu Lys Ser Phe Phe Leu Gln Pro Gly Glu Gln Leu Glu Gln Gly Ile
305                 310                 315                 320

Gln Asp Val Tyr Val Leu Ser Glu Gln Gln Gly Leu Leu Leu Arg Ala
                    325                 330                 335

Leu Gln Pro Leu Glu Glu Gly Glu Asp Glu Glu Lys Val Ser His Gln
                340                 345                 350

Ala Gly Asp His Trp Leu Ile Arg Gly Pro Leu Glu Tyr Val Pro Ser
                355                 360                 365

Ala Lys Val Glu Val Val Glu Glu Arg Gln Ala Ile Pro Leu Asp Glu
            370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                    405                 410                 415

Lys Glu Leu Pro Pro Gly Val Glu Glu Leu Leu Asn Lys Gly Gln Asp
                420                 425                 430

Pro Leu Ala Asp Arg Gly Glu Lys Asp Thr Ala Lys Ser Leu Gln Pro
            435                 440                 445

Leu Ala Pro Arg Asn Lys Thr Arg Val Val Ser Tyr Arg Val Pro His
                450                 455                 460

Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
                    485                 490                 495

Val Leu Ser Leu Ser Ala Gly Arg Pro Lys Arg Pro His Ala Arg Arg
                500                 505                 510

Ala Leu Cys Leu Leu Leu Gly Pro Asp Phe Phe Thr Asp Val Ile Thr
            515                 520                 525

Ile Glu Thr Ala Asp His Ala Arg Leu Gln Leu Gln Leu Ala Tyr Asn
                530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                    565                 570                 575

Ser Arg Val Arg Gly Ala Val Ala Ser Val Thr Phe Asp Asp Phe His
                580                 585                 590

Lys Asn Ser Ala Arg Ile Ile Arg Thr Ala Val Phe Gly Phe Glu Thr
            595                 600                 605

Ser Glu Ala Lys Gly Pro Asp Gly Met Ala Leu Pro Arg Pro Arg Asp
610                 615                 620

Gln Ala Val Phe Pro Gln Asn Gly Leu Val Val Ser Ser Val Asp Val
625                 630                 635                 640
```

Gln Ser Val Glu Pro Val Asp Gln Arg Thr Arg Asp Ala Leu Gln Arg
            645                 650                 655

Ser Val Gln Leu Ala Ile Glu Ile Thr Thr Asn Ser Gln Glu Ala Ala
                660                 665                 670

Ala Lys His Glu Ala Gln Arg Leu Glu Gln Glu Ala Arg Gly Arg Leu
            675                 680                 685

Glu Arg Gln Lys Ile Leu Asp Gln Ser Glu Ala Glu Lys Ala Arg Lys
        690                 695                 700

Glu Leu Leu Glu Leu Glu Ala Leu Ser Met Ala Val Glu Ser Thr Gly
705                 710                 715                 720

Thr Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Gln Arg Val Gln Lys Val Arg Glu Leu
        755                 760                 765

Glu Leu Val Tyr Ala Arg Ala Gln Leu Glu Leu Glu Val Ser Lys Ala
    770                 775                 780

Gln Gln Leu Ala Glu Val Glu Val Lys Lys Phe Lys Gln Met Thr Glu
785                 790                 795                 800

Ala Ile Gly Pro Ser Thr Ile Arg Asp Leu Ala Val Ala Gly Pro Glu
                805                 810                 815

Met Gln Val Lys Leu Leu Gln Ser Leu Gly Leu Lys Ser Thr Leu Ile
            820                 825                 830

Thr Asp Gly Ser Thr Pro Ile Asn Leu Phe Asn Thr Ala Phe Gly Leu
        835                 840                 845

Leu Gly Met Gly Pro Glu Gly Gln Pro Leu Gly Arg Arg Val Ala Ser
    850                 855                 860

Gly Pro Ser Pro Gly Glu Gly Ile Ser Pro Gln Ser Ala Gln Ala Pro
865                 870                 875                 880

Gln Ala Pro Gly Asp Asn His Val Val Pro Val Leu Arg
                885                 890

<210> SEQ ID NO 17
<211> LENGTH: 2682
<212> TYPE: DNA
<213> ORGANISM: Homo sapiens

<400> SEQUENCE: 17
atggcaactg aagagttcat catccgcatc cccccatacc actatatcca tgtgctggac      60
cagaacagca acgtgtcccg tgtggaggtc gggccaaaga cctacatccg gcaggacaat     120
gagagggtac tgtttgcccc catgcgcatg gtgaccgtcc ccccacgtca ctactgcaca     180
gtggccaacc ctgtgtctcg ggatgcccag ggcttggtgc tgtttgatgt cacagggcaa     240
gttcggcttc gccacgctga cctcgagatc cggctggccc aggacccctt ccccctgtac     300
ccaggggagg tgctggaaaa ggacatcaca cccctgcagg tggttctgcc caacactgcc     360
ctccatctaa aggcgctgct tgattttgag gataaagatg agacaaggt ggtggcagga     420 gatgagtggc ttttcgaggg acctggcacg tacatccccc ggaaggaagt ggaggtcgtg     480
gagatcattc aggccaccat catcaggcag aaccaggctc tgcggctcag ggcccgcaag     540
gagtgctggg accgggacgg caaggagagg gtgacagggg aagaatggct ggtcaccaca     600 gtagggggcgt acctcccagc ggtgtttgag gaggttctgg atttggtgga cgccgtcatc     660

| | |
|---|---|
| cttacggaaa agacagccct gcacctccgg gctcggcgga acttccggga cttcagggga | 720 |
| gtgtcccgcc gcactgggga ggagtggctg gtaacagtgc aggacacaga ggcccacgtg | 780 |
| ccagatgtcc acgaggaggt gctgggggtt gtgcccatca ccaccctggg ccccacaac | 840 |
| tactgcgtga ttctcgaccc tgtcggaccg gatggcaaga atcagctggg gcagaagcgc | 900 |
| gtggtcaagg gagagaagtc ttttttcctc cagccaggag agcagctgga caaggcatc | 960 |
| caggatgtgt atgtgctgtc ggagcagcag gggctgctgc tgagggccct gcagccctg | 1020 |
| gaggaggggg aggatgagga gaaggtctca caccaggctg ggaccactg gctcatccgc | 1080 |
| ggacccctgg agtatgtgcc atctgccaaa gtggaggtgg tggaggagcg ccaggccatc | 1140 |
| cctctagacg agaacgaggg catctatgtg caggatgtca agaccggaaa ggtgcgcgct | 1200 |
| gtgattggaa gcacctacat gctgacccag gacgaagtcc tgtgggagaa agagctgcct | 1260 |
| cccggggtgg aggagctgct gaacaagggg caggaccctc tggcagacag gggtgagaag | 1320 |
| gacacagcta agagcctcca gcccttggcg ccccggaaca agacccgtgt ggtcagctac | 1380 |
| cgcgtgcccc acaacgctgc ggtgcaggtg tacgactacc gagagaagcg agcccgcgtg | 1440 |
| gtcttcgggc tgagctggt gtcgctgggt cctgaggagc agttcacagt gttgtccctc | 1500 |
| tcagctgggc ggcccaagcg tccccatgcc cgccgtgcgc tctgcctgct gctggggcct | 1560 |
| gacttcttca cagacgtcat caccatcgaa acggcggatc atgccaggct gcaactgcag | 1620 |
| ctggcctaca ctggcacttt gaggtgaat gaccggaagg accccaaga gacggccaag | 1680 |
| ctcttttcag tgccagactt tgtaggtgat gcctgcaaag ccatcgcatc ccgggtgcgg | 1740 |
| ggggccgtgg cctctgtcac tttcgatgac ttccataaga actcagcccg catcattcgc | 1800 |
| actgctgtct ttggctttga gacctcggaa gcgaagggcc ccgatggcat ggccctgccc | 1860 |
| aggcccgggg accaggctgt cttcccccaa aacgggctgg tggtcagcag tgtggacgtg | 1920 |
| cagtcagtgg agcctgtgga tcagaggacc cgggacgccc tgcaacgcag cgtccagctg | 1980 |
| gccatcgaga tcaccaccaa ctcccaggaa gcggcggcca gcatgaggc tcagagactg | 2040 |
| gagcaggaag cccgcggccg gcttgagcgg cagaagatcc tggaccagtc agaagccgag | 2100 |
| aaagctcgca aggaactttt ggagctggag gctctgagca tggccgtgga gagcaccggg | 2160 |
| actgccaagg cggaggccga gtcccgtgcg gaggcagccc ggattgaggg agaagggtcc | 2220 |
| gtgctgcagg ccaagctaaa agcacaggcc ttggccattg aaacggaggc tgagctccag | 2280 |
| agggtccaga aggtccgaga gctggaactg gtctatgccc gggcccagct ggagctggag | 2340 |
| gtgagcaagc tcagcagct ggctgaggtg gaggtgaaga agttcaagca gatgacagag | 2400 |
| gccataggcc ccagcaccat cagggacctt gctgtggctg ggcctgagat gcaggtaaaa | 2460 |
| ctgctccagt ccctgggcct gaaatcaacc ctcatcaccg atggctccac tcccatcaac | 2520 |
| ctcttcaaca cagcctttgg gctgctgggg atggggcccg agggtcagcc cctgggcaga | 2580 |
| agggtggcca gtgggcccag ccctggggag gggatatccc cccagtctgc tcaggcccct | 2640 |
| caagctcctg gagacaacca cgtggtgcct gtactgcgct aa | 2682 |

<210> SEQ ID NO 18
<211> LENGTH: 861
<212> TYPE: PRT
<213> ORGANISM: Rattus norvegicus

<400> SEQUENCE: 18

Met Ala Thr Glu Glu Ala Ile Ile Arg Ile Pro Pro Tyr His Tyr Ile
1               5                   10                  15

His Val Leu Asp Gln Asn Ser Asn Val Ser Arg Val Glu Val Gly Pro
        20                  25                  30

Lys Thr Tyr Ile Arg Gln Asp Asn Glu Arg Val Leu Phe Ala Pro Val
            35                  40                  45

Arg Met Val Thr Val Pro Pro Arg His Tyr Cys Ile Val Ala Asn Pro
        50                  55                  60

Val Ser Arg Asp Thr Gln Ser Ser Val Leu Phe Asp Ile Thr Gly Gln
65                  70                  75                  80

Val Arg Leu Arg His Ala Asp Gln Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asn Gly Asp Lys Val Met Ala Gly Asp Glu Trp Leu
130                 135                 140

Phe Glu Gly Pro Gly Thr Tyr Ile Pro Gln Lys Glu Val Glu Val Val
145                 150                 155                 160

Glu Ile Ile Gln Ala Thr Val Ile Lys Gln Asn Gln Ala Leu Arg Leu
                165                 170                 175

Arg Ala Arg Lys Glu Cys Phe Asp Arg Glu Gly Lys Gly Arg Val Thr
            180                 185                 190

Gly Glu Glu Trp Leu Val Arg Ser Val Gly Ala Tyr Leu Pro Ala Val
        195                 200                 205

Phe Glu Glu Val Leu Asp Leu Val Asp Ala Val Ile Leu Thr Glu Lys
        210                 215                 220

Thr Ala Leu His Leu Arg Ala Leu Gln Asn Phe Arg Asp Leu Arg Gly
225                 230                 235                 240

Val Leu His Arg Thr Gly Glu Glu Trp Leu Val Thr Val Gln Asp Thr
                245                 250                 255

Glu Ala His Val Pro Asp Val Tyr Glu Glu Val Leu Gly Val Val Pro
            260                 265                 270

Ile Thr Thr Leu Gly Pro Arg His Tyr Cys Val Ile Leu Asp Pro Met
        275                 280                 285

Gly Pro Asp Gly Lys Asn Gln Leu Gly Gln Lys Arg Val Val Lys Gly
290                 295                 300

Glu Lys Ser Phe Phe Leu Gln Pro Gly Glu Arg Leu Glu Arg Gly Ile
305                 310                 315                 320

Gln Asp Val Tyr Val Leu Ser Glu Gln Gln Gly Leu Leu Leu Lys Ala
                325                 330                 335

Leu Gln Pro Leu Glu Glu Gly Glu Ser Glu Glu Lys Val Ser His Gln
            340                 345                 350

Ala Gly Asp Cys Trp Leu Ile Arg Gly Pro Leu Glu Tyr Val Pro Ser
        355                 360                 365

Ala Lys Val Glu Val Val Glu Glu Arg Gln Ala Ile Pro Leu Asp Gln
        370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Ser Gly Val Glu Glu Leu Leu Asn Leu Gly His Asp
            420                 425                 430

Pro Leu Ala Asp Arg Gly Gln Lys Gly Thr Ala Lys Pro Leu Gln Pro

```
                435                 440                 445
Ser Ala Pro Arg Asn Lys Thr Arg Val Val Ser Tyr Arg Val Pro His
450                 455                 460

Asn Ala Ala Val Gln Val Tyr Asp Tyr Arg Ala Lys Arg Ala Arg Val
465                 470                 475                 480

Val Phe Gly Pro Glu Leu Val Thr Leu Asp Pro Glu Glu Gln Phe Thr
                485                 490                 495

Val Leu Ser Leu Ser Ala Gly Arg Pro Lys Arg Pro His Ala Arg Arg
                500                 505                 510

Ala Leu Cys Leu Leu Leu Gly Pro Asp Phe Phe Thr Asp Val Ile Thr
                515                 520                 525

Ile Glu Thr Ala Asp His Ala Arg Leu Gln Leu Gln Leu Ala Tyr Asn
530                 535                 540

Trp His Phe Glu Leu Lys Asn Arg Asn Asp Pro Ala Glu Ala Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
                580                 585                 590

Lys Asn Ser Ala Arg Ile Ile Arg Met Ala Val Phe Gly Phe Glu Met
                595                 600                 605

Ser Glu Asp Thr Gly Pro Asp Gly Thr Leu Leu Pro Lys Ala Arg Asp
610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
                660                 665                 670

Ala Lys His Glu Ala Gln Arg Leu Glu Gln Glu Ala Arg Gly Arg Leu
                675                 680                 685

Glu Arg Gln Lys Ile Leu Asp Gln Ser Glu Ala Glu Lys Ala Arg Lys
690                 695                 700

Glu Leu Leu Glu Leu Glu Ala Met Ser Met Ala Val Glu Ser Thr Gly
705                 710                 715                 720

Asn Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
                740                 745                 750

Ile Glu Thr Glu Ala Glu Leu Glu Arg Val Lys Lys Val Arg Glu Met
                755                 760                 765

Glu Leu Ile Tyr Ala Arg Ala Gln Leu Glu Leu Val Ser Lys Ala
770                 775                 780

Gln Gln Leu Ala Asn Val Glu Ala Lys Lys Phe Lys Glu Met Thr Glu
785                 790                 795                 800

Ala Leu Gly Pro Gly Thr Ile Arg Asp Leu Ala Val Ala Gly Pro Glu
                805                 810                 815

Met Gln Val Lys Leu Leu Gln Ser Leu Gly Leu Lys Ser Thr Leu Ile
                820                 825                 830

Thr Asp Gly Ser Ser Pro Ile Asn Leu Phe Ser Thr Ala Phe Gly Leu
                835                 840                 845

Leu Gly Leu Gly Ser Asp Gly Gln Pro Pro Ala Gln Lys
850                 855                 860
```

<210> SEQ ID NO 19
<211> LENGTH: 2586
<212> TYPE: DNA
<213> ORGANISM: Rattus norvegicus

<400> SEQUENCE: 19

```
atggcaactg aagaggccat catccgcatc cccccatacc actacatcca tgtgctggac      60
cagaacagta atgtgtcccg tgtggaggtt ggaccaaaga cctacatccg gcaggacaat     120
gagagggtac tgtttgcccc agttcgcatg gtgaccgtcc ccccacgcca ctactgcata     180
gtggccaacc ctgtgtcccg ggacacccag agttctgtgt tatttgacat cacaggacaa     240
gtccgactcc ggcacgctga ccaggagatc cgactagccc aggacccctt ccccctgtat     300
ccaggggagg tgctggaaaa ggacatcacc ccactgcagg tggttctgcc caacacagca     360
ctgcatctta aggcgttgct ggactttgag ataagaatg gagacaaggt catggcagga     420
gacgagtggc tatttgaggg acctggcacc tacatcccac agaaggaagt ggaagtcgtg     480
gagatcattc aggccacagt catcaaacag aaccaagcac tgcggctaag ggcccgaaag     540
gagtgctttg accgggaggg caaggggcgc gtgacaggtg aggagtggct ggtccgatcc     600
gtgggggctt acctcccagc tgtctttgaa gaggtgctgg atctggtgga tgctgtgatc     660
cttacagaaa agactgccct gcacctccgg gctctgcaga acttcaggga ccttcgggga     720
gtgctccacc gcaccgggga ggaatggtta gtgacagtgc aggacacaga agcccatgtt     780
ccagatgtct atgaggaggt gcttgggta gtacccatca ccaccctggg acctcgacac     840
tactgtgtca ttcttgaccc aatgggacca gacggcaaga accagctggg acaaaagcgt     900
gttgtcaagg gagagaagtc cttttttcctc cagccaggag agaggctgga gcgaggcatc     960
caggatgtgt atgtgctgtc agagcagcag gggctgctac tgaaggcact gcagcccctg    1020
gaggagggag agagcgagga gaaggtctcc catcaggccg gagactgctg gctcatccgt    1080
gggcccctgg agtatgtgcc atctgcaaaa gtggaggtgg tggaggagcg tcaggctatc    1140
cctctggacc aaaatgaggg catctatgtg caggatgtca agacggggaa ggtgcgggct    1200
gtgattggaa gcacctacat gctgactcag gatgaagtcc tgtgggaaaa ggagctgcct    1260
tctggggtgg aggagctgct gaacttgggg catgaccctc tggcagacag gggtcagaag    1320
ggcacagcca agcccttca gccctcagct ccaaggaaca agaccccgagt ggtcagctac    1380
cgtgtcccgc acaatgcagc ggtgcaggtc tatgactaca gagccaagag agcccgtgtg    1440
gtctttgggc ccgagctagt gacactggat cctgaggagc agttcacagt attgtccctt    1500
tctgccgggc gacccaagcg tcctcatgcc cgccgtgcac tctgcctact gctgggacct    1560
gatttcttta ctgatgtcat caccatcgaa actgcagatc atgccaggtt gcagctgcag    1620
cttgcctaca actggcactt tgaactgaag aaccggaatg accctgcaga ggcagccaag    1680
cttttctccg tgcctgactt cgtgggtgac gcctgcaagg ccattgcatc ccgagtccgg    1740
ggggctgtag cctctgtcac cttttgatgac ttccataaaa actcagcccg gatcattcga    1800
atggctgttt ttggctttga gatgtctgaa gacacaggtc ctgatggcac actcctgccc    1860
aaggctcgag accaggcagt ctttcccccaa aacgggctgg tagtcagcag tgtggatgtg    1920
cagtcagtgg agcccgtgga ccagaggacc cgggatgccc ttcagcgcag cgttcagctg    1980
gccatcgaaa ttaccaccaa ctcccaggag gcagcagcca agcacgaggc tcagagactg    2040
gaacaggaag cccgtggtcg gcttgagagg cagaagatct tggaccagtc agaagctgaa    2100
```

```
aaagcccgca aggaactctt ggagcttgag gctatgagca tggctgtgga gagcacgggt   2160
aatgccaaag cagaggctga gtcccgtgca gaggcagcga ggatcgaagg agaaggctct   2220
gtgctgcagg ccaagctcaa ggcacaggcg ctagccattg agacggaggc tgagttggag   2280
cgagtaaaga aagtacgaga gatggaactg atctatgccc gggcccagtt ggagctggag   2340
gtgagcaagg cgcagcagct tgccaatgtg gaggcaaaga agttcaagga gatgacagag   2400
gcactgggcc ccggcaccat cagggacctg gctgtggccg ggccagagat gcaggtgaaa   2460
cttctccagt ccctgggcct gaaatccact ctcatcaccg atggctcgtc tcccatcaac   2520
ctcttcagca cagccttcgg gttgctgggg ctggggtctg atggtcagcc gccagcacag   2580
aagtga                                                              2586
```

```
<210> SEQ ID NO 20
<211> LENGTH: 12
<212> TYPE: PRT
<213> ORGANISM: Unknown
<220> FEATURE:
<223> OTHER INFORMATION: Description of Unknown: Cysteine-rich peptide
      (CP)

<400> SEQUENCE: 20

Met Ala Gly Cys Gly Cys Pro Cys Gly Cys Gly Ala
1               5                   10

<210> SEQ ID NO 21
<211> LENGTH: 905
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Gly Cys Gly Cys Pro Cys Gly Cys Gly Ala Met Ala Thr Glu
1               5                   10                  15

Glu Phe Ile Ile Arg Ile Pro Pro Tyr His Tyr Ile His Val Leu Asp
                20                  25                  30

Gln Asn Ser Asn Val Ser Arg Val Glu Val Gly Pro Lys Thr Tyr Ile
            35                  40                  45

Arg Gln Asp Asn Glu Arg Val Leu Phe Ala Pro Met Arg Met Val Thr
        50                  55                  60

Val Pro Pro Arg His Tyr Cys Thr Val Ala Asn Pro Val Ser Arg Asp
65                  70                  75                  80

Ala Gln Gly Leu Val Leu Phe Asp Val Thr Gly Gln Val Arg Leu Arg
                85                  90                  95

His Ala Asp Leu Glu Ile Arg Leu Ala Gln Asp Pro Phe Pro Leu Tyr
                100                 105                 110

Pro Gly Glu Val Leu Glu Lys Asp Ile Thr Pro Leu Gln Val Val Leu
            115                 120                 125

Pro Asn Thr Ala Leu His Leu Lys Ala Leu Leu Asp Phe Glu Asp Lys
        130                 135                 140

Asp Gly Asp Lys Val Val Ala Gly Asp Glu Trp Leu Phe Glu Gly Pro
145                 150                 155                 160

Gly Thr Tyr Ile Pro Arg Lys Glu Val Glu Val Glu Ile Ile Gln
                165                 170                 175

Ala Thr Ile Ile Arg Gln Asn Gln Ala Leu Arg Leu Arg Ala Arg Lys
            180                 185                 190
```

```
Glu Cys Trp Asp Arg Asp Gly Lys Glu Arg Val Thr Gly Glu Trp
        195                 200                 205

Leu Val Thr Thr Val Gly Ala Tyr Leu Pro Ala Val Phe Glu Val
    210                 215                 220

Leu Asp Leu Val Asp Ala Val Ile Leu Thr Glu Lys Thr Ala Leu His
225                 230                 235                 240

Leu Arg Ala Arg Arg Asn Phe Arg Asp Phe Arg Gly Val Ser Arg Arg
                245                 250                 255

Thr Gly Glu Glu Trp Leu Val Thr Val Gln Asp Thr Glu Ala His Val
            260                 265                 270

Pro Asp Val His Glu Glu Val Leu Gly Val Val Pro Ile Thr Thr Leu
        275                 280                 285

Gly Pro His Asn Tyr Cys Val Ile Leu Asp Pro Val Gly Pro Asp Gly
    290                 295                 300

Lys Asn Gln Leu Gly Gln Lys Arg Val Val Lys Gly Glu Lys Ser Phe
305                 310                 315                 320

Phe Leu Gln Pro Gly Glu Gln Leu Glu Gln Gly Ile Gln Asp Val Tyr
                325                 330                 335

Val Leu Ser Glu Gln Gln Gly Leu Leu Leu Arg Ala Leu Gln Pro Leu
            340                 345                 350

Glu Glu Gly Glu Asp Glu Glu Lys Val Ser His Gln Ala Gly Asp His
        355                 360                 365

Trp Leu Ile Arg Gly Pro Leu Glu Tyr Val Pro Ser Ala Lys Val Glu
    370                 375                 380

Val Val Glu Glu Arg Gln Ala Ile Pro Leu Asp Glu Asn Glu Gly Ile
385                 390                 395                 400

Tyr Val Gln Asp Val Lys Thr Gly Lys Val Arg Ala Val Ile Gly Ser
                405                 410                 415

Thr Tyr Met Leu Thr Gln Asp Glu Val Leu Trp Glu Lys Glu Leu Pro
            420                 425                 430

Pro Gly Val Glu Glu Leu Leu Asn Lys Gly Gln Asp Pro Leu Ala Asp
        435                 440                 445

Arg Gly Glu Lys Asp Thr Ala Lys Ser Leu Gln Pro Leu Ala Pro Arg
    450                 455                 460

Asn Lys Thr Arg Val Val Ser Tyr Arg Val Pro His Asn Ala Ala Val
465                 470                 475                 480

Gln Val Tyr Asp Tyr Arg Glu Lys Arg Ala Arg Val Val Phe Gly Pro
                485                 490                 495

Glu Leu Val Ser Leu Gly Pro Glu Glu Gln Phe Thr Val Leu Ser Leu
            500                 505                 510

Ser Ala Gly Arg Pro Lys Arg Pro His Ala Arg Arg Ala Leu Cys Leu
        515                 520                 525

Leu Leu Gly Pro Asp Phe Phe Thr Asp Val Ile Thr Ile Glu Thr Ala
    530                 535                 540

Asp His Ala Arg Leu Gln Leu Gln Leu Ala Tyr Asn Trp His Phe Glu
545                 550                 555                 560

Val Asn Asp Arg Lys Asp Pro Gln Glu Thr Ala Lys Leu Phe Ser Val
                565                 570                 575

Pro Asp Phe Val Gly Asp Ala Cys Lys Ala Ile Ala Ser Arg Val Arg
            580                 585                 590

Gly Ala Val Ala Ser Val Thr Phe Asp Asp Phe His Lys Asn Ser Ala
        595                 600                 605

Arg Ile Ile Arg Thr Ala Val Phe Gly Phe Glu Thr Ser Glu Ala Lys
```

Gly Pro Asp Gly Met Ala Leu Pro Arg Pro Arg Asp Gln Ala Val Phe
625                 630                 635                 640

Pro Gln Asn Gly Leu Val Val Ser Ser Val Asp Val Gln Ser Val Glu
            645                 650                 655

Pro Val Asp Gln Arg Thr Arg Asp Ala Leu Gln Arg Ser Val Gln Leu
        660                 665                 670

Ala Ile Glu Ile Thr Thr Asn Ser Gln Glu Ala Ala Lys His Glu
    675                 680                 685

Ala Gln Arg Leu Glu Gln Glu Ala Arg Gly Arg Leu Glu Arg Gln Lys
690                 695                 700

Ile Leu Asp Gln Ser Glu Ala Glu Lys Ala Arg Lys Glu Leu Leu Glu
705                 710                 715                 720

Leu Glu Ala Leu Ser Met Ala Val Glu Ser Thr Gly Thr Ala Lys Ala
                725                 730                 735

Glu Ala Glu Ser Arg Ala Glu Ala Ala Arg Ile Glu Gly Glu Gly Ser
            740                 745                 750

Val Leu Gln Ala Lys Leu Lys Ala Gln Ala Leu Ala Ile Glu Thr Glu
        755                 760                 765

Ala Glu Leu Gln Arg Val Gln Lys Val Arg Glu Leu Glu Leu Val Tyr
770                 775                 780

Ala Arg Ala Gln Leu Glu Leu Glu Val Ser Lys Ala Gln Gln Leu Ala
785                 790                 795                 800

Glu Val Glu Val Lys Lys Phe Lys Gln Met Thr Glu Ala Ile Gly Pro
                805                 810                 815

Ser Thr Ile Arg Asp Leu Ala Val Ala Gly Pro Glu Met Gln Val Lys
            820                 825                 830

Leu Leu Gln Ser Leu Gly Leu Lys Ser Thr Leu Ile Thr Asp Gly Ser
        835                 840                 845

Thr Pro Ile Asn Leu Phe Asn Thr Ala Phe Gly Leu Leu Gly Met Gly
850                 855                 860

Pro Glu Gly Gln Pro Leu Gly Arg Arg Val Ala Ser Gly Pro Ser Pro
865                 870                 875                 880

Gly Glu Gly Ile Ser Pro Gln Ser Ala Gln Ala Pro Gln Ala Pro Gly
                885                 890                 895

Asp Asn His Val Val Pro Val Leu Arg
            900                 905

<210> SEQ ID NO 22
<211> LENGTH: 2718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggcaggct gcggttgtcc atgcggttgt ggcgccatgg caactgaaga gttcatcatc      60
cgcatccccc cataccacta tatccatgtg ctggaccaga acagcaacgt gtcccgtgtg     120
gaggtcgggc caaagaccta catccggcag gacaatgaga gggtactgtt tgccccccatg    180 cgcatggtga ccgtcccccc acgtcactac tgcacagtgg ccaaccctgt gtctcgggat     240 gcccaggggct tggtgctgtt tgatgtcaca gggcaagttc ggcttcgcca cgctgacctc    300
gagatccggc tggcccagga ccccttcccc ctgtacccag gggaggtgct ggaaaaggac    360

-continued

```
atcacacccc tgcaggtggt tctgcccaac actgccctcc atctaaaggc gctgcttgat        420
tttgaggata aagatggaga caaggtggtg caggagatg agtggctttt cgagggacct         480
ggcacgtaca tcccccggaa ggaagtggag gtcgtggaga tcattcaggc caccatcatc       540
aggcagaacc aggctctgcg gctcagggcc cgcaaggagt gctgggaccg ggacggcaag       600
gagagggtga caggggaaga atggctggtc accacagtag gggcgtacct cccagcggtg       660
tttgaggagg ttctggattt ggtggacgcc gtcatcctta cggaaaagac agccctgcac       720
ctccgggctc ggcggaactt ccgggacttc aggggagtgt cccgccgcac tggggaggag       780
tggctggtaa cagtgcagga cacagaggcc cacgtgccag atgtccacga ggaggtgctg       840
ggggttgtgc ccatcaccac cctgggcccc cacaactact gcgtgattct cgaccctgtc       900 ggaccgggatg gcaagaatca gctggggcag aagcgcgtgg tcaagggaga gaagtcttt     960 ttcctccagc caggagagca gctggaacaa ggcatccagg atgtgtatgt gctgtcggag      1020 cagcagggggc tgctgctgag ggccctgcag cccctggagg aggggagga tgaggagaag     1080 gtctcacacc aggctgggga ccactggctc atccgcggac ccctggagta tgtgccatct    1140
gccaaagtgg aggtggtgga ggagcgccca gccatccctc tagacgagaa cgagggcatc    1200
tatgtgcagg atgtcaagac cggaaaggtg cgcgctgtga ttggaagcac ctacatgctg    1260
acccaggacg aagtcctgtg ggagaaagag ctgcctcccg gggtggagga gctgctgaac    1320
aaggggcagg accctctggc agacagggt gagaaggaca cagctaagag cctccagccc     1380
ttggcgcccc ggaacaagac ccgtgtggtc agctaccgcg tgccccacaa cgctgcggtg    1440
caggtgtacg actaccgaga gaagcgagcc cgcgtggtct cgggcctga gctggtgtcg    1500 ctgggtcctg aggagcagtt cacagtgttg tccctctcag ctgggcggcc caagcgtccc    1560
catgcccgcc gtgcgctctg cctgctgctg gggcctgact tcttcacaga cgtcatcacc    1620
atcgaaacgg cggatcatgc caggctgcaa ctgcagctgg cctacaactg gcactttgag   1680
gtgaatgacc ggaaggaccc ccaagagacg gccaagctct tttcagtgcc agactttgta   1740
ggtgatgcct gcaaagccat cgcatcccgg gtgcggggg ccgtggcctc tgtcactttc   1800
gatgacttcc ataagaactc agcccgcatc attcgcactg ctgtctttgg ctttgagacc   1860
tcggaagcga agggccccga tggcatggcc ctgcccaggc cccgggacca ggctgtcttc    1920
ccccaaaacg ggctggtggt cagcagtgtg gacgtgcagt cagtggagcc tgtggatcag   1980
aggacccggg acgccctgca acgcagcgtc cagctggcca tcgagatcac caccaactcc   2040
caggaagcgg cggccaagca tgaggctcag agactggagc aggaagcccg cggccggctt    2100
gagcggcaga agatcctgga ccagtcagaa gccgagaaag ctcgcaagga acttttggag   2160
ctggaggctc tgagcatggc cgtggagagc accgggactg ccaaggcgga ggccgagtcc    2220
cgtgcggagg cagcccggat tgagggagaa gggtccgtgc tgcaggccaa gctaaaagca   2280
caggccttgg ccattgaaac ggaggctgag ctccagaggg tccagaaggt ccgagagctg   2340
gaactggtct atgcccgggc ccagctggag ctggaggtga gcaaggctca gcagctggct    2400
gaggtggagg tgaagaagtt caagcagatg acagaggcca taggccccag caccatcagg   2460
gaccttgctg tggctgggcc tgagatgcag gtaaaactgc tccagtccct gggcctgaaa   2520
tcaaccctca tcaccgatgg ctccactccc atcaacctct tcaacacagc ctttgggctg   2580
ctggggatgg ggcccgaggg tcagcccctg gcagaaggg tggccagtgg gcccagccct    2640
ggggagggga tatcccccca gtctgctcag gcccctcaag ctcctggaga caaccacgtg    2700
gtgcctgtac tgcgctaa                                                  2718
```

<210> SEQ ID NO 23
<211> LENGTH: 873
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Ala Gly Cys Gly Cys Pro Cys Gly Cys Gly Ala Met Ala Thr Glu
1               5                   10                  15

Glu Ala Ile Ile Arg Ile Pro Pro Tyr His Tyr Ile His Val Leu Asp
            20                  25                  30

Gln Asn Ser Asn Val Ser Arg Val Glu Val Gly Pro Lys Thr Tyr Ile
        35                  40                  45

Arg Gln Asp Asn Glu Arg Val Leu Phe Ala Pro Val Arg Met Val Thr
    50                  55                  60

Val Pro Pro Arg His Tyr Cys Ile Val Ala Asn Pro Val Ser Arg Asp
65                  70                  75                  80

Thr Gln Ser Ser Val Leu Phe Asp Ile Thr Gly Gln Val Arg Leu Arg
                85                  90                  95

His Ala Asp Gln Glu Ile Arg Leu Ala Gln Asp Pro Phe Pro Leu Tyr
            100                 105                 110

Pro Gly Glu Val Leu Glu Lys Asp Ile Thr Pro Leu Gln Val Val Leu
        115                 120                 125

Pro Asn Thr Ala Leu His Leu Lys Ala Leu Leu Asp Phe Glu Asp Lys
    130                 135                 140

Asn Gly Asp Lys Val Met Ala Gly Asp Glu Trp Leu Phe Glu Gly Pro
145                 150                 155                 160

Gly Thr Tyr Ile Pro Gln Lys Glu Val Glu Val Glu Ile Ile Gln
                165                 170                 175

Ala Thr Val Ile Lys Gln Asn Gln Ala Leu Arg Leu Arg Ala Arg Lys
            180                 185                 190

Glu Cys Phe Asp Arg Glu Gly Lys Gly Arg Val Thr Gly Glu Glu Trp
        195                 200                 205

Leu Val Arg Ser Val Gly Ala Tyr Leu Pro Ala Val Phe Glu Glu Val
    210                 215                 220

Leu Asp Leu Val Asp Ala Val Ile Leu Thr Glu Lys Thr Ala Leu His
225                 230                 235                 240

Leu Arg Ala Leu Gln Asn Phe Arg Asp Leu Arg Gly Val Leu His Arg
                245                 250                 255

Thr Gly Glu Glu Trp Leu Val Thr Val Gln Asp Thr Glu Ala His Val
            260                 265                 270

Pro Asp Val Tyr Glu Glu Val Leu Gly Val Val Pro Ile Thr Thr Leu
        275                 280                 285

Gly Pro Arg His Tyr Cys Val Ile Leu Asp Pro Met Gly Pro Asp Gly
    290                 295                 300

Lys Asn Gln Leu Gly Gln Lys Arg Val Val Lys Gly Glu Lys Ser Phe
305                 310                 315                 320

Phe Leu Gln Pro Gly Glu Arg Leu Glu Arg Gly Ile Gln Asp Val Tyr
                325                 330                 335

Val Leu Ser Glu Gln Gln Gly Leu Leu Leu Lys Ala Leu Gln Pro Leu
            340                 345                 350

Glu Glu Gly Glu Ser Glu Glu Lys Val Ser His Gln Ala Gly Asp Cys
```

```
                    355                 360                 365
Trp Leu Ile Arg Gly Pro Leu Glu Tyr Val Pro Ser Ala Lys Val Glu
    370                 375                 380

Val Val Glu Glu Arg Gln Ala Ile Pro Leu Asp Gln Asn Glu Gly Ile
385                 390                 395                 400

Tyr Val Gln Asp Val Lys Thr Gly Lys Val Arg Ala Val Ile Gly Ser
                    405                 410                 415

Thr Tyr Met Leu Thr Gln Asp Glu Val Leu Trp Glu Lys Glu Leu Pro
                420                 425                 430

Ser Gly Val Glu Glu Leu Leu Asn Leu Gly His Asp Pro Leu Ala Asp
            435                 440                 445

Arg Gly Gln Lys Gly Thr Ala Lys Pro Leu Gln Pro Ser Ala Pro Arg
        450                 455                 460

Asn Lys Thr Arg Val Val Ser Tyr Arg Val Pro His Asn Ala Ala Val
465                 470                 475                 480

Gln Val Tyr Asp Tyr Arg Ala Lys Arg Ala Arg Val Val Phe Gly Pro
                    485                 490                 495

Glu Leu Val Thr Leu Asp Pro Glu Glu Gln Phe Thr Val Leu Ser Leu
                500                 505                 510

Ser Ala Gly Arg Pro Lys Arg Pro His Ala Arg Arg Ala Leu Cys Leu
            515                 520                 525

Leu Leu Gly Pro Asp Phe Phe Thr Asp Val Ile Thr Ile Glu Thr Ala
        530                 535                 540

Asp His Ala Arg Leu Gln Leu Gln Leu Ala Tyr Asn Trp His Phe Glu
545                 550                 555                 560

Leu Lys Asn Arg Asn Asp Pro Ala Glu Ala Lys Leu Phe Ser Val
                    565                 570                 575

Pro Asp Phe Val Gly Asp Ala Cys Lys Ala Ile Ala Ser Arg Val Arg
                580                 585                 590

Gly Ala Val Ala Ser Val Thr Phe Asp Asp Phe His Lys Asn Ser Ala
            595                 600                 605

Arg Ile Ile Arg Met Ala Val Phe Gly Phe Glu Met Ser Glu Asp Thr
        610                 615                 620

Gly Pro Asp Gly Thr Leu Leu Pro Lys Ala Arg Asp Gln Ala Val Phe
625                 630                 635                 640

Pro Gln Asn Gly Leu Val Val Ser Ser Val Asp Val Gln Ser Val Glu
                    645                 650                 655

Pro Val Asp Gln Arg Thr Arg Asp Ala Leu Gln Arg Ser Val Gln Leu
                660                 665                 670

Ala Ile Glu Ile Thr Thr Asn Ser Gln Glu Ala Ala Lys His Glu
            675                 680                 685

Ala Gln Arg Leu Glu Gln Glu Ala Arg Gly Arg Leu Glu Arg Gln Lys
        690                 695                 700

Ile Leu Asp Gln Ser Glu Ala Glu Lys Ala Arg Lys Glu Leu Leu Glu
705                 710                 715                 720

Leu Glu Ala Met Ser Met Ala Val Glu Ser Thr Gly Asn Ala Lys Ala
                    725                 730                 735

Glu Ala Glu Ser Arg Ala Glu Ala Ala Arg Ile Glu Gly Glu Gly Ser
                740                 745                 750

Val Leu Gln Ala Lys Leu Lys Ala Gln Ala Leu Ala Ile Glu Thr Glu
            755                 760                 765

Ala Glu Leu Glu Arg Val Lys Lys Val Arg Glu Met Glu Leu Ile Tyr
        770                 775                 780
```

| Ala | Arg | Ala | Gln | Leu | Glu | Leu | Glu | Val | Ser | Lys | Ala | Gln | Gln | Leu | Ala |
|---|---|---|---|---|---|---|---|---|---|---|---|---|---|---|---|
| 785 | | | | 790 | | | | | 795 | | | | | 800 | |

Asn Val Glu Ala Lys Lys Phe Lys Glu Met Thr Glu Ala Leu Gly Pro
                    805                  810                815

Gly Thr Ile Arg Asp Leu Ala Val Ala Gly Pro Glu Met Gln Val Lys
        820                  825              830

Leu Leu Gln Ser Leu Gly Leu Lys Ser Thr Leu Ile Thr Asp Gly Ser
          835                  840              845

Ser Pro Ile Asn Leu Phe Ser Thr Ala Phe Gly Leu Leu Gly Leu Gly
850                  855                860

Ser Asp Gly Gln Pro Pro Ala Gln Lys
865                  870

<210> SEQ ID NO 24
<211> LENGTH: 2622
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 24

```
atggcaggct gcggttgtcc atgcggttgt ggcgccatgg caactgaaga ggccatcatc      60
cgcatccccc cataccacta catccatgtg ctggaccaga acagtaatgt gtcccgtgtg     120
gaggttggac caaagaccta catccggcag acaatgagag ggtactgtt tgccccagtt     180
cgcatggtga ccgtcccccc acgccactac tgcatagtgg ccaaccctgt gtcccgggac     240
acccagagtt ctgtgttatt tgacatcaca ggacaagtcc gactccggca cgctgaccag     300
gagatccgac tagcccagga ccccttcccc ctgtatccag gggaggtgct ggaaaaggac     360
atcaccccac tgcaggtggt tctgcccaac acagcactgc atcttaaggc gttgctggac     420
tttgaggata gaatggaga caaggtcatg gcaggagacg agtggctatt tgagggacct     480
ggcacctaca tcccacagaa ggaagtggaa gtcgtggaga tcattcaggc cacagtcatc     540
aaacagaacc aagcactgcg gctaagggcc gaaaggagt gctttgaccg ggagggcaag     600
gggcgcgtga caggtgagga gtggctggtc cgatccgtgg gggcttacct cccagctgtc     660
tttgaagagg tgctggatct ggtggatgct gtgatcctta cagaaaagac tgccctgcac     720
ctccgggctc tgcagaactt cagggacctt cggggagtgc tccaccgcac cggggaggaa     780
tggttagtga cagtgcagga cacagaagcc catgttccag atgtctatga ggaggtgctt     840
ggggtagtac ccatcaccac cctgggacct cgacactact gtgtcattct tgacccaatg     900
ggaccagacg gcaagaacca gctgggacaa aagcgtgttg tcaagggaga gaagtccttt     960
ttcctccagc caggagagag gctggagcga ggcatccagg atgtgtatgt gctgtcagag    1020
cagcaggggc tgctactgaa ggcactgcag cccctggagg agggagagag cgaggagaag    1080
gtctcccatc aggccggaga ctgctggctc atccgtgggc ccctggagta tgtgccatct    1140
gcaaaagtgg aggtggtgga ggagcgtcag gctatccctc tggaccaaaa tgagggcatc    1200
tatgtgcagg atgtcaagac ggggaaggtg cgggctgtga ttggaagcac ctacatgctg    1260
actcaggatg aagtcctgtg ggaaaaggag ctgccttctg ggtggagga gctgctgaac    1320
ttggggcatg accctctggc agacaggggt cagaagggca gccaagcc ccttcagccc    1380
tcagctccaa ggaacaagac ccgagtggtc agctaccgtg tcccgcacaa tgcagcggtg    1440
caggtctatg actacagagc caagagagcc cgtgtggtct ttgggcccga gctagtgaca    1500
```

-continued

```
ctggatcctg aggagcagtt cacagtattg tccctttctg ccgggcgacc caagcgtcct   1560
catgcccgcc gtgcactctg cctactgctg ggacctgatt tctttactga tgtcatcacc   1620
atcgaaactg cagatcatgc caggttgcag ctgcagcttg cctacaactg cactttgaa    1680
ctgaagaacc ggaatgaccc tgcagaggca gccaagcttt tctccgtgcc tgacttcgtg   1740
ggtgacgcct gcaaggccat tgcatcccga gtccgggggg ctgtagcctc tgtcaccttt   1800
gatgacttcc ataaaaactc agcccggatc attcgaatgg ctgttttttgg ctttgagatg  1860
tctgaagaca caggtcctga tggcacactc ctgcccaagg ctcgagacca ggcagtcttt   1920
ccccaaaacg ggctggtagt cagcagtgtg gatgtgcagt cagtggagcc cgtggaccag   1980
aggacccggg atgcccttca gcgcagcgtt cagctggcca tcgaaattac caccaactcc   2040
caggaggcag cagccaagca cgaggctcag agactggaac aggaagcccg tggtcggctt   2100
gagaggcaga agatcttgga ccagtcagaa gctgaaaaag cccgcaagga actcttggag   2160
cttgaggcta tgagcatggc tgtggagagc acgggtaatg ccaaagcaga ggctgagtcc   2220
cgtgcagagg cagcgaggat cgaaggagaa ggctctgtgc tgcaggccaa gctcaaggca   2280
caggcgctag ccattgagac ggaggctgag ttggagcgag taaagaaagt acgagagatg   2340
gaactgatct atgcccgggc ccagttggag ctggaggtga gcaaggcgca gcagcttgcc   2400
aatgtggagg caaagaagtt caaggagatg acagaggcac tgggccccgg caccatcagg   2460
gacctggctg tggccgggcc agagatgcag gtgaaacttc tccagtccct gggcctgaaa   2520
tccactctca tcaccgatgg ctcgtctccc atcaacctct tcagcacagc cttcgggttg   2580
ctggggctgg ggtctgatgg tcagccgcca gcacagaagt ga                      2622
```

<210> SEQ ID NO 25
<211> LENGTH: 2627
<212> TYPE: PRT
<213> ORGANISM: Homo sapiens

<400> SEQUENCE: 25

```
Met Glu Lys Leu His Gly His Val Ser Ala His Pro Asp Ile Leu Ser
1               5                   10                  15

Leu Glu Asn Arg Cys Leu Ala Met Leu Pro Asp Leu Gln Pro Leu Glu
            20                  25                  30

Lys Leu His Gln His Val Ser Thr His Ser Asp Ile Leu Ser Leu Lys
        35                  40                  45

Asn Gln Cys Leu Ala Thr Leu Pro Asp Leu Lys Thr Met Glu Lys Pro
    50                  55                  60

His Gly Tyr Val Ser Ala His Pro Asp Ile Leu Ser Leu Glu Asn Gln
65                  70                  75                  80

Cys Leu Ala Thr Leu Ser Asp Leu Lys Thr Met Glu Lys Pro His Gly
                85                  90                  95

His Val Ser Ala His Pro Asp Ile Leu Ser Leu Glu Asn Arg Cys Leu
            100                 105                 110

Ala Thr Leu Pro Ser Leu Lys Ser Thr Val Ser Ala Ser Pro Leu Phe
        115                 120                 125

Gln Ser Leu Gln Ile Ser His Met Thr Gln Ala Asp Leu Tyr Arg Val
    130                 135                 140

Asn Asn Ser Asn Cys Leu Leu Ser Glu Pro Pro Ser Trp Arg Ala Gln
145                 150                 155                 160

His Phe Ser Lys Gly Leu Asp Leu Ser Thr Cys Pro Ile Ala Leu Lys
                165                 170                 175
```

-continued

```
Ser Ile Ser Ala Thr Glu Thr Ala Gln Glu Ala Thr Leu Gly Arg Trp
            180                 185                 190

Phe Asp Ser Glu Glu Lys Lys Gly Ala Glu Thr Gln Met Pro Ser Tyr
            195                 200                 205

Ser Leu Ser Leu Gly Glu Glu Glu Val Glu Asp Leu Ala Val Lys
210                 215                 220

Leu Thr Ser Gly Asp Ser Glu Ser His Pro Glu Pro Thr Asp His Val
225                 230                 235                 240

Leu Gln Glu Lys Lys Met Ala Leu Leu Ser Leu Leu Cys Ser Thr Leu
            245                 250                 255

Val Ser Glu Val Asn Met Asn Asn Thr Ser Asp Pro Thr Leu Ala Ala
            260                 265                 270

Ile Phe Glu Ile Cys Arg Glu Leu Ala Leu Leu Glu Pro Glu Phe Ile
            275                 280                 285

Leu Lys Ala Ser Leu Tyr Ala Arg Gln Gln Leu Asn Val Arg Asn Val
            290                 295                 300

Ala Asn Asn Ile Leu Ala Ile Ala Ala Phe Leu Pro Ala Cys Arg Pro
305                 310                 315                 320

His Leu Arg Arg Tyr Phe Cys Ala Ile Val Gln Leu Pro Ser Asp Trp
            325                 330                 335

Ile Gln Val Ala Glu Leu Tyr Gln Ser Leu Ala Glu Gly Asp Lys Asn
            340                 345                 350

Lys Leu Val Pro Leu Pro Ala Cys Leu Arg Thr Ala Met Thr Asp Lys
            355                 360                 365

Phe Ala Gln Phe Asp Glu Tyr Gln Leu Ala Lys Tyr Asn Pro Arg Lys
            370                 375                 380

His Arg Ala Lys Arg His Pro Arg Arg Pro Arg Ser Pro Gly Met
385                 390                 395                 400

Glu Pro Pro Phe Ser His Arg Cys Phe Pro Arg Tyr Ile Gly Phe Leu
            405                 410                 415

Arg Glu Glu Gln Arg Lys Phe Glu Lys Ala Gly Asp Thr Val Ser Glu
            420                 425                 430

Lys Lys Asn Pro Pro Arg Phe Thr Leu Lys Lys Leu Val Gln Arg Leu
            435                 440                 445

His Ile His Lys Pro Ala Gln His Val Gln Ala Leu Leu Gly Tyr Arg
            450                 455                 460

Tyr Pro Ser Asn Leu Gln Leu Phe Ser Arg Ser Arg Leu Pro Gly Pro
465                 470                 475                 480

Trp Asp Ser Ser Arg Ala Gly Lys Arg Met Lys Leu Ser Arg Pro Glu
            485                 490                 495

Thr Trp Glu Arg Glu Leu Ser Leu Arg Gly Asn Lys Ala Ser Val Trp
            500                 505                 510

Glu Glu Leu Ile Glu Asn Gly Lys Leu Pro Phe Met Ala Met Leu Arg
            515                 520                 525

Asn Leu Cys Asn Leu Leu Arg Val Gly Ile Ser Ser Arg His His Glu
            530                 535                 540

Leu Ile Leu Gln Arg Leu Gln His Gly Lys Ser Val Ile His Ser Arg
545                 550                 555                 560

Gln Phe Pro Phe Arg Phe Leu Asn Ala His Asp Ala Ile Asp Ala Leu
            565                 570                 575

Glu Ala Gln Leu Arg Asn Gln Ala Leu Pro Phe Pro Ser Asn Ile Thr
            580                 585                 590
```

```
Leu Met Arg Arg Ile Leu Thr Arg Asn Glu Lys Asn Arg Pro Arg Arg
            595                 600                 605

Arg Phe Leu Cys His Leu Ser Arg Gln Gln Leu Arg Met Ala Met Arg
        610                 615                 620

Ile Pro Val Leu Tyr Glu Gln Leu Lys Arg Glu Lys Leu Arg Val His
625                 630                 635                 640

Lys Ala Arg Gln Trp Lys Tyr Asp Gly Glu Met Leu Asn Arg Tyr Arg
                645                 650                 655

Gln Ala Leu Glu Thr Ala Val Asn Leu Ser Val Lys His Ser Leu Pro
            660                 665                 670

Leu Leu Pro Gly Arg Thr Val Leu Val Tyr Leu Thr Asp Ala Asn Ala
        675                 680                 685

Asp Arg Leu Cys Pro Lys Ser Asn Pro Gln Gly Pro Pro Leu Asn Tyr
    690                 695                 700

Ala Leu Leu Leu Ile Gly Met Met Ile Thr Arg Ala Glu Gln Val Asp
705                 710                 715                 720

Val Val Leu Cys Gly Gly Asp Thr Leu Lys Thr Ala Val Leu Lys Ala
                725                 730                 735

Glu Glu Gly Ile Leu Lys Thr Ala Ile Lys Leu Gln Ala Gln Val Gln
            740                 745                 750

Glu Phe Asp Glu Asn Asp Gly Trp Ser Leu Asn Thr Phe Gly Lys Tyr
        755                 760                 765

Leu Leu Ser Leu Ala Gly Gln Arg Val Pro Val Asp Arg Val Ile Leu
    770                 775                 780

Leu Gly Gln Ser Met Asp Asp Gly Met Ile Asn Val Ala Lys Gln Leu
785                 790                 795                 800

Tyr Trp Gln Arg Val Asn Ser Lys Cys Leu Phe Val Gly Ile Leu Leu
                805                 810                 815

Arg Arg Val Gln Tyr Leu Ser Thr Asp Leu Asn Pro Asn Asp Val Thr
            820                 825                 830

Leu Ser Gly Cys Thr Asp Ala Ile Leu Lys Phe Ile Ala Glu His Gly
        835                 840                 845

Ala Ser His Leu Leu Glu His Val Gly Gln Met Asp Lys Ile Phe Lys
    850                 855                 860

Ile Pro Pro Pro Gly Lys Thr Gly Val Gln Ser Leu Arg Pro Leu
865                 870                 875                 880

Glu Glu Asp Thr Pro Ser Pro Leu Ala Pro Val Ser Gln Gln Gly Trp
                885                 890                 895

Arg Ser Ile Arg Leu Phe Ile Ser Ser Thr Phe Arg Asp Met His Gly
            900                 905                 910

Glu Arg Asp Leu Leu Leu Arg Ser Val Leu Pro Ala Leu Gln Ala Arg
        915                 920                 925

Ala Ala Pro His Arg Ile Ser Leu His Gly Ile Asp Leu Arg Trp Gly
    930                 935                 940

Val Thr Glu Glu Glu Thr Arg Arg Asn Arg Gln Leu Glu Val Cys Leu
945                 950                 955                 960

Gly Glu Val Glu Asn Ala Gln Leu Phe Val Gly Ile Leu Gly Ser Arg
                965                 970                 975

Tyr Gly Tyr Ile Pro Pro Ser Tyr Asn Leu Pro Asp His Pro His Phe
            980                 985                 990

His Trp Ala Gln Gln Tyr Pro Ser  Gly Arg Ser Val Thr  Glu Met Glu
        995                 1000                1005

Val Met  Gln Phe Leu Asn Arg  Asn Gln Arg Leu Gln  Pro Ser Ala
```

-continued

```
            1010                1015                1020

Gln Ala Leu Ile Tyr Phe Arg Asp Ser Ser Phe Leu Ser Ser Val
        1025                1030                1035

Pro Asp Ala Trp Lys Ser Asp Phe Val Ser Glu Ser Glu Glu Ala
        1040                1045                1050

Ala Cys Arg Ile Ser Glu Leu Lys Ser Tyr Leu Ser Arg Gln Lys
        1055                1060                1065

Gly Ile Thr Cys Arg Arg Tyr Pro Cys Glu Trp Gly Val Ala
        1070                1075                1080

Ala Gly Arg Pro Tyr Val Gly Leu Glu Glu Phe Gly Gln Leu
        1085                1090                1095

Val Leu Gln Asp Val Trp Asn Met Ile Gln Lys Leu Tyr Leu Gln
        1100                1105                1110

Pro Gly Ala Leu Leu Glu Gln Pro Val Ser Ile Pro Asp Asp Asp
        1115                1120                1125

Leu Val Gln Ala Thr Phe Gln Gln Leu Gln Lys Pro Pro Ser Pro
        1130                1135                1140

Ala Arg Pro Arg Leu Leu Gln Asp Thr Val Gln Gln Leu Met Leu
        1145                1150                1155

Pro His Gly Arg Leu Ser Leu Val Thr Gly Gln Ser Gly Gln Gly
        1160                1165                1170

Lys Thr Ala Phe Leu Ala Ser Leu Val Ser Ala Leu Gln Ala Pro
        1175                1180                1185

Asp Gly Ala Lys Val Ala Pro Leu Val Phe Phe His Phe Ser Gly
        1190                1195                1200

Ala Arg Pro Asp Gln Gly Leu Ala Leu Thr Leu Leu Arg Arg Leu
        1205                1210                1215

Cys Thr Tyr Leu Arg Gly Gln Leu Lys Glu Pro Gly Ala Leu Pro
        1220                1225                1230

Ser Thr Tyr Arg Ser Leu Val Trp Glu Leu Gln Gln Arg Leu Leu
        1235                1240                1245

Pro Lys Ser Ala Glu Ser Leu His Pro Gly Gln Thr Gln Val Leu
        1250                1255                1260

Ile Ile Asp Gly Ala Asp Arg Leu Val Asp Gln Asn Gly Gln Leu
        1265                1270                1275

Ile Ser Asp Trp Ile Pro Lys Lys Leu Pro Arg Cys Val His Leu
        1280                1285                1290

Val Leu Ser Val Ser Ser Asp Ala Gly Leu Gly Glu Thr Leu Glu
        1295                1300                1305

Gln Ser Gln Gly Ala His Val Leu Ala Leu Gly Pro Leu Glu Ala
        1310                1315                1320

Ser Ala Arg Ala Arg Leu Val Arg Glu Glu Leu Ala Leu Tyr Gly
        1325                1330                1335

Lys Arg Leu Glu Glu Ser Pro Phe Asn Asn Gln Met Arg Leu Leu
        1340                1345                1350

Leu Val Lys Arg Glu Ser Gly Arg Pro Leu Tyr Leu Arg Leu Val
        1355                1360                1365

Thr Asp His Leu Arg Leu Phe Thr Leu Tyr Glu Gln Val Ser Glu
        1370                1375                1380

Arg Leu Arg Thr Leu Pro Ala Thr Val Pro Leu Leu Leu Gln His
        1385                1390                1395

Ile Leu Ser Thr Leu Glu Lys Glu His Gly Pro Asp Val Leu Pro
        1400                1405                1410
```

```
Gln Ala Leu Thr Ala Leu Glu Val Thr Arg Ser Gly Leu Thr Val
1415                1420                1425

Asp Gln Leu His Gly Val Leu Ser Val Trp Arg Thr Leu Pro Lys
1430                1435                1440

Gly Thr Lys Ser Trp Glu Glu Ala Val Ala Ala Gly Asn Ser Gly
1445                1450                1455

Asp Pro Tyr Pro Met Gly Pro Phe Ala Cys Leu Val Gln Ser Leu
1460                1465                1470

Arg Ser Leu Leu Gly Glu Gly Pro Leu Glu Arg Pro Gly Ala Arg
1475                1480                1485

Leu Cys Leu Pro Asp Gly Pro Leu Arg Thr Ala Ala Lys Arg Cys
1490                1495                1500

Tyr Gly Lys Arg Pro Gly Leu Glu Asp Thr Ala His Ile Leu Ile
1505                1510                1515

Ala Ala Gln Leu Trp Lys Thr Cys Asp Ala Asp Ala Ser Gly Thr
1520                1525                1530

Phe Arg Ser Cys Pro Pro Glu Ala Leu Gly Asp Leu Pro Tyr His
1535                1540                1545

Leu Leu Gln Ser Gly Asn Arg Gly Leu Leu Ser Lys Phe Leu Thr
1550                1555                1560

Asn Leu His Val Val Ala Ala His Leu Glu Leu Gly Leu Val Ser
1565                1570                1575

Arg Leu Leu Glu Ala His Ala Leu Tyr Ala Ser Ser Val Pro Lys
1580                1585                1590

Glu Glu Gln Lys Leu Pro Glu Ala Asp Val Ala Val Phe Arg Thr
1595                1600                1605

Phe Leu Arg Gln Gln Ala Ser Ile Leu Ser Gln Tyr Pro Arg Leu
1610                1615                1620

Leu Pro Gln Gln Ala Ala Asn Gln Pro Leu Asp Ser Pro Leu Cys
1625                1630                1635

His Gln Ala Ser Leu Leu Ser Arg Arg Trp His Leu Gln His Thr
1640                1645                1650

Leu Arg Trp Leu Asn Lys Pro Arg Thr Met Lys Asn Gln Gln Ser
1655                1660                1665

Ser Ser Leu Ser Leu Ala Val Ser Ser Ser Pro Thr Ala Val Ala
1670                1675                1680

Phe Ser Thr Asn Gly Gln Arg Ala Ala Val Gly Thr Ala Asn Gly
1685                1690                1695

Thr Val Tyr Leu Leu Asp Leu Arg Thr Trp Gln Glu Glu Lys Ser
1700                1705                1710

Val Val Ser Gly Cys Asp Gly Ile Ser Ala Cys Leu Phe Leu Ser
1715                1720                1725

Asp Asp Thr Leu Phe Leu Thr Ala Phe Asp Gly Leu Leu Glu Leu
1730                1735                1740

Trp Asp Leu Gln His Gly Cys Arg Val Leu Gln Thr Lys Ala His
1745                1750                1755

Gln Tyr Gln Ile Thr Gly Cys Cys Leu Ser Pro Asp Cys Arg Leu
1760                1765                1770

Leu Ala Thr Val Cys Leu Gly Gly Cys Leu Lys Leu Trp Asp Thr
1775                1780                1785

Val Arg Gly Gln Leu Ala Phe Gln His Thr Tyr Pro Lys Ser Leu
1790                1795                1800
```

```
Asn Cys Val Ala Phe His Pro Glu Gly Gln Val Ile Ala Thr Gly
1805                1810                1815

Ser Trp Ala Gly Ser Ile Ser Phe Phe Gln Val Asp Gly Leu Lys
1820                1825                1830

Val Thr Lys Asp Leu Gly Ala Pro Gly Ala Ser Ile Arg Thr Leu
1835                1840                1845

Ala Phe Asn Val Pro Gly Gly Val Val Ala Val Gly Arg Leu Asp
1850                1855                1860

Ser Met Val Glu Leu Trp Ala Trp Arg Glu Gly Ala Arg Leu Ala
1865                1870                1875

Ala Phe Pro Ala His His Gly Phe Val Ala Ala Ala Leu Phe Leu
1880                1885                1890

His Ala Gly Cys Gln Leu Leu Thr Ala Gly Glu Asp Gly Lys Val
1895                1900                1905

Gln Val Trp Ser Gly Ser Leu Gly Arg Pro Arg Gly His Leu Gly
1910                1915                1920

Ser Leu Ser Leu Ser Pro Ala Leu Ser Val Ala Leu Ser Pro Asp
1925                1930                1935

Gly Asp Arg Val Ala Val Gly Tyr Arg Ala Asp Gly Ile Arg Ile
1940                1945                1950

Tyr Lys Ile Ser Ser Gly Ser Gln Gly Ala Gln Gly Gln Ala Leu
1955                1960                1965

Asp Val Ala Val Ser Ala Leu Ala Trp Leu Ser Pro Lys Val Leu
1970                1975                1980

Val Ser Gly Ala Glu Asp Gly Ser Leu Gln Gly Trp Ala Leu Lys
1985                1990                1995

Glu Cys Ser Leu Gln Ser Leu Trp Leu Leu Ser Arg Phe Gln Lys
2000                2005                2010

Pro Val Leu Gly Leu Ala Thr Ser Gln Glu Leu Leu Ala Ser Ala
2015                2020                2025

Ser Glu Asp Phe Thr Val Gln Leu Trp Pro Arg Gln Leu Leu Thr
2030                2035                2040

Arg Pro His Lys Ala Glu Asp Phe Pro Cys Gly Thr Glu Leu Arg
2045                2050                2055

Gly His Glu Gly Pro Val Ser Cys Cys Ser Phe Ser Thr Asp Gly
2060                2065                2070

Gly Ser Leu Ala Thr Gly Gly Arg Asp Arg Ser Leu Leu Cys Trp
2075                2080                2085

Asp Val Arg Thr Pro Lys Thr Pro Val Leu Ile His Ser Phe Pro
2090                2095                2100

Ala Cys His Arg Asp Trp Val Thr Gly Cys Ala Trp Thr Lys Asp
2105                2110                2115

Asn Leu Leu Ile Ser Cys Ser Ser Asp Gly Ser Val Gly Leu Trp
2120                2125                2130

Asp Pro Glu Ser Gly Gln Arg Leu Gly Gln Phe Leu Gly His Gln
2135                2140                2145

Ser Ala Val Ser Ala Val Ala Val Glu Glu His Val Val Ser
2150                2155                2160

Val Ser Arg Asp Gly Thr Leu Lys Val Trp Asp His Gln Gly Val
2165                2170                2175

Glu Leu Thr Ser Ile Pro Ala His Ser Gly Pro Ile Ser His Cys
2180                2185                2190

Ala Ala Ala Met Glu Pro Arg Ala Ala Gly Gln Pro Gly Ser Glu
```

```
              2195                2200                2205
Leu Leu Val Val Thr Val Gly Leu Asp Gly Ala Thr Arg Leu Trp
    2210                2215                2220

His Pro Leu Leu Val Cys Gln Thr His Thr Leu Leu Gly His Ser
    2225                2230                2235

Gly Pro Val Arg Ala Ala Ala Val Ser Glu Thr Ser Gly Leu Met
    2240                2245                2250

Leu Thr Ala Ser Glu Asp Gly Ser Val Arg Leu Trp Gln Val Pro
    2255                2260                2265

Lys Glu Ala Asp Asp Thr Cys Ile Pro Arg Ser Ser Ala Ala Val
    2270                2275                2280

Thr Ala Val Ala Trp Ala Pro Asp Gly Ser Met Ala Val Ser Gly
    2285                2290                2295

Asn Gln Ala Gly Glu Leu Ile Leu Trp Gln Glu Ala Lys Ala Val
    2300                2305                2310

Ala Thr Ala Gln Ala Pro Gly His Ile Gly Ala Leu Ile Trp Ser
    2315                2320                2325

Ser Ala His Thr Phe Phe Val Leu Ser Ala Asp Glu Lys Ile Ser
    2330                2335                2340

Glu Trp Gln Val Lys Leu Arg Lys Gly Ser Ala Pro Gly Asn Leu
    2345                2350                2355

Ser Leu His Leu Asn Arg Ile Leu Gln Glu Asp Leu Gly Val Leu
    2360                2365                2370

Thr Ser Leu Asp Trp Ala Pro Asp Gly His Phe Leu Ile Leu Ala
    2375                2380                2385

Lys Ala Asp Leu Lys Leu Leu Cys Met Lys Pro Gly Asp Ala Pro
    2390                2395                2400

Ser Glu Ile Trp Ser Ser Tyr Thr Glu Asn Pro Met Ile Leu Ser
    2405                2410                2415

Thr His Lys Glu Tyr Gly Ile Phe Val Leu Gln Pro Lys Asp Pro
    2420                2425                2430

Gly Val Leu Ser Phe Leu Arg Gln Lys Glu Ser Gly Glu Phe Glu
    2435                2440                2445

Glu Arg Leu Asn Phe Asp Ile Asn Leu Glu Asn Pro Ser Arg Thr
    2450                2455                2460

Leu Ile Ser Ile Thr Gln Ala Lys Pro Glu Ser Glu Ser Ser Phe
    2465                2470                2475

Leu Cys Ala Ser Ser Asp Gly Ile Leu Trp Asn Leu Ala Lys Cys
    2480                2485                2490

Ser Pro Glu Gly Glu Trp Thr Thr Gly Asn Met Trp Gln Lys Lys
    2495                2500                2505

Ala Asn Thr Pro Glu Thr Gln Thr Pro Gly Thr Asp Pro Ser Thr
    2510                2515                2520

Cys Arg Glu Ser Asp Ala Ser Met Asp Ser Asp Ala Ser Met Asp
    2525                2530                2535

Ser Glu Pro Thr Pro His Leu Lys Thr Arg Gln Arg Arg Lys Ile
    2540                2545                2550

His Ser Gly Ser Val Thr Ala Leu His Val Leu Pro Glu Leu Leu
    2555                2560                2565

Val Thr Ala Ser Lys Asp Arg Asp Val Lys Leu Trp Glu Arg Pro
    2570                2575                2580

Ser Met Gln Leu Leu Gly Leu Phe Arg Cys Glu Gly Ser Val Ser
    2585                2590                2595
```

```
Cys Leu Glu Pro Trp Leu Gly Ala Asn Ser Thr Leu Gln Leu Ala
    2600            2605                2610

Val Gly Asp Val Gln Gly Asn Val Tyr Phe Leu Asn Trp Glu
    2615            2620                2625

<210> SEQ ID NO 26
<211> LENGTH: 7884
<212> TYPE: DNA
<213> ORGANISM: Homo sapiens

<400> SEQUENCE: 26
atggaaaaac tccatgggca tgtgtctgcc catccagaca tcctctcctt ggagaaccgg     60
tgcctggcta tgctccctga cttacagccc ttggagaaac tacatcagca tgtatctacc    120
cactcagata tcctctcctt gaagaaccag tgcctagcca cgcttcctga cctgaagacc    180
atggaaaaac cacatggata tgtgtctgcc cacccagaca tcctctcctt ggagaaccag    240
tgcctggcca cactttctga cctgaagacc atggagaaac cacatggaca tgtttctgcc    300
cacccagaca tcctctcctt ggagaaccgg tgcctggcca ccctccctag tctaaagagc    360
actgtgtctg ccagccccct tgttccagag tctacagata tctcacatga cgcaagctgat    420 ttgtaccgtg tgaacaacag caattgcctg ctctctgagc ctccaagttg gaggctcag    480 catttctcta agggactaga cctttcaacc tgccctatag ccctgaaatc catctctgcc    540
acagagacag ctcaggaagc aactttgggt cgttggtttg attcagaaga agagaaaggg    600
gcagagaccc aaatgccttc ttatagtctg agcttgggag aggaggagga ggtggaggat    660
ctggccgtga agctcacctc tggagactct gaatctcatc cagagcctac tgaccatgtc    720
cttcaggaaa agaagatggc tctactgagc ttgctgtgct ctactctggt ctcagaagta    780
aacatgaaca atacatctga ccccaccctg gctgccattt ttgaaatctg tcgtgaactt    840
gccctcctgg agcctgagtt tatcctcaag gcatctttgt atgccaggca gcagctgaac    900
gtccggaatg tggccaataa catcttggcc attgctgctt tcttgccggc gtgtcgcccc    960
cacctgcgac gatatttctg tgccattgtc cagctgcctt ctgactggat ccaggtggct   1020
gagctttacc agagcctggc tgagggagat aagaataagc tggtgcccct gcccgcctgt   1080
ctccgtactg ccatgacgga caaatttgcc cagtttgacg agtaccagct ggctaagtac   1140
aaccctcgga agcaccgggc caagagacac ccccgccggc cacccccgctc tccagggatg   1200 gagcctccat tttctcacag atgttttcca aggtacatag ggtttctcag agaagagcag   1260
agaaagtttg agaaggccgg tgatacagtg tcagagaaaa agaatcctcc aaggttcacc   1320
ctgaagaagc tggttcagcg actgcacatc cacaagcctg cccagcacgt tcaagccctg   1380
ctgggttaca gataccctc caacctacag ctcttttctc gaagtcgcct tcctgggcct   1440
tgggattcta gcagagctgg gaagaggatg aagctgtcta ggccagagac ctgggagcgg   1500
gagctgagcc tacgggggaa caaagcgtcg gtctgggagg aactcattga aaatgggaag   1560
cttcccttca tggccatgct tcggaacctg tgcaacctgc tgcgggttgg aatcagttcc   1620
cgccaccatg agctcattct ccagagactc agcatggga agtcggtgat ccacagtcgg   1680
cagtttccat tcagatttct taacgcccat gatgccattt atgccctcga ggctcaactc   1740
agaaatcaag cattgcccct tccttcgaat ataacactga tgaggcggat actaactaga   1800
aatgaaaaga accgtcccag gcggaggttt ctttgccacc taagccgtca gcagcttcgt   1860
atggcaatga ggataccgt gttgtatgag cagctcaaga gggagaagct gagagtacac   1920
```

```
aaggccagac agtggaaata tgatggtgag atgctgaaca ggtaccgaca ggccctagag    1980
acagctgtga acctctctgt gaagcacagc ctgcccctgc tgccaggccg cactgtcttg    2040
gtctatctga cagatgctaa tgcagacagg ctctgtccaa agagcaaccc acaagggccc    2100
ccgctgaact atgcactgct gttgattggg atgatgatca cgaggcgga gcaggtggac    2160 gtcgtgctgt gtggaggtga cactctgaag actgcagtgc ttaaggcaga agaaggcatc    2220
ctgaagactg ccatcaagct ccaggctcaa gtccaggagt ttgatgaaaa tgatggatgg    2280
tccctgaata cttttgggaa atacctgctg tctctggctg gccaaagggt tcctgtggac    2340
agggtcatcc tccttggcca aagcatggat gatggaatga taaatgtggc caaacagctt    2400
tactggcagc gtgtgaattc caagtgcctc tttgttggta tcctcctaag aagggtacaa    2460
tacctgtcaa cagatttgaa tcccaatgat gtgacactct caggctgtac tgatgcgata    2520
ctgaagttca ttgcagagca tggggcctcc catcttctgg aacatgtggg ccaaatggac    2580
aaaatattca agattccacc acccccagga aagacagggg tccagtctct ccggccactg    2640
gaagaggaca ctccaagccc cttggctcct gtttcccagc aaggatggcg cagcatccgg    2700
cttttcattt catccacttt ccgagacatg cacggggagc gggacctgct gctgaggtct    2760
gtgctgccag cactgcaggc ccgagcggcc cctcaccgta tcagccttca cggaatcgac    2820
ctccgctggg gcgtcactga ggaggagacc cgtaggaaca gacaactgga agtgtgcctt    2880
ggggaggtgg agaacgcaca gctgtttgtg gggattctgg gctcccgtta tggatacatt    2940 cccccccagct acaaccttcc tgaccatcca cacttccact gggcccagca gtacccttca    3000
gggcgctctg tgacagagat ggaggtgatg cagttcctga accggaacca acgtctgcag    3060
ccctctgccc aagctctcat ctacttccgg gattccagct tcctcagctc tgtgccagat    3120
gcctggaaat ctgactttgt ttctgagtct gaagaggccg catgtcggat ctcagaactg    3180
aagagctacc taagcagaca gaaagggata acctgccgca gatacccctg tgagtggggg    3240
ggtgtggcag ctgccggcc ctatgttggc gggctgaggg agtttgggca gttggttctg    3300
caggatgtat ggaatatgat ccagaagctc tacctgcagc ctggggccct gctggagcag    3360
ccagtgtcca tcccagacga tgacttggtc caggccacct tccagcagct gcagaagcca    3420
ccgagtcctg cccggccacg ccttcttcag gacacagtgc aacagctgat gctgccccac    3480
ggaaggctga gcctggtgac ggggcagtca ggacagggca agacagcctt cctggcatct    3540
cttgtgtcag ccctgcaggc tcctgatggg gccaaggtgg caccattagt cttcttccac    3600
ttttctgggg ctcgtcctga ccagggtctt gccctcactc tgctcagacg cctctgtacc    3660
tatctgcgtg gccaactaaa agagccaggt gccctcccca gcacctaccg aagcctggtg    3720
tgggagctgc agcagaggct gctgcccaag tctgctgagt ccctgcatcc tggccagacc    3780
caggtcctga tcatcgatgg ggctgatagg ttagtggacc agaatgggca gctgatttca    3840
gactggatcc caaagaagct tccccggtgt gtacacctgg tgctgagtgt gtctagtgat    3900
gcaggcctag gggagaccct tgagcagagc agggtgccc acgtgctggc cttgggggcct    3960 ctggaggcct ctgctcgggc ccggctggtg agagaggagc tggccctgta cgggaagcgg    4020
ctggaggagt caccatttaa caaccagatg cgactgctgc tggtgaagcg ggaatcaggc    4080
cggccgctct acctgcgctt ggtcaccgat cacctgaggc tcttcacgct gtatgagcag    4140
gtgtctgaga gactccggac cctgcctgcc actgtccccc tgctgctgca gcacatcctg    4200
agcacactgg agaaggagca cgggcctgat gtccttcccc aggccttgac tgccctagaa    4260
gtcacacgga gtggtttgac tgtggaccag ctgcacggag tgctgagtgt gtggcggaca    4320
```

```
ctaccgaagg ggactaagag ctgggaagaa gcagtggctg ctggtaacag tggagacccc    4380
taccccatgg gcccgtttgc ctgcctcgtc cagagtctgc gcagtttgct aggggagggc    4440
cctctggagc gccctggtgc ccggctgtgc ctccctgatg ggcccctgag aacagcagct    4500
aaacgttgct atgggaagag gccagggcta gaggacacgg cacacatcct cattgcagct    4560
cagctctgga agacatgtga cgctgatgcc tcaggcacct tccgaagttg ccctcctgag    4620
gctctgggag acctgcctta ccacctgctc cagagcggga accgtggact tctttcgaag    4680
ttccttacca acctccatgt ggtggctgca cacttggaat tgggtctggt ctctcggctc    4740
ttggaggccc atgccctcta tgcttcttca gtccccaaag aggaacaaaa gctcccggag    4800
gctgacgttg cagtgtttcg caccttcctg aggcagcagg cttcaatcct cagccagtac    4860
ccccggctcc tgccccagca ggcagccaac cagcccctgg actcacctct ttgccaccaa    4920
gcctcgctgc tctcccggag atggcacctc caacacacac tacgatggct aataaaccc    4980
cggaccatga aaatcagca aagctccagc ctgtctctgg cagtttcctc atcccctact    5040
gctgtggcct tctccaccaa tgggcaaaga gcagctgtgg gcactgccaa tgggacagtt    5100
tacctgttgg acctgagaac ttggcaggag gagaagtctg tggtgagtgg ctgtgatgga    5160
atctctgctt gtttgttcct ctccgatgat acactctttc ttactgcctt cgacgggctc    5220
ctggagctct gggacctgca gcatggttgt cgggtgctgc agactaaggc tcaccagtac    5280
caaatcactg gctgctgcct gagcccagac tgccggctgc tagccaccgt gtgcttggga    5340
ggatgcctaa agctgtggga cacagtccgt gggcagctgg ccttccagca cacctacccc    5400
aagtccctga actgtgttgc cttccaccca gaggggcagg taatagccac aggcagctgg    5460
gctggcagca tcagcttctt ccaggtggat gggctcaaag tcaccaagga cctgggggca    5520
cccggagcct ctatccgtac cttggccttc aatgtgcctg ggggggttgt ggctgtgggc    5580
cggctggaca gtatggtgga gctgtgggcc tggcagaaag gggcacggct ggctgccttc    5640
cctgcccacc atggctttgt tgctgctgcg cttttcctgc atgcgggttg ccagttactg    5700
acggctggag aggatggcaa ggttcaggtg tggtcagggt ctctgggtcg gcccgtggg    5760
cacctgggtt cccttctctc ctctcctgcc ctctctgtgg cactcagccc agatggtgat    5820
cgggtggctg ttggatatcg agcggatggc attaggatct acaaaatctc ttcaggttcc    5880
caggggctc agggtcaggc actggatgtg gcagtgtccg ccctggcctg gctaagcccc    5940
aaggtattgg tgagtggtgc agaagatggg tccttgcagg gctgggcact caaggaatgc    6000
tcccttcagt ccctctggct cctgtccaga ttccagaagc ctgtgctagg actgccact    6060
tcccaggagc tcttggcttc tgcctcagag gatttcacag tgcagctgtg gccaaggcag    6120
ctgctgacgc ggccacacaa ggcagaagac tttcctgtg gcactgagct gcggggacat    6180
gagggccctg tgagctgctg tagtttcagc actgatggag gcagcctggc caccggggc    6240
cgggatcgga gtccctctg ctgggacgtg aggacaccca aaccctgt tttgatccac    6300
tccttccctg cctgtcaccg tgactgggtc actggctgtg cctggaccaa agataaccta    6360
ctgatatcct gctccagtga tggctctgtg gggctctggg acccagagtc aggacagcgg    6420
cttggtcagt tcctgggtca tcagagtgct gtgagcgctg tggcagctgt ggaggagcac    6480
gtggtgtctg tgagccggga tgggaccttg aaagtgtggg accatcaagg cgtggagctg    6540
accagcatcc ctgctcactc aggacccatt agccactgtg cagctgccat ggagccccgt    6600
gcagctggac agcctgggtc agagcttctg gtggtaaccg tcgggctaga tggggccaca    6660
```

-continued

```
cggttatggc atccactctt ggtgtgccaa acccacaccc tcctgggaca cagcggccca    6720
gtccgtgctg ctgctgtttc agaaacctca ggcctcatgc tgaccgcctc tgaggatggt    6780
tctgtacggc tctggcaggt tcctaaggaa gcagatgaca catgtatacc aaggagttct    6840
gcagccgtca ctgctgtggc ttgggcacca gatggttcca tggcagtatc tggaaatcaa    6900
gctggggaac taatcttgtg caggaagct aaggctgtgg ccacagcaca ggctccaggc     6960
cacattggtg ctctgatctg gtcctcggca cacacctttt tgtcctcag tgctgatgag     7020
aaaatcagcg agtggcaagt gaaactgcgg aagggttcgg cacccggaaa tttgagtctt    7080
cacctgaacc gaattctaca ggaggactta ggggtgctga caagtctgga ttgggctcct    7140
gatggtcact ttctcatctt ggccaaagca gatttgaagt tactttgcat gaagccaggg    7200
gatgctccat ctgaaatctg gagcagctat acagaaaatc ctatgatatt gtccacccac    7260
aaggagtatg catatttgt cctgcagccc aaggatcctg gagttctttc tttcttgagg     7320
caaaaggaat caggagagtt tgaagagagg ctgaactttg atataaactt agagaatcct    7380
agtaggaccc taatatcgat aactcaagcc aaacctgaat ctgagtcctc attttgtgt     7440
gccagctctg atgggatcct atggaacctg ccaaatgca gcccagaagg agaatggacc     7500
acaggtaaca tgtggcagaa aaagcaaac actccagaaa cccaaactcc agggacagac    7560
ccatctacct gcagggaatc tgatgccagc atggatagtg atgccagcat ggatagtgag    7620
ccaacaccac atctaaagac acggcagcgt agaaagattc actcgggctc tgtcacagcc    7680
ctccatgtgc tacctgagtt gctggtgaca gcttcgaagg acagagatgt taagctatgg    7740
gagagaccca gtatgcagct gctgggcctg ttccgatgcg aagggtcagt gagctgcctg    7800
gaaccttggc tgggcgctaa ctccaccctg cagcttgccg tgggagacgt gcagggcaat    7860
gtgtactttc tgaattggga atga                                           7884
```

<210> SEQ ID NO 27
<211> LENGTH: 2629
<212> TYPE: PRT
<213> ORGANISM: Rattus norvegicus

<400> SEQUENCE: 27

```
Met Glu Lys Leu Cys Gly Tyr Val Pro Val His Pro Asp Ile Leu Ser
1               5                   10                  15

Leu Lys Asn Arg Cys Leu Thr Met Leu Ser Asp Ile Gln Pro Leu Glu
            20                  25                  30

Lys Ile His Gly Gln Arg Ser Val Asn Pro Asp Ile Leu Ser Leu Glu
        35                  40                  45

Asn Arg Cys Leu Thr Leu Leu Pro Asp Leu Gln Pro Met Glu Lys Ile
    50                  55                  60

His Gly Gln Arg Ser Val His Pro Asp Ile Leu Ser Ser Glu Asn Arg
65                  70                  75                  80

Cys Leu Thr Leu Leu Pro Asp Leu Gln Ser Leu Glu Lys Leu Cys Gly
                85                  90                  95

His Met Ser Ser His Pro Asp Val Leu Ser Leu Glu Asn Arg Cys Leu
            100                 105                 110

Ala Thr Leu Pro Thr Val Lys Arg Thr Val Ser Gly Pro Leu Leu
        115                 120                 125

Gln Cys Leu His Arg Ser His Thr Ala Gln Ala Asp Leu Arg Asp Pro
    130                 135                 140

Asn Phe Arg Asn Cys Leu Phe Pro Glu Pro Pro Thr Ile Glu Ala Pro
145                 150                 155                 160
```

```
Cys Phe Leu Lys Glu Leu Asp Leu Pro Thr Gly Pro Arg Ala Leu Lys
            165                 170                 175

Ser Met Ser Ala Thr Ala Arg Val Gln Glu Val Ala Leu Gly Gln Arg
            180                 185                 190

Cys Val Ser Glu Gly Lys Glu Leu Gln Glu Glu Lys Glu Ser Ala Glu
            195                 200                 205

Val Pro Met Pro Leu Tyr Ser Leu Ser Leu Gly Gly Glu Glu Glu Glu
210                 215                 220

Val Val Gly Ala Pro Val Leu Lys Leu Thr Ser Gly Asp Ser Asp Ser
225                 230                 235                 240

His Pro Glu Thr Thr Asp Gln Ile Leu Gln Glu Lys Lys Met Ala Leu
            245                 250                 255

Leu Thr Leu Leu Cys Ser Ala Met Ala Ser Ser Val Asn Val Lys Asp
            260                 265                 270

Ala Ser Asp Pro Thr Arg Ala Ser Ile His Glu Val Cys Ser Ala Leu
            275                 280                 285

Ala Pro Leu Glu Pro Glu Phe Ile Leu Lys Ala Ser Leu Tyr Ala Arg
            290                 295                 300

Gln Gln Leu Asn Leu Arg Asp Ile Ala Asn Ile Val Leu Ala Val Ala
305                 310                 315                 320

Ala Leu Leu Pro Ala Cys Arg Pro His Val Arg Arg Tyr Tyr Ser Ala
            325                 330                 335

Ile Val His Leu Pro Ser Asp Trp Ile Gln Val Ala Glu Phe Tyr Gln
            340                 345                 350

Ser Leu Ala Glu Gly Asp Glu Lys Lys Leu Val Pro Leu Pro Ala Cys
            355                 360                 365

Leu Arg Ala Ala Met Thr Asp Lys Phe Ala Gln Phe Asp Glu Tyr Gln
            370                 375                 380

Leu Ala Lys Tyr Asn Pro Arg Lys His Arg Ser Lys Thr Arg Ser Arg
385                 390                 395                 400

Gln Pro Pro Arg Pro Gln Arg Thr Lys Pro Pro Phe Ser Glu Ser Gly
            405                 410                 415

Lys Cys Phe Pro Lys Ser Val Trp Pro Leu Lys Asn Glu Gln Ile Ser
            420                 425                 430

Phe Glu Ala Ala Tyr Asn Ala Val Ser Glu Lys Lys Arg Leu Pro Arg
            435                 440                 445

Phe Thr Leu Lys Lys Leu Val Glu Gln Leu His Ile His Glu Pro Ala
            450                 455                 460

Gln His Val Gln Ala Leu Leu Gly Tyr Arg Tyr Pro Ser Thr Leu Glu
465                 470                 475                 480

Leu Phe Ser Arg Ser His Leu Pro Gly Pro Trp Asp Ser Ser Arg Ala
            485                 490                 495

Gly Gln Arg Met Lys Leu Gln Arg Pro Glu Thr Trp Glu Arg Glu Leu
            500                 505                 510

Ser Leu Arg Gly Asn Arg Ala Ser Val Trp Glu Glu Leu Ile Asp Asn
            515                 520                 525

Gly Lys Leu Pro Phe Met Ala Met Leu Arg Asn Leu Cys Asn Leu Leu
530                 535                 540

Arg Thr Gly Ile Ser Ala His His Glu Leu Val Leu Gln Arg Leu
545                 550                 555                 560

Gln His Glu Lys Ser Val Ile His Ser Arg Gln Phe Pro Phe Arg Phe
            565                 570                 575
```

```
Leu Asn Ala His Asp Ser Leu Asp Arg Leu Glu Ala Gln Leu Arg Ser
            580                 585                 590

Lys Ala Ser Pro Phe Pro Ser Asn Thr Thr Leu Met Lys Arg Ile Met
        595                 600                 605

Ile Arg Asn Ser Lys Lys Ile Lys Arg Pro Ala Asn Pro Arg Tyr Leu
    610                 615                 620

Cys Thr Leu Thr Gln Arg Gln Leu Arg Ala Ala Met Ala Ile Pro Val
625                 630                 635                 640

Met Tyr Glu His Leu Lys Arg Glu Lys Leu Arg Leu His Lys Ala Arg
                645                 650                 655

Gln Trp Thr Cys Asp Leu Glu Leu Leu Glu Arg Tyr Arg Gln Ala Leu
                660                 665                 670

Glu Thr Ala Val Asn Ile Ser Val Lys His Asn Leu Pro Pro Leu Pro
            675                 680                 685

Gly Arg Thr Leu Leu Val Tyr Leu Thr Asp Ala Asn Ala Asn Arg Leu
        690                 695                 700

Cys Pro Lys Ser His Leu Gln Gly Pro Pro Leu Asn Tyr Val Leu Leu
705                 710                 715                 720

Leu Ile Gly Met Met Met Ala Arg Ala Glu Gln Thr Thr Val Trp Leu
                725                 730                 735

Cys Gly Thr Gly Thr Val Lys Thr Pro Val Leu Thr Ala Asp Glu Gly
                740                 745                 750

Ile Leu Lys Thr Ala Ile Lys Leu Gln Ala Gln Val Gln Glu Leu Glu
            755                 760                 765

Glu Asn Asp Glu Trp Pro Leu Glu Thr Phe Glu Lys Tyr Leu Leu Ser
        770                 775                 780

Leu Ala Val Arg Arg Thr Pro Ile Asp Arg Val Ile Leu Phe Gly Gln
785                 790                 795                 800

Arg Met Asp Thr Glu Leu Leu Asn Val Ala Lys Gln Ile Ile Trp Gln
                805                 810                 815

His Val Asn Ser Lys Cys Leu Phe Val Ser Val Leu Leu Arg Lys Met
                820                 825                 830

Gln Tyr Met Ser Pro Asn Leu Asn Pro Asn Asp Val Thr Leu Ser Gly
            835                 840                 845

Cys Thr Asp Gly Ile Leu Lys Phe Ile Ala Glu His Gly Ala Ser Arg
850                 855                 860

Leu Leu Glu His Val Gly Gln Leu Asp Lys Ile Phe Lys Ile Pro Pro
865                 870                 875                 880

Pro Pro Gly Lys Thr Lys Val Ser Pro Leu Arg Pro Leu Glu Glu Asn
                885                 890                 895

Asn Pro Gly Pro Phe Val Pro Ile Ser Gln His Gly Trp Arg Asn Ile
            900                 905                 910

Arg Leu Phe Ile Ser Ser Thr Phe Arg Asp Met His Gly Glu Arg Asp
        915                 920                 925

Leu Leu Met Arg Ser Val Leu Pro Ala Leu Gln Ala Arg Ala Phe Pro
    930                 935                 940

His Arg Ile Ser Leu His Ala Ile Asp Leu Arg Trp Gly Ile Thr Glu
945                 950                 955                 960

Glu Glu Thr Arg Arg Asn Arg Gln Leu Glu Val Cys Leu Gly Glu Val
                965                 970                 975

Glu Asn Ser Gln Leu Phe Val Gly Ile Leu Gly Ser Arg Tyr Gly Tyr
            980                 985                 990

Thr Pro Pro Ser Tyr Asp Leu Pro  Asp His Pro His Phe  His Trp Thr
```

-continued

```
            995                 1000                1005
Gln Arg Tyr Pro Ser Gly Arg Ser Val Thr Glu Met Glu Val Met
        1010                1015                1020

Gln Phe Leu Asn Arg Gly Gln Arg Ser Glu Pro Ser Asp Gln Ala
        1025                1030                1035

Leu Ile Tyr Phe Arg Asp Pro Gly Phe Leu Ser Ser Val Pro Asp
        1040                1045                1050

Val Trp Lys Pro Asp Phe Ile Ser Glu Ser Glu Glu Ala Ala His
        1055                1060                1065

Arg Val Ser Glu Leu Lys Arg Phe Leu Gln Glu Gln Lys Glu Val
        1070                1075                1080

Thr Cys Arg Arg Tyr Ser Cys Glu Trp Gly Val Ala Ala Ala Gly
        1085                1090                1095

Arg Pro Tyr Thr Gly Gly Leu Glu Glu Phe Gly Gln Leu Val Leu
        1100                1105                1110

Gln Asp Val Trp Ser Val Ile Gln Lys Arg Tyr Leu Gln Pro Gly
        1115                1120                1125

Ala Gln Leu Glu Gln Pro Gly Ser Ile Ser Glu Glu Asp Leu Ile
        1130                1135                1140

Gln Ala Ser Phe Gln Gln Leu Lys Ser Pro Pro Ser Pro Ala Arg
        1145                1150                1155

Pro Arg Leu Leu Gln Asp Thr Val Gln Gln Leu Met Leu Pro His
        1160                1165                1170

Gly Arg Leu Ser Leu Val Ile Gly Gln Ala Gly Gln Gly Lys Thr
        1175                1180                1185

Ala Phe Leu Ala Ser Leu Val Ser Ala Leu Lys Val Pro Asp Gln
        1190                1195                1200

Pro Asn Val Ala Pro Phe Val Phe Phe His Phe Ser Ala Ala Arg
        1205                1210                1215

Pro Asp Gln Cys Leu Ala Phe Asn Leu Leu Arg Arg Leu Cys Thr
        1220                1225                1230

His Leu His Gln Lys Leu Gly Glu Pro Ser Ala Leu Pro Ser Thr
        1235                1240                1245

Tyr Arg Gly Leu Val Trp Glu Leu Gln Gln Lys Leu Leu Leu Lys
        1250                1255                1260

Ser Ala Gln Trp Leu Gln Pro Gly Gln Thr Leu Val Leu Ile Ile
        1265                1270                1275

Asp Gly Ala Asp Lys Leu Val Asp His Asn Gly Gln Leu Ile Ser
        1280                1285                1290

Asp Trp Ile Pro Lys Ser Leu Pro Arg Arg Val His Leu Val Leu
        1295                1300                1305

Ser Val Ser Ser Asp Ser Gly Leu Gly Glu Thr Leu Gln Gln Ser
        1310                1315                1320

Gln Ser Ala Tyr Val Val Ala Leu Gly Ser Leu Val Pro Ser Ser
        1325                1330                1335

Arg Ala Gln Leu Val Arg Glu Glu Leu Ala Leu Tyr Gly Lys Arg
        1340                1345                1350

Leu Glu Glu Ser Pro Phe Asn Asn Gln Met Arg Leu Leu Leu Ala
        1355                1360                1365

Lys Gln Gly Ser Ser Leu Pro Leu Tyr Leu His Leu Val Thr Asp
        1370                1375                1380

Tyr Leu Arg Leu Phe Thr Leu Tyr Glu Gln Val Ser Glu Arg Leu
        1385                1390                1395
```

-continued

```
Arg Thr Leu Pro Ala Thr Leu Pro Leu Leu Leu Gln His Ile Leu
    1400            1405            1410

Ser Thr Leu Glu Gln Glu His Gly His Asn Val Leu Pro Gln Ala
    1415            1420            1425

Leu Thr Ala Leu Glu Val Thr His Ser Gly Leu Thr Val Asp Gln
    1430            1435            1440

Leu His Ala Val Leu Ser Thr Trp Leu Thr Leu Pro Lys Glu Thr
    1445            1450            1455

Lys Ser Trp Glu Glu Ala Val Ala Ala Ser His Ser Gly Asn Leu
    1460            1465            1470

Tyr Pro Leu Ala Pro Phe Ala Tyr Leu Val Gln Ser Leu Arg Ser
    1475            1480            1485

Leu Leu Gly Glu Gly Pro Val Glu Arg Pro Gly Ala Arg Leu Cys
    1490            1495            1500

Leu Ser Asp Gly Pro Leu Arg Thr Ala Val Lys Arg Arg Tyr Gly
    1505            1510            1515

Lys Arg Leu Gly Leu Glu Lys Thr Ala His Val Leu Ile Ala Ala
    1520            1525            1530

His Leu Trp Lys Met Cys Asp Pro Asp Ala Ser Gly Thr Phe Arg
    1535            1540            1545

Ser Cys Pro Pro Glu Ala Leu Lys Asp Leu Pro Tyr His Leu Leu
    1550            1555            1560

Gln Ser Gly Asn His Gly Leu Leu Ala Lys Phe Leu Thr Asn Leu
    1565            1570            1575

His Val Val Ala Ala Tyr Leu Glu Val Gly Leu Val Pro Asp Leu
    1580            1585            1590

Leu Glu Ala Tyr Glu Leu Tyr Ala Ser Ser Lys Pro Glu Val Asn
    1595            1600            1605

Gln Lys Leu Pro Glu Ala Asp Val Ala Val Phe His Asn Phe Leu
    1610            1615            1620

Lys Gln Gln Ala Ser Leu Leu Thr Gln Tyr Pro Leu Leu Leu Leu
    1625            1630            1635

Gln Gln Ala Ala Ser Gln Pro Glu Glu Ser Pro Val Cys Cys Gln
    1640            1645            1650

Ala Pro Leu Leu Thr Gln Arg Trp His Asn Gln Cys Ile Leu Lys
    1655            1660            1665

Trp Ile Asn Lys Pro Gln Thr Leu Lys Gly Gln Gln Ser Leu Ser
    1670            1675            1680

Leu Pro Ile Ser Ser Ser Pro Thr Ala Val Ala Phe Ser Pro Asn
    1685            1690            1695

Gly Gln Arg Ala Ala Val Gly Thr Ala Gly Gly Thr Ile Tyr Leu
    1700            1705            1710

Leu Asn Leu Arg Thr Trp Gln Glu Glu Lys Ala Leu Val Ser Gly
    1715            1720            1725

Cys Asp Gly Ile Ser Ser Phe Ala Phe Leu Ser Asp Thr Ala Leu
    1730            1735            1740

Phe Leu Thr Thr Phe Asp Gly Leu Leu Glu Leu Trp Asp Leu Gln
    1745            1750            1755

His Gly Cys Trp Val Phe Gln Thr Lys Ala His Gln Tyr Gln Ile
    1760            1765            1770

Thr Gly Cys Cys Leu Ser Pro Asp Arg Arg Leu Leu Ala Thr Val
    1775            1780            1785
```

-continued

| | | | | | | | | | | | |
|---|---|---|---|---|---|---|---|---|---|---|---|
| Cys | Leu | Gly | Gly | Tyr | Val | Lys | Leu | Trp | Asp | Thr | Val | Gln | Gly | Gln |
| | 1790 | | | | 1795 | | | | 1800 | | |

Leu Ala Phe Gln Tyr Thr His Pro Lys Ser Leu Asn Cys Ile Thr
1805 1810 1815

Phe His Pro Glu Gly Gln Val Val Ala Thr Gly Asn Trp Ser Gly
1820 1825 1830

Ile Val Thr Phe Phe Gln Ala Asp Gly Leu Lys Val Thr Lys Glu
1835 1840 1845

Leu Gly Gly Pro Gly Pro Ser Val Arg Thr Leu Ala Phe Ser Ala
1850 1855 1860

Pro Gly Lys Val Val Ala Leu Gly Arg Ile Asp Gly Thr Val Glu
1865 1870 1875

Leu Trp Ala Trp Gln Glu Gly Thr Arg Leu Ala Ala Phe Pro Ala
1880 1885 1890

Gln Cys Gly Gly Val Ser Thr Val Leu Phe Leu His Ala Gly Gly
1895 1900 1905

Arg Phe Leu Thr Ala Gly Glu Asp Gly Lys Ala Gln Leu Trp Ser
1910 1915 1920

Gly Phe Leu Gly Arg Pro Arg Gly Cys Leu Gly Ser Leu Tyr Leu
1925 1930 1935

Ser Pro Ala Leu Ser Val Ala Leu Asn Pro Asp Gly Asp Gln Val
1940 1945 1950

Ala Val Gly Tyr Arg Gly Asp Gly Ile Lys Ile Tyr Arg Ile Ser
1955 1960 1965

Ser Gly Pro Gln Glu Ala Gln Cys Gln Glu Leu Asn Val Ala Val
1970 1975 1980

Ser Ala Leu Val Trp Leu Ser Pro Ser Val Leu Val Ser Gly Ala
1985 1990 1995

Glu Asp Gly Ser Leu His Gly Trp Met Leu Arg Arg Asn Ser Leu
2000 2005 2010

Gln Ser Leu Trp Leu Ser Ser Val Cys Gln Lys Pro Val Leu Gly
2015 2020 2025

Leu Ala Ala Ser Gln Glu Phe Leu Ala Ser Ala Ser Glu Asp Phe
2030 2035 2040

Thr Val Arg Leu Trp Pro Arg Gln Leu Leu Thr Gln Pro His Ala
2045 2050 2055

Val Glu Glu Leu Pro Cys Ala Ala Glu Leu Arg Gly His Glu Gly
2060 2065 2070

Pro Val Cys Cys Cys Ser Phe Ser Pro Asp Gly Arg Ile Leu Ala
2075 2080 2085

Thr Ala Gly Arg Asp Arg Asn Leu Leu Cys Trp Asp Val Lys Val
2090 2095 2100

Ala Gln Ala Pro Leu Leu Ile His Thr Phe Ser Ser Cys His Arg
2105 2110 2115

Asp Trp Ile Thr Gly Cys Thr Trp Thr Lys Asp Asn Ile Leu Ile
2120 2125 2130

Ser Cys Ser Ser Asp Gly Ser Val Gly Leu Trp Asn Pro Glu Ala
2135 2140 2145

Gly Gln Gln Leu Gly Gln Phe Pro Gly His Gln Ser Ala Val Ser
2150 2155 2160

Ala Val Val Ala Val Glu Glu His Ile Val Ser Val Ser Arg Asp
2165 2170 2175

Gly Thr Leu Lys Val Trp Asp Arg Gln Gly Val Glu Leu Thr Ser

```
                    2180                2185                2190
Ile Pro Ala His Ser Gly Pro Ile Ser Gln Cys Ala Ala Ala Leu
    2195                2200                2205
Glu Pro Arg Pro Ala Gly Gln Pro Gly Ser Glu Leu Met Val Val
    2210                2215                2220
Thr Val Gly Leu Asp Gly Ala Thr Lys Leu Trp His Pro Leu Leu
    2225                2230                2235
Val Cys Gln Ile His Thr Leu Gln Gly His Ser Gly Pro Val Thr
    2240                2245                2250
Ala Ala Ala Ala Ser Glu Ala Ser Gly Leu Leu Leu Thr Ser Asp
    2255                2260                2265
Asn Ser Ser Val Arg Leu Trp Gln Ile Pro Lys Glu Ala Asp Asp
    2270                2275                2280
Thr Cys Lys Pro Arg Ser Ser Ala Val Ile Thr Ala Val Ala Trp
    2285                2290                2295
Ala Pro Asp Gly Ser Leu Val Val Ser Gly Asn Glu Ala Gly Glu
    2300                2305                2310
Leu Thr Leu Trp Gln Lys Ala Gln Ala Val Ala Thr Ala Arg Ala
    2315                2320                2325
Pro Gly Arg Val Ser Asp Leu Ile Trp Cys Ser Ala Asn Ala Phe
    2330                2335                2340
Phe Val Leu Ser Ala Asn Glu Asn Val Ser Glu Trp Gln Val Glu
    2345                2350                2355
Leu Arg Lys Gly Ser Thr Cys Thr Asn Phe Arg Leu Tyr Leu Lys
    2360                2365                2370
Arg Val Leu Gln Glu Asp Leu Gly Val Leu Thr Gly Met Ala Leu
    2375                2380                2385
Ala Pro Asp Gly Gln Ser Leu Ile Leu Met Lys Glu Asp Val Glu
    2390                2395                2400
Leu Leu Gln Met Lys Pro Gly Ser Thr Pro Ser Ser Ile Cys Arg
    2405                2410                2415
Arg Tyr Ala Val His Ser Ser Ile Leu Cys Thr Ser Lys Asp Tyr
    2420                2425                2430
Gly Leu Phe Tyr Leu Gln Gln Gly Asn Ser Gly Ser Leu Ser Ile
    2435                2440                2445
Leu Glu Gln Glu Glu Ser Gly Lys Phe Glu Lys Thr Leu Asp Phe
    2450                2455                2460
Asn Leu Asn Leu Asn Asn Pro Asn Gly Ser Pro Val Ser Ile Thr
    2465                2470                2475
Gln Ala Glu Pro Glu Ser Gly Ser Ser Leu Leu Cys Ala Thr Ser
    2480                2485                2490
Asp Gly Met Leu Trp Asn Leu Ser Glu Cys Thr Pro Glu Gly Glu
    2495                2500                2505
Trp Val Val Asp Asn Ile Trp Gln Lys Lys Ser Arg Asn Pro Lys
    2510                2515                2520
Ser Arg Thr Pro Gly Thr Asp Ser Ser Pro Gly Leu Phe Cys Met
    2525                2530                2535
Asp Ser Trp Val Glu Pro Thr His Leu Lys Ala Arg Gln Cys Lys
    2540                2545                2550
Lys Ile His Leu Gly Ser Val Thr Ala Leu His Val Leu Pro Gly
    2555                2560                2565
Leu Leu Val Thr Ala Ser Glu Asp Arg Asp Val Lys Leu Trp Glu
    2570                2575                2580
```

Arg Pro Ser Met Gln Leu Leu Gly Leu Phe Arg Cys Glu Gly Pro
2585                2590                2595

Val Ser Cys Leu Glu Pro Trp Met Glu Pro Ser Ser Pro Leu Gln
2600                2605                2610

Leu Ala Val Gly Asp Ala Gln Gly Asn Leu Tyr Phe Leu Ser Trp
2615                2620                2625

Glu

<210> SEQ ID NO 28
<211> LENGTH: 7890
<212> TYPE: DNA
<213> ORGANISM: Rattus norvegicus

<400> SEQUENCE: 28

```
atggagaaac tctgtggtta tgtgcctgtc cacccagaca tcctctcctt gaagaatcgg      60
tgcctgacca tgctctctga catccaaccc ctggagaaaa tacatggaca gagatctgtc     120
aacccagaca tcctgtcctt ggagaaccgg tgcctgacct tgctccctga tctccagccc     180
atggagaaaa tacatggaca gagatctgtc cacccagaca tcctctcctc agagaaccgg     240
tgtctgacct tgctccctga cctccagtcc ctggagaagc tatgtggaca tatgtctagt     300
cacccagacg tcctctcttt ggagaaccga tgtcttgcta ccctcccgac tgtaaagaga     360
actgtttcga gtggcccctt gctccagtgt cttcacagat tcatacggc acaagctgat      420 ctgcgtgacc cgaactttcg caactgcctg ttccctgagc ctcctaccat agaggctcca     480
tgtttcttga aggaactaga ccttccaact ggacccaggg ccctgaaatc catgtctgct     540
acagctcgag ttcaggaagt agctttgggt cagcggtgcg tctcagaagg aaaggaattg     600
caggaagaaa agaaagcgc agaagtcccg atgcctttgt acagtctaag cttgggggga      660
gaagaagaag aagtggtggg ggcaccggtc ctaaaactca catctggaga ctctgactct     720 cacccctgaaa ccactgacca gatcctgcag gagaagaaga tggctctctt gaccttgctg     780
tgctcagcta tggcctcaag tgtgaatgtg aaagatgcct ccgatcctac ccgggcatct     840
atccatgaag tctgcagtgc gctggccccc ttggaacctg agttcatcct taaggcatct     900
ttgtatgcta ggcagcagct taacctccgg acatagcca atatagtgtt ggccgtggct      960
gccctcttgc cagcctgccg ccccccatgta cgacggtatt actctgccat tgttcacctg    1020
ccttcagact ggatccaggt agccgagttc taccagagcc tggcagaagg ggatgagaag    1080
aagttggtgc cctgcctgc ctgcctccgt gctgccatga ctgacaaatt tgcccagttt      1140
gatgagtacc agctagcgaa gtacaaccca cggaaacacc gatccaagac acgttcccgc    1200
cagccacccc gccctcaaag gacaaaaacct ccatttttcag agagtgggaa atgttttcca    1260
aagagcgttt ggcccttaa aaacgaacag atttcgttcg aagcagctta taatgcagtg     1320
tcagagaaga aaaggctacc aaggttcact ctgaagaagt tggtagagca actgcatatc    1380
catgagcctg cgcagcatgt ccaggccctg ctgggctaca ggtacccatc caccctagag    1440
ctcttttctc ggagtcatct ccctgggcca tgggactcta gcagggctgg gcaacggatg    1500
aagctccaaa ggccagagac ctgggagcgg gagctgagct acgtggaaa cagagcttct     1560 gtgtgggagg aactcataga caatgggaaa ctccccttca tggccatgct ccggaacctg    1620
tgtaacctgc tgcggactgg gatcagtgcc caccaccatg aactcgttct ccagagactc    1680
cagcatgaga atctgtgat tcacagtcgg cagtttccat tcagattcct taatgctcac    1740
gactctctcg atagactcga ggctcagctc agaagtaaag catcgcccct cccttccaat    1800
```

```
acaacattga tgaagcggat aatgattaga aactcaaaaa aaatcaagag acctgccaac    1860
ccgaggtacc tgtgcaccct gacgcagcgg cagcttcggg cggcaatggc tatcccggtg    1920
atgtatgagc atctcaagcg ggagaaactg aggctgcaca aggccagaca gtggacctgt    1980
gaccttgagt tgctgagcg gtatcgccag gccctggaaa cggccgtgaa catctctgta    2040
aagcacaacc taccccgct gccaggccga accctcttgg tctatctcac agatgcaaat    2100
gccaacagac tttgtcccaa gagtcacttg caagggcctc ccctgaacta tgtgctgctg    2160
ttgatcggga tgatgatggc tcgggcggag cagacgacag tttggctgtg tgggacagga    2220
actgtgaaga caccagtact tacagccgac gaaggtatcc tgaagactgc catcaaactt    2280
caggctcaag tccaggagtt agaagaaaat gatgagtggc ccctggaaac ttttgagaag    2340
tacctgctat ctctggctgt gcgaaggacc cctattgaca gggtcatcct gttcggccaa    2400
aggatggata cggagctgct gaatgtagcc aaacagatta tctggcagca tgtgaattcc    2460
aagtgcctct tcgtcagtgt cctcctacgg aaaatgcagt acatgtcacc aaatttgaat    2520
cccaatgatg tgacgctctc gggctgcact gacgggatcc tgaagttcat tgcggagcat    2580
ggagcctctc gtcttctgga acatgtgggc caactagata agatattcaa gatccctcca    2640
cccccaggaa agacaaaggt ctcacctctc cggccgctgg aggagaacaa ccctggtccc    2700
ttcgttccta tttcccagca tggatggcgc aacatccggc ttttcatttc gtccactttc    2760
cgagacatgc atggggaacg agacttgctg atgcgatctg ttctgccagc gctgcaggcc    2820
cgagcgttcc cccaccgcat cagccttcac gccattgacc tgcgctgggg aatcacggag    2880
gaagagaccc gcaggaacag acaactggaa gtgtgccttg gggaggtgga gaactctcag    2940
ctgttcgtgg ggatcctggg ctcccgctat ggctatactc cccccagcta tgatctgcct    3000
gaccacccc actttcactg gacccagcga taccttcgg ggcgctctgt aacagagatg    3060
gaggtgatgc agttcctgaa ccgtggccaa cgctcggaac cctctgacca agctctcatc    3120
tacttccgag atcctggttt ccttagctct gtgccagatg tctggaaacc tgactttatt    3180
tccgagtcag aagaggctgc acatcgggtc tcagaactga agagattcct acaggaacag    3240
aaagaggtta cctgccgcag gtactcctgt gaatggggag gcgtagcagc cggccggccc    3300
tatactgggg gcctggagga gtttggacag ttggttctcc aagatgtgtg gagcgtgatc    3360
cagaagcgtt acctgcagcc tggggcccag ttggagcagc caggatccat ctcagaagag    3420
gatttgatcc aggccagctt tcagcagctg aagagcccac cgagtcccgc acggccacgc    3480
cttcttcagg ataccgtgca acagctgatg ctgcccacg ggaggctgag cctagtgatt    3540
gggcaggcag acagggaaa gactgccttc ctggcatccc ttgtgtcggc cctgaaggtt    3600
cccgaccagc ccaatgtggc cccgttcgtt ttcttccact tttcagcagc ccgccctgac    3660
cagtgtcttg ctttcaacct cctcagacgc ctctgtaccc atctgcatca aaaactggga    3720
gagccgagcg ctctccccag cacttacaga ggcctggtgt gggaactgca gcagaagctg    3780
ctcctcaaat ctgcccagtg gctgcaacca ggccagactt tggtccttat tatcgacggg    3840
gcagataagt tggtggacca taatggacag ctgatttcag actggatccc caagtctctt    3900
ccgcggcgag tacacctggt gctgagtgtg tctagtgact caggcctggg agagaccctt    3960
cagcaaagtc agagtgctta tgtggtggcc ttggggtctt tggtcccgtc ttcaagggct    4020
cagcttgtga gagaagagct agcactgtat gggaaacggc tggaggagtc acctttaac    4080
aaccagatgc ggctgctgct ggcaaagcag gggtcaagcc tgccactgta cctgcacctc    4140
```

```
gtcactgact acctgaggct tttcacactg tacgaacagg tgtctgagag acttcgaacc   4200
ctgcccgcca ctctcccact gctgctgcag cacatcctga gcaccttgga gcaagagcat   4260
ggccataacg tccttcctca agctttgact gcccttgagg tcacgcacag tggtctgact   4320
gtggaccagc tgcatgcagt cctgagcacg tggttgactt tgcccaagga gactaagagc   4380
tgggaagagg cagtggctgc cagtcacagt ggaaacctct acccctggc tccatttgcc    4440 taccttgtcc agagtctacg cagtttacta ggcgagggcc ccgtggagcg ccctggcgcc   4500
cgtctctgcc tctctgatgg gcctctgagg acagcagtta aacgtcgcta tgggaaaagg   4560
ctggggctag agaagactgc gcatgtcctc attgcagctc acctctggaa gatgtgtgac   4620
cctgatgcct caggcacctt ccgaagttgc cctcccgagg ctctgaaaga tttaccttac   4680
cacctgctcc agagcgggaa ccatggtctc cttgcaaagt tccttaccaa cctccatgtg   4740
gtggctgcat atctggaagt gggtctagtc ccggacctct tggaggctta cgagctctat   4800
gcttcttcaa agcctgaagt gaaccagaag ctcccggagg cagatgttgc tgtattccac   4860
aacttcctga acaacaggc ttcactcctt acccagtatc ctttgctcct gctccagcag    4920
gcagctagcc agcctgaaga gtcacctgtt tgctgccagg ccccctgct cacccagcgg    4980 tggcacaacc agtgcatact gaaatggatt aataaacccc agaccttgaa gggtcagcaa   5040
agcttgtctc tgccaatttc ctcatcccca actgctgtgg ccttctctcc taatgggcaa   5100
agagcagctg tggggactgc tggtgggaca atttacctgt tgaacttgag aacctggcag   5160
gaggagaagg ctctggtgag tggctgtgat gggatttcct cttcgcgtt cctgtcagac    5220 actgctcttt tccttaccac cttcgatggg ctcctggagc tttgggacct gcaacatggt   5280
tgttgggtgt tccagaccaa ggcccaccag taccaaatca ctggctgctg cctgagccca   5340
gaccgccgcc tgctggccac cgtgtgtttg ggaggatacg taaagctgtg ggacacagtc   5400
cagggccagc tggctttcca gtacacccat cccaagtctc taaactgcat caccttccac   5460
ccagagggga aggtggtagc cacaggcaac tggtctggca tcgtgacctt cttccaggca   5520
gatggactca aagtcaccaa ggaactaggg ggcccaggac cctctgttcg tacgctggca   5580
ttcagtgcac ccgggaaggt tgtggctcta ggccggatag atgggacagt ggagctgtgg   5640
gcctggcaag agggcacacg gctggcagcc ttccctgcac agtgtggcgg tgtctccacc   5700
gttcttttct tgcatgctgg aggccggttc ctgacggctg gggaagatgg caaggctcag   5760
ttatggtcag gatttcttgg ccggcccagg ggttgcctgg gctctcttta tctttctcct   5820
gcgctctctg tggctctcaa cccagacggt gaccaggtgg ctgttgggta ccgaggagat   5880
ggcattaaaa tctacagaat ttcttcaggt ccccaggagg ctcaatgcca agagctaaat   5940
gtggcggtgt ctgcactggt ctggctgagt cccagcgtct tggtgagtgg tgcagaagat   6000
ggctccctgc atggctggat gctcaggaga aactcccttc agtccctgtg gctgtcatcc   6060
gtgtgccaga gcctgtgct ggggctggct gcctcccagg agttcttggc ttctgcctca    6120
gaggacttca cggtgcgact gtggccaaga cagctgctga cacagccaca tgcagtagaa   6180
gagttgccct gtgcggctga actccgggga cacgaggggc cggtgtgctg ctgtagcttc   6240
agcccggatg gacgcatctt ggccacagcg ggcaggatc ggaatctcct ctgctgggac    6300
gtcaaggtag cccaagcccc tctcctgatt cacacgttct cgtcctgtca tcgagactgg   6360
atcactggct gtacgtggac caaagacaac atcctgatct cctgctctag tgatggctct   6420
gtgggactct ggaacccaga ggcaggacag caacttggcc agttcccagg tcaccagagt   6480
gccgtgagcg ctgtggttgc tgtggaggaa cacattgtat ctgtgagtcg ggatgggacc   6540
```

-continued

```
ttgaaagtgt gggaccgtca gggtgtggag ctgaccagca tccctgccca ttccggaccc    6600
attagccagt gtgcggctgc tctggaaccc cgtccagctg dacagcctgg atcagagctt    6660
atggtggtga ctgttggact ggatgggggcc acaaagctgt ggcatcccct gttggtgtgc   6720
caaatacata ccctgcaggg acacagtggt ccagtcacag ctgctgctgc ttcagaggcc    6780
tcaggcctcc tgctgacctc agacaatagc tctgtacgac tctggcagat ccctaaggaa    6840
gcagatgata cctgcaaacc taggagttct gcggtcatca ccgctgtggc gtgggcacca    6900
gatggttctc tggtggtgtc tggaaatgaa gctggggaac taacgctgtg cagaaagcg     6960 caggctgtgg ctacggcacg ggctccaggc cgcgtcagtg acctgatctg gtgctccgca    7020
aatgcattct tgttctcag tgctaatgaa aatgtcagtg agtggcaagt ggaactgagg     7080
aaaggttcaa catgcaccaa tttcagactt tatctgaaga gagttctgca ggaggacttg    7140
ggagtcttga caggtatggc cctggcgcct gacggccagt ctctcatttt gatgaaagag    7200
gatgtagaat tgctacagat gaagcccggg tctactccat cttcgatctg caggaggtat    7260
gcagtgcatt cttctatact gtgcaccagc aaagactatg gcctgtttta cctgcagcag    7320
ggaaactctg gatctctttc tatcttggag caggaggagt cagggaagtt tgaaaagacc    7380
ctggacttca atctgaactt aaataatcct aatgggtccc cagtatcaat cactcaggct    7440
gaacctgagt ctgggtcctc gcttttgtgt gctacctctg atgggatgct gtggaactta    7500
tctgagtgta ccccagaagg agagtgggtc gtagataaca tctggcagaa aaaatcaaga    7560
aaccctaaaa gtcgaactcc ggggacagat tcgtccccag gcttattctg catggatagc    7620
tgggtagaac ccacacattt aaaggcacgg cagtgtaaaa agattcactt gggctctgtc    7680
acggccctcc atgtgctgcc cggattgctg gtgactgctt cagaggacag agatgttaag    7740
ctgtgggaga gacccagtat gcagctgctc ggcttgttcc gatgtgaagg gccggtgagc    7800
tgtctggaac cttggatgga gcccagctct cccctgcagc ttgctgtggg agatgcacaa    7860
ggaaacttgt attttctatc ttgggaatga                                     7890
```

<210> SEQ ID NO 29
<211> LENGTH: 98
<212> TYPE: RNA
<213> ORGANISM: Homo sapiens

<400> SEQUENCE: 29

```
ggcuggcuuu agcucagcgg uuacuucgac aguucuuuaa uugaaacaag caaccugucu    60 gggguuguucg agacccgcgg gcgcucucca guccuuuu                           98
```

<210> SEQ ID NO 30
<211> LENGTH: 88
<212> TYPE: RNA
<213> ORGANISM: Homo sapiens

<400> SEQUENCE: 30

```
ggcuggcuuu agcucagcgg uuacuucgag uacauuguaa ccaccucucu ggguugguucg   60 agacccgcgg gugcuuucca gcucuuuu                                       88
```

<210> SEQ ID NO 31
<211> LENGTH: 88
<212> TYPE: RNA
<213> ORGANISM: Homo sapiens

<400> SEQUENCE: 31

```
ggcuggcuuu agcucagcgg uuacuucgcg ugucaucaaa ccaccucucu ggguuguucg    60
agacccgcgg gcgcucucca gcccucuu                                      88
```

<210> SEQ ID NO 32
<211> LENGTH: 143
<212> TYPE: RNA
<213> ORGANISM: Rattus norvegicus

<400> SEQUENCE: 32

```
ggccagcuuu agcucagcgg uuacuucgac gugcuccagu uugagcaggc uauguaacgu    60
ggucgguucg agcaacacaa ccagccgcuu gccaucugg ugagugguug guucgagacc    120
cgcgggcgcu cucuggcccu uuu                                           143
```

<210> SEQ ID NO 33
<211> LENGTH: 814
<212> TYPE: DNA
<213> ORGANISM: Homo sapiens

<400> SEQUENCE: 33

```
atcactctct ttaatcacta ctcacagtaa cctcaactcc tgccacaatg tacaggatgc    60
aactcctgtc ttgcattgca ctaagtcttg cacttgtcac aaacagtgca cctacttcaa   120
gttctacaaa gaaaacacag ctacaactgg agcatttact gctggattta cagatgattt   180
tgaatggaat taataattac aagaatccca aactcaccag gatgctcaca tttaagtttt   240
acatgcccaa gaaggccaca gaactgaaac atcttcagtg tctagaagaa gaactcaaac   300
ctctggagga agtgctaaat ttagctcaaa gcaaaaactt tcacttaaga cccagggact   360
taatcagcaa tatcaacgta atagttctgg aactaagggg atctgaaaca acattcatgt   420
gtgaatatgc tgatgagaca gcaaccattg tagaatttct gaacagatgg attacctttt   480
gtcaaagcat catctcaaca ctgacttgat aattaagtgc ttcccactta aaacgtatca   540
ggccttctat ttatttaaat atttaaattt tatatttatt gttgaatgta tggtttgcta   600
cctattgtaa ctattattct taatcttaaa actataaata tggatctttt atgattcttt   660
ttgtaagccc taggggctct aaaatggttt cacttattta tcccaaaata tttattatta   720
tgttgaatgt taaatatagt atctatgtag attggttagt aaaactattt aataaatttg   780
ataaatataa aaaaaaaaaa aaaaaaaaaa aaaa                               814
```

<210> SEQ ID NO 34
<211> LENGTH: 153
<212> TYPE: PRT
<213> ORGANISM: Homo sapiens

<400> SEQUENCE: 34

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95
```

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 35
<211> LENGTH: 1589
<212> TYPE: DNA
<213> ORGANISM: Homo sapiens

<400> SEQUENCE: 35

| | |
|---|---:|
| gaattcctct ggtcctcatc caggtgcgcg ggaagcaggt gcccaggaga gaggggataa | 60 |
| tgaagattcc atgctgatga tcccaaagat tgaacctgca gaccaagcgc aaagtagaaa | 120 |
| ctgaaagtac actgctggcg gatcctacgg aagttatgga aaaggcaaag cgcagagcca | 180 |
| cgccgtagtg tgtgccgccc cccttgggat ggatgaaact gcagtcgcgg cgtgggtaag | 240 |
| aggaaccagc tgcagagatc accctgccca acacagactc ggcaactccg cggaagacca | 300 |
| gggtcctggg agtgactatg gcggtgaga gcttgctcct gctccagttg cggtcatcat | 360 |
| gactacgccc gcctccgca gaccatgttc catgtttctt ttaggtatat ctttggactt | 420 |
| cctcccctga tccttgttct gttgccagta gcatcatctg attgtgatat tgaaggtaaa | 480 |
| gatggcaaac aatatgagag tgttctaatg gtcagcatcg atcaattatt ggacagcatg | 540 |
| aaagaaattg gtagcaattg cctgaataat gaatttaact ttttttaaaag acatatctgt | 600 |
| gatgctaata aggaaggtat gttttttattc cgtgctgctc gcaagttgag gcaatttctt | 660 |
| aaaatgaata gcactggtga ttttgatctc cacttattaa agtttcaga aggcacaaca | 720 |
| atactgttga actgcactgg ccaggttaaa ggaagaaaac cagctgccct gggtgaagcc | 780 |
| caaccaacaa agagtttgga agaaaataaa tctttaaagg aacagaaaaa actgaatgac | 840 |
| ttgtgtttcc taaagagact attacaagag ataaaaactt gttggaataa aattttgatg | 900 |
| ggcactaaag aacactgaaa atatggagt ggcaatatag aaacacgaac tttagctgca | 960 |
| tcctccaaga atctatctgc ttatgcagtt tttcagagtg gaatgcttcc tagaagttac | 1020 |
| tgaatgcacc atggtcaaaa cggattaggg catttgagaa atgcatattg tattactaga | 1080 |
| agatgaatac aaacaatgga aactgaatgc tccagtcaac aaactatttc ttatatatgt | 1140 |
| gaacatttat caatcagtat aattctgtac tgattttttgt aagacaatcc atgtaaggta | 1200 |
| tcagttgcaa taatacttct caaacctgtt taaatatttc aagacattaa atctatgaag | 1260 |
| tatataatgg tttcaaagat tcaaaattga cattgcttta ctgtcaaaat aattttatgg | 1320 |
| ctcactatga atctattata ctgtattaag agtgaaaatt gtcttcttct gtgctggaga | 1380 |
| tgttttagag ttaacaatga tatatggata atgccggtga gaataagaga gtcataaacc | 1440 |
| ttaagtaagc aacagcataa caaggtccaa gatacctaaa agagatttca agagatttaa | 1500 |
| ttaatcatga atgtgtaaca cagtgccttc aataaatggt atagcaaatg ttttgacatg | 1560 |
| aaaaaaggac aatttcaaaa aaataaaat | 1589 |

<210> SEQ ID NO 36
<211> LENGTH: 177
<212> TYPE: PRT

<213> ORGANISM: Homo sapiens

<400> SEQUENCE: 36

```
Met Phe His Val Ser Phe Arg Tyr Ile Phe Gly Leu Pro Pro Leu Ile
1               5                   10                  15
Leu Val Leu Leu Pro Val Ala Ser Ser Asp Cys Asp Ile Glu Gly Lys
            20                  25                  30
Asp Gly Lys Gln Tyr Glu Ser Val Leu Met Val Ser Ile Asp Gln Leu
        35                  40                  45
Leu Asp Ser Met Lys Glu Ile Gly Ser Asn Cys Leu Asn Asn Glu Phe
    50                  55                  60
Asn Phe Phe Lys Arg His Ile Cys Asp Ala Asn Lys Glu Gly Met Phe
65                  70                  75                  80
Leu Phe Arg Ala Ala Arg Lys Leu Arg Gln Phe Leu Lys Met Asn Ser
                85                  90                  95
Thr Gly Asp Phe Asp Leu His Leu Leu Lys Val Ser Glu Gly Thr Thr
            100                 105                 110
Ile Leu Leu Asn Cys Thr Gly Gln Val Lys Gly Arg Lys Pro Ala Ala
        115                 120                 125
Leu Gly Glu Ala Gln Pro Thr Lys Ser Leu Glu Glu Asn Lys Ser Leu
    130                 135                 140
Lys Glu Gln Lys Lys Leu Asn Asp Leu Cys Phe Leu Lys Arg Leu Leu
145                 150                 155                 160
Gln Glu Ile Lys Thr Cys Trp Asn Lys Ile Leu Met Gly Thr Lys Glu
                165                 170                 175
His
```

<210> SEQ ID NO 37
<211> LENGTH: 1968
<212> TYPE: DNA
<213> ORGANISM: Homo sapiens

<400> SEQUENCE: 37

```
actccgggtg gcaggcgccc gggggaatcc cagctgactc gctcactgcc ttcgaagtcc      60
ggcgccccc gggagggaac tgggtggccg caccctcccg gctgcggtgg ctgtcgcccc     120
ccaccctgca gccaggactc gatggaggta cagagctcgg cttctttgcc ttgggagggg     180
agtggtggtg gttgaaaggg cgatggaatt tccccgaaa gcctacgccc agggcccctc     240
ccagctccag cgttaccctc cggtctatcc tactggccga gctgccccgc cttctcatgg     300
ggaaaactta gccgcaactt caattttgg ttttcctt aatgacactt ctgaggctct     360
cctagccatc ctcccgcttc cggaggagcg cagatcgcag gtcccttgc ccctggcgtg     420
cgactcccta ctgcgctgcg ctcttacggc gttccaggct gctggctagc gcaaggcggg     480
ccgggcaccc cgcgctccgc tgggagggtg agggacgcgc gtctggcggc cccagccaag     540
ctgcgggttt ctgagaagac gctgtcccgc agccctgagg gctgagttct gcacccagtc     600
aagctcagga aggccaagaa aagaatccat tccaatatat ggccatgtgg ctctttggag     660
caatgttcca tcatgttcca tgctgctgac gtcacatgga gcacagaaat caatgttagc     720
agatagccag cccatacaag atcgtattgt attgtaggag gcatcgtgga tggatggctg     780
ctggaaaccc cttgccatag ccagctcttc ttcaatactt aaggatttac cgtggctttg     840
agtaatgaga atttcgaaac cacatttgag aagtatttcc atccagtgct acttgtgttt     900
acttctaaac agtcattttc taactgaagc tggcattcat gtcttcattt tgggctgttt     960
```

| | |
|---|---|
| cagtgcaggg cttcctaaaa cagaagccaa ctgggtgaat gtaataagtg atttgaaaaa | 1020 |
| aattgaagat cttattcaat ctatgcatat tgatgctact ttatatacgg aaagtgatgt | 1080 |
| tcaccccagt tgcaaagtaa cagcaatgaa gtgctttctc ttggagttac aagttatttc | 1140 |
| acttgagtcc ggagatgcaa gtattcatga tacagtagaa atctgatca tcctagcaaa | 1200 |
| caacagtttg tcttctaatg ggaatgtaac agaatctgga tgcaaagaat gtgaggaact | 1260 |
| ggaggaaaaa aatattaaag aattttttgca gagttttgta catattgtcc aaatgttcat | 1320 |
| caacacttct tgattgcaat tgattctttt taaagtgttt ctgttattaa caaacatcac | 1380 |
| tctgctgctt agacataaca aaacactcgg catttcaaat gtgctgtcaa acaagttttt | 1440 |
| tctgtcaaga agatgatcag accttggatc agatgaactc ttagaaatga aggcagaaaa | 1500 |
| atgtcattga gtaatatagt gactatgaac ttctctcaga cttactttac tcattttttt | 1560 |
| aatttattat tgaaattgta catatttgtg gaataatgta aaatgttgaa taaaaatatg | 1620 |
| tacaagtgtt gttttttaag ttgcactgat attttacctc ttattgcaaa atagcatttg | 1680 |
| tttaagggtg atagtcaaat tatgtattgg tggggctggg taccaatgct gcaggtcaac | 1740 |
| agctatgctg gtaggctcct gcctgtgtgg aaccactgac tactggctct cattgacttc | 1800 |
| cttactaagc atagcaaaca gaggaagaat ttgttatcag taagaaaaag aagaactata | 1860 |
| tgtgaatcct cttctttaca ctgtaattta gttattgatg tataaagcaa ctgttatgaa | 1920 |
| ataaagaaat tgcaataact ggcaaaaaaa aaaaaaaaa aaaaaaaa | 1968 |

<210> SEQ ID NO 38
<211> LENGTH: 160
<212> TYPE: PRT
<213> ORGANISM: Homo sapiens

<400> SEQUENCE: 38

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160
```

<210> SEQ ID NO 39
<211> LENGTH: 2347
<212> TYPE: DNA
<213> ORGANISM: Homo sapiens

<400> SEQUENCE: 39

-continued

```
ctgtttcagg gccattggac tctccgtcct gcccagagca agatgtgtca ccagcagttg      60
gtcatctctt ggttttccct ggttttctg gcatctcccc tcgtggccat atgggaactg      120
aagaaagatg tttatgtcgt agaattggat tggtatccgg atgcccctgg agaaatggtg     180
gtcctcacct gtgacacccc tgaagaagat ggtatcacct ggaccttgga ccagagcagt    240
gaggtcttag gctctggcaa aaccctgacc atccaagtca aagagtttgg agatgctggc    300
cagtacacct gtcacaaagg aggcgaggtt ctaagccatt cgctcctgct gcttcacaaa    360
aaggaagatg gaatttggtc cactgatatt ttaaaggacc agaaagaacc caaaataag    420 acctttctaa gatgcgaggc caagaattat tctggacgtt tcacctgctg gtggctgacg    480
acaatcagta ctgatttgac attcagtgtc aaaagcagca gaggctcttc tgaccccaa    540 ggggtgacgt gcggagctgc tacactctct gcagagagag tcagagggga caacaaggag   600
tatgagtact cagtggagtg ccaggaggac agtgcctgcc cagctgctga ggagagtctg   660
cccattgagg tcatggtgga tgccgttcac aagctcaagt atgaaaacta caccagcagc   720
ttcttcatca gggacatcat caaacctgac ccacccaaga acttgcagct gaagccatta   780
aagaattctc ggcaggtgga ggtcagctgg gagtaccctg acacctggag tactccacat   840
tcctacttct ccctgacatt ctgcgttcag gtccagggca agagcaagag agaaaagaaa   900
gatagagtct tcacggacaa gacctcagcc acggtcatct gccgcaaaaa tgccagcatt   960
agcgtgcggg cccaggaccg ctactatagc tcatcttgga gcgaatgggc atctgtgccc  1020
tgcagttagg ttctgatcca ggatgaaaat ttggaggaaa agtggaagat attaagcaaa  1080
atgtttaaag acacaacgga atagacccaa aaagataatt tctatctgat ttgctttaaa  1140 acgtttttt aggatcacaa tgatatcttt gctgtatttg tatagttaga tgctaaatgc   1200
tcattgaaac aatcagctaa tttatgtata gattttccag ctctcaagtt gccatgggcc   1260
ttcatgctat ttaaatattt aagtaattta tgtatttatt agtatattac tgttattaa    1320 cgtttgtctg ccaggatgta tggaatgttt catactctta tgacctgatc catcaggatc   1380
agtccctatt atgcaaaatg tgaatttaat tttatttgta ctgacaactt ttcaagcaag   1440
gctgcaagta catcagtttt atgacaatca ggaagaatgc agtgttctga taccagtgcc  1500
atcatacact tgtgatggat gggaacgcaa gagatactta catggaaacc tgacaatgca   1560
aacctgttga gaagatccag gagaacaaga tgctagttcc catgtctgtg aagcttcct   1620 ggagatggtg ttgataaagc aatttagggc cacttacact tctaagcaag tttaatcttt   1680
ggatgcctga attttaaaag ggctagaaaa aaatgattga ccagcctggg aaacataaca   1740
agaccccgtc tctacaaaaa aaatttaaaa ttagccaggc gtggtggctc atgcttgtgg   1800
tcccagctgt tcaggaggat gaggcaggag gatctcttga gcccaggagg tcaaggctat   1860
ggtgagccgt gattgtgcca ctgcatacca gcctaggtga cagaatgaga ccctgtctca   1920 aaaaaaaaa tgattgaaat taaaattcag ctttagcttc catggcagtc ctcaccccca   1980
cctctctaaa agacacagga ggatgacaca gaaacaccgt aagtgtctgg aaggcaaaaa   2040
gatcttaaga ttcaagagag aggacaagta gttatggcta aggacatgaa attgtcagaa   2100
tggcaggtgg cttcttaaca gccctgtgag aagcagacag atgcaaagaa atctggaat    2160 cccttttctca ttagcatgaa tgaacctgat acacaattat gaccagaaaa tatggctcca   2220
tgaaggtgct acttttaagt aatgtatgtg cgctctgtaa agtgattaca tttgtttcct   2280
gtttgtttat ttatttattt attttgcat tctgaggctg aactaataaa aactcttctt    2340
``` tgtaatc                                                                    2347

<210> SEQ ID NO 40
<211> LENGTH: 328
<212> TYPE: PRT
<213> ORGANISM: Homo sapiens

<400> SEQUENCE: 40

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 41
<211> LENGTH: 1444
<212> TYPE: DNA
<213> ORGANISM: Homo sapiens

<400> SEQUENCE: 41

```
tttcattttg ggccgagctg gaggcggcgg ggccgtcccg gaacggctgc ggccgggcac     60
cccgggagtt aatccgaaag cgccgcaagc cccgcgggcc ggccgcaccg cacgtgtcac    120
cgagaagctg atgtagagag agacacagaa ggagacagaa agcaagagac cagagtcccg    180
ggaaagtcct gccgcgcctc gggacaatta taaaaatgtg gcccctgggt cagcctccc    240
agccaccgcc ctcacctgcc gcggccacag gtctgcatcc agcggctcgc cctgtgtccc    300
tgcagtgccg gctcagcatg tgtccagcgc gcagcctcct ccttgtggct accctggtcc    360
tcctggacca cctcagtttg gccagaaacc tccccgtggc cactccagac ccaggaatgt    420
tcccatgcct tcaccactcc caaaacctgc tgagggccgt cagcaacatg ctccagaagg    480
ccagacaaac tctagaattt tacccttgca cttctgaaga gattgatcat gaagatatca    540
caaaagataa aaccagcaca gtggaggcct gtttaccatt ggaattaacc aagaatgaga    600
gttgcctaaa ttccagagag acctctttca taactaatgg gagttgcctg gcctccagaa    660
agacctcttt tatgatggcc ctgtgcctta gtagtattta tgaagacttg aagatgtacc    720
aggtggagtt caagaccatg aatgcaaagc ttctgatgga tcctaagagg cagatctttc    780
tagatcaaaa catgctggca gttattgatg agctgatgca ggccctgaat tcaacagtg    840
agactgtgcc acaaaaatcc tcccttgaag aaccggattt ttataaaact aaaatcaagc    900
tctgcatact tcttcatgct ttcagaattc gggcagtgac tattgataga gtgatgagct    960
atctgaatgc ttcctaaaaa gcgaggtccc tccaaaccgt tgtcattttt ataaaacttt   1020
gaaatgagga aactttgata ggatgtggat taagaactag ggagggggaa agaaggatgg   1080
gactattaca tccacatgat acctctgatc aagtattttt gacatttact gtggataaat   1140
tgtttttaag ttttcatgaa tgaattgcta agaagggaaa atatccatcc tgaaggtgtt   1200
tttcattcac tttaatagaa gggcaaatat ttataagcta tttctgtacc aaagtgtttg   1260
tggaaacaaa catgtaagca taacttattt taaaatattt atttatataa cttggtaatc   1320
atgaaagcat ctgagctaac ttatatttat ttatgttata tttattaaat tatttatcaa   1380
gtgtatttga aaatattttt taagtgttct aaaaataaaa gtattgaatt aaagtgaaaa   1440
aaaa                                                                1444
```

<210> SEQ ID NO 42
<211> LENGTH: 253
<212> TYPE: PRT
<213> ORGANISM: Homo sapiens

<400> SEQUENCE: 42

```
Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
                20                  25                  30

Leu Ser Met Cys Pro Ala Arg Ser Leu Leu Val Ala Thr Leu Val
            35                  40                  45

Leu Leu Asp His Leu Ser Leu Ala Arg Asn Leu Pro Val Ala Thr Pro
        50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
```

```
            100                 105                 110
Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
                180                 185                 190

Met Leu Ala Val Ile Asp Glu Leu Met Gln Ala Leu Asn Phe Asn Ser
            195                 200                 205

Glu Thr Val Pro Gln Lys Ser Ser Leu Glu Glu Pro Asp Phe Tyr Lys
            210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```

<210> SEQ ID NO 43
<211> LENGTH: 787
<212> TYPE: DNA
<213> ORGANISM: Homo sapiens

<400> SEQUENCE: 43

```
ggctaaagtt ctctggagga tgtggctgca gagcctgctg ctcttgggca ctgtggcctg     60
cagcatctct gcacccgccc gctcgcccag ccccagcacg cagccctggg agcatgtgaa    120
tgccatccag gaggcccggc gtctcctgaa cctgagtaga cactgctg ctgagatgaa     180
tgaaacagta gaagtcatct cagaaatgtt tgacctccag gagccgacct gcctacagac    240
ccgcctggag ctgtacaagc agggcctgcg gggcagcctc accaagctca agggccccctt   300
gaccatgatg gccagccact acaagcagca ctgccctcca accccggaaa cttcctgtgc    360
aacccagatt atcacctttg aaagtttcaa agagaacctg aaggactttc tgcttgtcat    420
ccccttgac tgctgggagc cagtccagga gtgagaccgg ccagatgagg ctggccaagc     480
cggggagctg ctctctcatg aaacaagagc tagaaactca ggatggtcat cttggaggga    540
ccaaggggtg ggccacagcc atggtgggag tggcctggac ctgccctggg ccacactgac    600
cctgatacag gcatggcaga agaatgggaa tattttatac tgacagaaat cagtaatatt    660
tatatattta tatttttaaa atatttattt atttatttat ttaagttcat attccatatt    720
tattcaagat gttttaccgt aataattatt attaaaaata tgcttctact tgaaaaaaaa    780
aaaaaaa                                                             787
```

<210> SEQ ID NO 44
<211> LENGTH: 144
<212> TYPE: PRT
<213> ORGANISM: Homo sapiens

<400> SEQUENCE: 44

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30
```

```
Val Asn Ala Ile Gln Glu Ala Arg Arg Leu Leu Asn Leu Ser Arg Asp
         35                  40                  45
Thr Ala Ala Glu Met Asn Glu Thr Val Glu Val Ile Ser Glu Met Phe
 50                  55                  60
Asp Leu Gln Glu Pro Thr Cys Leu Gln Thr Arg Leu Glu Leu Tyr Lys
 65                  70                  75                  80
Gln Gly Leu Arg Gly Ser Leu Thr Lys Leu Lys Gly Pro Leu Thr Met
                 85                  90                  95
Met Ala Ser His Tyr Lys Gln His Cys Pro Pro Thr Pro Glu Thr Ser
                100                 105                 110
Cys Ala Thr Gln Ile Ile Thr Phe Glu Ser Phe Lys Glu Asn Leu Lys
            115                 120                 125
Asp Phe Leu Leu Val Ile Pro Phe Asp Cys Trp Glu Pro Val Gln Glu
130                 135                 140
```

<210> SEQ ID NO 45
<211> LENGTH: 2545
<212> TYPE: DNA
<213> ORGANISM: Homo sapiens

<400> SEQUENCE: 45

| | | |
|---|---|---|
| atccaataca ggagtgactt ggaactccat tctatcacta tgaagaaaag tggtgttctt | 60 |
| ttcctcttgg gcatcatctt gctggttctg attggagtgc aaggaacccc agtagtgaga | 120 |
| aagggtcgct gttcctgcat cagcaccaac caagggacta tccacctaca atccttgaaa | 180 |
| gaccttaaac aatttgcccc aagcccttcc tgcgagaaaa ttgaaatcat tgctacactg | 240 |
| aagaatggag ttcaaacatg tctaaaccca gattcagcag atgtgaagga actgattaaa | 300 |
| aagtgggaga acaggtcag ccaaaagaaa aagcaaaaga tgggaaaaa acatcaaaaa | 360 |
| aagaaagttc tgaaagttcg aaaatctcaa cgttctcgtc aaaagaagac tacataagag | 420 |
| accacttcac caataagtat tctgtgttaa aaatgttcta ttttaattat accgctatca | 480 |
| ttccaaagga ggatggcata taatacaaag gcttattaat ttgactagaa aatttaaaac | 540 |
| attactctga aattgtaact aaagttagaa agttgatttt aagaatccaa acgttaagaa | 600 |
| ttgttaaagg ctatgattgt ctttgttctt ctaccaccca ccagttgaat tcatcatgc | 660 |
| ttaaggccat gattttagca atacccatgt ctacacagat gttcacccaa ccacatccca | 720 |
| ctcacaacag ctgcctggaa gagcagccct aggcttccac gtactgcagc tccagagag | 780 |
| tatctgaggc acatgtcagc aagtcctaag cctgttagca tgctggtgag ccaagcagtt | 840 |
| tgaaattgag ctggacctca ccaagctgct gtggccatca acctctgtat ttgaatcagc | 900 |
| ctacaggcct cacacacaat gtgtctgaga gattcatgct gattgttatt gggtatcacc | 960 |
| actggagatc accagtgtgt ggctttcaga gcctcctttc tggctttgga agccatgtga | 1020 |
| ttccatcttg cccgctcagg ctgaccactt tatttctttt tgttcccctt tgcttcattc | 1080 |
| aagtcagctc ttctccatcc taccacaatg cagtgccttt cttctctcca gtgcacctgt | 1140 |
| catatgctct gatttatctg agtcaactcc tttctcatct tgtccccaac accccacaga | 1200 |
| agtgctttct tctcccaatt catcctcact cagtccagct tagttcaagt cctgcctctt | 1260 |
| aaataaacct ttttgacac acaaattatc ttaaaactcc tgtttcactt ggttcagtac | 1320 |
| cacatgggtg aacactcaat ggttaactaa ttcttgggtg tttatcctat ctctccaacc | 1380 |
| agattgtcag ctccttgagg gcaagagcca cagtatattt ccctgtttct tccacagtgc | 1440 |
| ctaataatac tgtggaacta ggttttaata atttttttaat tgatgttgtt atgggcagga | 1500 |

```
tggcaaccag accattgtct cagagcaggt gctggctctt cctggctac tccatgttgg    1560 ctagcctctg gtaacctctt acttattatc ttcaggacac tcactacagg gaccagggat   1620
gatgcaacat ccttgtcttt ttatgacagg atgtttgctc agcttctcca acaataagaa   1680
gcacgtggta aaacacttgc ggatattctg gactgttttt aaaaaatata cagtttaccg   1740
aaaatcatat aatcttacaa tgaaaaggac tttatagatc agccagtgac caacctttc   1800 ccaaccatac aaaaattcct ttcccgaag gaaaagggct ttctcaataa gcctcagctt    1860
tctaagatct aacaagatag ccaccgagat ccttatcgaa actcatttta ggcaaatatg   1920
agttttattg tccgtttact tgtttcagag tttgtattgt gattatcaat taccacacca   1980
tctcccatga agaaagggaa cggtgaagta ctaagcgcta gaggaagcag ccaagtcggt   2040
tagtggaagc atgattggtg cccagttagc ctctgcagga tgtggaaacc tccttccagg   2100
ggaggttcag tgaattgtgt aggagaggtt gtctgtggcc agaatttaaa cctatactca   2160
ctttcccaaa ttgaatcact gctcacactg ctgatgattt agagtgctgt ccggtggaga   2220
tcccacccga acgtcttatc taatcatgaa actcccagt tccttcatgt aacttccctg    2280
aaaaatctaa gtgtttcata aatttgagag tctgtgaccc acttaccttg catctcacag   2340
gtagacagta taactaac aaccaaagac tacatattgt cactgacaca cacgttataa     2400
tcatttatca tatatataca tacatgcata cactctcaaa gcaaataatt tttcacttca   2460
aaacagtatt gacttgtata ccttgtaatt tgaaatattt tctttgttaa aatagaatgg   2520
tatcaataaa tagaccatta atcag                                         2545
```

<210> SEQ ID NO 46
<211> LENGTH: 125
<212> TYPE: PRT
<213> ORGANISM: Homo sapiens

<400> SEQUENCE: 46

```
Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Val Leu Lys
            100                 105                 110

Val Arg Lys Ser Gln Arg Ser Arg Gln Lys Lys Thr Thr
        115                 120                 125
```

<210> SEQ ID NO 47
<211> LENGTH: 1184
<212> TYPE: DNA
<213> ORGANISM: Homo sapiens

<400> SEQUENCE: 47

```
gggggagaca ttcctcaatt gcttagacat attctgagcc tacagcagag gaacctccag    60
tctcagcacc atgaatcaaa ctgccattct gatttgctgc cttatctttc tgactctaag   120
```

```
tggcattcaa ggagtacctc tctctagaac tgtacgctgt acctgcatca gcattagtaa      180
tcaacctgtt aatccaaggt ctttagaaaa acttgaaatt attcctgcaa gccaattttg      240
tccacgtgtt gagatcattg ctacaatgaa aagaagggt gagaagagat gtctgaatcc       300
agaatcgaag gccatcaaga atttactgaa agcagttagc aaggaaaggt ctaaaagatc      360
tccttaaaac cagaggggag caaaatcgat gcagtgcttc caaggatgga ccacacagag      420
gctgcctctc ccatcacttc cctacatgga gtatatgtca agccataatt gttcttagtt      480
tgcagttaca ctaaaaggtg accaatgatg gtcaccaaat cagctgctac tactcctgta      540
ggaaggttaa tgttcatcat cctaagctat tcagtaataa ctctaccctg cactataat       600 gtaagctcta ctgaggtgct atgttcttag tggatgttct gaccctgctt caaatatttc      660
cctcaccttt cccatcttcc aagggtacta aggaatcttt ctgctttggg gtttatcaga      720
attctcagaa tctcaaataa ctaaaaggta tgcaatcaaa tctgcttttt aaagaatgct      780
ctttacttca tggacttcca ctgccatcct cccaaggggc ccaaattctt tcagtggcta      840
cctacataca attccaaaca catacaggaa ggtagaaata tctgaaaatg tatgtgtaag      900
tattcttatt taatgaaaga ctgtacaaag tagaagtctt agatgtatat atttcctata      960
ttgttttcag tgtacatgga ataacatgta attaagtact atgtatcaat gagtaacagg     1020 aaaatttaa aaatacagat agatatatgc tctgcatgtt acataagata aatgtgctga      1080
atggttttca aaataaaaat gaggtactct cctggaaata ttaagaaaga ctatctaaat     1140
gttgaaagat caaaggtta ataaagtaat tataactaaa aaaa                       1184

<210> SEQ ID NO 48
<211> LENGTH: 98
<212> TYPE: PRT
<213> ORGANISM: Homo sapiens

<400> SEQUENCE: 48

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
                20                  25                  30

Ile Ser Ile Ser Asn Gln Pro Val Asn Pro Arg Ser Leu Glu Lys Leu
            35                  40                  45

Glu Ile Ile Pro Ala Ser Gln Phe Cys Pro Arg Val Glu Ile Ile Ala
        50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 49
<211> LENGTH: 1179
<212> TYPE: DNA
<213> ORGANISM: Homo sapiens

<400> SEQUENCE: 49
aaaacaaaac atttgagaaa cacggctcta aactcatgta aagagtgcat gaaggaaagc       60
aaaaacagaa atggaaagtg cccagaaagc attaagaaag tggaaatcag tatgttccct     120
atttaaggca tttgcaggaa gcaaggcctt cagagaacct agagcccaag gttcagagtc     180
```

```
acccatctca gcaagcccag aagtatctgc aatatctacg atggcctcgc cctttgcttt      240
actgatggtc ctggtggtgc tcagctgcaa gtcaagctgc tctctgggct gtgatctccc      300
tgagacccac agcctggata acaggaggac cttgatgctc ctggcacaaa tgagcagaat      360
ctctccttcc tcctgtctga tggacagaca tgactttgga tttccccagg aggagtttga      420
tggcaaccag ttccagaagg ctccagccat ctctgtcctc catgagctga tccagcagat      480
cttcaacctc tttaccacaa aagattcatc tgctgcttgg gatgaggacc tcctagacaa      540
attctgcacc gaactctacc agcagctgaa tgacttggaa gcctgtgtga tgcaggagga      600
gagggtggga gaaactcccc tgatgaatgc ggactccatc ttggctgtga agaaatactt      660
ccgaagaatc actctctatc tgacagagaa gaaatacagc ccttgtgcct gggaggttgt      720
cagagcagaa atcatgagat ccctctcttt atcaacaaac ttgcaagaaa gattaaggag      780
gaaggaataa catctggtcc aacatgaaaa caattcttat tgactcatac accaggtcac      840
gctttcatga attctgtcat ttcaaagact ctcacccctg ctataactat gaccatgctg      900
ataaactgat ttatctattt aaatatttat ttaactattc ataagattta aattattttt      960
gttcatataa cgtcatgtgc acctttacac tgtggttagt gtaataaaac atgttcctta     1020
tatttactca atccattatt ttgtgttgtt cattaaactt ttactatagg aacttcctgt     1080
atgtgttcat tctttaatat gaattcccta gcctgactgt gcaacctgat tagagaataa     1140
agggtatatt ttatttgctt atcattatta tatgtaaga                            1179
```

<210> SEQ ID NO 50
<211> LENGTH: 189
<212> TYPE: PRT
<213> ORGANISM: Homo sapiens

<400> SEQUENCE: 50

```
Met Ala Ser Pro Phe Ala Leu Leu Met Val Leu Val Val Leu Ser Cys
1               5                   10                  15

Lys Ser Ser Cys Ser Leu Gly Cys Asp Leu Pro Glu Thr His Ser Leu
            20                  25                  30

Asp Asn Arg Arg Thr Leu Met Leu Leu Ala Gln Met Ser Arg Ile Ser
        35                  40                  45

Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185
```

<210> SEQ ID NO 51
<211> LENGTH: 985
<212> TYPE: DNA
<213> ORGANISM: Homo sapiens

<400> SEQUENCE: 51

```
gcggagctgg gtgcgagcgc cctaccgctt tcgctttccc ttcgcggtgc ccactccact      60
ccttgtgcgg cgctaggccc cccgtcccgg tcatggccat gctcagggtc cagcccgagg     120
cccaagccaa ggtggatgtg tttcgtgaag acctctgtac caagacagag aacctgctcg     180
ggagctattt ccccaagaag atttctgagc tggatgcatt tttaaaggag ccagctctca     240
atgaagccaa cttgagcaat ctgaaggccc cattggacat cccagtgcct gatccagtca     300
aggagaaaga gaaagaggag cggaagaaac agcaggagaa ggaagacaag gatgaaaaga     360
agaaggggga ggatgaagac aaaggtcctc cctgtggccc agtgaactgc aatgaaaaga     420
tcgtggtcct tctgcagcgc ttgaagcctg agatcaagga tgtcattgag cagctcaacc     480
tggtcaccac ctggttgcag ctgcagatac tcggattga ggatggtaac aattttggag     540
tggctgtcca ggagaaggtg tttgagctga tgaccagcct ccacaccaag ctagaaggct     600
tccacactca aatctctaag tatttctctg agcgtggtga tgcagtgact aaagcagcca     660
agcagcccca tgtgggtgat tatcggcagc tggtgcacga gctggatgag gcagagtacc     720
gggacatccg gctgatggtc atggagatcc gcaatgctta tctgtgtta tatgacatca     780
tcctgaagaa cttcgagaag ctcaagaagc ccaggggaga aacaaaggga atgatctatt     840
gagagccctc tctcccattc tgtgatgagt acagcagaga ccttcctgct ttttactggg     900
gactccagat ttttccccaaa cttgcttctg ttgagatttt tccctcacct tgcctctcag     960
gcacaataaa tatagttata ccact                                            985
```

<210> SEQ ID NO 52
<211> LENGTH: 249
<212> TYPE: PRT
<213> ORGANISM: Homo sapiens

<400> SEQUENCE: 52

```
Met Ala Met Leu Arg Val Gln Pro Glu Ala Gln Ala Lys Val Asp Val
1               5                   10                  15

Phe Arg Glu Asp Leu Cys Thr Lys Thr Glu Asn Leu Leu Gly Ser Tyr
            20                  25                  30

Phe Pro Lys Lys Ile Ser Glu Leu Asp Ala Phe Leu Lys Glu Pro Ala
        35                  40                  45

Leu Asn Glu Ala Asn Leu Ser Asn Leu Lys Ala Pro Leu Asp Ile Pro
    50                  55                  60

Val Pro Asp Pro Val Lys Glu Lys Glu Lys Glu Arg Lys Lys Gln
65                  70                  75                  80

Gln Glu Lys Glu Asp Lys Asp Glu Lys Lys Gly Glu Asp Glu Asp
            85                  90                  95

Lys Gly Pro Pro Cys Gly Pro Val Asn Cys Asn Glu Lys Ile Val Val
        100                 105                 110

Leu Leu Gln Arg Leu Lys Pro Glu Ile Lys Asp Val Ile Glu Gln Leu
    115                 120                 125

Asn Leu Val Thr Thr Trp Leu Gln Leu Gln Ile Pro Arg Ile Glu Asp
130                 135                 140

Gly Asn Asn Phe Gly Val Ala Val Gln Glu Lys Val Phe Glu Leu Met
145                 150                 155                 160
```

Thr Ser Leu His Thr Lys Leu Glu Gly Phe His Thr Gln Ile Ser Lys
              165                 170                 175

Tyr Phe Ser Glu Arg Gly Asp Ala Val Thr Lys Ala Ala Lys Gln Pro
            180                 185                 190

His Val Gly Asp Tyr Arg Gln Leu Val His Glu Leu Asp Glu Ala Glu
        195                 200                 205

Tyr Arg Asp Ile Arg Leu Met Val Met Glu Ile Arg Asn Ala Tyr Ala
    210                 215                 220

Val Leu Tyr Asp Ile Ile Leu Lys Asn Phe Glu Lys Leu Lys Lys Pro
225                 230                 235                 240

Arg Gly Glu Thr Lys Gly Met Ile Tyr
                245

<210> SEQ ID NO 53
<211> LENGTH: 694
<212> TYPE: DNA
<213> ORGANISM: Homo sapiens

<400> SEQUENCE: 53
catcactcac accttgcatt tcacccctgc atcccagtcg ccctgcagcc tcacacagat      60
cctgcacaca cccagacagc tggcgctcac acattcaccg ttggcctgcc tctgttcacc     120
ctccatggcc ctgctactgg ccctcagcct gctggttctc tggacttccc cagccccaac     180
tctgagtggc accaatgatg ctgaagactg ctgcctgtct gtgacccaga aacccatccc     240
tgggtacatc gtgaggaact tccactacct tctcatcaag gatggctgca gggtgcctgc     300
tgtagtgttc accacactga ggggccgcca gctctgtgca cccccagacc agccctgggt     360
agaacgcatc atccagagac tgcagaggac ctcagccaag atgaagcgcc gcagcagtta     420
acctatgacc gtgcagaggg agcccggagt ccgagtcaag cattgtgaat tattacctaa     480
cctggggaac cgaggaccag aaggaaggac caggcttcca gctcctctgc accagacctg     540
accagccagg acagggcctg gggtgtgtgt gagtgtgagt gtgagcgaga gggtgagtgt     600
ggtcagagta agctgctccc accccagat tgcaatgcta ccaataaagc cgcctggtgt     660
ttacaactaa aaaaaaaaaa aaaaaaaaa aaaa                                 694

<210> SEQ ID NO 54
<211> LENGTH: 97
<212> TYPE: PRT
<213> ORGANISM: Homo sapiens

<400> SEQUENCE: 54

Ala Leu Leu Leu Ala Leu Ser Leu Leu Val Leu Trp Thr Ser Pro Ala
1               5                   10                  15

Pro Thr Leu Ser Gly Thr Asn Asp Ala Glu Asp Cys Cys Leu Ser Val
            20                  25                  30

Thr Gln Lys Pro Ile Pro Gly Tyr Ile Val Arg Asn Phe His Tyr Leu
        35                  40                  45

Leu Ile Lys Asp Gly Cys Arg Val Pro Ala Val Val Phe Thr Thr Leu
    50                  55                  60

Arg Gly Arg Gln Leu Cys Ala Pro Pro Asp Gln Pro Trp Val Glu Arg
65                  70                  75                  80

Ile Ile Gln Arg Leu Gln Arg Thr Ser Ala Lys Met Lys Arg Arg Ser
                85                  90                  95

Ser

```
<210> SEQ ID NO 55
<211> LENGTH: 856
<212> TYPE: DNA
<213> ORGANISM: Homo sapiens

<400> SEQUENCE: 55
cacagacatg gctcagtcac tggctctgag cctccttatc ctggttctgg cctttggcat    60
ccccaggacc caaggcagtg atggagggc tcaggactgt tgcctcaagt acagccaaag   120
gaagattccc gccaaggttg tccgcagcta ccggaagcag gaaccaagct taggctgctc   180
catcccagct atcctgttct tgccccgcaa gcgctctcag gcagagctat gtgcagaccc   240
aaaggagctc tgggtgcagc agctgatgca gcatctggac aagacaccat ccccacagaa   300
accagcccag gctgcagga aggacagggg ggcctccaag actggcaaga aggaaaggg    360 ctccaaaggc tgcaagagga ctgagcggtc acagacccct aaagggccat agcccagtga   420
gcagcctgga gccctggaga ccccaccagc ctcaccagcg cttgaagcct gaacccaaga   480
tgcaagaagg aggctatgct caggggccct ggagcagcca ccccatgctg gccttgccac   540
actctttctc ctgctttaac caccccatct gcattcccag ctctaccctg catggctgag   600
ctgcccacag caggccaggt ccagagagac cgaggaggga gagtctccca gggagcatga   660
gaggaggcag caggactgtc cccttgaagg agaatcatca ggaccctgga cctgatacgg   720
ctccccagta caccccacct cttccttgta aatatgattt atacctaact gaataaaaag   780
ctgttctgtc ttcccaccca aaaaaaaaaa aaaaaaaaaa aaaaaaaaaa aaaaaaaaaa   840
aaaaaaaaaa aaaaa                                                   856

<210> SEQ ID NO 56
<211> LENGTH: 134
<212> TYPE: PRT
<213> ORGANISM: Homo sapiens

<400> SEQUENCE: 56

Met Ala Gln Ser Leu Ala Leu Ser Leu Leu Ile Leu Val Leu Ala Phe
  1               5                  10                  15

Gly Ile Pro Arg Thr Gln Gly Ser Asp Gly Ala Gln Asp Cys Cys
                 20                  25                  30

Leu Lys Tyr Ser Gln Arg Lys Ile Pro Ala Lys Val Val Arg Ser Tyr
         35                  40                  45

Arg Lys Gln Glu Pro Ser Leu Gly Cys Ser Ile Pro Ala Ile Leu Phe
     50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                 85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
        130

<210> SEQ ID NO 57
<211> LENGTH: 1669
<212> TYPE: DNA
<213> ORGANISM: Homo sapiens

<400> SEQUENCE: 57
```

```
ctccctcagc aaggacagca gaggaccagc taagagggag agaagcaact acagacccccc    60
cctgaaaaca accctcagac gccacatccc ctgacaagct gccaggcagg ttctcttcct   120
ctcacatact gacccacggc tccaccctct ctccctgga aaggacacca tgagcactga    180
aagcatgatc cgggacgtgg agctggccga ggaggcgctc cccaagaaga caggggggcc    240
ccagggctcc aggcggtgct tgttcctcag cctcttctcc ttcctgatcg tggcaggcgc   300
caccacgctc ttctgcctgc tgcactttgg agtgatcggc cccagagggg aagagttccc    360
cagggacctc tctctaatca gccctctggc ccaggcagtc agatcatctt ctcgaacccc   420
gagtgacaag cctgtagccc atgttgtagc aaaccctcaa gctgaggggc agctccagtg    480
gctgaaccgc cgggccaatg ccctcctggc caatggcgtg gagctgagag ataaccagct    540
ggtggtgcca tcagagggcc tgtacctcat ctactcccag gtcctcttca agggccaagg    600
ctgcccctcc acccatgtgc tcctcaccca caccatcagc cgcatcgccg tctcctacca    660
gaccaaggtc aacctcctct ctgccatcaa gagcccctgc cagagggaga ccccagaggg    720
ggctgaggcc aagccctggt atgagcccat ctatctggga ggggtcttcc agctggagaa    780
gggtgaccga ctcagcgctg agatcaatcg gcccgactat ctcgactttg ccgagtctgg    840
gcaggtctac tttgggatca ttgccctgtg aggaggacga acatccaacc ttcccaaacg    900
cctcccctgc cccaatccct ttattacccc ctccttcaga cacctcaac ctcttctggc    960
tcaaaaagag aattgggggc ttagggtcgg aacccaagct tagaacttta agcaacaaga   1020
ccaccacttc gaaacctggg attcaggaat gtgtggcctg cacagtgaag tgctggcaac   1080
cactaagaat tcaaactggg gcctccagaa ctcactgggg cctacagctt tgatccctga   1140
catctggaat ctggagacca gggagccttt ggttctggcc agaatgctgc aggacttgag   1200
aagacctcac ctagaaattg acacaagtgg accttaggcc ttcctctctc cagatgtttc   1260
cagacttcct tgagacacgg agcccagccc tccccatgga gccagctccc tctatttatg   1320
tttgcacttg tgattatta ttatttattt attatttat tatttacaga tgaatgtatt   1380
tatttgggag accggggtat cctgggggac ccaatgtagg agctgccttg gctcagacat   1440
gttttccgtg aaaacggagc tgaacaatag gctgttccca tgtagccccc tggcctctgt   1500
gccttctttt gattatgttt tttaaaatat ttatctgatt aagttgtcta aacaatgctg   1560
atttggtgac caactgtcac tcattgctga gcctctgctc cccaggggag ttgtgtctgt   1620
aatcgcccta ctattcagtg gcgagaaata agtttgctt agaaaagaa            1669
```

<210> SEQ ID NO 58
<211> LENGTH: 233
<212> TYPE: PRT
<213> ORGANISM: Homo sapiens

<400> SEQUENCE: 58

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

```
Ser Arg Thr Pro Ser Asp Lys Pro Val Ala His Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

```
<210> SEQ ID NO 59
<211> LENGTH: 1077
<212> TYPE: DNA
<213> ORGANISM: Homo sapiens

<400> SEQUENCE: 59
ggggaccaaa gaggctgggc cccgccatgg gccagacggc aggcgacctt ggctggcggc      60
tcagcctgtt gctgcttccc ttgctcctgg ttcaagctgg tgtctgggga ttcccaaggc     120
ccccagggag gccccagctg agcctgcagg agctgcggag ggagttcaca gtcagcctgc     180
atctcgccag gaagctgctc gccgaggttc ggggccaggc ccaccgcttt gcggaatctc     240
acctgccagg agtgaacctg tacctcctgc ccctgggaga gcagctccct gatgtttccc     300
tgaccttcca ggcctggcgc cgcctctctg acccggagct ctctgcttc atctccacca     360
cgcttcagcc cttccatgcc ctgctggag ggctggggac ccagggccgc tggaccaaca     420
tggagaggat gcagctgtgg gccatgaggc tggacctccg cgatctgcag cggcacctcc     480
gcttccaggt gctggctgca ggattcaacc tcccggagga ggaggaggag aagaggagg      540
aggaggagga ggagaggaag gggctgctcc caggggcact gggcagcgcc ttacagggcc     600
cggcccaggt gtcctggccc cagctcctct ccacctaccg cctgctgcac tccttggagc     660
tcgtcttatc tcgggccgtg cgggagttgc tgctgctgtc caaggctggg cactcagtct     720
ggcccttggg gttcccaaca ttgagccccc agccctgatc ggtggcttct tagcccctg     780
ccccccaccc tttagaactt taggactgga gtcttggcat cagggcagcc ttcgcatcat     840
cagccttgga caagggaggg ctcttccagc ccctgcccc aggccctacc cagtaactga     900
aagcccctct ggtcctcgcc agctatttat ttcttggata tttatttatt gtttagggag     960
atgatggttt atttattgtc ttggggcccg atggtcctcc tcgggccaag cccccatgct    1020
gggtgcccaa taaagcactc tcatccataa aaaaaaaaaa aaaaaaaaaa aaaaaaa       1077
```

```
<210> SEQ ID NO 60
<211> LENGTH: 243
<212> TYPE: PRT
```

<213> ORGANISM: Homo sapiens

<400> SEQUENCE: 60

```
Met Gly Gln Thr Ala Gly Asp Leu Gly Trp Arg Leu Ser Leu Leu Leu
1               5                   10                  15
Leu Pro Leu Leu Leu Val Gln Ala Gly Val Trp Gly Phe Pro Arg Pro
            20                  25                  30
Pro Gly Arg Pro Gln Leu Ser Leu Gln Glu Leu Arg Arg Glu Phe Thr
        35                  40                  45
Val Ser Leu His Leu Ala Arg Lys Leu Leu Ala Glu Val Arg Gly Gln
50                  55                  60
Ala His Arg Phe Ala Glu Ser His Leu Pro Gly Val Asn Leu Tyr Leu
65                  70                  75                  80
Leu Pro Leu Gly Glu Gln Leu Pro Asp Val Ser Leu Thr Phe Gln Ala
                85                  90                  95
Trp Arg Arg Leu Ser Asp Pro Glu Arg Leu Cys Phe Ile Ser Thr Thr
            100                 105                 110
Leu Gln Pro Phe His Ala Leu Leu Gly Gly Leu Gly Thr Gln Gly Arg
        115                 120                 125
Trp Thr Asn Met Glu Arg Met Gln Leu Trp Ala Met Arg Leu Asp Leu
130                 135                 140
Arg Asp Leu Gln Arg His Leu Arg Phe Gln Val Leu Ala Ala Gly Phe
145                 150                 155                 160
Asn Leu Pro Glu Glu Glu Glu Glu Glu Glu Glu Glu Glu Glu Glu Glu
                165                 170                 175
Arg Lys Gly Leu Leu Pro Gly Ala Leu Gly Ser Ala Leu Gln Gly Pro
            180                 185                 190
Ala Gln Val Ser Trp Pro Gln Leu Leu Ser Thr Tyr Arg Leu Leu His
        195                 200                 205
Ser Leu Glu Leu Val Leu Ser Arg Ala Val Arg Glu Leu Leu Leu Leu
210                 215                 220
Ser Lys Ala Gly His Ser Val Trp Pro Leu Gly Phe Pro Thr Leu Ser
225                 230                 235                 240
Pro Gln Pro
```

<210> SEQ ID NO 61
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttcccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tcccctccga cggccccgta     420
atgcagaaga agaccatggg ctgggaggcc tcctccgagc ggatgtaccc cgaggacggc     480
gccctgaagg gcgagatcaa gcagaggctg aagctgaagg acggcggcca ctacgacgct     540
```

```
gaggtcaaga ccacctacaa ggccaagaag cccgtgcagc tgcccggcgc ctacaacgtc      600
aacatcaagt tggacatcac ctcccacaac gaggactaca ccatcgtgga acagtacgaa      660
cgcgccgagg ccgccactc caccggcggc atggacgagc tgtacaagta a                711
```

<210> SEQ ID NO 62
<211> LENGTH: 1605
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
atggctcaga tgatgactct gagcctcctt agcctggtcc tggctctctg catccctgg       60 acccaaggca gtgatggagg gggtcaggac tgctgcctta agtacagcca agagaaaatt      120
ccctacagta ttgtccgagg ctataggaag caagaaccaa gtttaggctg tcccatcccg      180
gcaatcctgt tctcaccccg gaagcactct aagcctgagc tatgtgcaaa ccctgaggaa      240
ggctgggtgc agaacctgat gcgccgcctg gaccagcctc cagccccagg gaaacaaagc      300
cccggctgca ggaagaaccg gggaacctct aagtctggaa agaaaggaaa gggctccaag      360
ggctgcaaga gaactgaaca gacacagccc tcaagaggaa gatccatggt gagcaagggc      420
gaggaggata acatggccat catcaaggag ttcatgcgct tcaaggtgca catggagggc      480
tccgtgaacg gccacgagtt cgagatcgag ggcgagggcg agggccgccc ctacgagggc      540
acccagaccg ccaagctgaa ggtgaccaag ggtggccccc tgcccttcgc ctgggacatc      600
ctgtcccctc agttcatgta cggctccaag gcctacgtga agcaccccgc cgacatcccc      660
gactacttga agctgtcctt ccccgagggc ttcaagtggg agcgcgtgat gaacttcgag      720
gacggcggcg tggtgaccgt gacccaggac tcctccctgc aggacggcga gttcatctac      780
aaggtgaagc tgcgcggcac caacttcccc tccgacggcc ccgtaatgca gaagaagacc      840
atgggctggg aggcctcctc cgagcggatg taccccgagg acggcgccct gaagggcgag      900
atcaagcaga ggctgaagct gaaggacggc ggccactacg acgctgaggt caagaccacc      960
tacaaggcca agaagcccgt gcagctgccc ggcgcctaca acgtcaacat caagttggac     1020
atcacctccc acaacgagga ctacaccatc gtggaacagt acgaacgcgc cgagggccgc     1080
cactccaccg gcggcatgga cgagctgtac aagtaatgca cacaacactg gcaggatgct     1140
gtgccttgga cagaactcct cagtctacag acagaggatg gcttctggaa acttacacca     1200
gaactgggac ttatattaaa tcttaataca aatggtttgc acagctttct taaacaaaaa     1260
ggcattcaat tctctaggtgt aaaaggaaga gaatgtctcc tggacctaat tgccacaatg     1320
ctggtactac agtttattcg caccaggttg gaaaagagg gaatagtgtt caaatcactg     1380
atgaaaatgg atgacccttc tatttccagg aatattccct gggcttttga ggcaataaag     1440
caagcaagtg aatgggtaag aagaactgaa ggacagtacc catctatctg cccacggctt     1500
gaactgggga acgactggga ctctgccacc aagcagttgc tgggactcca gcccataagc     1560
actgtgtccc ctcttcatag agtcctccat tacagtcaag ctaa                     1605
```

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
gcgcggatcc ccatggctca gatgatg                                              27

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcgcagatct tcctcttgag ggctgtgtct g                                         31

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccccactagt ccagttctca gtcactggct ctg                                       33

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccccgctagc tggcccttta ggggtctgtg                                           30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccccgctagc tgcacacaac actggcagga                                           30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggggctcgag ttagccttga ctgtaatgga                                           30

<210> SEQ ID NO 69
<211> LENGTH: 252
<212> TYPE: PRT
<213> ORGANISM: Homo sapiens

<400> SEQUENCE: 69

-continued

```
Ala Asn Leu Arg Leu Pro Met Ala Ser Ala Leu Pro Glu Ala Leu Cys
1               5                   10                  15

Ser Gln Ser Arg Thr Thr Pro Val Asp Leu Cys Leu Leu Glu Glu Ser
            20                  25                  30

Val Gly Ser Leu Glu Gly Ser Arg Cys Pro Val Phe Ala Phe Gln Ser
        35                  40                  45

Ser Asp Thr Glu Ser Asp Glu Leu Ser Glu Val Leu Gln Asp Ser Cys
    50                  55                  60

Phe Leu Gln Ile Lys Cys Asp Thr Lys Asp Asp Ser Ile Pro Cys Phe
65                  70                  75                  80

Leu Glu Leu Lys Glu Glu Asp Glu Ile Val Cys Thr Gln His Trp Gln
                85                  90                  95

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

Val Lys Gly Arg Glu Cys Leu Leu Asp Leu Ile Ala Thr Met Leu Val
145                 150                 155                 160

Leu Gln Phe Ile Arg Thr Arg Leu Glu Lys Glu Gly Ile Val Phe Lys
                165                 170                 175

Ser Leu Met Lys Met Asp Asp Pro Ser Ile Ser Arg Asn Ile Pro Trp
            180                 185                 190

Ala Phe Glu Ala Ile Lys Gln Ala Ser Glu Trp Val Arg Arg Thr Glu
        195                 200                 205

Gly Gln Tyr Pro Ser Ile Cys Pro Arg Leu Glu Leu Gly Asn Asp Trp
    210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250
```